United States Patent
Feinberg

(10) Patent No.: US 10,927,415 B2
(45) Date of Patent: Feb. 23, 2021

(54) METHODS FOR IDENTIFYING CANCER RISK

(75) Inventor: Andrew P. Feinberg, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 558 days.

(21) Appl. No.: 12/625,240

(22) Filed: Nov. 24, 2009

(65) Prior Publication Data
US 2010/0167940 A1 Jul. 1, 2010

Related U.S. Application Data

(60) Provisional application No. 61/118,169, filed on Nov. 26, 2008.

(51) Int. Cl.
*C12Q 1/6886* (2018.01)

(52) U.S. Cl.
CPC ..... *C12Q 1/6886* (2013.01); *C12Q 2600/154* (2013.01); *Y10T 436/143333* (2015.01)

(58) Field of Classification Search
None
See application file for complete search history.

(56) References Cited

U.S. PATENT DOCUMENTS

| 7,211,390 B2 * | 5/2007 | Rothberg et al. ............ 435/6.1 |
| 2006/0183128 A1 * | 8/2006 | Berlin et al. ................... 435/6 |
| 2008/0095764 A1 | 4/2008 | Parsons et al. |
| 2008/0166728 A1 * | 7/2008 | Kruglyak et al. ............. 435/6 |

OTHER PUBLICATIONS

Takai et al. Comprehensive analysis of CpG islands in human chromosomes 21 and 22. PNAS 99(6):3740-3745 (2002).*
Hackenberg et al. CpGcluster: a distance-based algorithm for CpG-island detection. BMC Bioinformatics 7:446; 13 pages (2006).*
Glass et al. CG dinucleotide clustering is a species-specific property of the genome. Nucleic Acids Research 35(20):6798-6807 (2007).*
Akan et al. DNA sequence and structural properties as predictors of human and mouse promoters. Gene 410:165-176, published online Dec. 23, 2007.*
Irizarry et al. A species-generalized probabilistic model-based definition of CpG islands. Mammalian Genome 20(9-10):674-80, published online Sep. 24, 2009.*
Feinberg, A. P. & Tycko, B. The history of cancer epigenetics. Nat. Rev. Cancer 4, 143-153, 2004.*
Pini et al. Evidence That General Genomic Hypomethylation and Focal Hypermethylation Are Two Independent Molecular Events of Non-Hodgkin's Lymphoma. Oncology Research 14:399-405 (2004).*
Genbank AL021528 [online] Jan. 6, 2005 [retrieved on Sep. 14, 2012] retrieved from http://www.ncbi.nlm.nih.gov/nuccore/3115987?sat=34& satkey=2682059.*
Zare et al. Qualitative analysis of Adenomatous Polyposis Coli promoter: Hypermethylation, engagement and effects on survival of patients with esophageal cancer in a high risk region of the world, a potential molecular marker. BMC Cancer 9:24, Jan. 17, 2009 (12 pages).*
GenBank Accession No. NC_000020 [online] Jun. 6, 2016 [retrieved on Sep. 4, 2016] retrieved from http://www.ncbi.nlm.nih.gov/nuccore/NC_000020.*
GenBank Accession No. NM_024701 [online] Aug. 25, 2016 [retrieved on Sep. 4, 2016] retrieved from http://www.ncbi.nlm.nih.gov/nuccore/nm_024701.*
Oue et al., DNA methylation of multiple genes in gastric carcinoma: Association with histolgical type and CpG island methylator phenotype. Cancer Sci 2002, 94(10):901-905; abstract, p. 902 fig 1 RAR beta gene.
Sakamoto et al., Cell type-specific methylation profiles occurring disproportionately in CpG-less regions that delineate developmental similarity. Genes Cells 2007, 12(10):1123-1132; p. 1126 left col. para 1, Supplement 2 Zfpm 1 gene and fibroblast growth factor gene 14 (fgf14).
Irizarry, et al., Comprehensive high-throughput arrays for relative methylation (CHAR). Genome Research, May 2008, 18(5):780-790; abstract.
Youssef et al., Methylation and regulation of expression of different retinoic acid receptor beta isoforms in human colon cancer. Cancer Biol Ther. 2004, 3(1):82-86; abstract.
Irizarry et al., The human colon cancer methylome shows similar hypo- and hypermethylation at conserved tissue-specific CpGisland shores. Nature Genetics ePub Jan. 19, 2009.41(2);178-186; p. 179 right col. para 2.

* cited by examiner

*Primary Examiner* — Samuel C Woolwine
(74) *Attorney, Agent, or Firm* — DLA Piper LLP (US)

(57) ABSTRACT

Provided herein are tissue-specific differential methylated regions (T-DMRs) and cancer-related differential methylated regions (C-DMRs) and methods of use thereof. In one embodiment of the invention, there are provided methods of detecting a cell proliferative disorder by detecting altered methylation in one or more DMRs identified herein. In another embodiment of the invention, there are provided methods of determining clinical outcome by detecting altered methylation in one or more DMRs identified herein.

6 Claims, 40 Drawing Sheets
Specification includes a Sequence Listing.

SEQUENCE LISTING

<160> NUMBER OF SEQ ID NOS: 144

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tcctgaggaa tcaacacttc                                           20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cagatgccat gggtctcttg                                           20

<210> SEQ ID NO 3
<211> LENGTH: 20
<212> TYPE: DNA
<213> ORGANISM: Artificial Sequence
<220> FEATURE:
<223> OTHER INFORMATION: Primer -continued

```
<400> SEQUENCE: 3
acgtcgagcc ggctcctgga                                              20

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ataatgaggt atagaggtta ta                                           22

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aacatctata tcaacaaact aa                                           22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
gaggttatat ttgtttttgt tt                                           22

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aactctaccc aaaaatcaaa a                                            21

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ggttttgttt tagttttg                                                18

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
caaaactaaa acaaaacc                                                18

<210> SEQ ID NO 10
<211> LENGTH: 24
```

```
<212> TYPE: DNA
<213> ORGANISM: Artificial Sequence
<220> FEATURE:
<223> OTHER INFORMATION: Primer

<400> SEQUENCE: 10
gatatagtag gttttaggat gtgt                                          24

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ttaccacact attttaatta atataacct                                     29

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aggatgtgtt ttattgagta ta                                            22

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
aaaaccattt atatttttaa aact                                          24

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tgttttattg agtataaatg                                               20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
gtggtttata tttgtaattt                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
```
gaattatttg aggttaggtg                                             20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tgattaatat ggtgaaattt                                             20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ttaaaaatat aaaaattagt                                             20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ggaggttaag gtaggagaat                                             20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gttgtagtga gttaagaata                                             20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gaggtgatta tagggagtat                                             20

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
aaccctaaaa tttttctttt attc                                        24

<210> SEQ ID NO 23
<211> LENGTH: 18
<212> TYPE: DNA
<213> ORGANISM: Artificial Sequence

```
<220> FEATURE:
<223> OTHER INFORMATION: Primer

<400> SEQUENCE: 23
gttttggggt agtaatag                                                  18

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
ctaaacatca ttaaaaaact a                                              21

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25 ggtttttag ggaatgtgtt                                                 20

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
aaagaggtat tattatttat atattttgtg g                                   31

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
tattaaactt aaacctaaaa tttcacatc                                      29

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
ggtagtttta ggaaaattag g                                              21

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
aactattaat aaccctaaat cc                                             22
```

```
<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gtattattta attgattatt                                                 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
atatttgtga atttgagatt                                                 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ttggggttgg taaatgtagg                                                 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
aatgagattt aatttattag                                                 20

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
taggtttggt tttgtttatt tag                                             23

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
caataaccta aatactacca taatt                                           25

<210> SEQ ID NO 36
<211> LENGTH: 22
<212> TYPE: DNA
<213> ORGANISM: Artificial Sequence
<220> FEATURE:
<223> OTHER INFORMATION: Primer
```

<400> SEQUENCE: 36
gttgtttagg attgtaaaat at                                            22

<210> SEQ ID NO 37
<211> LENGTH: 18
<212> TYPE: DNA
<213> ORGANISM: Artificial Sequence
<220> FEATURE:
<223> OTHER INFORMATION: Primer

<400> SEQUENCE: 37
aaaaaaacca actacctc                                                 18

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
ttgtttttag ttaattag                                                 18

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
gtatagtgga tttttggagg t                                             21

<210> SEQ ID NO 40
<211> LENGTH: 18
<212> TYPE: DNA
<213> ORGANISM: Artificial Sequence
<220> FEATURE:
<223> OTHER INFORMATION: Primer

<400> SEQUENCE: 40
ctaattaact aaaaacaa                                                 18

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
acctccaaaa atccactata c                                             21

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
aaggagtata ataagtagag tgtg                                          24

<210> SEQ ID NO 43

```
<211> LENGTH: 23
<212> TYPE: DNA
<213> ORGANISM: Artificial Sequence
<220> FEATURE:
<223> OTHER INFORMATION: Primer

<400> SEQUENCE: 43
aaaacacctc cctaaattat caa                                              23

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
gtagaagggt tgtgatagga t                                                21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
cctccctaaa ttatcaactt c                                                21

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gaagggttgt gataggattt                                                  20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
ataaataaaa atattgttta                                                  20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
attttagtat tttgggaggt                                                  20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
```
aaatataaaa attagttggg                                                  20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
ggaggttgag gtaggagatt                                                  20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
aggtagaggt tgtagtgagt                                                  20

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
gttgattgtt ttttagtttt ttt                                              23

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
cccaacccaa aaataactat a                                                21

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
aaatttgatt ttggttttag gaga                                             24

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
actcccccat ctatacattt taa                                              23

<210> SEQ ID NO 56
<211> LENGTH: 24
<212> TYPE: DNA

```
<213> ORGANISM: Artificial Sequence
<220> FEATURE:
<223> OTHER INFORMATION: Primer

<400> SEQUENCE: 56
gtattgagta tgttttgtag ggtt                                            24

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
cttcacttaa caaaaaaata t                                               21

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
gaaaatgatt atgagtaaat ttggg                                           25

<210> SEQ ID NO 59
<211> LENGTH: 26
<212> TYPE: DNA
<213> ORGANISM: Artificial Sequence
<220> FEATURE:
<223> OTHER INFORMATION: Primer

<400> SEQUENCE: 59
cttaaaaata aaaataacaa cccacc                                          26

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
gagtaaattt ggggttattg t                                               21

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
ccaattttca accaacctat a                                               21

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
agaatagtaa taattatagt                                                 20
```

```
<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tagttattgt aaaaatgaat                                           20

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
ttgttaaaat ttttgttttt                                           20

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
tagttgttaa gtataattta                                           20

<210> SEQ ID NO 66
<211> LENGTH: 26
<212> TYPE: DNA
<213> ORGANISM: Artificial Sequence
<220> FEATURE:
<223> OTHER INFORMATION: Primer

<400> SEQUENCE: 66 tgtatttta gtagagatag ggttag                                     26

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67
tctattaaca taactcaaaa caacc                                     25

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
ttagtagaga tagggttagg                                           20

<210> SEQ ID NO 69
<211> LENGTH: 21
<212> TYPE: DNA
<213> ORGANISM: Artificial Sequence
<220> FEATURE:
```

<223> OTHER INFORMATION: Primer

<400> SEQUENCE: 69
caaaacaacc tctccacata a                                          21

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70 gatttttga tttaatggtt                                             20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
ttaaaatagg ttaagataaa                                            20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
taattttgtt gattttttta                                            20

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
tatttttaaa tataattata                                            20

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
tagatattga atagaatgtt ggaga                                      25

<210> SEQ ID NO 75
<211> LENGTH: 25
<212> TYPE: DNA
<213> ORGANISM: Artificial Sequence
<220> FEATURE:
<223> OTHER INFORMATION: Primer

<400> SEQUENCE: 75
attatttcca ttcctctcaa aatac                                      25

```
<210> SEQ ID NO 76
<211> LENGTH: 24
<212> TYPE: DNA
<213> ORGANISM: Artificial Sequence
<220> FEATURE:
<223> OTHER INFORMATION: Primer

<400> SEQUENCE: 76
agaatgttgg agatttttttt aatg                                         24

<210> SEQ ID NO 77
<211> LENGTH: 24
<212> TYPE: DNA
<213> ORGANISM: Artificial Sequence
<220> FEATURE:
<223> OTHER INFORMATION: Primer

<400> SEQUENCE: 77
cctttttttt ataataccta aact                                          24

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78 agatttttttt aatgttttga                                              20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
gaagaattat gagtttttat                                               20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
gaaaatagga attttagtgt                                               20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
aggtaatata gatgttggta                                               20

<210> SEQ ID NO 82
<211> LENGTH: 20
<212> TYPE: DNA
<213> ORGANISM: Artificial Sequence
<220> FEATURE:
<223> OTHER INFORMATION: Primer
```

```
<400> SEQUENCE: 82
taaggtagtt attggagatt                                               20

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
attggggaag atttttattt agag                                          24

<210> SEQ ID NO 84
<211> LENGTH: 24
<212> TYPE: DNA
<213> ORGANISM: Artificial Sequence
<220> FEATURE:
<223> OTHER INFORMATION: Primer

<400> SEQUENCE: 84
ctaaatccca aattctccat atac                                          24

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
agattgaata tttggttatt aag                                           23

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
ctctaaaatc cttcccctta a                                             21

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
atttagtgta gataaaggtg                                               20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
gagtttaaat aatttttag                                                20

<210> SEQ ID NO 89
<211> LENGTH: 20
```

-continued

<212> TYPE: DNA
<213> ORGANISM: Artificial Sequence
<220> FEATURE:
<223> OTHER INFORMATION: Primer

<400> SEQUENCE: 89
ggaatattta aagatatttt                                              20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
taggtgttat tttgatttta                                              20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
aaatttagtt aagtagtgta                                              20

<210> SEQ ID NO 92
<211> LENGTH: 22
<212> TYPE: DNA
<213> ORGANISM: Artificial Sequence
<220> FEATURE:
<223> OTHER INFORMATION: Primer

<400> SEQUENCE: 92
tttagagtgg agaagaaatg tt                                           22

<210> SEQ ID NO 93
<211> LENGTH: 25
<212> TYPE: DNA
<213> ORGANISM: Artificial Sequence
<220> FEATURE:
<223> OTHER INFORMATION: Primer

<400> SEQUENCE: 93
atattccaca ttaaacatat accac                                        25

<210> SEQ ID NO 94
<211> LENGTH: 23
<212> TYPE: DNA
<213> ORGANISM: Artificial Sequence
<220> FEATURE:
<223> OTHER INFORMATION: Primer

<400> SEQUENCE: 94
gtttaatggg attagagtga ttt                                          23

<210> SEQ ID NO 95
<211> LENGTH: 24
<212> TYPE: DNA
<213> ORGANISM: Artificial Sequence
<220> FEATURE:
<223> OTHER INFORMATION: Primer

<400> SEQUENCE: 95
ataaaaaacc tttcaaatta acac                                              24

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
gtgattttat gatggtattg                                                   20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
gagttaggtt tggaaggaag                                                   20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
atgtgttgtt ttgtataaga                                                   20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
aaggaagggt tttattaaat                                                   20

<210> SEQ ID NO 100
<211> LENGTH: 25
<212> TYPE: DNA
<213> ORGANISM: Artificial Sequence
<220> FEATURE:
<223> OTHER INFORMATION: Primer

<400> SEQUENCE: 100
tatttagggt tatttggttt ttttt                                             25

<210> SEQ ID NO 101
<211> LENGTH: 25
<212> TYPE: DNA
<213> ORGANISM: Artificial Sequence
<220> FEATURE:
<223> OTHER INFORMATION: Primer

<400> SEQUENCE: 101
aacctaactc cctacccact tatct                                             25

<210> SEQ ID NO 102
<211> LENGTH: 23
<212> TYPE: DNA
<213> ORGANISM: Artificial Sequence

```
<220> FEATURE:
<223> OTHER INFORMATION: Primer

<400> SEQUENCE: 102
ggattgtatt agaaaaatat agt                                          23

<210> SEQ ID NO 103
<211> LENGTH: 19
<212> TYPE: DNA
<213> ORGANISM: Artificial Sequence
<220> FEATURE:
<223> OTHER INFORMATION: Primer

<400> SEQUENCE: 103
acccatattt ccctcctat                                               19

<210> SEQ ID NO 104
<211> LENGTH: 18
<212> TYPE: DNA
<213> ORGANISM: Artificial Sequence
<220> FEATURE:
<223> OTHER INFORMATION: Primer

<400> SEQUENCE: 104
ctacaactct atttaccc                                                18

<210> SEQ ID NO 105
<211> LENGTH: 25
<212> TYPE: DNA
<213> ORGANISM: Artificial Sequence
<220> FEATURE:
<223> OTHER INFORMATION: Primer

<400> SEQUENCE: 105
tattttattg tgggagtttt tggag                                        25

<210> SEQ ID NO 106
<211> LENGTH: 29
<212> TYPE: DNA
<213> ORGANISM: Artificial Sequence
<220> FEATURE:
<223> OTHER INFORMATION: Primer

<400> SEQUENCE: 106
aataatcaca tttctcactt ttaccacta                                    29

<210> SEQ ID NO 107
<211> LENGTH: 21
<212> TYPE: DNA
<213> ORGANISM: Artificial Sequence
<220> FEATURE:
<223> OTHER INFORMATION: Primer

<400> SEQUENCE: 107
tgggagtttt tggagtatag t                                            21

<210> SEQ ID NO 108
<211> LENGTH: 23
<212> TYPE: DNA
<213> ORGANISM: Artificial Sequence
<220> FEATURE:
<223> OTHER INFORMATION: Primer

<400> SEQUENCE: 108
tatatttacc tatattccta tct                                          23
```

<210> SEQ ID NO 109
<211> LENGTH: 23
<212> TYPE: DNA
<213> ORGANISM: Artificial Sequence
<220> FEATURE:
<223> OTHER INFORMATION: Primer

<400> SEQUENCE: 109
aataaaatac atttattatc att                                              23

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
ttttgtgttt tgttgtggtg tg                                               22

<210> SEQ ID NO 111
<211> LENGTH: 25
<212> TYPE: DNA
<213> ORGANISM: Artificial Sequence
<220> FEATURE:
<223> OTHER INFORMATION: Primer

<400> SEQUENCE: 111
ctaactccaa actccaaaac catta                                            25

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
ggaaatgaga tttattgaga g                                                21

<210> SEQ ID NO 113
<211> LENGTH: 21
<212> TYPE: DNA
<213> ORGANISM: Artificial Sequence
<220> FEATURE:
<223> OTHER INFORMATION: Primer

<400> SEQUENCE: 113
ctctccttct attacaacta a                                                21

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
tagttattgg taatttttag                                                  20

<210> SEQ ID NO 115
<211> LENGTH: 25
<212> TYPE: DNA
<213> ORGANISM: Artificial Sequence
<220> FEATURE:
<223> OTHER INFORMATION: Primer

```
<400> SEQUENCE: 115
ttgattttga tttgttagtt gtttg                                    25

<210> SEQ ID NO 116
<211> LENGTH: 24
<212> TYPE: DNA
<213> ORGANISM: Artificial Sequence
<220> FEATURE:
<223> OTHER INFORMATION: Primer

<400> SEQUENCE: 116
tattccaata tacccatc accc                                       24

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
ggggtttagg agtaaaggtt                                          20

<210> SEQ ID NO 118
<211> LENGTH: 23
<212> TYPE: DNA
<213> ORGANISM: Artificial Sequence
<220> FEATURE:
<223> OTHER INFORMATION: Primer

<400> SEQUENCE: 118
ctaccctata aaaaatctt aaa                                       23

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
attcccaaaa atacccctaat                                         20

<210> SEQ ID NO 120
<211> LENGTH: 22
<212> TYPE: DNA
<213> ORGANISM: Artificial Sequence
<220> FEATURE:
<223> OTHER INFORMATION: Primer

<400> SEQUENCE: 120
ttgttgtgga ggagtttgtt ag                                       22

<210> SEQ ID NO 121
<211> LENGTH: 22
<212> TYPE: DNA
<213> ORGANISM: Artificial Sequence
<220> FEATURE:
<223> OTHER INFORMATION: Primer

<400> SEQUENCE: 121
tccaacctac tccttataaa tc                                       22

<210> SEQ ID NO 122
```

<211> LENGTH: 22
<212> TYPE: DNA
<213> ORGANISM: Artificial Sequence
<220> FEATURE:
<223> OTHER INFORMATION: Primer

<400> SEQUENCE: 122
tggtttgtat gaaagggaat at                                            22

<210> SEQ ID NO 123
<211> LENGTH: 25
<212> TYPE: DNA
<213> ORGANISM: Artificial Sequence
<220> FEATURE:
<223> OTHER INFORMATION: Primer

<400> SEQUENCE: 123
cctactcctt ataaatcaaa acacc                                         25

<210> SEQ ID NO 124
<211> LENGTH: 17
<212> TYPE: DNA
<213> ORGANISM: Artificial Sequence
<220> FEATURE:
<223> OTHER INFORMATION: Primer

<400> SEQUENCE: 124
tttagttgta ttgtttt                                                  17

<210> SEQ ID NO 125
<211> LENGTH: 23
<212> TYPE: DNA
<213> ORGANISM: Artificial Sequence
<220> FEATURE:
<223> OTHER INFORMATION: Primer

<400> SEQUENCE: 125
gtgtggttag aggtataagt aga                                           23

<210> SEQ ID NO 126
<211> LENGTH: 25
<212> TYPE: DNA
<213> ORGANISM: Artificial Sequence
<220> FEATURE:
<223> OTHER INFORMATION: Primer

<400> SEQUENCE: 126
tcaaccctct caaaacttat tccta                                         25

<210> SEQ ID NO 127
<211> LENGTH: 25
<212> TYPE: DNA
<213> ORGANISM: Artificial Sequence
<220> FEATURE:
<223> OTHER INFORMATION: Primer

<400> SEQUENCE: 127
gtagagggaa gaaaagattt ttttt                                         25

<210> SEQ ID NO 128
<211> LENGTH: 18
<212> TYPE: DNA
<213> ORGANISM: Artificial Sequence
<220> FEATURE:
<223> OTHER INFORMATION: Primer

<400> SEQUENCE: 128
cccaatcctc ccccttc                                              18

<210> SEQ ID NO 129
<211> LENGTH: 19
<212> TYPE: DNA
<213> ORGANISM: Artificial Sequence
<220> FEATURE:
<223> OTHER INFORMATION: Primer

<400> SEQUENCE: 129
ttgtagatta ttttatttg                                            19

<210> SEQ ID NO 130
<211> LENGTH: 25
<212> TYPE: DNA
<213> ORGANISM: Artificial Sequence
<220> FEATURE:
<223> OTHER INFORMATION: Primer

<400> SEQUENCE: 130
tgggtgggtg tagatatttt gttat                                     25

<210> SEQ ID NO 131
<211> LENGTH: 25
<212> TYPE: DNA
<213> ORGANISM: Artificial Sequence
<220> FEATURE:
<223> OTHER INFORMATION: Primer

<400> SEQUENCE: 131
acaatcctac acacacaaac cttta                                     25

<210> SEQ ID NO 132
<211> LENGTH: 23
<212> TYPE: DNA
<213> ORGANISM: Artificial Sequence
<220> FEATURE:
<223> OTHER INFORMATION: Primer

<400> SEQUENCE: 132
tagtgaaagt tttgggaaat tta                                       23

<210> SEQ ID NO 133
<211> LENGTH: 23
<212> TYPE: DNA
<213> ORGANISM: Artificial Sequence
<220> FEATURE:
<223> OTHER INFORMATION: Primer

<400> SEQUENCE: 133
ctacacacac aaacctttaa taa                                       23

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
attcatttta aaaataatc c                                          21

<210> SEQ ID NO 135
<211> LENGTH: 30
<212> TYPE: DNA

```
<213> ORGANISM: Artificial Sequence
<220> FEATURE:
<223> OTHER INFORMATION: Primer

<400> SEQUENCE: 135
tattaattaa attgttttta ggaaggtaat                                          30

<210> SEQ ID NO 136
<211> LENGTH: 25
<212> TYPE: DNA
<213> ORGANISM: Artificial Sequence
<220> FEATURE:
<223> OTHER INFORMATION: Primer

<400> SEQUENCE: 136
aaatttacat aaaaccacaa caaac                                              25

<210> SEQ ID NO 137
<211> LENGTH: 22
<212> TYPE: DNA
<213> ORGANISM: Artificial Sequence
<220> FEATURE:
<223> OTHER INFORMATION: Primer

<400> SEQUENCE: 137
gtttttagga aggtaattag aa                                                 22

<210> SEQ ID NO 138
<211> LENGTH: 24
<212> TYPE: DNA
<213> ORGANISM: Artificial Sequence
<220> FEATURE:
<223> OTHER INFORMATION: Primer

<400> SEQUENCE: 138
tacaaaaact taccaaatct atat                                               24

<210> SEQ ID NO 139
<211> LENGTH: 19
<212> TYPE: DNA
<213> ORGANISM: Artificial Sequence
<220> FEATURE:
<223> OTHER INFORMATION: Primer

<400> SEQUENCE: 139
aaattttaag aagttagta                                                     19

<210> SEQ ID NO 140
<211> LENGTH: 26
<212> TYPE: DNA
<213> ORGANISM: Artificial Sequence
<220> FEATURE:
<223> OTHER INFORMATION: Primer

<400> SEQUENCE: 140
gattaatgag ttatagagag atgttg                                             26

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
aaggagttaa aagtttttgg ag                                                 22
```

```
<210> SEQ ID NO 142
<211> LENGTH: 24
<212> TYPE: DNA
<213> ORGANISM: Artificial Sequence
<220> FEATURE:
<223> OTHER INFORMATION: Primer

<400> SEQUENCE: 142
gtttaggttt tttattttat aatg                                              24

<210> SEQ ID NO 143
<211> LENGTH: 21
<212> TYPE: DNA
<213> ORGANISM: Artificial Sequence
<220> FEATURE:
<223> OTHER INFORMATION: Primer

<400> SEQUENCE: 143
taagatttgg tgagggtttg t                                                 21

<210> SEQ ID NO 144
<211> LENGTH: 14
<212> TYPE: DNA
<213> ORGANISM: Artificial Sequence
<220> FEATURE:
<223> OTHER INFORMATION: Primer

<400> SEQUENCE: 144
gggtgattta tgaa                                                         14
```

METHODS FOR IDENTIFYING CANCER RISK

RELATED APPLICATION DATA

This application claims the benefit of priority under 35 U.S.C. § 119(e) of U.S. Ser. No. 61/118,169, filed Nov. 26, 2008, the entire content of which is incorporated herein by reference.

STATEMENT OF GOVERNMENT SUPPORT

This invention was made in part with government support under Grant Nos. P50HG003233 and R37CA54358 awarded by the National Institutes of Health. The United States government has certain rights in this invention.

BACKGROUND OF THE INVENTION

Field of the Invention

The present invention relates generally to differentially methylated regions (DMRs) in the genome outside CpG islands, and more specifically to methods for detecting the presence of or a risk for a hyperproliferative disorder by detecting an alteration in methylation status of such DMRs.

Background Information

Epigenetics is the study of non-sequence information of chromosome DNA during cell division and differentiation. The molecular basis of epigenetics is complex and involves modifications of the activation or inactivation of certain genes. Additionally, the chromatin proteins associated with DNA may be activated or silenced. Epigenetic changes are preserved when cells divide. Most epigenetic changes only occur within the course of one individual organism's lifetime, but some epigenetic changes are inherited from one generation to the next.

One example of an epigenetic mechanism is DNA methylation (DNAm), a covalent modification of the nucleotide cytosine. In particular, it involves the addition of methyl groups to cytosine nucleotides in the DNA, to convert cytosine to 5-methylcytosine. DNA methylation plays an important role in determining whether some genes are expressed or not. Abnormal DNA methylation is one of the mechanisms underlying the changes observed with aging and development of many cancers.

Cancers have historically been linked to genetic changes such as DNA sequence mutations. Evidence now supports that a relatively large number of cancers originate, not from mutations, but from epigenetic changes such as inappropriate DNA methylation. In some cases, hypermethylation of DNA results the an inhibition of expression of critical genes, such as tumor suppressor genes or DNA repair genes, allowing cancers to develop. In other cases, hypomethylation of genes modulates expression, which contributes to the development of cancer.

Epigenetics has led to an epigenetic progenitor model of cancer that epigenetic alterations affecting tissue-specific division and differentiation are the predominant mechanism by which epigenetic changes cause cancer. In other words, it is believed that aberrant methylation patterns may play multiple roles in cancer, such as the silencing of tumor suppressor genes, and the over-expression of oncogenes.

Since the discovery of altered DNA methylation in human cancer, the focus has largely been on specific genes of interest and regions assumed to be important functionally, such as promoters and CpG islands, and there has not been a comprehensive genome-scale understanding of the relationship between DNA methylation loss and gain in cancer and in normal differentiation.

SUMMARY OF THE INVENTION

The present invention is based on the discovery that some tissue-specific or cancer-related alterations in DNA methylation occur not only in promoters or CpG islands, but in sequences up to 2 kb distant from such CpG islands (such sequences are termed "CpG island shores"). In accordance with this discovery, there are provided herein differentially methylated regions (DMRs) and methods of use thereof.

In one embodiment of the invention, there are provided methods of diagnosis including detecting a cell proliferative disorder. The methods involve comparing the methylation status of one or more nucleic acid sequences in a sample from a subject suspected of having the disorder, with the proviso that the one or more nucleic acid sequences are outside of a promoter region of a gene and outside of a CpG island, and wherein the nucleic acid sequence is up to about 2 kb in distance from a CpG island, to the methylation status of the one or more nucleic acid sequences in a sample from a corresponding normal tissue or individual not having a cell proliferative disorder, wherein an alteration in methylation status is indicative of a cell proliferative disorder.

In certain embodiments, the cell proliferative disorder is cancer. In some embodiments, the nucleic acid sequence is within a gene; alternatively, the nucleic acid sequence is upstream or downstream of a gene. In particular embodiments, the one or more nucleic acid sequence is selected from the group consisting of the DMRs set forth in Tables 1-4, 6, 7, 9, 11, 14-16, 18, the DPP6 gene, the MRPL36 gene, the MEST gene, the GATA-2 gene, the RARRES2 gene, and any combination thereof. In some embodiments the alteration in methylation status is hypomethylation; in other embodiments the alteration in methylation status is hypermethylation. In embodiments using more than one DMR, the alteration in methylation status of some may be hypomethylation, whereas others may be hypermethylation.

In another embodiment of the invention, there are provided methods of determining a clinical outcome. Such methods are accomplished by comparing the methylation status of one or more nucleic acid sequences in a sample from a subject prior to undergoing a therapeutic regimen for a disease or disorder, wherein the disease or disorder is associated with altered methylation of the one or more nucleic acid sequences, with the proviso that the one or more nucleic acid sequences are outside of a promoter region of a gene and outside of a CpG island, and wherein the nucleic acid sequence is up to about 2 kb in distance from a CpG island, to the methylation status of the one or more nucleic acid, sequences in a sample from the individual after the therapeutic regimen has been initiated, wherein change in methylation status is indicative a positive clinical outcome. In particular embodiments, the one or more nucleic acid sequence is selected from the group consisting of the DMRs set forth in Tables 1-4, 6, 7, 9, 11, 14-16, 18, the DPP6 gene, the MRPL36 gene, the MEST gene, the GATA-2 gene, the RARRES2 gene, and any combination thereof. In some embodiments the change in methylation status is hypomethylation; in other embodiments the change in methylation status is hypermethylation. In embodiments using more than one DMR, the change in methylation status of some may be hypomethylation, whereas others may be hypermethylation.

In another embodiment of the invention, there are provided methods for providing a methylation map of a region of genomic DNA by performing comprehensive high-throughput array-based relative methylation (CHARM) analysis on, for example, a sample of labeled, digested genomic DNA. In some embodiments, the method may further include bisulfate pyrosequencing of the genomic DNA, for example.

In still another embodiment of the invention, there are provided methods of detecting a methylation status profile of the nucleic acid of a cancer cell from a tumor or biological sample. Such methods include hybridizing labeled and digested nucleic acid of a cancer cell from a tumor or biological sample to a DNA microarray comprising at least 100 nucleic acid sequences, with the proviso that the nucleic acid sequences are outside of a promoter region of a gene and outside of a CpG island, and wherein the nucleic acid sequence is up to about 2 kb in distance from a CpG island and determining a pattern of methylation from the hybridizing of step a), thereby detecting a methylation profile. In particular embodiments, the method further includes comparing the methylation profile to a methylation profile from hybridization of the microarray with labeled and digested nucleic acid from control "normal" cells. In certain embodiments, the one or more nucleic acid sequence is selected from the group consisting of the DMRs set forth in Tables 1-4, 6, 7, 9, 11, 14-16, 18, the DPP6 gene, the MRPL36 gene, the MEST gene, the GATA-2 gene, the RARRES2 gene, and any combination thereof.

In yet another embodiment of the present invention, there are provided methods for prognosis of a cancer in a subject known to have or suspected of having a cancer associated with altered methylation of one or more nucleic acid sequences. The method includes obtaining a tissue sample or biological sample containing nucleic acid from a subject; and assaying the methylation status of one or more nucleic acid sequences, with the proviso that the one or more nucleic acid sequences are outside of a promoter region of a gene and outside of a CpG island, and wherein the nucleic acid sequence is up to about 2 kb in distance from a CpG island bodily fluid; wherein the presence of altered methylation in the sample from the subject, relative to a corresponding sample from a normal sample, is indicative that the subject is a good for therapy of cancer. In some embodiments, the one or more nucleic acid sequence is selected from the group consisting of the DMRs set forth in Tables 1-4, 6, 7, 9, 11, 14-16, 18, the DPP6 gene, the MRPL36 gene, the MEST gene, the GATA-2 gene, the RARRES2 gene, and any combination thereof.

In another embodiment of the invention, there is provided a plurality of nucleic acid sequences, wherein the nucleic acid sequences are outside of a promoter region of a gene and outside of a CpG island, and wherein the nucleic acid sequence is up to about 2 kb in distance from a CpG island, and wherein the nucleic acid sequences are differentially methylated in cancer, In some embodiments, the nucleic acid sequence are selected from the group consisting of the DMR sequences as set forth in Tables 1-4, 6, 7, 9, 11, 14-16, 18, the MRPL36 gene, the MEST gene, the GATA-2 gene, and the RARRES2 gene. In one aspect, the plurality is a microarray.

In another embodiment of the invention, there is provided a plurality of nucleic acid sequences, wherein the nucleic acid sequences are outside of a promoter region of a gene and outside of a CpG island, and wherein the nucleic acid sequence is up to about 2 kb in distance from a CpG island, and wherein the nucleic acid sequences are differentially methylated in tissues derived from the three different embryonic lineages. In some embodiments, the plurality of nucleic acid sequences are selected from one or more of the sequences as set forth in FIG. 5a, FIG. 5b, Tables 1, 2, 4, 7, 9, 10, 12-14, and 17. In one aspect, the plurality is a microarray.

Figure 1A:
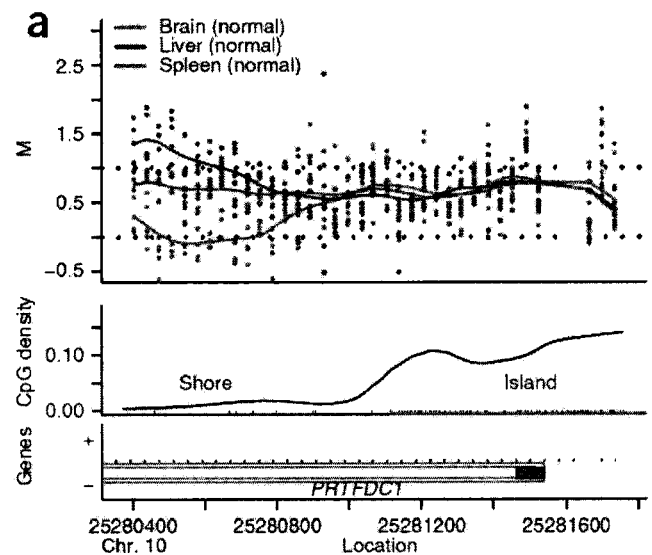
FIG. 1A shows a plot of M value versus genomic location for brain, liver, and spleen (upper panel) and a plot of CpG density versus genomic location over the same region (lower panel) for a T-DMR located in a CpG island shore.

D, SLIT and NTRK-like family, member 1 (SLITRK1); E, FEZ family zinc finger 2 (FEZF2), (n) equals the number of samples analyzed by pyrosequencing.

FIGS. 14A-D shows box plots of bisulfite pyrosequencing confirming the prevalence of 4 hypomethylated C-DMR shores in a large set of colon tumor and normal mucosa samples. Box-plots represent DNA methylation level measured using bisulfite pyrosequencing. A, transmembrane protein 14A (TMEM14A); B, glutamate-rich 1 (ERICH1); C, family with sequence similarity 70, member B (FAM70C); D, prostate transmembrane protein, androgen induced 1 (TMEPAI), (n) equals the number of samples analyzed by pyrosequencing.

Figure 15:
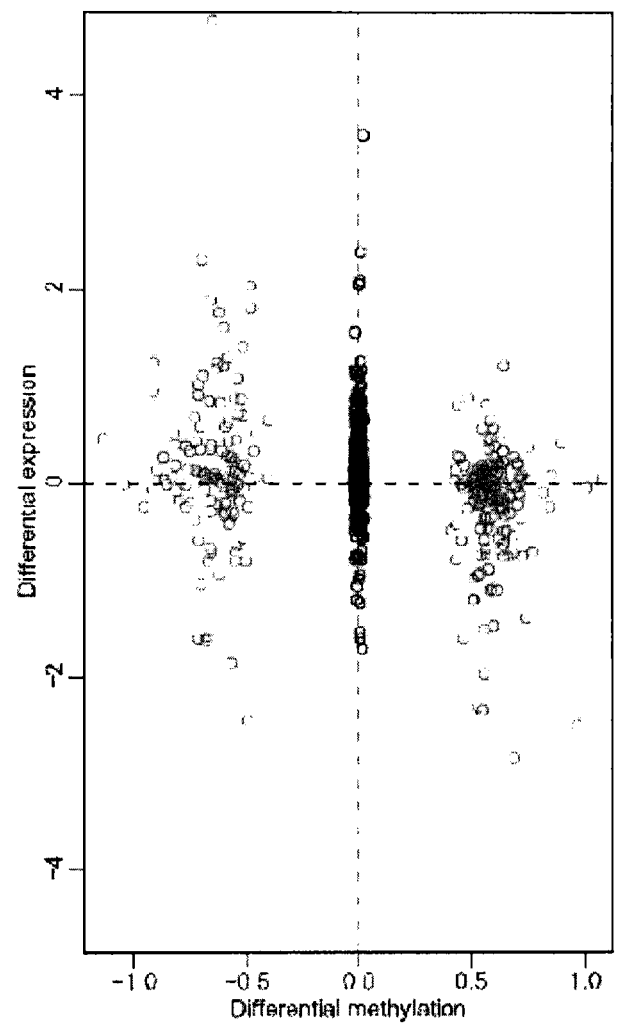

FIG. 15 shows a plot of log (base 2) ratios of colon tumor to normal expression against delta M values for colon tumor and normal DNAm.

Figure 16:
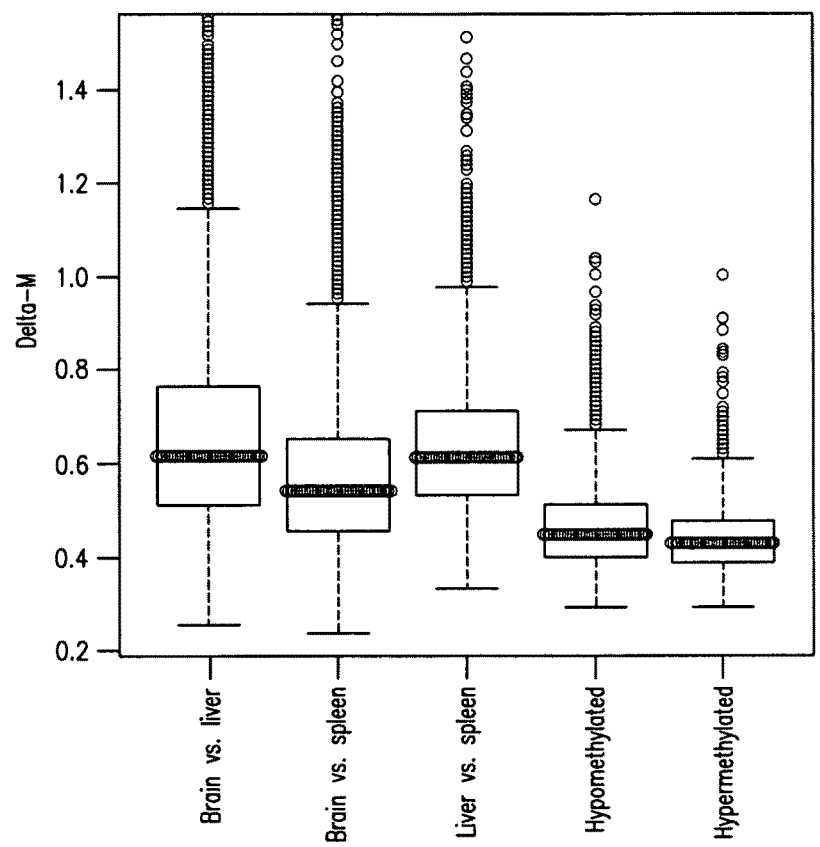

FIG. 16 shows a plot of average delta M values stratified into T-DMRs, hypermethylated C-DMRs and hypomethylated C-DMRs. T-DMRs were further stratified according to brain versus liver, brain versus spleen, and liver versus spleen pair-wise comparisons. The box-plots represent absolute values of the delta Ms.

Figure 17:
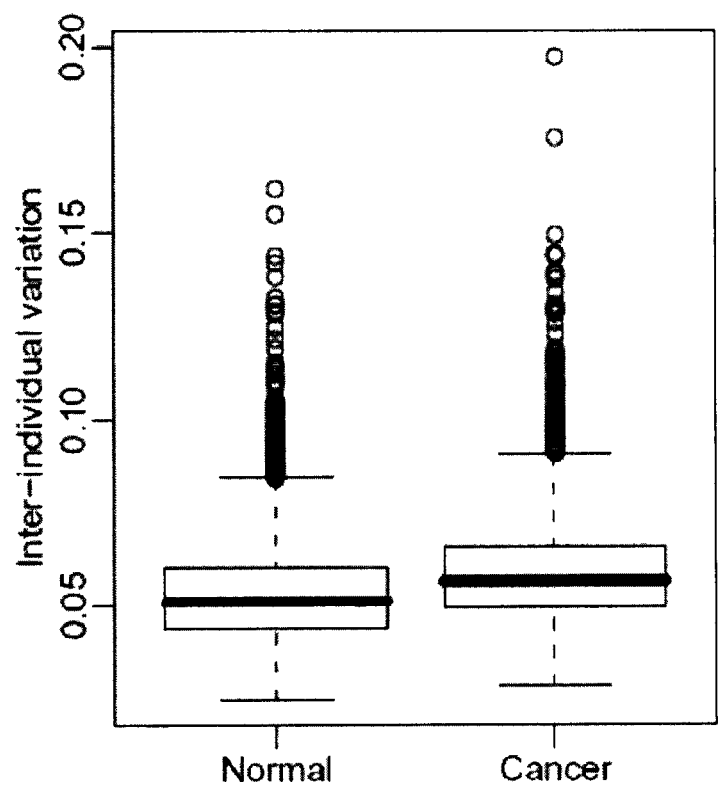

FIG. 17 shows a plot the average inter-individual standard deviation of the M-values for C-DMRs. The box-plots represent these values for normal colon mucosa and colon tumors.

Figure 18A:
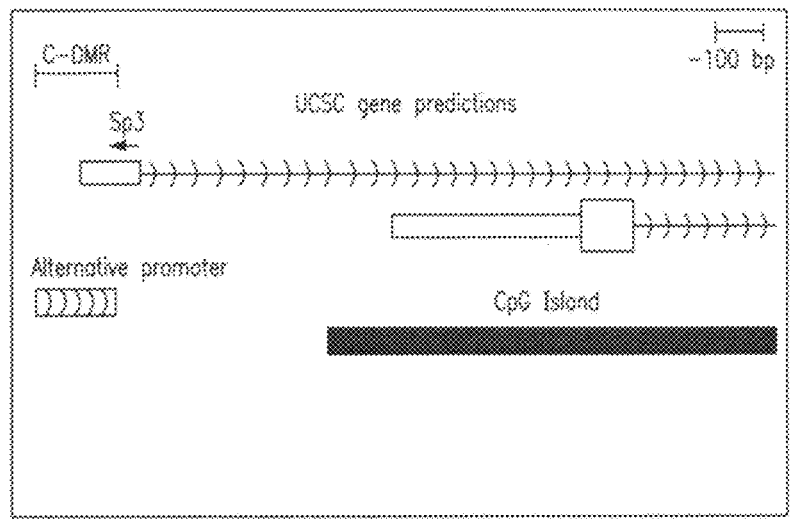

FIG. 18A shows a schematic overview of the PIP5K1A gene locus. C-DMR represents the genomic region that is hypomethylated in colon tumors as compared to normals.

Figure 18B:
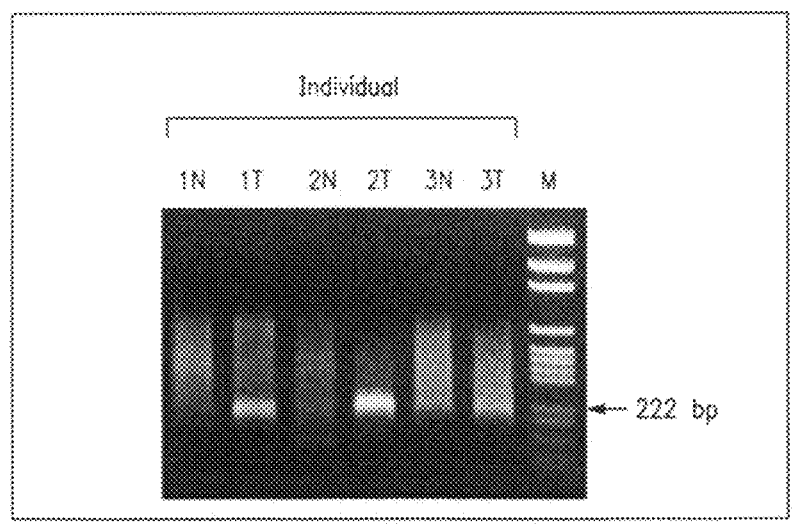

FIG. 18B shows a photograph of a gel in which the arrow indicates a 220 bp fragment present in 3 colon tumors but not normal mucosa from the same individual amplified by the Sp3 primer and the 5' RACE anchor primer.

Figure 19:
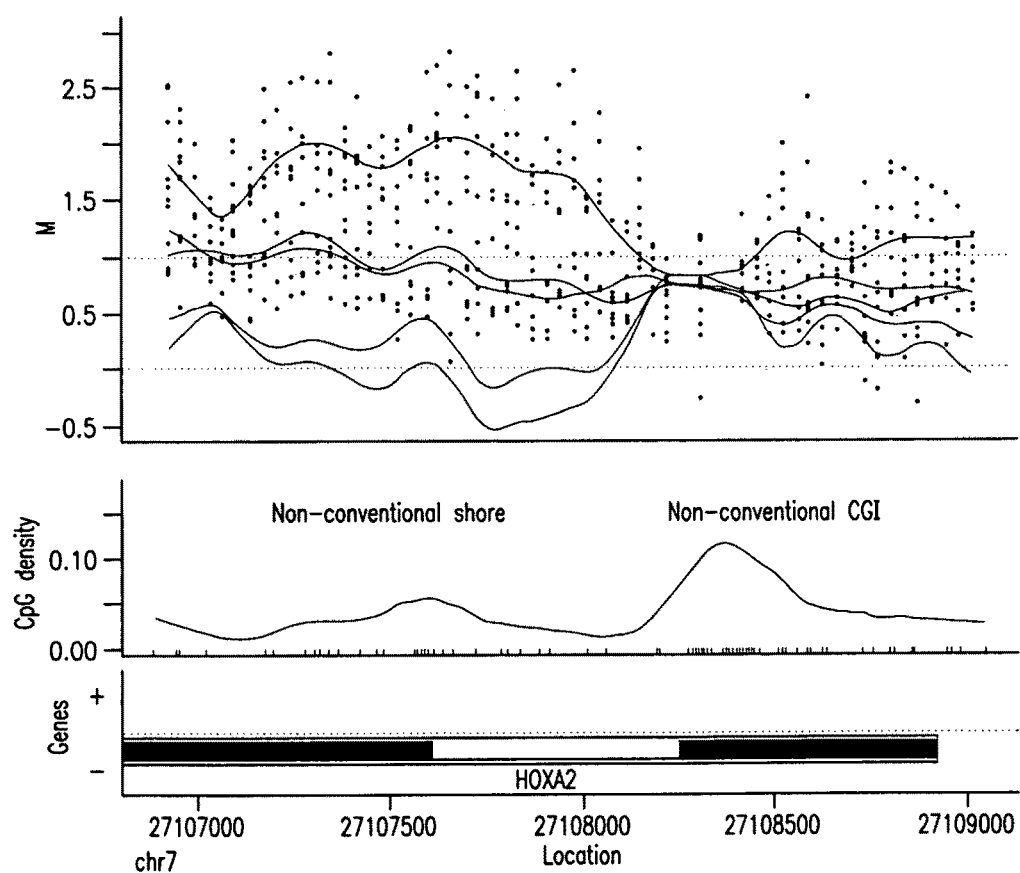

FIG. 19 shows an example of C-DMR that is not adjacent to a conventionally defined CpG island. The upper panel is a plot of M value versus genomic location for brain, liver, spleen, normal colon, colon tumor. The middle panel provides the location of CpG dinucleotides with tick marks on the x-axis. The lower panel provides gene annotation for the genomic region.

Figure 20:
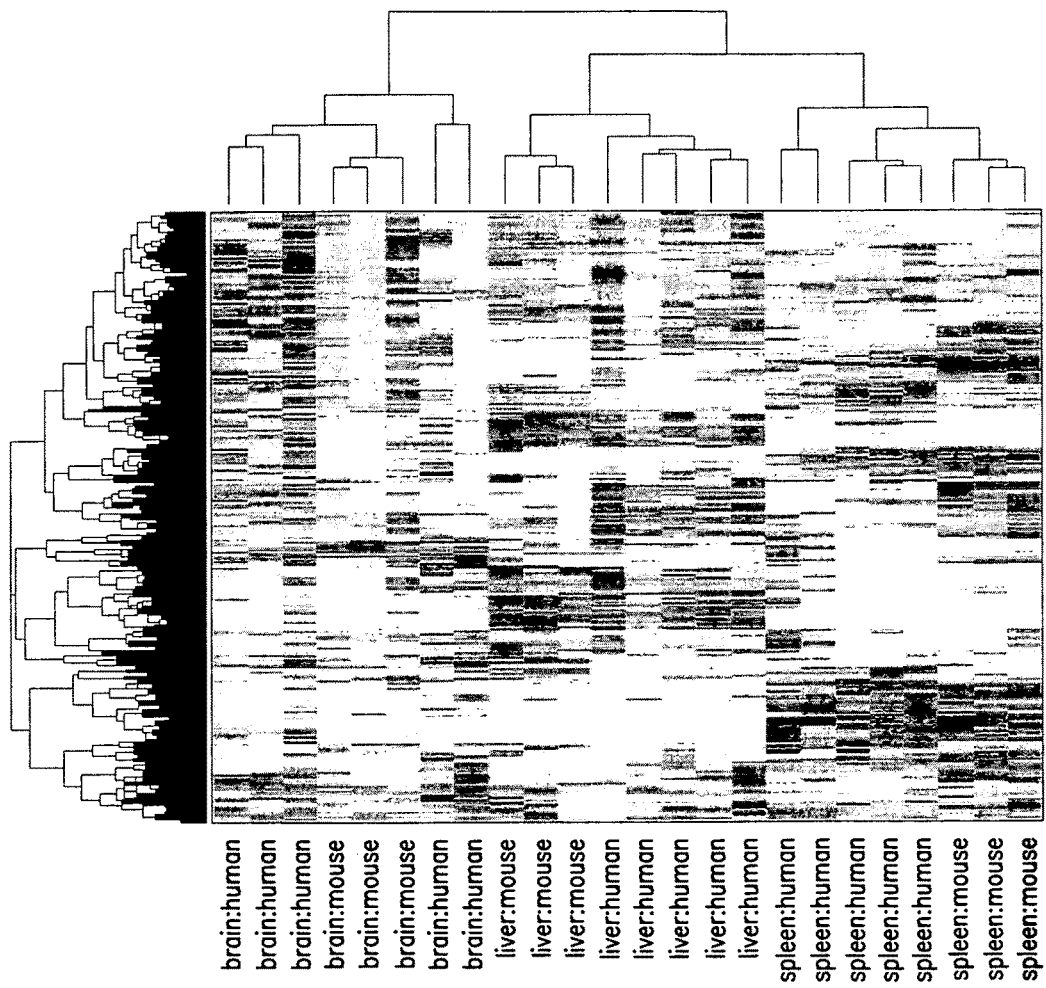

FIG. 20 shows a plot of hierarchical clustering. Columns represent individual samples, and rows represent regions corresponding to mouse T-DMRs. The heatmap displays M values, with some being more methylated and some being less methylated.

DETAILED DESCRIPTION OF THE INVENTION

The present invention is based on the discovery that some tissue-specific or cancer-related alterations in DNA methylation occur not only in promoters or CpG islands, but in sequences up to 2 kb distant (termed "CpG island shores"). In accordance with this discovery, there are provided herein tissue-specific differential methylated regions (T-DMRs) and cancer-related differential methylated regions (C-DMRs) and methods of use thereof. Accordingly, in one embodiment of the invention, there are provided methods of detecting a cell proliferative disorder. The methods involve comparing the methylation status of one or more nucleic acid sequences in a sample from a subject suspected of having the disorder, with the proviso that the one or more nucleic acid sequences are outside of a promoter region of a gene and outside of a CpG island, and wherein the nucleic acid sequence is up to about 2 kb in distance from a CpG island, to the methylation status of the one or more nucleic acid sequences in a sample from a corresponding normal tissue or individual not having a cell proliferative disorder, wherein an alteration in methylation status is indicative of a cell proliferative disorder. In some embodiments the alteration in methylation status is hypomethylation; in other embodiments the alteration in methylation status is hypermethylation. In embodiments using more than one DMR, the alteration in methylation status of some may be hypomethylation, whereas others may be hypermethylation.

In some embodiments methylation status is converted to an M value. As used herein an M value, can be a log ratio of intensities from total (Cy3) and McrBC-fractionated DNA (Cy5): positive and negative M values are quantitatively associated with methylated and unmethylated sites, respectively.

Hypomethylation of a DMR is present when there is a measurable decrease in methylation of the DMR. In some embodiments, a DMR can be determined to be hypomethylated when less than 50% of the methylation sites analyzed are not methylated. Hypermethylation of a DMR is present when there is a measurable increase in methylation of the DMR. In some embodiments, a DMR can be determined to be hypermethylated when more than 50% of the methylation sites analyzed are methylated. Methods for determining methylation states are provided herein and are known in the art. In some embodiments methylation status is converted to an M value. As used herein an M value, can be a log ratio of intensities from total (Cy3) and McrBC-fractionated DNA (Cy5): positive and negative M values are quantitatively associated with methylated and unmethylated sites, respectively. M values are calculated as described in the Examples. In some embodiments, M values which range from ±0.5 to 0.5 represent unmethylated sites as defined by the control probes, and values from 0.5 to 1.5 represent baseline levels of methylation.

In particular embodiments, the one or more nucleic acid sequence is selected from the C'-DMRs provided herein. In one aspect, the one or more nucleic acid sequence is selected from the group consisting of the DMRs set forth in Tables 1-4, 6, 7, 9, 11, 14-16, 18, the DPP6 gene, the MRPL36 gene, the MEST gene, the GATA-2 gene, the RARRES2 gene, and any combination thereof. In some embodiments, the nucleic acid sequence is within a gene; alternatively, the nucleic acid sequence is upstream or downstream of a gene.

In particular embodiments, the one or more nucleic acid sequence is selected from the T-DMRs provided herein. In one aspect, the one or more nucleic acid sequence is selected from the group consisting of the DMRs set forth in FIG. 5a, FIG. 5b, Tables 1, 2, 4, 7, 9, 10, 12-14, and 17. Such T-DMRs may be used to distinguish between the tissue types representing the three embryonic lineages: endodermal, mesodermal, and ectodermal.

The biological sample can be virtually any biological sample, particularly a sample that contains RNA or DNA from the subject. The biological sample can be a tissue sample which contains about 1 to about 10,000,000, about 1000 to about 10,000,000, or about 1,000,000 to about 10,000,000 somatic cells. However, it is possible to obtain samples that contain smaller numbers of cells, even a single cell in embodiments that utilize an amplification protocol such as PCR. The sample need not contain any intact cells, so long as it contains sufficient biological material (e.g., protein or genetic material, such as RNA or DNA) to assess methylation status of the one or more DMRs.

In some embodiments, a biological or tissue sample can be drawn from any tissue that is susceptible to cancer. A biological or tissue sample may be obtained by surgery, biopsy, swab, stool, or other collection method. In some embodiments, the sample is derived from blood, plasma, serum, lymph, nerve-cell containing tissue, cerebrospinal fluid, biopsy material, tumor tissue, bone marrow, nervous tissue, skin, hair, tears, fetal material, amniocentesis material, uterine tissue, saliva, feces, or sperm. In particular embodiments, the biological sample for methods of the present invention can be, for example, a sample from colorectal tissue, or in certain embodiments, can be a blood sample, or a fraction of a blood sample such as a peripheral blood lymphocyte (PBL) fraction. Methods for isolating PBLs from whole blood are well known in the art. In addition, it is possible to use a blood sample and enrich the small amount of circulating cells from a tissue of interest, e.g., colon, breast, lung, prostate, head and neck, etc. using a method known in the art.

As disclosed above, the biological sample can be a blood sample. The blood sample can be obtained using methods known in the art, such as finger prick or phlebotomy. Suitably, the blood sample is approximately 0.1 to 20 ml, or alternatively approximately 1 to 15 ml with the volume of blood being approximately 10 ml.

Accordingly, in one embodiment, the identified cancer risk is for colorectal cancer, and the biological sample is a tissue sample obtained from the colon, blood, or a stool sample. In another embodiment, the identified cancer risk is for stomach cancer or esophageal cancer, and the tissue may be obtained by endoscopic biopsy or aspiration, or stool sample or saliva sample. In another embodiment, the identified cancer risk is esophageal cancer, and the tissue is obtained by endoscopic biopsy, aspiration, or oral or saliva sample. In another embodiment, the identified cancer risk is leukemia/lymphoma and the tissue sample is blood.

In the present invention, the subject is typically a human but also can be any mammal, including, but not limited to, a dog, cat, rabbit, cow, bird, rat, horse, pig, or monkey.

As mentioned above, for certain embodiments of the present invention, the method is performed as part of a regular checkup. Therefore, for these methods the subject has not been diagnosed with cancer, and typically for these present embodiments it is not known that a subject has a hyperproliferative disorder, such as a cancer.

Methods of the present invention identify a risk of developing cancer for a subject. A cancer can include, but is not limited to, colorectal cancer, esophageal cancer, stomach cancer, leukemia/lymphoma, lung cancer, prostate cancer, uterine cancer, breast cancer, skin cancer, endocrine cancer, urinary cancer, pancreas cancer, other gastrointestinal cancer, ovarian cancer, cervical cancer, head cancer, neck cancer, and adenomas. In one aspect, the cancer is colorectal cancer.

A hyperproliferative disorder includes, but is not limited to, neoplasms located in the following: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital. In certain embodiments, the hyperproliferative disorder is a cancer. In one aspect, the cancer is colorectal cancer.

In another embodiment, the present invention provides a method for managing health of a subject. The method includes performing the method for identifying an increased risk of developing cancer discussed above and performing a traditional cancer detection method. For example a traditional cancer detection method can be performed if the method for identifying cancer risk indicates that the subject is at an increased risk for developing cancer. Many traditional cancer detection methods are known and can be included in this aspect of the invention. The traditional cancer detection method can include, for example, one or more of chest X-ray, carcinoembryonic antigen (CEA) level determination, colorectal examination, endoscopic examination, MRI, CAT scanning, or other imaging such as gallium scanning, and barium imaging, and sigmoidoscopy/colonoscopy, a breast exam, or a prostate specific antigen (PSA) assay.

Numerous methods for analyzing methylation status of a gene are known in the art and can be used in the methods of the present invention to identify either hypomethylation or hypermethylation of the one or more DMRs. In some embodiments, the determining of methylation status is performed by one or more techniques selected from the group consisting of a nucleic acid amplification, polymerase chain reaction (PCR), methylation specific PCR, bisulfite pyrosequenceing, single-strand conformation polymorphism (SSCP) analysis, restriction analysis, microarray technology, and proteomics. As illustrated in the Examples herein, analysis of methylation can be performed by bisulfite genomic sequencing. Bisulfite treatment modifies DNA converting unmethylated, but not methylated, cytosines to uracil. Bisulfite treatment can be carried out using the METHYLEASY bisulfite modification kit (Human Genetic Signatures).

In some embodiments, bisulfite pyrosequencing, which is a sequencing-based analysis of DNA methylation that quantitatively measures multiple, consecutive CpG sites individually with high accuracy and reproducibility, may be used. Exemplary primers for such analysis are set forth in Table 8.

It will be recognized that depending on the site bound by the primer and the direction of extension from a primer, that the primers listed above can be used in different pairs. Furthermore, it will be recognized that additional primers can be identified within the DMRs, especially primers that allow analysis of the same methylation sites as those analyzed with primers that correspond to the primers disclosed herein.

Altered methylation can be identified by identifying a detectable difference in methylation. For example, hypomethylation can be determined by identifying whether after bisulfite treatment a uracil or a cytosine is present a particular location. If uracil is present after bisulfite treatment, then the residue is unmethylated. Hypomethylation is present when there is a measurable decrease in methylation.

In an alternative embodiment, the method for analyzing methylation of the DMR can include amplification using a primer pair specific for methylated residues within a DMR. In these embodiments, selective hybridization or binding of at least one of the primers is dependent on the methylation state of the target DNA sequence (Herman et al., *Proc. Natl. Acad. Sci. USA,* 93:9821 (1996)). For example, the amplification reaction can be preceded by bisulfite treatment, and the primers can selectively hybridize to target sequences in a manner that is dependent on bisulfite treatment. For example, one primer can selectively bind to a target sequence only when one or more base of the target sequence is altered by bisulfite treatment, thereby being specific for a methylated target sequence.

Other methods are known in the art for determining methylation status of a DMR, including, but not limited to, array-based methylation analysis and Southern blot analysis.

Methods using an amplification reaction, for example methods above for detecting hypomethylation or hyprmethylation of one or more DMRs, can utilize a real-time detection amplification procedure. For example, the method can utilize molecular beacon technology (Tyagi S., et al., *Nature Biotechnology*, 14: 303 (1996)) or Taqman™ technology (Holland, P. M., et al., *Proc. Natl. Acad. Sci. USA*, 88:7276 (1991)).

Also methyl light (Trinh B N, Long T I, Laird P W. DNA methylation analysis by MethyLight technology, Methods, 25(4):456-62 (2001), incorporated herein in its entirety by reference), Methyl Heavy (Epigenomics, Berlin, Germany), or SNuPE (single nucleotide primer extension) (See e.g., Watson D., et al., *Genet Res.* 75(3):269-74 (2000)). Can be used in the methods of the present invention related to identifying altered methylation of DMRs.

As used herein, the term "selective hybridization" or "selectively hybridize" refers to hybridization under moderately stringent or highly stringent physiological conditions, which can distinguish related nucleotide sequences from unrelated nucleotide sequences.

As known in the art, in nucleic acid hybridization reactions, the conditions used to achieve a particular level of stringency will vary, depending on the nature of the nucleic acids being hybridized. For example, the length, degree of complementarity, nucleotide sequence composition (for example, relative GC:AT content), and nucleic acid type, i.e., whether the oligonucleotide or the target nucleic acid sequence is DNA or RNA, can be considered in selecting hybridization conditions. An additional consideration is whether one of the nucleic acids is immobilized, for example, on a filter. Methods for selecting appropriate stringency conditions can be determined empirically or estimated using various formulas, and are well known in the art (see, for example, Sambrook et al., supra, 1989).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

The degree of methylation in the DNA associated with the DMRs being assessed, may be measured by fluorescent in situ hybridization (FISH) by means of probes which identify and differentiate between genomic DNAs, associated with the DMRs being assessed, which exhibit different degrees of DNA methylation. FISH is described in the Human chromosomes: principles and techniques (Editors, Ram S. Verma, Arvind Babu Verma, Ram S.) 2nd ed., New York: McGraw-Hill, 1995, and de Capoa A., Di Leandro M., Grappelli C., Menendez F., Poggesi I., Giancotti P., Marotta, M. R., Spano A., Rocchi M., Archidiacono N., Niveleau A. Computer-assisted analysis of methylation status of individual interphase nuclei in human cultured cells. *Cytometry.* 31:85-92, 1998 which is incorporated herein by reference. In this case, the biological sample will typically be any which contains sufficient whole cells or nuclei to perform short term culture. Usually, the sample will be a tissue sample that contains 10 to 10,000, or, for example, 100 to 10,000, whole somatic cells.

Additionally, as mentioned above, methyl light, methyl heavy, and array-based methylation analysis can be performed, by using bisulfite treated DNA that is then PCR-amplified, against microarrays of oligonucleotide target sequences with the various forms corresponding to unmethylated and methylated DNA.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template In another aspect, the present invention includes kits that are useful for carrying out the methods of the present invention. The components contained in the kit depend on a number of factors, including: the particular analytical technique used to detect methylation or measure the degree of methylation or a change in methylation, and the one or more DMRs is being assayed for methylation status.

Accordingly, the present invention provides a kit for determining a methylation status of one or more differentially methylated region (DMR) of the invention. In some embodiments, the one or more T-DMRs are selected from one or more of the sequences as set forth in Tables 1-4, 6, 7, 9, 11, 14-16, the MRPL36 gene, the MEST gene, the GATA-2 gene, and the RARRES2 gene. In another embodiment, the one or more T-DMRs are selected from one or more of the sequences as set forth in FIG. 5a, FIG. 5b, Tables 1 2, 4, 7, 9, 10, 12-14, and 17. The kit includes an oligonucleotide probe, primer, or primer pair, or combination thereof for carrying out a method for detecting hypomethylation, as discussed above. For example, the probe, primer, or primer pair, can be capable of selectively hybridizing to the DMR either with or without prior bisulfite treatment of the DMR. The kit can further include one or more detectable labels.

The kit can also include a plurality of oligonucleotide probes, primers, or primer pairs, or combinations thereof, capable of selectively hybridizing to the DMR with or without prior bisulfite treatment of the DMR. The kit can include an oligonucleotide primer pair that hybridizes under stringent conditions to all or a portion of the DMR only after bisulfite treatment. In one aspect, the kit can provide reagents for bisulfite pyrosequencing including one or more primer pairs set forth in Table 8. The kit can include instructions on using kit components to identify, for example, the presence of cancer or an increased risk of developing cancer.

The studies provided herein focused on three key questions. First, where are DNA methylation changes that distinguish tissue types? Taking a comprehensive genome-wide approach, three normal tissue types representing the three embryonic lineages—liver (endodermal), spleen (mesodermal) and brain (ectodermal)—obtained from five autopsies were examined. A difference from previous methylation studies of tissues, aside from the genome-wide design herein, is that in the present studies, tissues were obtained from the same individual, thus controlling for potential interindividual variability. Second, where are DNAm alterations in cancer, and what is the balance between hypomethylation and hypermethylation? For this purpose, 13 colorectal cancers and matched normal mucosa from the subjects were examined. Third, what is the functional role of these methylation changes? To this end, a comparative epigenomics study of tissue methylation in the mouse, as well as gene expression analyses were carried out.

To examine DNAm on a genome-wide scale, comprehensive high-throughput array-based relative methylation (CHARM) analysis, which is a microarray-based method agnostic to preconceptions about DNAm, including location relative to genes and CpG content was carried out. The resulting quantitative measurements of DNAm, denoted with M, are log ratios of intensities from total (Cy3) and McrBC-fractionated DNA (Cy5): positive and negative M values are quantitatively associated with methylated and unmethylated sites, respectively. For each sample, ~4.6 million CpG sites across the genome were analyzed using a custom-designed NimbleGen HD2 microarray, including all of the classically defined CpG islands as well as all nonrepetitive lower CpG density genomic regions of the genome. 4,500 control probes were included to standardize these M values so that unmethylated regions were associated, on average, with values of 0. CHARM is 100% specific at 90% sensitivity for known methylation marks identified by other methods (for example, in promoters) and includes the approximately half of the genome not identified by conventional region preselection. The CHARM results were also extensively corroborated by quantitative bisulfite pyrosequencing analysis.

Provided herein is a genome-wide analysis of DNA methylation addressing variation among normal tissue types, variation between cancer and normal, and variation between human and mouse, revealing several surprising relationships among these three types of epigenetic variation, supported by extensive bisulfite pyrosequencing and functional analysis. First, most tissue-specific DNAm was found to occur, not at CpG islands, but at CpG island shores (sequences up to 2 kb distant from CpG islands). The identification of these regions opens the door to functional studies, such as those investigating the mechanism of targeting DNAm to these regions and the role of differential methylation of shores. Supporting a functional role for shores, gene expression was closely linked to T-DMR and C-DMR methylation, particularly for switches from 'none' to 'some' methylation. The relationship between shore methylation and gene expression was confirmed by 5-aza-2'-deoxycytidine and DNA methyltransferase knockout experiments altering expression of the same genes. Another mechanism for shores supported by this study is regulation of alternative transcripts, supported by mapping and RACE experiments.

Although 76% of T-DMRs identified herein were in CpG island shores, at least for the three tissues examined here, 24% were not adjacent to conventionally defined CpG islands. However, many of these regions were nevertheless shores of CpG-enriched sequences (for an example, see FIG. 13). We are currently developing a novel algorithm for CpG island definition based on hidden Markov modeling that will likely increase the fraction of T-DMRs in CpG island shores. The 'CpG clusters' recently identified (Glass et al., Nucleic Acids Res 35:6798-6807, 2007) are not CpG island shores (only 4% of shore DMRs map to them), although the shores of these clusters, like the shores of CpG islands, are enriched for DMRs. Note that the variation in DNAm is still not within the dense CpG regions as defined by any of these definitions but in CpG shores.

A second key finding of the studies provided herein is that T-DMRs are highly conserved between human and mouse, and the methylation itself is sufficiently conserved to completely discriminate tissue types regardless of species of origin. This was true even for T-DMRs located >2 kb from transcriptional start sites. The incorporation of epigenetic data, such as DNAm, in evolutionary studies as done here, should greatly enhance the identification of conserved elements that regulate differentiation. Greater DNAm heterogeneity was found in human than in mouse (at least in an inbred strain), even for DMRs located >2 kb from a gene promoter. While not wishing to be bound to any particular theory, this result suggests that the conservation of DNAm between human and mouse may have a strong genetic basis, consistent with a greater degree of tissue DNAm homogeneity in the inbred mouse strain.

A third key finding of the studies provided herein is that most cancer-related changes in DNAm, that is, C-DMRs, at least for colon cancer, correspond to T-DMRs, and that these changes are similarly divided between hypomethylation and hypermethylation and also involve CpG island shores. Thus, epigenetic changes in cancer largely involve the same DMRs as epigenetic changes in normal differentiation. These results have important implications for studies such as the Cancer Genome Atlas, in that most altered DNA methylation in cancer does not involve CpG islands, and thus these studies would benefit from analysis of CpG island shores. Similarly, high-throughput sequencing efforts based on reduced representation analysis of CpG islands per se are unlikely to identify most DNAm variation in normal tissues or in cancer.

Finally, GO annotation analysis suggests that DNAm changes in cancer reflect development and pluripotency-associated genes, and differentiated cellular functions for lineages other than the colon. These data are consistent with the epigenetic progenitor model of cancer (Feinberg et al., Nat Rev Genet. 7:21-33, 2006), which proposes that epigenetic alterations affecting tissue-specific differentiation are the predominant mechanism by which epigenetic changes cause cancer. The genes identified in the studies provided herein will themselves be of considerable interest for further study, as will be the potential regulatory regions that did not lie in close proximity to annotated genes.

The following example is provided to further illustrate the advantages and features of the present invention, but are not intended to limit the scope of the invention. While they are typical of those that might be used, other procedures,

EXAMPLE

The Human Colon Cancer Methylome Shows Similar Hypo- and Hypermethylation at Conserved Tissue-Specific CpG Island Shores It has been shown that alterations in DNA methylation (DNAm) occur in cancer, including hypomethylation of oncogenes and hypermethylation of tumor suppressor genes. However, most studies of cancer methylation have assumed that functionally important DNAm will occur in promoters, and that most DNAm changes in cancer occur in CpG islands. This example illustrates that most methylation alterations in colon cancer occur not in promoters, and also not in CpG islands, but in sequences up to 2 kb distant, which are termed herein 'CpG island shores'. CpG island shore methylation was strongly related to gene expression, and it was highly conserved in mouse, discriminating tissue types regardless of species of origin. There was a notable overlap (45-65%) of the locations of colon cancer-related methylation changes with those that distinguished normal tissues, with hypermethylation enriched closer to the associated CpG islands, and hypomethylation enriched further from the associated CpG island and resembling that of non-colon normal tissues. Thus, methylation changes in cancer are at sites that vary normally in tissue differentiation, consistent with the epigenetic progenitor model of cancer, which proposes that epigenetic alterations affecting tissue-specific differentiation are the predominant mechanism by which epigenetic changes cause cancer.

Samples. Snap-frozen colon tumors and dissected normal mucosa were obtained from the same subjects. For the tissue studies, human postmortem brain, liver and spleen tissues, from the same individual, were obtained.

Genomic DNA isolation and McrBC fractionation. Genomic DNA isolation was carried out using the MasterPure DNA purification kit (Epicentre) as recommended by the manufacturer. For each sample, 5 m of genomic DNA was digested, fractionated, labeled and hybridized to a CHARM microarray (Irizarrry et al., Genome Res 18:771-9, 2008).

CHARM microarray design. CHARM microarrays were prepared as previously described (Irizarrry et al., Genome Res 18:771-9, 2008) and additionally included a set of 4,500 probes, totaling 148,500 base pairs across 30 genomic regions as controls. As these control probes represent genomic regions without CpG sites and hence cannot be methylated, they were used to normalize and standardize array data. The observed M values were standardized so that the average in the control regions was 0. Therefore, M values of 0 for other probes on the array were associated with no methylation.

Figure 8A:
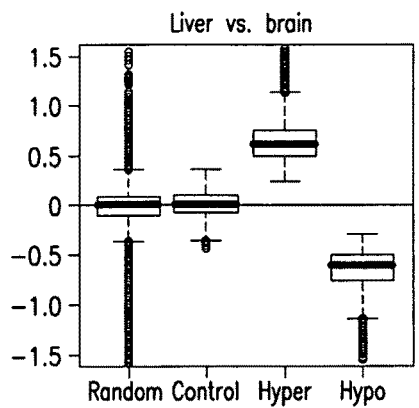
FIGS. 8A-D show box plots of average ΔM values over all DMRs compared to randomly chosen regions and unmethylated control regions matched for length.
Figure 8B:
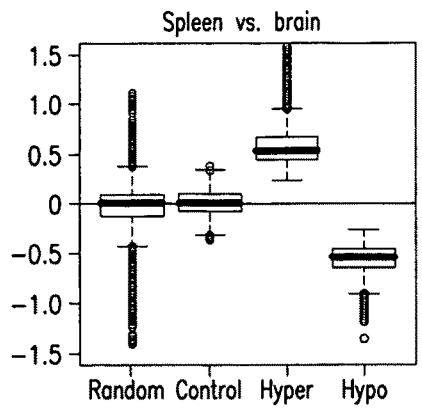
Figure 8C:
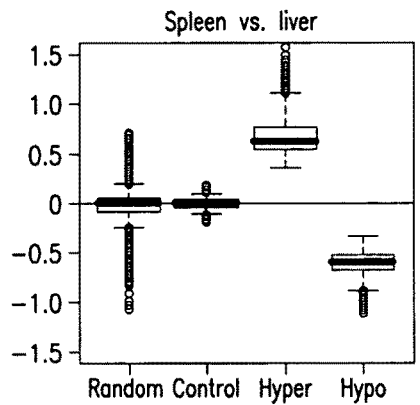
Figure 8D:
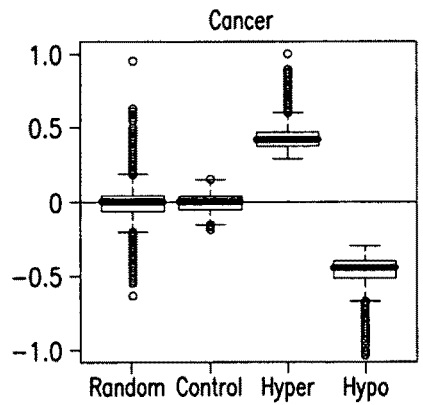
Figure 8E:
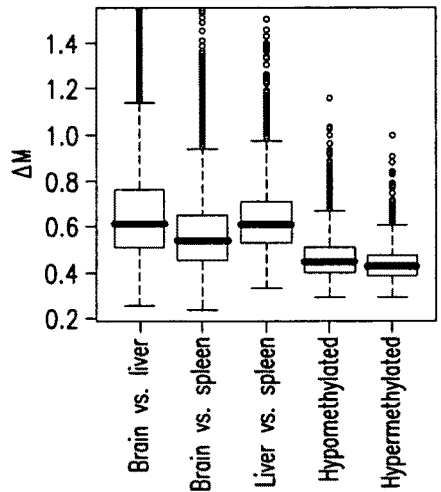
FIG. 8E shows box plots of ΔM for pairwise comparison.
Figure 8F:
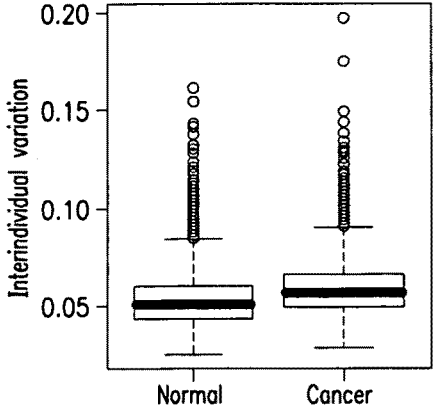
FIG. 8F shows box plots of the average inter-individual standard deviation of the ΔM value for normal mucosa and colon tumors.

CHARM DNA methylation analysis. McrBC fractionation was conducted followed by CHARM array hybridization for all human tissue samples as previously described (Irizarrry et al., Genome Res 18:771-9, 2008). For each probe, average M values were computed across the five samples in each tissue type. Differential methylation was quantified for each pairwise tissue comparison by the difference of averaged M values ($\Delta M$). Replicates were used to estimate probe-specific s.d., which provided standard errors (s.e.m.) for $\Delta M$. z scores ($\Delta M$/s.e.m.(:$\Delta M$)) were calculated and grouped contiguous statistically significant values into regions. Because millions of z scores were examined, statistical confidence calculation needed to account for multiple comparisons. Therefore false discovery rates (FDR) were computed and a list with an FDR of 5% was reported. Statistical significance of the regions was assessed as described below. C-DMRs were determined using the same procedure described above with the following exception: because greater heterogeneity was observed in the cancer samples (FIG. 8f), $\Delta M$ was not divided by the standard errors, as this would penalize regions of highly variable M values. For all expression microarray analysis, RMA was used for processing and then the samples were averaged in each tissue, and the difference (equivalent to average log ratio) computed. Mouse T-DMRs were determined using the same statistical procedures as described above for the T-DMRs and were then mapped to the human genome using the UCSC liftOver tool. To correct for possible 'array' effects, each T-DMR was standardized by subtracting the mean of M across all samples within a species and divided by s.d. across all samples within a species. A list of all mouse T-DMRs is provided in Table 17. Overlap of C-DMRs with T-DMRs was determined by adding the number of regions.

Statistical significance of DMRs. Contiguous regions composed of probes with z scores associated with P values smaller than 0.001 were grouped into regions. The area of each region (length multiplied by $\Delta M$) was used to define statistical significance. A permutation test was used to form a null distribution for these areas and the empirical Bayes approach described. The effect of fragment length on M values observed using CHARM was tested by computing the expected DNA fragment size based on McrBC recognition sites. Next, the $\Delta M$ values were stratified for each probe, from the colon tumor and normal mucosa comparison, by fragment size. The results showed no relationship between fragment size and $\Delta M$.

Bisulfite pyrosequencing. Isolation of genomic DNA for all bisulfite pyrosequencing validation was done using the MasterPure DNA purification kit (Epicentre) as recommended by the manufacturer. For validation of shore regions, 1 μg of genomic DNA from each sample was bisulfite-treated using an EpiTect kit (Qiagen) according to the manufacturer's specifications. Converted genomic DNA was PCR-amplified using unbiased nested primers and carried out quantitative pyrosequencing using a PSQ HS96 (Biotage) to determine percentage methylation at each CpG site. Primer sequences and annealing temperatures are provided in Table 8. For bisulfite pyrosequencing of C-DMRs in 34-65 colon tumor and 30-61 normal mucosa samples, 500 ng of genomic DNA was bisulfite-treated using the EZ-96 DNA Methylation Gold kit (Zymo Research) as specified by the manufacturer. Converted genomic DNA was PCR-amplified using unbiased nested primers followed by pyrosequencing using a PSQ HS96 (Biotage). Bisulfite pyrosequencing was done as previously described (Tort et al., Nat Protocols 2:2265-75, 2007). Percent methylation was determined at each CpG site using the Q-CpG methylation software (Biotage). Table 6 provides the genomic location of CpG sites measured in the CpG shore and associated CpG island bisulfite pyrosequencing assays. Genomic coordinates for all CpG sites measured in the set of ~50 colon tumor and normal samples are provided in Methods online. The genomic coordinates for CpG sites measured in colon tumor and normal samples representing DLX5C, ERICH1, FAM70B, SLITRK1, FEZF2, LRFN5, TMEM14A, TMEPAI, and HOXA3 are chr7:96493826, 96493847; chr8: 847868,847870; chr13:113615615; chr13: 83352935; chr3:62335457,62335482,62335504; chr14:411-48241,41148246,41148252; chr6:52638087; chr20:

55707264; and chr7:27130446,27130448,27130450, respectively. Primer sequences and annealing temperatures for all bisulfite pyrosequencing reactions are provided in Table 7.

Total RNA isolation. Total RNA was isolated for Affymetrix microarray analysis from all human tissues using the RNEASY Mini kit (Qiagen) as specified by the manufacturer. All samples were DNase treated using the on-column DNase digestion kit (Qiagen) as recommended. Total RNA concentration was measured and RNA quality was determined by using an RNA 6000 Nano Lab chip kit and running the chip on a 2100 Bioanalyzer (Agilent).

Affymetrix microarray expression analysis. Genome-wide transcriptional analysis was done on a total of five liver and five brain samples from the same individuals using Affymetrix U133A GeneChip microarrays. The raw microarray gene expression data was obtained for the brain and liver tissue from The Stanley Medical Research Institute (SMRI) online genomics database (see URLs section below). The five individuals selected were unaffected controls from the SMRI Array collection. Genome-wide transcriptional profiling was also carried out on four colon tumor and four matched normal mucosa using Affymetrix U133 Plus 2.0 microarrays. One microgram of high-quality total RNA was amplified, labeled and hybridized according to the manufacturer's (Affymetrix) specifications and data was normalized as previously described (Irizarry et al. Biostatistics 4:249-64, 2003; and Bolstad et al., Bioinformatics 19:185-93, 1999).

Quantitative real-time PCR. Quantitative real time PCR was performed on high quality total RNA samples, determined using Agilent Bioanalyzer and RNA Nano 6000 chips, using pre-optimized Taqman assays (Applied Biosystems). A summary of assay identification numbers can be found in Table 9. Total RNA was prepared for quantitative real-time PCR using the Trizol method (Invitrogen) for FZD3, RBM38, NDN and SEMA3C and the RNEASY mini kit (Qiagen) was used to isolate total RNA for ZNF804A, CHRM2 and NQO1. cDNA was prepared for quantitative real-time PCR using the QUANTITECT RT kit (Qiagen) with Turbo DNase to eliminate genomic DNA. TaqMan assays (Applied Biosystems) were used to determine relative gene expression and analyzed experiments on a 7900HT detection system. Taqman assays (Applied Biosystems) were used to determine relative gene expression and experiments were analyzed on a 7900HT detection system. Human ACTB was used as an endogenous control. Relative expression differences were calculated using the ΔΔCt method (Livak and Schmittgen, Methods 25:402-8, 2001).

5' RACE PCR. 5' RACE experiments were done using a second generation RACE kit (Roche Applied Science) as specified by the manufacturer's protocol. RACE PCR products were directly sequenced with 3100 Genetic Analyzer (AB Applied Biosystems). The sequences for our gene specific primers are: PIP5K1A cDNA synthesis (PIP5K1A-Sp1): TCCTGAGGAATCAACACTTC (SEQ ID NO:1); first round PIP5K1A primer (PIP5K1A-Sp2): CAGATGC-CATGGGTCTCTTG (SEQ ID NO:2); second round PIP5K1A primer (PIP5K1A-Sp3): ACGTCGAGCCGGCTCCTGGA (SEQ ID NO:3).

Soft agar assay for colony growth. HeLa and HCT116 cell lines were purchased from American Type Culture Collection (ATCC) and cultured using media and conditions recommended by the supplier. Cells were transfected with sequence verified full-length cDNAs of NQO1, ZNF804A, and CHRM2, and empty expression plasmid constructs obtained from Open Biosystems (Huntsville, Ala.) using Fugene (Roche) following supplied protocols. After 48 hours cells were harvested by trypsin treatment and resuspended in quadruplets at 5000 cells/35 mm well in 0.35% agar overlaid over 0.5% agar. The culture media contained 1×DMEM, 10% fetal bovine serum, 100 units/ml penicillin/streptomycin. Cells were incubated in a humidified $CO_2$ incubator (37° C., 5% $CO_2$) for 17 days followed by staining with 0.005% Crystal Violet for 2 hours. Colonies were counted under a light microscope.

GO annotation. GO annotation was analyzed using the Bioconductor Gostats package to find enriched categories (P<0.01).

URLs. Complete set of T-DMR plots is on the internet at rafalab.jhsph.edu/t-dmr3000.pdf; complete set of C DMR plots is on the internet at rafalab.jhsph.edu/c-dmr-all.pdf. The Stanley Medical Research Institute (SMRI) online genomics database is available at stanleygenomics.org.

Accession codes. NCBI GEO: Gene expression microarray data was submitted under accession number GSE13471.

Figure 9:
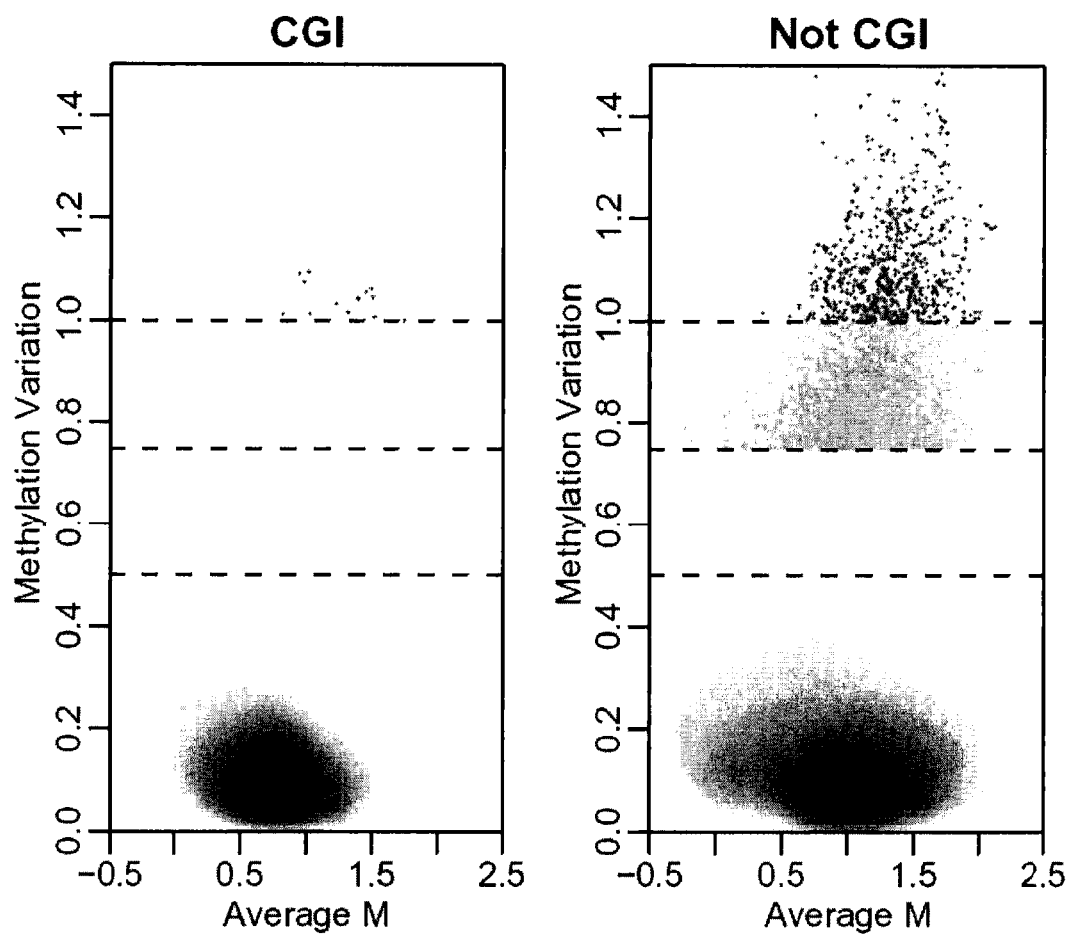
FIG. 9 shows plots of M values for CHARM probes located within a CGI (left plot) and outside a CGI (right plot).
Figure 10A:
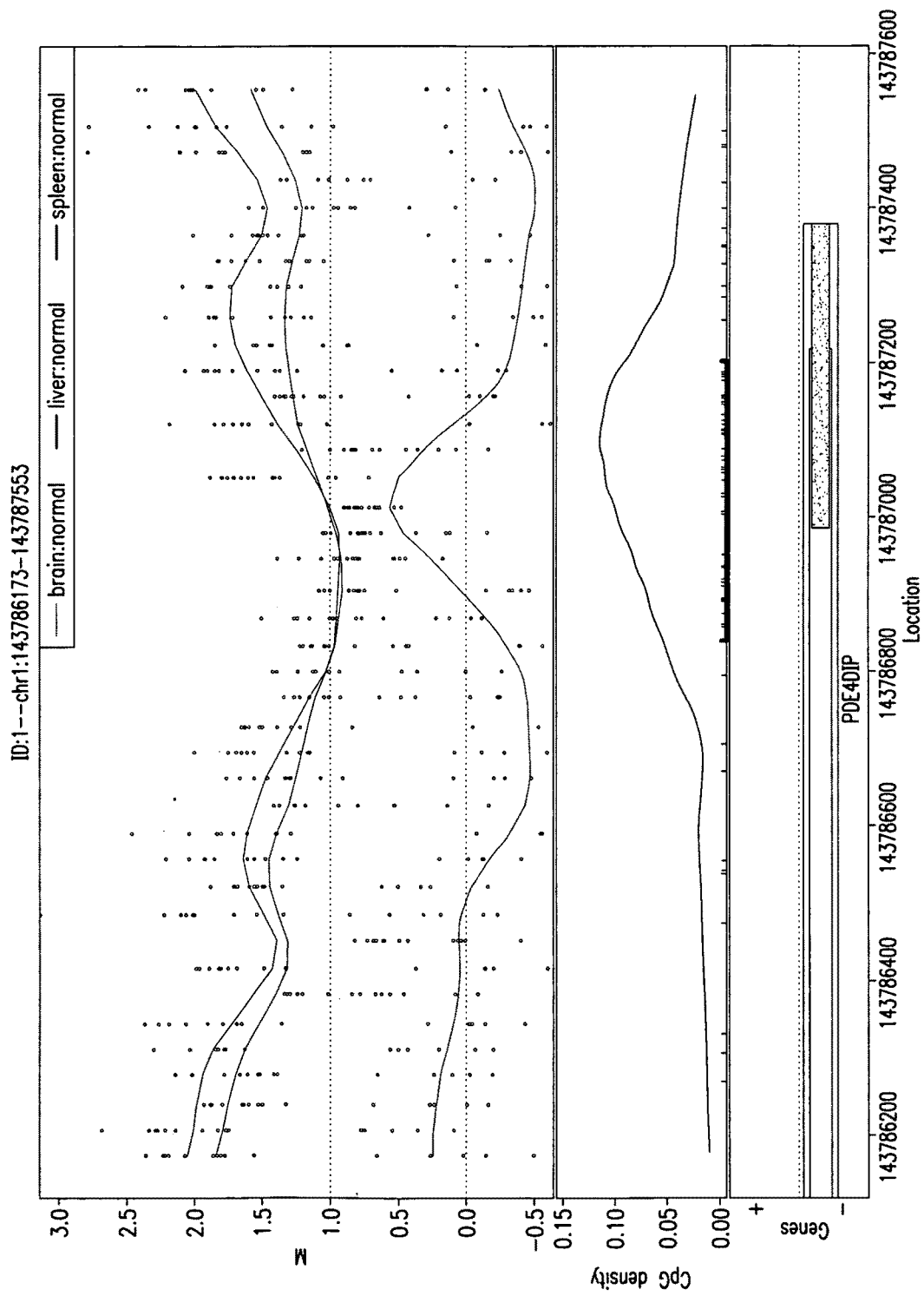
FIGS. 10A-J show representative plots of 10 T-DMRs. The upper panels are plots of M value versus genomic location for brain, liver, and spleen. The middle panels provide the location of CpG dinucleotides with tick marks on the x-axis. The lower panels provide gene annotation for the genomic region.
Figure 10B:
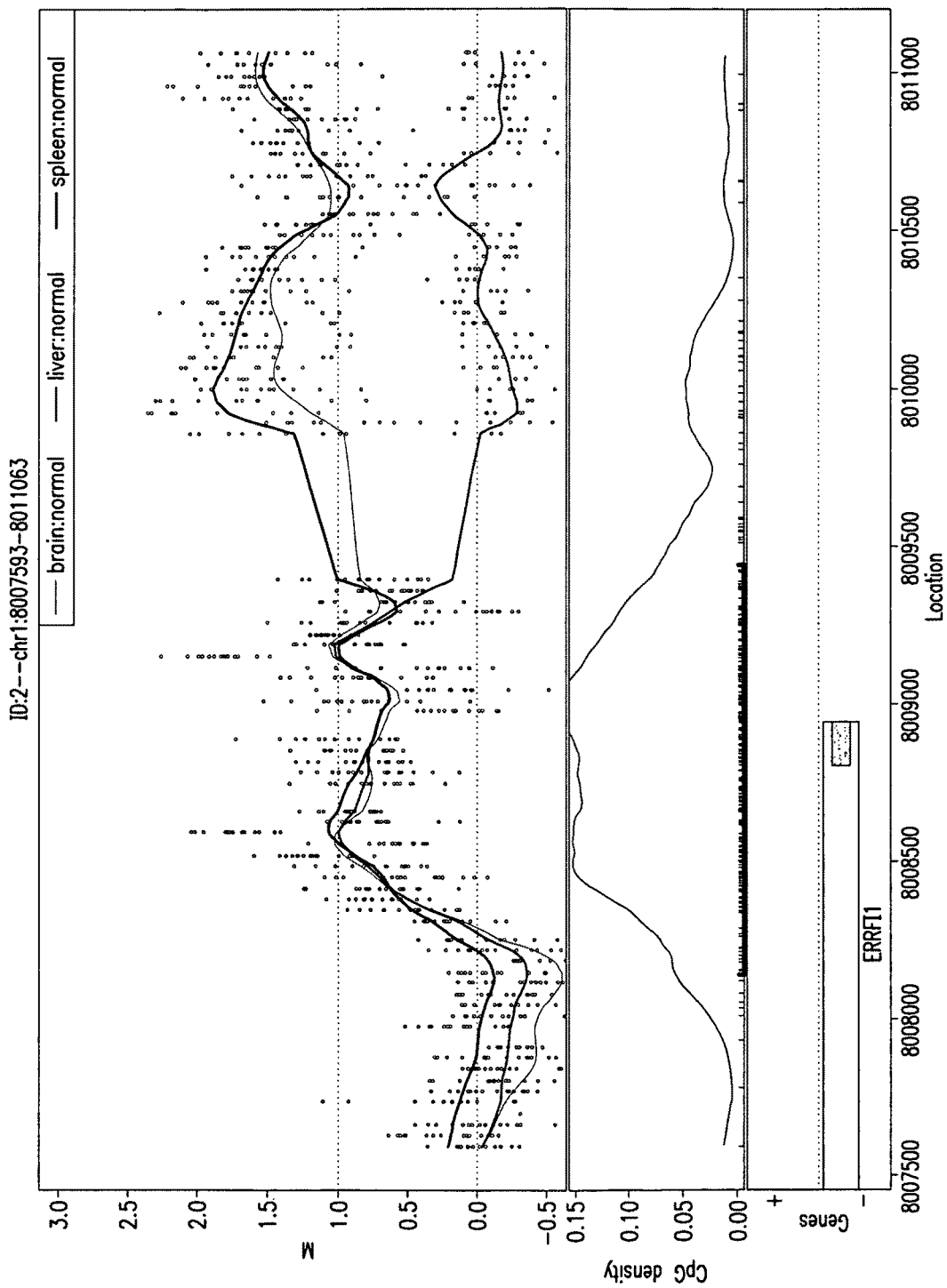
Figure 10C:
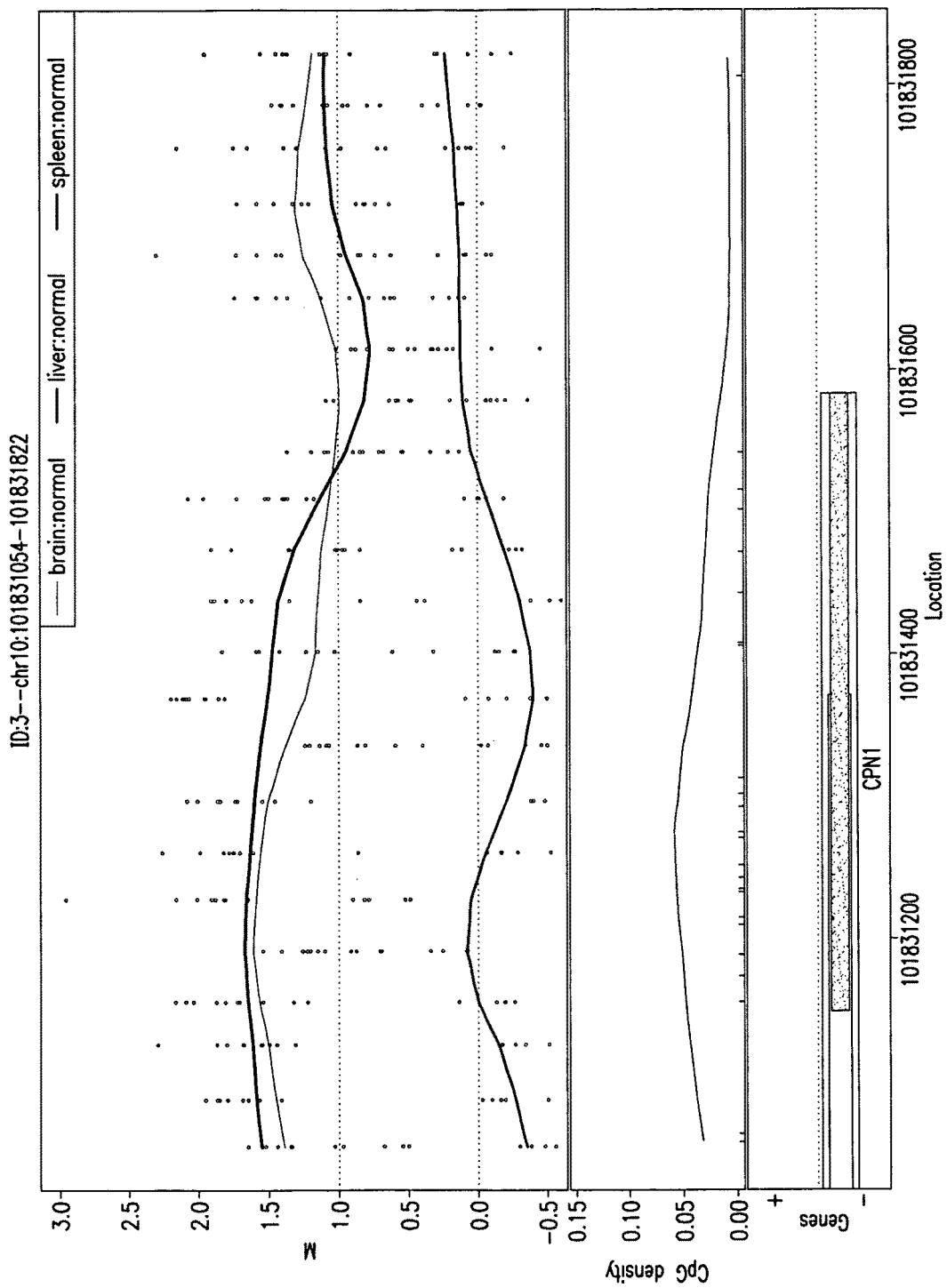
Figure 10D:
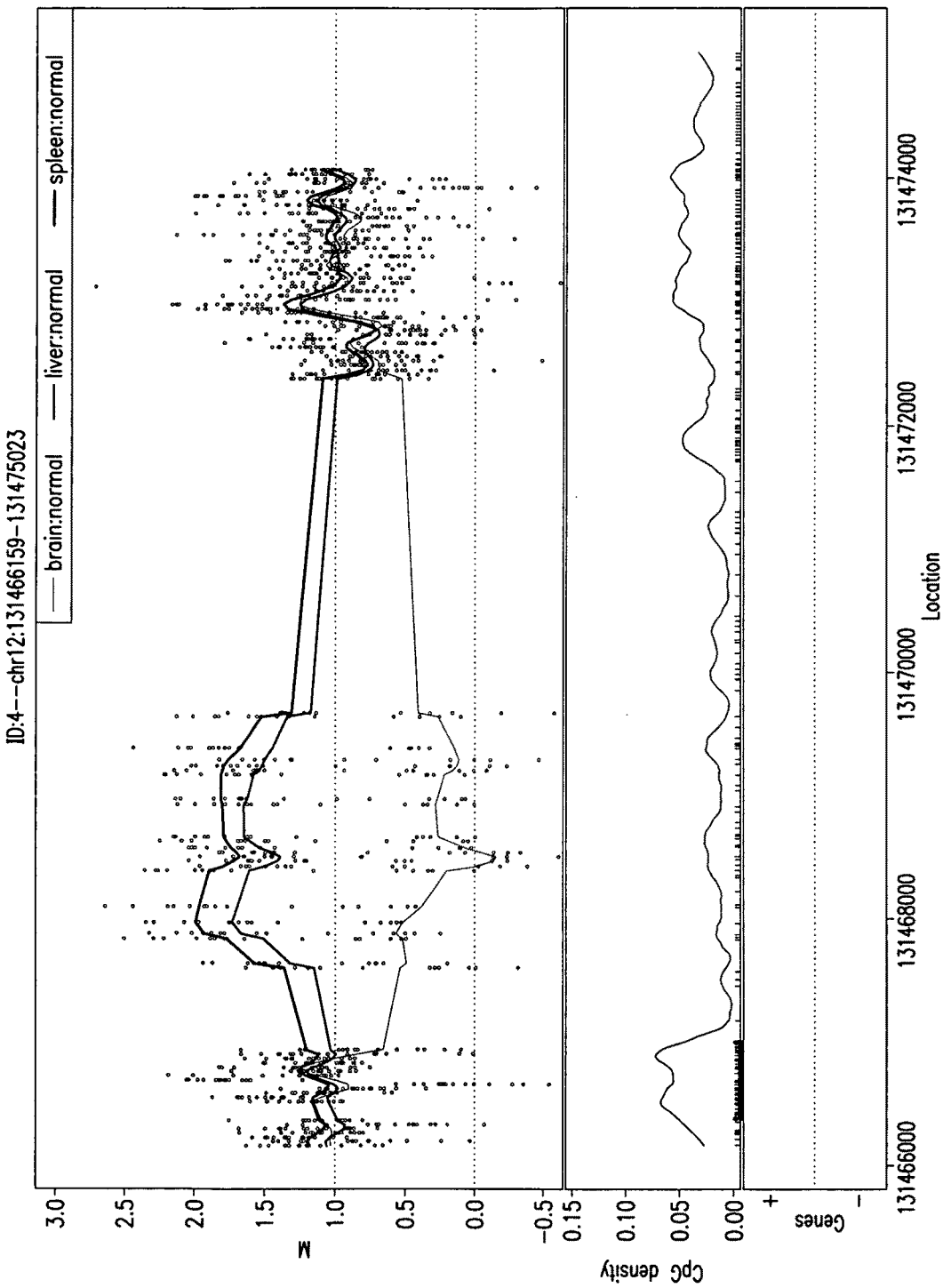
Figure 10E:
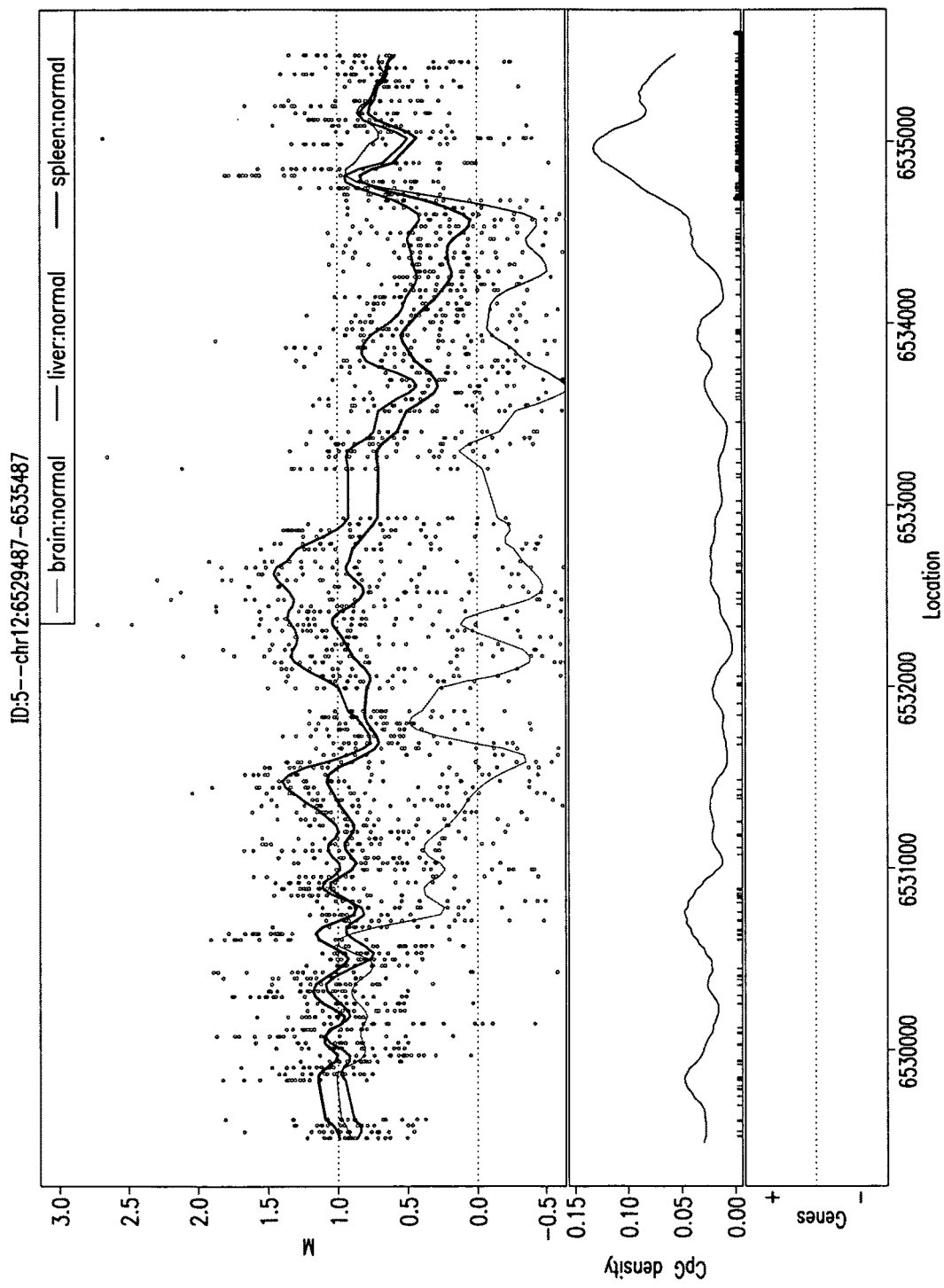
Figure 10F:
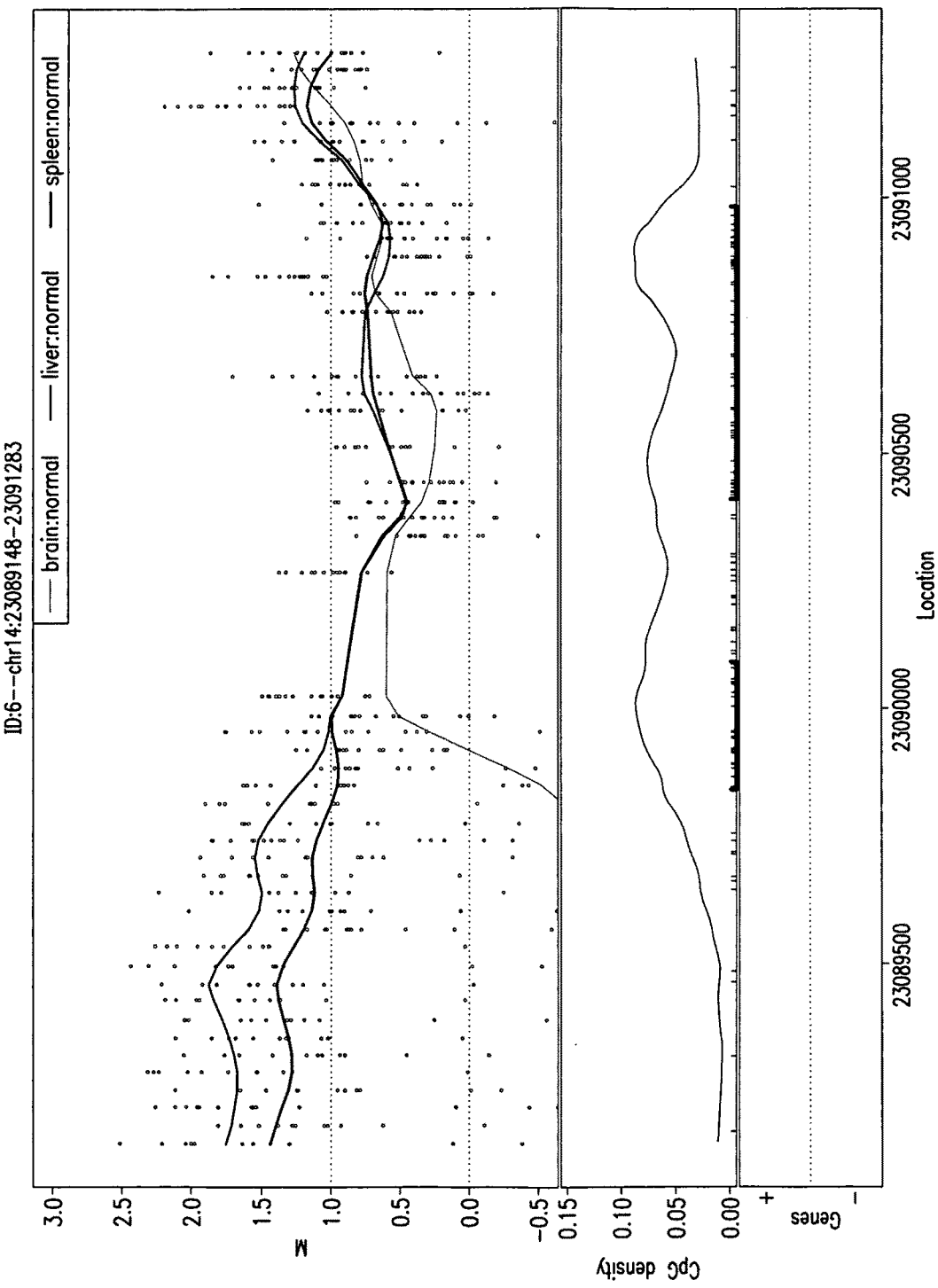
Figure 10G:
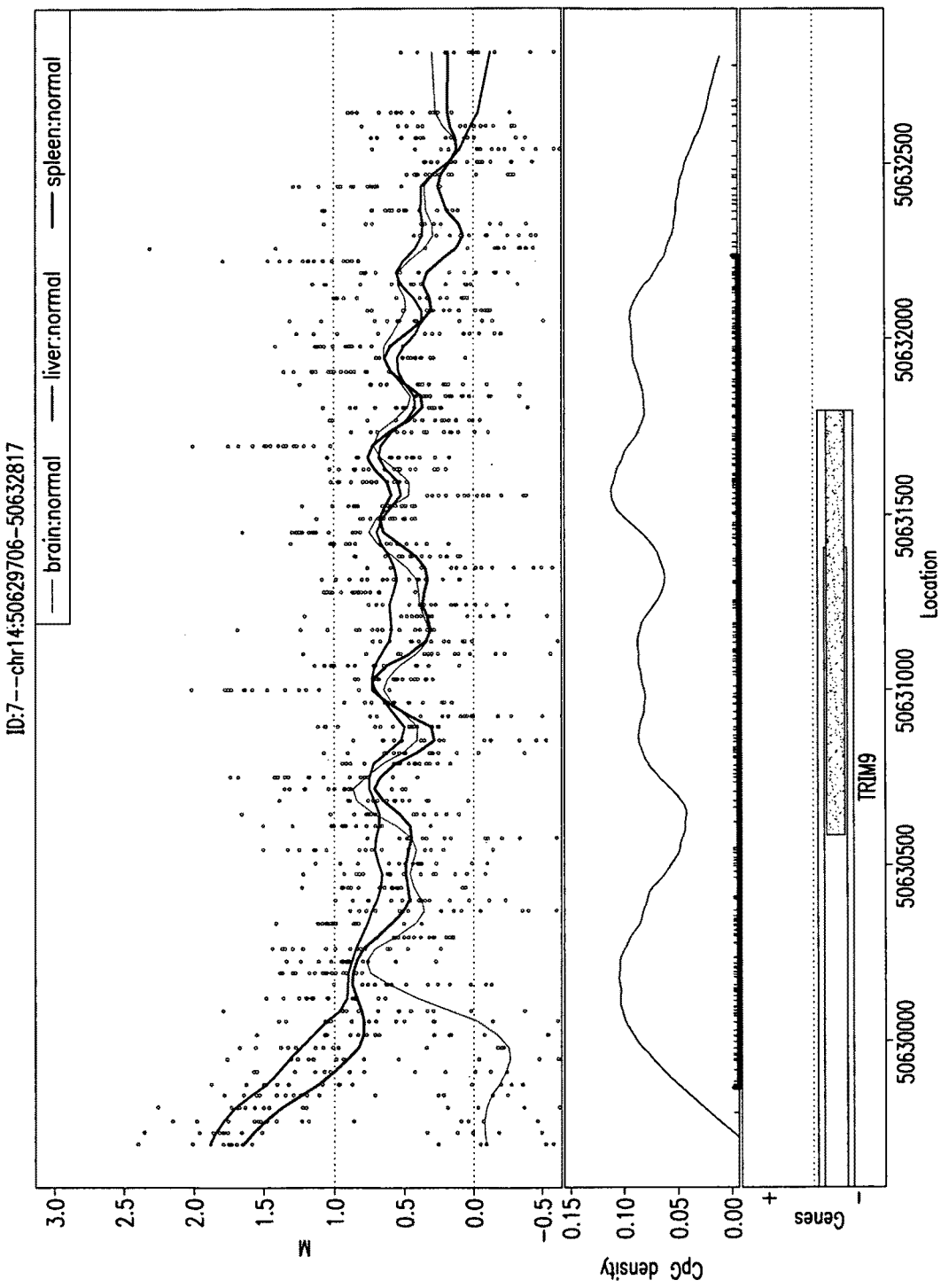
Figure 10H:
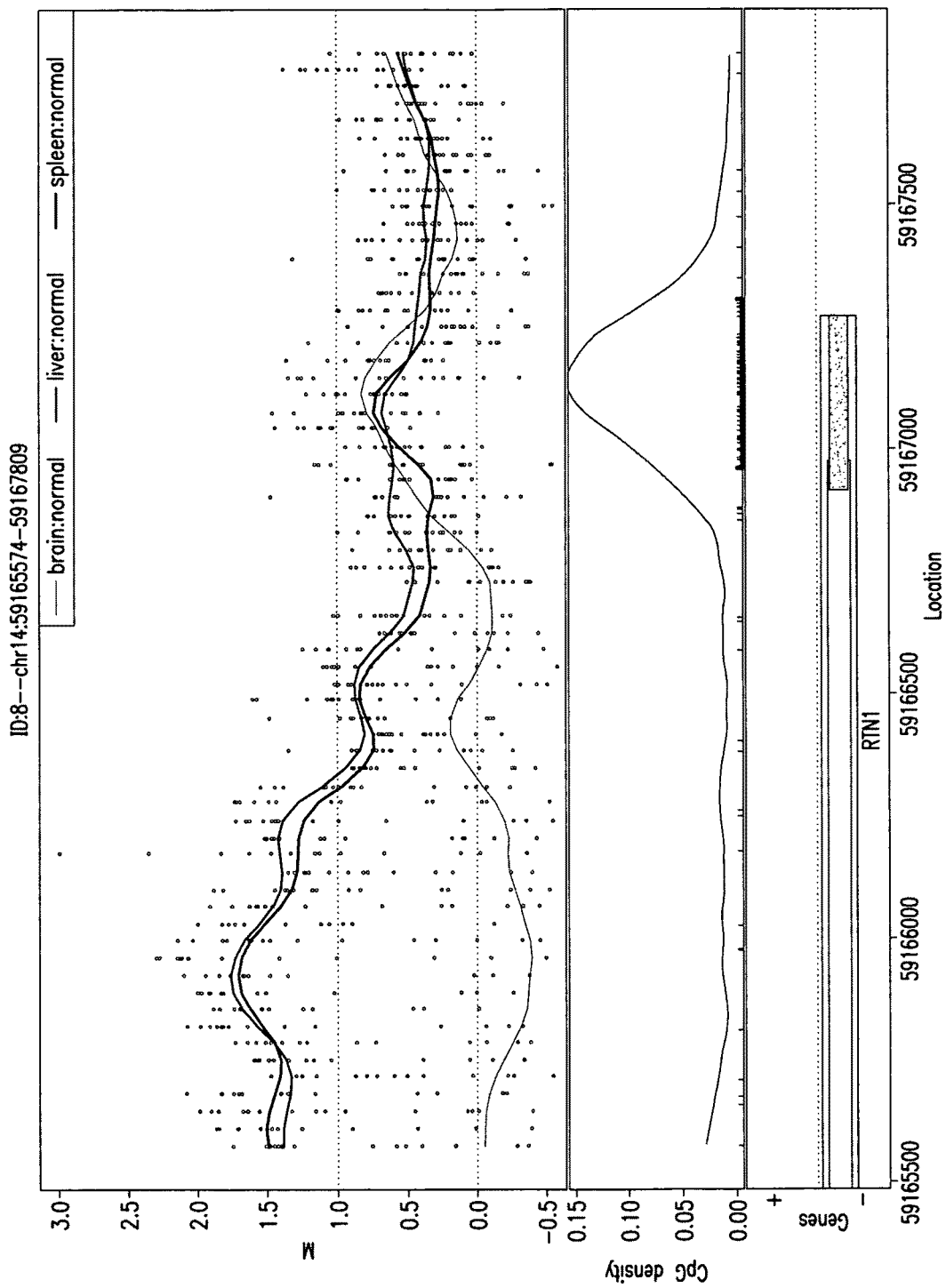
Figure 10I:
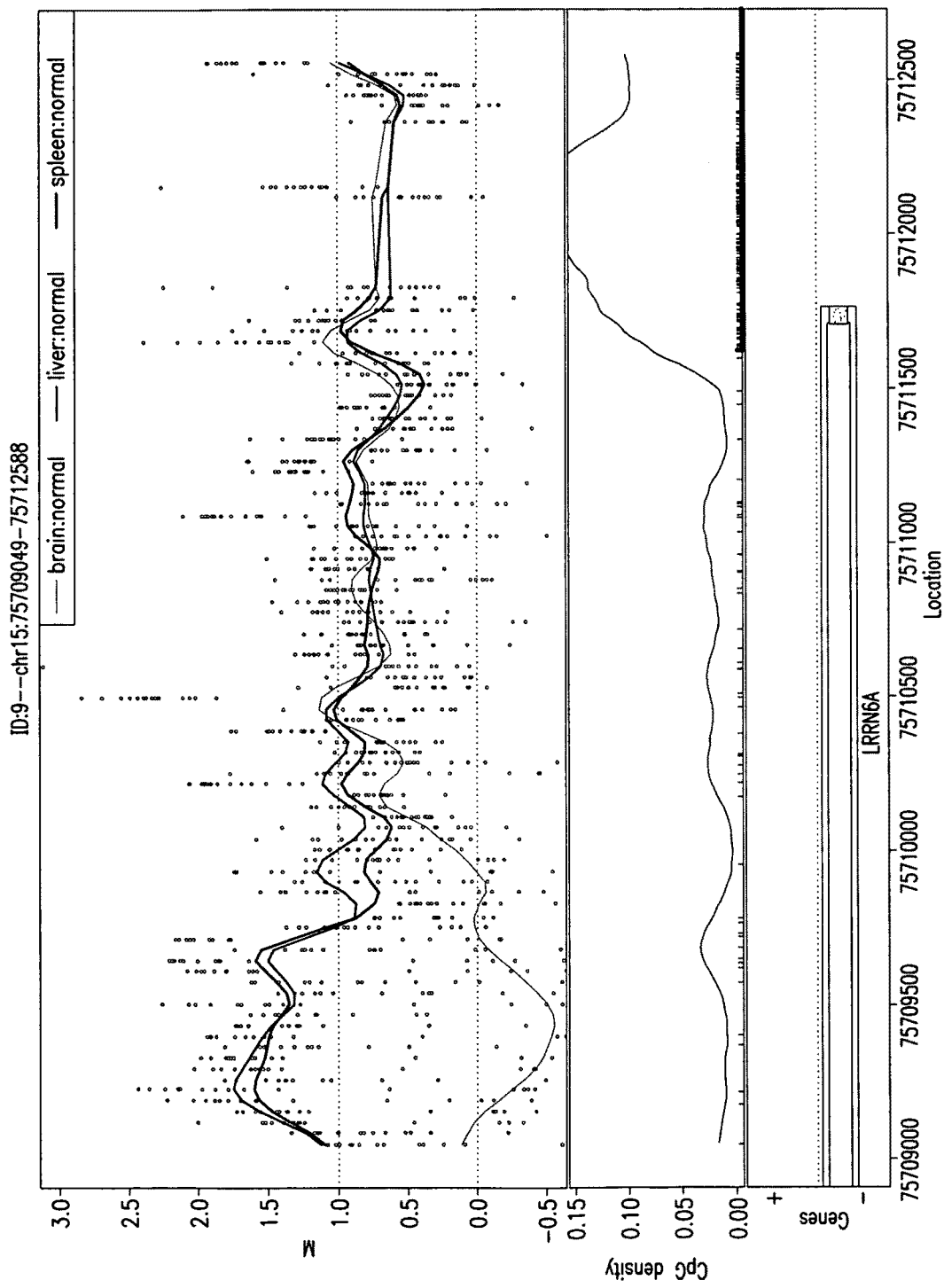
Figure 10J:
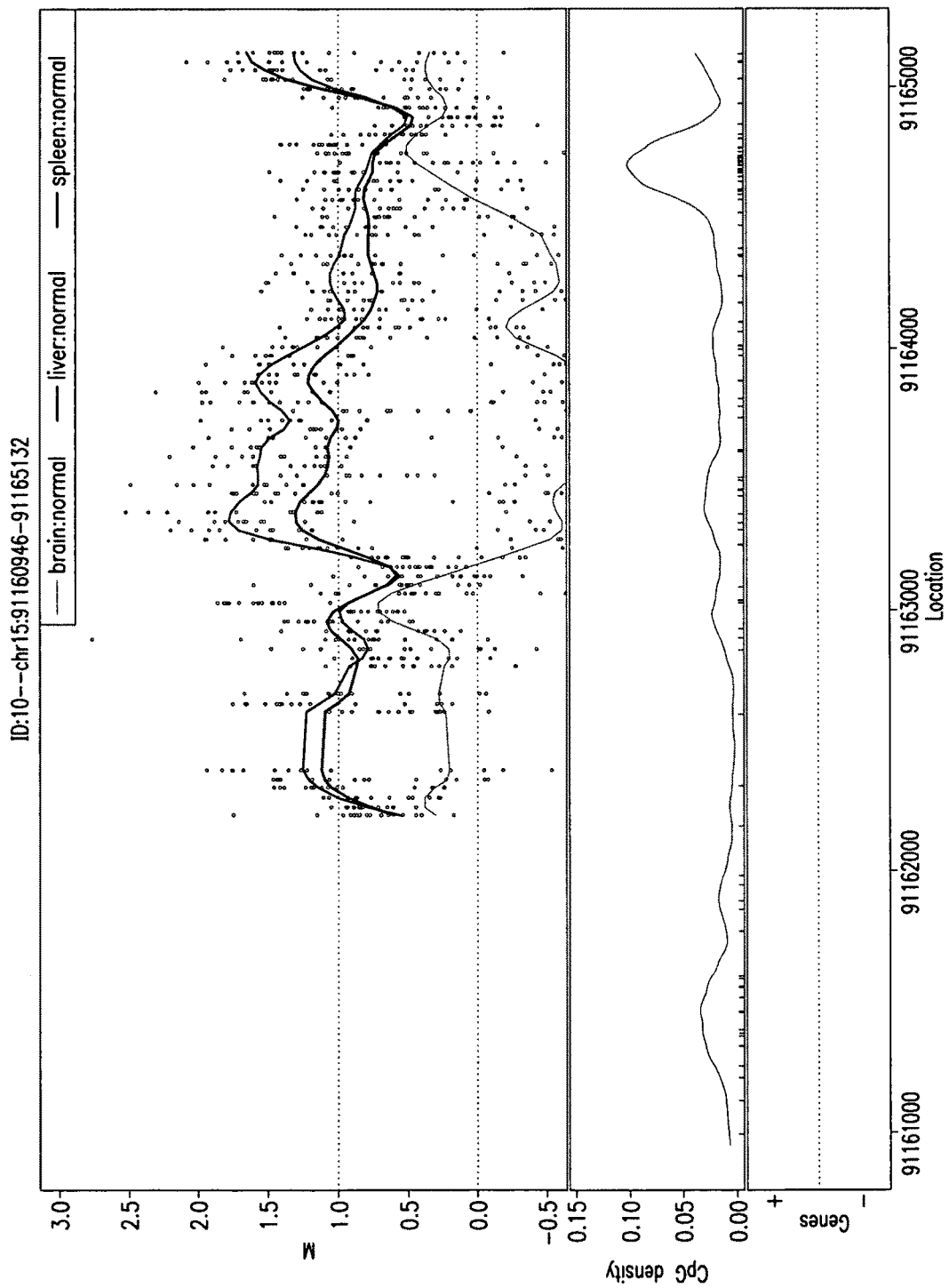

Most tissue-specific DNAm occurs in 'CpG island shores.' Because CHARM is not biased for CpG island or promoter sequences, objective data on tissue-specific methylation could be obtained. 16,379 tissue differential methylation regions (T-DMRs), defined as regions with M values for one tissue consistently different than that for the others at a false discovery rate (FDR) of 5% (see Methods) were identified. The median size of a T-DMR was 255 bp. Previous studies of tissue- or cancer-specific DNAm have focused on promoters and/or CpG islands, which have been defined as regions with a GC fraction greater than 0.5 and an observed-to-expected ratio of CpG greater than 0.6 (Feinberg, A. P. & Tycko, B., Nat. Rev. Cancer 4, 143-153, 2004; and Gardiner-Garden, M. & Frommer, M., J. Mol. Biol. 196, 261-282, 1987). It has previously been reported that the degree of differences in DNAm of promoters in somatic cells is relatively low in conventionally defined CpG islands and higher at promoters with intermediate CpG density. Two recent studies identified a relatively small fraction, 4-8%, of CpG islands with tissue-specific methylation. It was also found herein that DNAm variation is uncommon in CpG islands (FIG. 9).

Figure 1B:
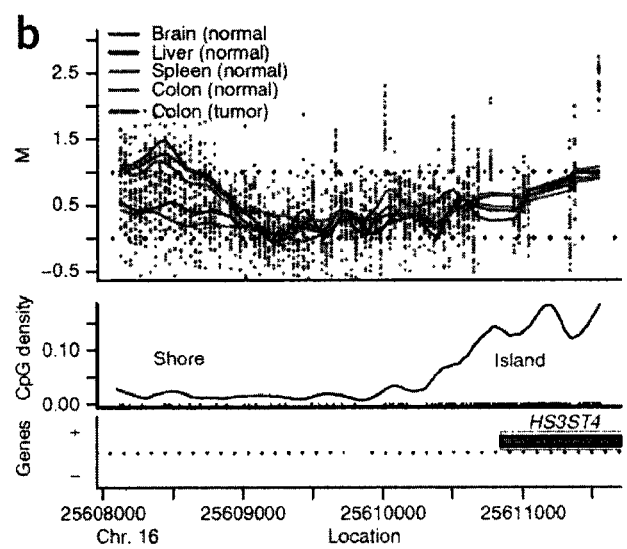
FIG. 1B shows a plot of M value versus genomic location for brain, liver, spleen, normal colon, and colon tumor (upper panel) and a plot of CpG density versus genomic location over the same region (lower panel) for a C-DMR located in a CpG island shore that overlaps with a T-DMR.
Figure 2:
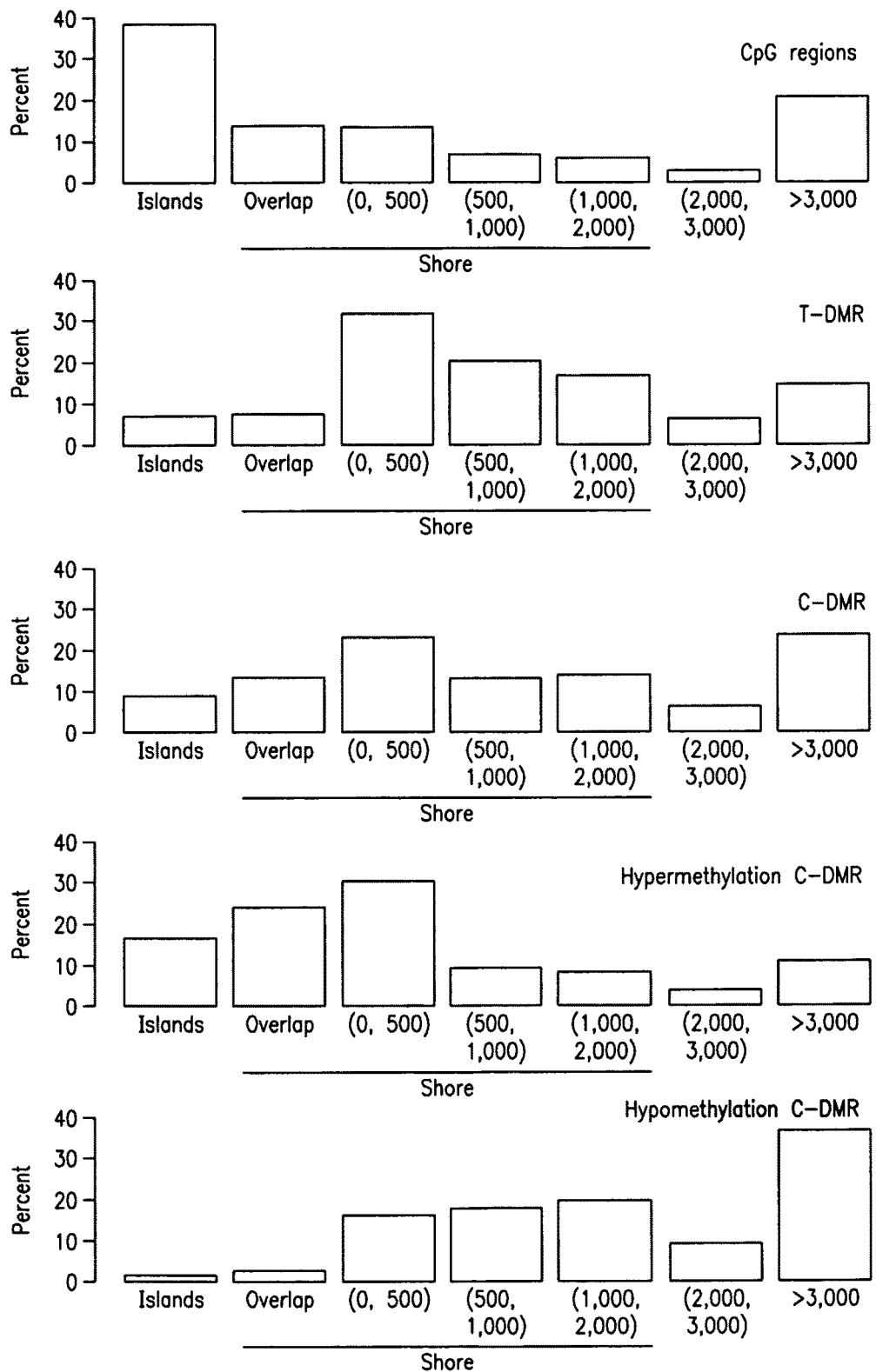
FIG. 2 shows plots depicting the distribution of distance of T-DMRs and C-DMRs from CpG islands.

The genome-wide approach of CHARM also enabled the finding of an unexpected physical relationship between CpG islands and DNAm variation, namely that 76% of T-DMRs were located within 2 kb of islands in regions denoted herein as 'CpG island shores.' For example, for the T-DMR in the PRTFDC1 gene, which encodes a brain-specific phosphoribosyltransferase that is relatively hypomethylated in the brain, the spreading of M values among the tissues begins ~200 bp from the CpG island and at a point where the CpG density associated with the island has fallen to ⅒ the density in the island itself (FIG. 1). The association of T-DMRs with CpG island shores was not due to an arbitrary definition of CpG islands but to a true association of these DNAm differences near but not in the regions of dense CpG content (Table 10 describes some of the identified T-DMR regions. The complete set of T-DMRs is available on the Nature Genetics website (nature.com/naturegenetics) see "Supplementary Data 1" in the Supplementary Information for Irizarry et al., Nature Genetics 41(2):178-186). Plots similar to those in FIG. 1 for 10 of the T-DMRs are provided in FIG. 10A-J; the complete set of T-DMRs plots, ordered by statistical significance, are available online at rafalab.jhsph.edu/t-dmr3000.pdf). The distribution of T-DMRs by distance from the respective islands showed that DNAm variation is distributed over a ~2 kb shore, and that although CpG islands are enriched on the arrays, because of their high CpG content (33% of CHARM probes are in islands), only 6% of T-DMRs are in islands, compared to 76% in shores; an additional 18% of T-DMRs were located greater than 2 kb from the respective islands (FIG. 2). The localization of T-DMRs also occurred largely outside of promoters (96%), as CpG islands are localized primarily within promoters. Furthermore, more than half (52%) of T-DMRs were greater than 2 kb from the nearest annotated gene. The distribution of the distance to islands remained essentially unchanged when we used FDR cutoffs of 0.01, 0.05 and 0.10.

The array-based result that the differential methylation was in CpG island shores rather than in the associated islands was confirmed by carrying out bisulfite pyrosequencing analysis on over 100 CpG sites in the islands and shores associated with four genes, three T-DMRs and one cancer differential methylation region. At all 101 sites, the DMR was confirmed to lie within the shore rather than the island (Table 1). For example, PCDH9, which encodes a brain-specific protocadherin, was relatively hypomethylated in the brain at all 6 sites examined in the CpG island shore but unmethylated in both brain and spleen at all 18 sites examined in the associated island (Table 1). Differential methylation of an additional four CpG island shores was also confirmed by bisulfite pyrosequencing of 39 total CpG sites, and all showed statistically significant differences in DNAm ($P<0.05$) (Table 2). These data verify the sensitivity of CHARM for detecting subtle differences in DNAm. Furthermore, they confirm that most normal differential methylation takes place at CpG island shores.

FIG. 1 illustrates that most tissue-specific differential DNA methylation was located at CpG island shores. (a) An example of a T-DMR located at a CpG island shore in the PRTFDC1 gene. The upper panel is a plot of M value versus genomic location for brain, liver and spleen. Each point represents the methylation level of an individual sample for a given probe. The curve represents averaged smoothed M values, described in detail in the Methods. Because of the scale and standardization used, M values that range from −0.5 to 0.5 represented unmethylated sites as defined by the control probes, and values from 0.5 to 1.5 represent baseline levels of methylation. The middle panel provides the location of CpG dinucleotides with tick marks on the x axis. CpG density was calculated across the region using a standard density estimator and is represented by the smoothed line. The location of the CpG island was denoted on the x axis. The lower panel provides gene annotation for the genomic region. The thin outer line represents the transcript, the thin inner lines represent a coding region. Filled in boxes represent exons. On the y axis, plus and minus marks denote sense and antisense gene transcription, respectively. (b) An example of a C-DMR that was located in a CpG island shore and that overlapped a T-DMR. Liver was hypomethylated relative to brain and spleen tissues. Hypomethylation of colon tumor was observed in comparison to matched normal colon tissue and overlapped the region of liver hypomethylation.

FIG. 9 illustrates that genome-wide DNAm analysis showed methylation variation was more common outside of CpG islands than within them. The average M value was computed for four sets of normal brain, liver, spleen and colon. Methylation variation across tissues was determined using the standard deviation across tissues of within tissue-averaged M. For all CHARM probes located within a CGI, left plot, and all CHARM probes located outside of a CGI, right plot, a smooth scatter plot was used to represent distribution of values from high to low number of points. Where tissue M variation was greater than 0.75 points were used, and where greater than 1.0, other points were used.

Figure 3A:
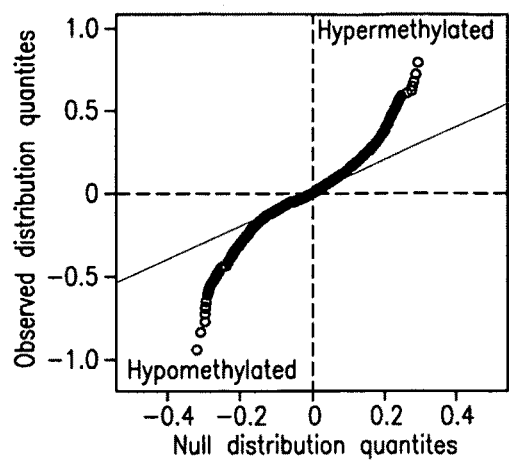
FIG. 3A shows a quantile-quantile plot depicting the number of sites of hypomethylation and hypermethylation in colon cancer.
Figure 3B:
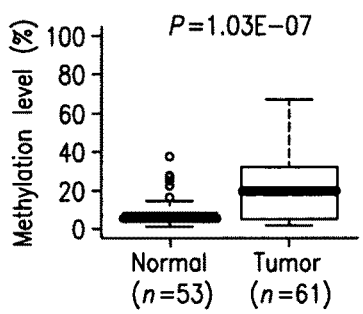
FIGS. 3B-J show box plots depicting the degree of DNA methylation of the indicated C-DMRs as measured by bisulfite pyrosequencing.
Figure 3C:
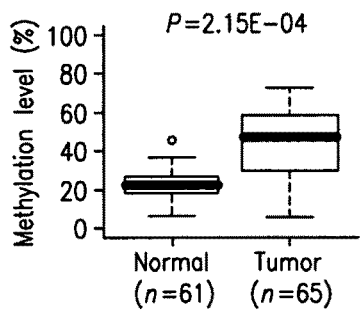
Figure 3D:
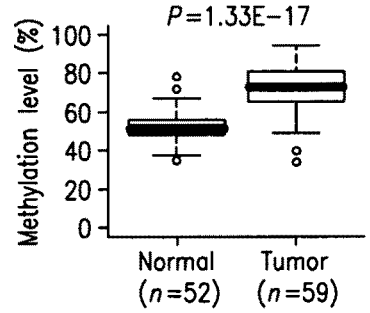
Figure 3E:
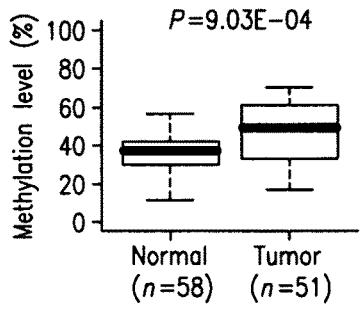
Figure 3F:
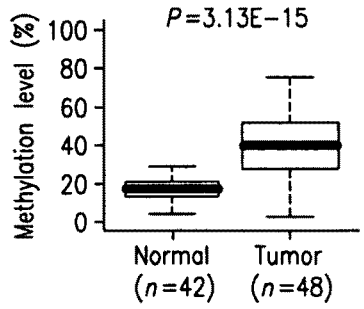
Figure 3G:
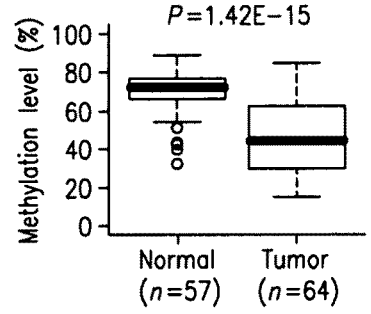
Figure 3H:
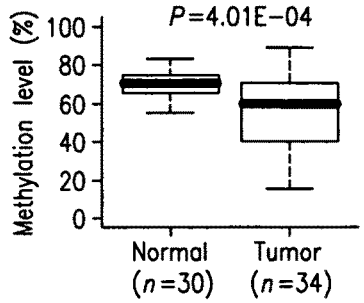
Figure 3I:
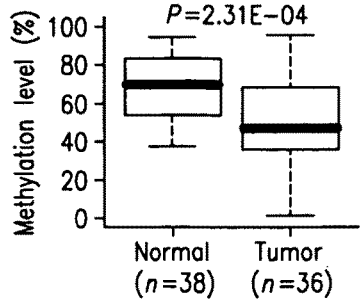
Figure 3J:
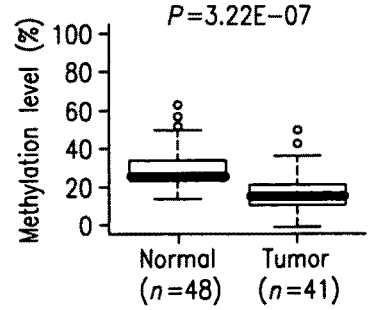

Similar CpG island shore hypo- and hypermethylation in cancer. The same comprehensive genome-wide was used approach to address cancer-specific DNA methylation. The focus was on colorectal cancer, a paradigm for cancer epigenetics because of the availability of subject-matched normal mucosa, the cell type from which the tumors arise. DNAm was analyzed on 13 colon cancers and matched normal mucosa from the same individuals, identifying 2,707 regions showing differential methylation in cancers (C-DMRs) with an FDR of 5% (Table 11 describes some of the identified C-DMR regions. The complete set of C-DMRs is available on the Nature Genetics website (nature.com/naturegenetics) see "Supplementary Data 2" in the Supplementary Information for Irizarry et al., Nature Genetics 41(2):178-186). Plots similar to those in FIG. 1 for 10 of the C-DMRs are provided in FIGS. 12A-J; the complete set of C-DMRs plots, ordered by statistical significance, are available online at rafalab.jhsph.edu/c-dmr-all.pdf). These C-DMRs were similarly divided between those showing hypomethylation in the cancer (compared to the normal colon) and those showing hypermethylation (1,199 (44%) and 1,508 (56%), respectively). The CHARM arrays, like other tiling arrays, do not contain repetitive sequences, so the abundance of hypomethylation was not due to enrichment for repetitive DNA, which has been shown to be hypomethylated in cancer. This similarity in amount of hypomethylation and hypermethylation was also shown in a quantile-quantile plot, in which quantiles for the observed average difference between tumor and normal sample Ms are plotted against quantiles from a null distribution constructed with the control (M=0) regions (FIG. 3A).

Although both hypomethylation and hypermethylation in cancer involved CpG island shores, there were subtle differences in the precise regions that were altered. The hypermethylation extended to include portions of the associated CpG islands in 24% of cases (termed 'overlap' in FIG. 2), which could account for the island hypermethylation frequently reported in cancer, even though that is not the predominant site of modification. In contrast, the hypomethylation extended to between 2 and 3 kb from the associated island in 10% of cases and was not associated with an island in 35% of cases (FIG. 2).

To confirm differential methylation in colon tumors, additional bisulfite pyrosequencing validation of nine C-DMRs, including five regions showing hypermethylation and four regions with hypomethylation, in an average of 50 primary cancer and normal mucosal samples per gene was carried out. For all of the genes, the pyrosequencing data matched the CHARM data (P values ranging from $10^{-4}$ to $10^{-17}$) (FIGS. 3b-j and Table 3). Thus, CHARM was precise in identifying both T-DMRs and C-DMRs.

Our screening process was effective at identifying known targets of altered DNAm in cancer. For example, 10 of the 25 most statistically significant C-DMRs have previously been reported to show altered DNAm in cancer, for example, WNK2, hypermethylated in glioblastoma (Hong, et al., Proc. Natl. Acad. Sci. USA 104:10974-10979, 2007) and HOXA6, hypermethylated in lymphoid malignancies (Strathdee et al., Clin. Cancer Res. 13, 5048-5055, 2007). However, hundreds of genes not previously described were also identified by this screening. For example, for hypermethylation, we identified genes encoding GATA-2, an important regulator of hematopoetic differentiation (Cantor et al., J. Exp. Med. 205, 611-624, 2008), and RARRES2, whose expression is decreased in intestinal adenomas (Segditsas et al., Hum. Mol. Genet. 17:3864-3875, 2008). For hypomethylation, we identified genes encoding DPP6, a biomarker for melanoma (Jaeger et al., Clin. Cancer Res. 13, 806-815, 2007), MRPL36, a DNA helicase that confers susceptibility to breast cancer (Seal et al., Nat. Genet. 38, 1239-1241, 2006), and MEST, a known target of hypomethylation and loss of imprinting in breast cancer (Pedersen et al., Cancer Res. 59:5449-5451, 1999). Note that although previous T-DMR screens have focused on CpG islands, which we show account for only 8% of T-DMRs, our screen did identify CpG island loci validated by others as well, for example, PAX6, OSR1 and HOXC12. Thus, cancer, like normal tissues, involves changes in DNAm in CpG island shores, with comparable amounts of hypomethylation and hypermethylation but with subtle differences in the precise distribution of these alterations with respect to the associated CpG island. These differences will have important functional implications for gene expression, as discussed later.

FIG. 2 illustrates the distribution of distance of T-DMRs and C-DMRs from CpG islands. In the plots, bars denoted "Islands" were regions that cover or overlap more than 50% of a CpG island. Bars denoted "Overlap" were regions that overlap 0.1-50% of a CpG island. Regions denoted by (0, 500) did not overlap islands but are located <500 bp of islands. Regions denoted by (500, 1,000) were located >500 and ≤1,000 bp from an island. Regions denoted by (1,000, 2,000) were regions >1,000 bp and ≤2,000 bp from an island. Regions denoted by (2000, 3000) were located >2,000 bp and ≤3,000 bp from an island. Regions denoted >3,000 were >3,000 bp from an island. The percentage of each class was provided for CpG regions (the CHARM arrays themselves, null hypothesis), tissue-specific differentially methylated regions (T-DMRs), cancer-specific differentially methylated regions (C-DMRs), and the latter subdivided into regions of cancer-specific hypermethylation and hypomethylation.

FIG. 3 illustrates similar numbers of sites of hypomethylation and hypermethylation in colon cancer. (a) A quantile-quantile plot showed a similar number of sites of hypomethylation and hypermethylation in colon cancer. The quantiles of the differences in M values between tumor and normal colon tissues were plotted against the quantiles of a null distribution formed using the differences seen in the control regions. Points deviating from the diagonal were not expected by chance, and a similar proportion is seen for hypomethylation and hypermethylation in cancer. (b-j) Bisulfite pyrosequencing confirms the prevalence of five hypermethylated and four hypomethylated C-DMR shores in a large set of colon tumor and normal mucosa samples. Box plots represent degree of DNA methylation as measured using bisulfite pyrosequencing. (b) DLX5 (distal-less homeobox 5). (c) LRFN5 (leucine-rich repeat and fibronectin type III domain containing 5). (d) HOXA3 (homeobox A3). (e) SLITRK1 (SLIT and NTRK like family, member 1). (f) FEZF2 (FEZ family zinc finger 2). (g) TMEM14A (transmembrane protein 14A). (h) ERICH1 (glutamate-rich 1). (i) FAM70B (family with sequence similarity 70, member B). (j) PMEPA1 (prostate transmembrane protein, androgen induced 1). n, number of samples analyzed by pyrosequencing.

Figure 4:
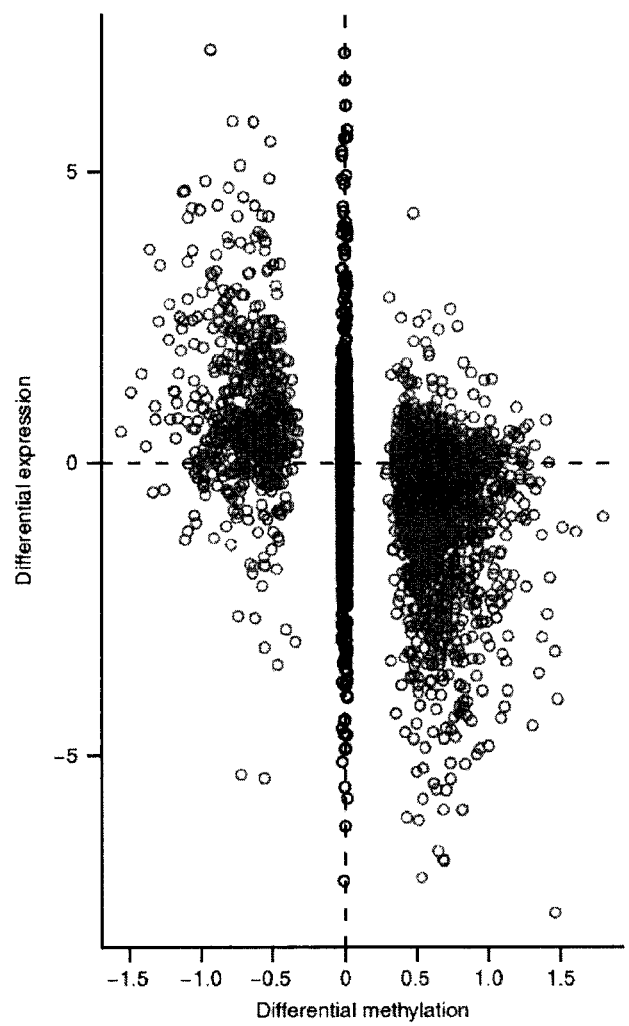
FIG. 4 shows a plot of differential gene expression versus differential methylation for brain and liver T-DMR.

Gene expression is linked to non-CpG-island methylation. Because the identification of CpG island shores was unexpected, the functional relationship between their differential methylation and the expression of associated genes was explored. To address tissue- and cancer-specific DNAm, gene expression was analyzed across the genome in five primary brains and livers from the same autopsy specimens, and in four colon cancers and subject-matched normal mucosa; all samples were from subjects for whom genome-wide methylation analysis data had been collected. Methylation of T-DMRs showed a strong inverse relationship with differential gene expression, even though these DMRs were not CpG islands but rather CpG island shores. The relationship between DNAm and gene expression was greater for DMRs in which one of the two measured points had approximately no methylation ('none-to-some' methylation compared to 'some-to-more' or 'some-to-less' methylation), particularly for hypomethylation (FIG. 4). The significant association of gene expression with T-DMRs was true even when the DMR was 300-2,000 bp from the transcription start site, for example, average log-ratio values of 0.84 and 0.35 ($P<10^{-37}$ and $10^{-4}$) for some-to-none and some-to-more/less methylation, respectively, comparing liver to brain expression (FIG. 4). Moreover, when T-DMRs were related to changes in gene expression from over 242 samples, representing 20 different tissue types, it was found that 5,352 of the 8,910 genes that were differentially expressed across the 20 tissues were within 2 kb of a T-DMR, much more than expected by chance ($P<10^{-15}$). For C-DMRs as well, even though there were fewer of them than T-DMRs, there was a significant association of gene expression with DNAm: $P<10^{-6}$ and $P<10^{-3}$ for hypermethylation and hypomethylation, respectively; again, the relation was much more marked when one of the two measured points had no methylation (FIGS. 10A-J; the complete set is available on the Nature Genetics website (nature.com/naturegenetics) see "Supplementary FIG. 2" in the Supplementary Information for Irizarry et al., Nature Genetics 41(2):178-186).

The inverse relationship between DNAm and transcription was validated at eight CpG island shores, two T-DMRs and six C-DMRs in tissues and colon cancers, respectively, using quantitative real-time PCR. Both of the T-DMRs were in shores, one located 844 bp upstream of the promoter and one within the gene body. Similarly, all six of the C-DMRs assayed were in shores, with five located in the gene promoter and one within the gene body (Table 4). These quantitative data provided additional support for a strong relationship between differential methylation in CpG island shores and transcription of associated genes. This functional relationship between gene expression and shore methylation applies to shores located within 2 kb of an annotated transcriptional start site but leaves open the possibility of additional regulatory function for shores located in intragenic regions or gene deserts.

FIG. 4 shows that gene expression was strongly correlated with T-DMRs at CpG island shores. For each brain versus liver T-DMR, the closest annotated gene on the Affymetrix HGU133A microarray was found, resulting in a total of 2,041 geneT-DMR pairs. Plotted are log (base 2) ratios of liver to brain expression against ΔM values for liver and brain DNAm. Dots represented T-DMRs located within 300 bp from the corresponding gene's transcriptional start site (TSS). Dots represented T-DMRs that were located from 300 to 2,000 bp from the TSS of an annotated gene. Dots, in the middle, represented log ratios for all genes further than 2 kb from an annotated TSS.

FIG. 10 illustrates that most tissue-specific differential DNA methylation were located at CpG island shores. The top 50 T-DMRs, ordered by statistical significance. Displays are as in FIG. 1a. The upper panels are plots of M value versus genomic location for brain, liver, and spleen. Each point represents the methylation level of an individual sample for a given probe. The curve represents averaged smoothed M values, described in detail in the Methods. Due to the scale and standardization used, M values which range from −0.5 to 0.5 represented unmethylated sites as defined by the control probes, and values from 0.5 to 1.5 represented baseline levels of methylation. The middle panels provide the location of CpG dinucleotides with tick marks on the x-axis. CpG density was calculated across the region using a standard density estimator and is represented by the smoothed line. The location of the CpG island was denoted on the x-axis. The lower panels provide gene annotation for the genomic region. The thin outer line represents the transcript, the thin inner lines represent a coding region. Filled in boxes represent exons. On the y-axis, plus and minus marks denote sense and antisense gene transcription respectively.

Figure 5A:
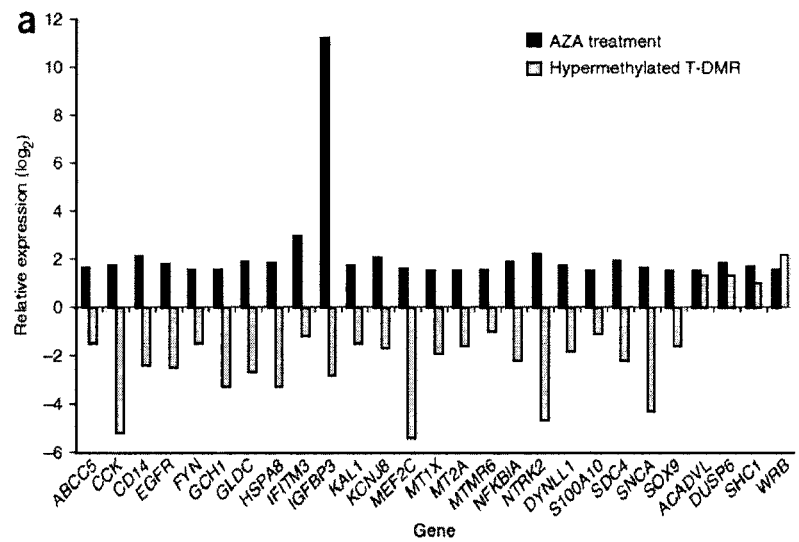
FIG. 5 shows plots of the relative expression of hypermethylated T-DMR when treated with 5-aza-2' deoxycytidine (FIG. 5A) or in a double knockout of DNA methyltransferase 1 and 3b (FIG. 5B).
Figure 5B:
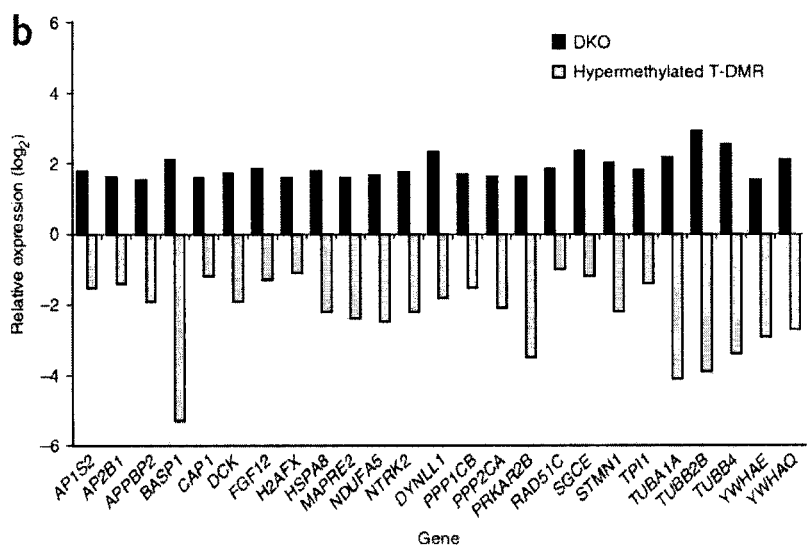

Shore-linked silencing reversed by methyltransferase inhibition. The previous data, although compelling, are associative in nature. For a more functional analysis, DNA methylation and gene expression data from tissues studied in the current work were compared to a rigorous analysis using hundreds of expression microarray experiments published earlier (Gius et al., Cancer Cell 6:361-371, 2004), which tested the effects on gene expression of 5-aza-2'-deoxycytidine (AZA), and also to double DNA methyltransferase 1 and 3B somatic cell knockout (DKO) experiments. Genes from the present study that had DMRs meeting an FDR <0.05 and that showed differential expression in the tissues at P<0.05 were compared to genes that had significant P values after AZA or DKO. Of 27 DMRs that showed relative hypermethylation with gene silencing in tissues, 23 were activated by AZA (FIG. 5a and Tables 12 and 13). Similarly, of 25 DMRs that showed relative hypermethylation with gene silencing in tissues, all 25 were activated by DKO (FIG. 5b and Tables 12 and 13). Thus, both chemical and genetic demethylation cause changes in gene expression similar to those associated with increased methylation of CpG island shores.

FIG. 5 shows that genes downregulated in association with T-DMR shore hypermethylation were activated by 5-aza-2'-deoxycytidine treatment of colon cancer cell line HCT116 and knockout of DNA methyltrasferase 1 and 3b in HCT116. (a) Genes significantly upregulated (P<0.05) after treatment of HCT116 cells with 5-aza-2'-deoxycytidine (AZA) that were also associated with a relatively hypermethylated T-DMR showing a significant change in gene expression (P<0.05): 23/27 genes are activated by AZA. (b) Genes significantly upregulated (P<0.05) after knockout of DNA methyltransferases 1 and 3b (DKO) in HCT116 cells that were also associated with a relatively hypermethylated T-DMRs showing a significant change in gene expression (P<0.05): 25/25 genes were activated by DKO. Plotted are log (base 2) ratios of expression of AZA/untreated, DKO/HCT116 and relatively hypermethylated/hypomethylated tissue.

DMRs are associated with alternative transcription. The question as to what the function of differential methylation at CpG island shores might be was next addressed. One possibility was alternative transcription. Both the T-DMRs and C-DMRs often involved alternative transcripts, as defined by cap analysis gene expression (CAGE): 68% and 70% of the T-DMRs and C-DMRs, respectively, were not within 500 bp of an annotated transcriptional start site but were within 500 bp of an alternative transcriptional start site. By chance, only 58% were expect to have this relationship (P<10$^{-15}$). These results suggested that DNA methylation might regulate alternative transcription in normal differentiation and cancer. Rapid amplification of cDNA ends (RACE) experiments were therefore carried out in order to confirm the presence of alternative transcripts and their differential expression in cancer. Three colon tumor and subject-matched normal mucosa were examined at the PIP5K1A locus, a C-DMR that is hypomethylated in colon tumors, and confirmed that an alternative RNA transcript is produced in colon tumors compared to their matched normal counterparts (B online). Thus, a key function for differential methylation during differentiation may be alternative transcription, and the role of altered DNAm in cancer may in part be disruption of the regulatory control of specific promoter usage.

Figure 11A:
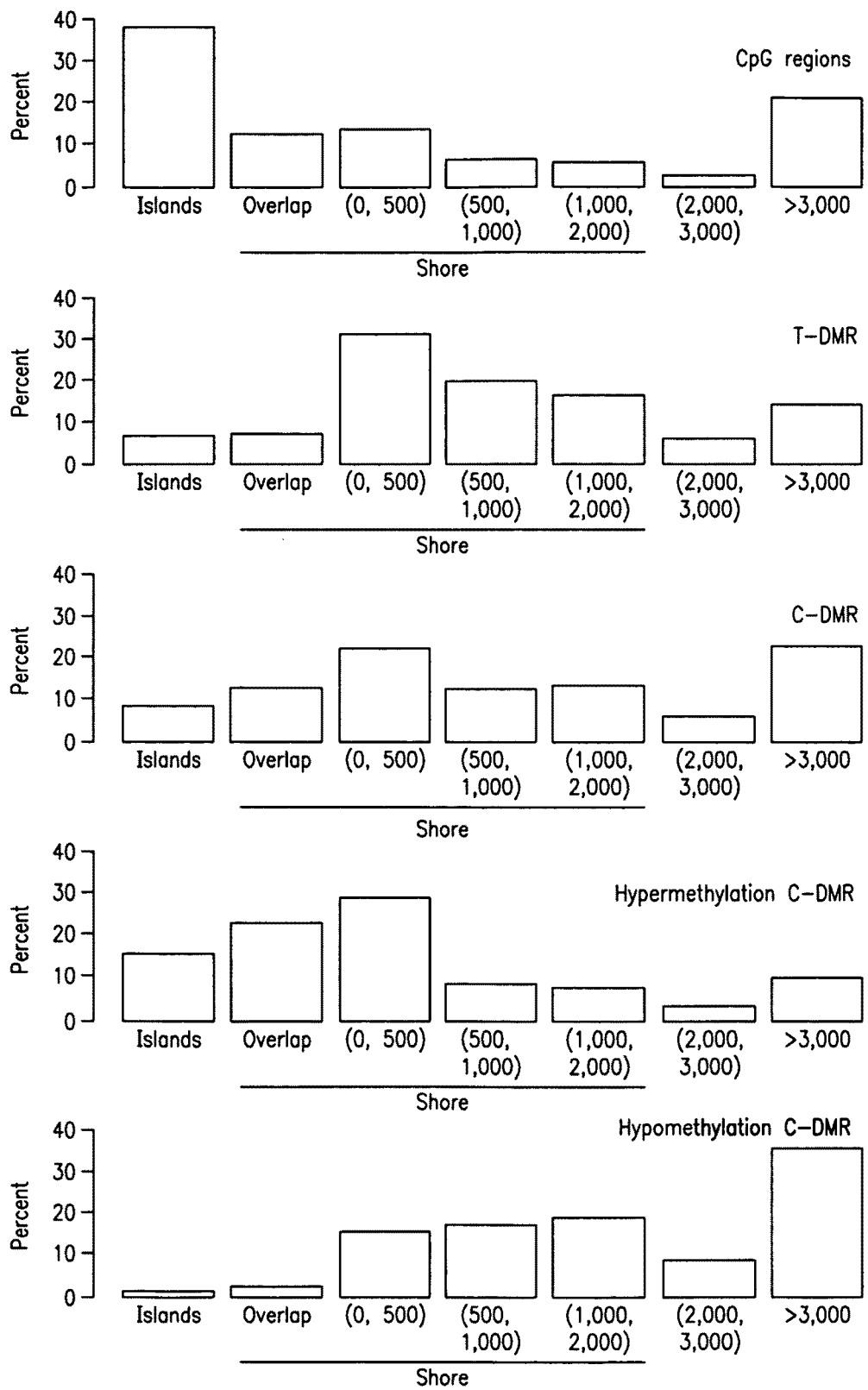
FIGS. 11A-C show plots of the distribution of distance of T-DMRs and C-DMRs from CpG islands using different FDR cutoff values (0.01, 0.05, and 0.10, for FIGS. 11A, 11B, and 11C, respectively.
Figure 11B:
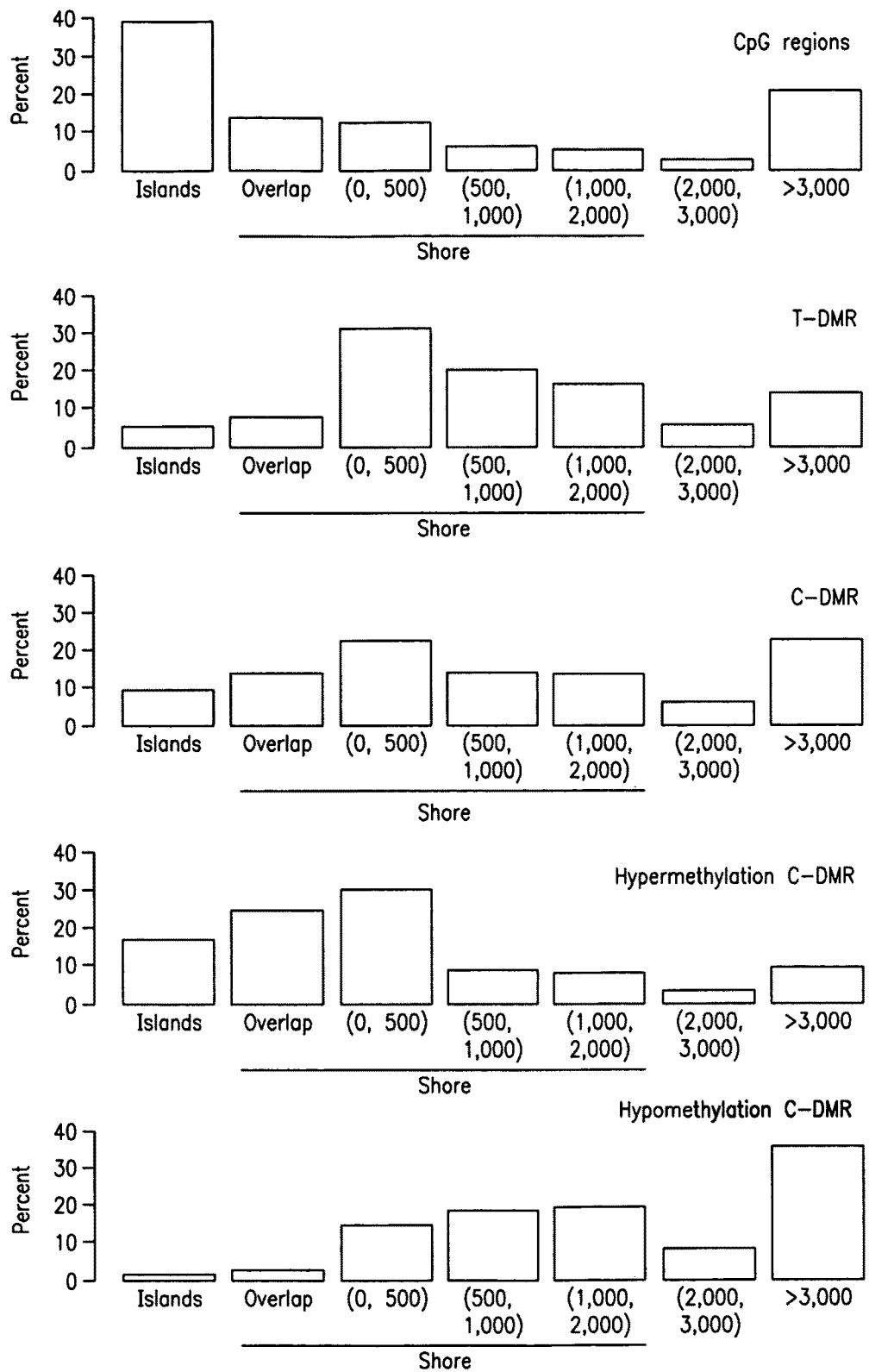
Figure 11C:
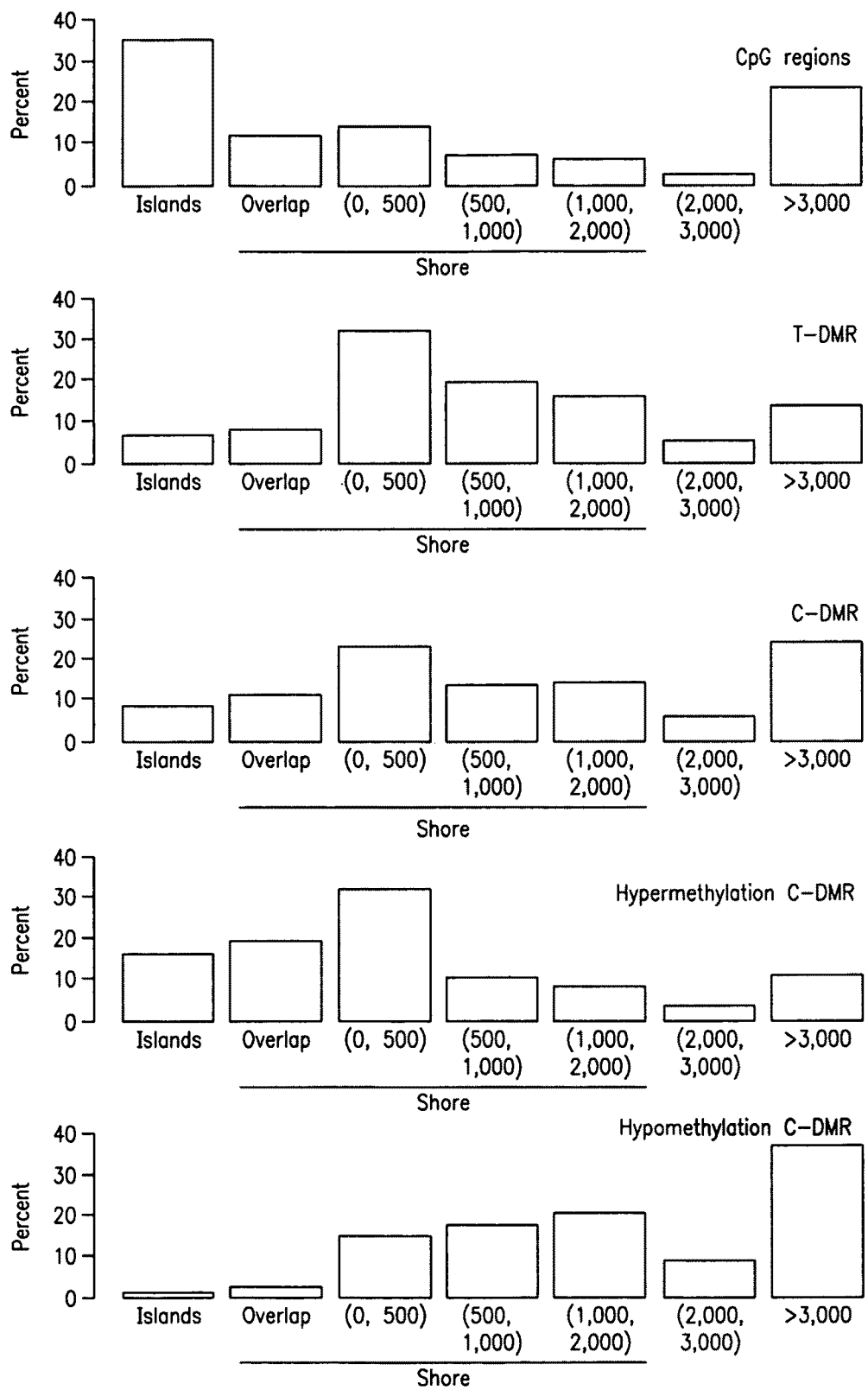
Figure 12A:
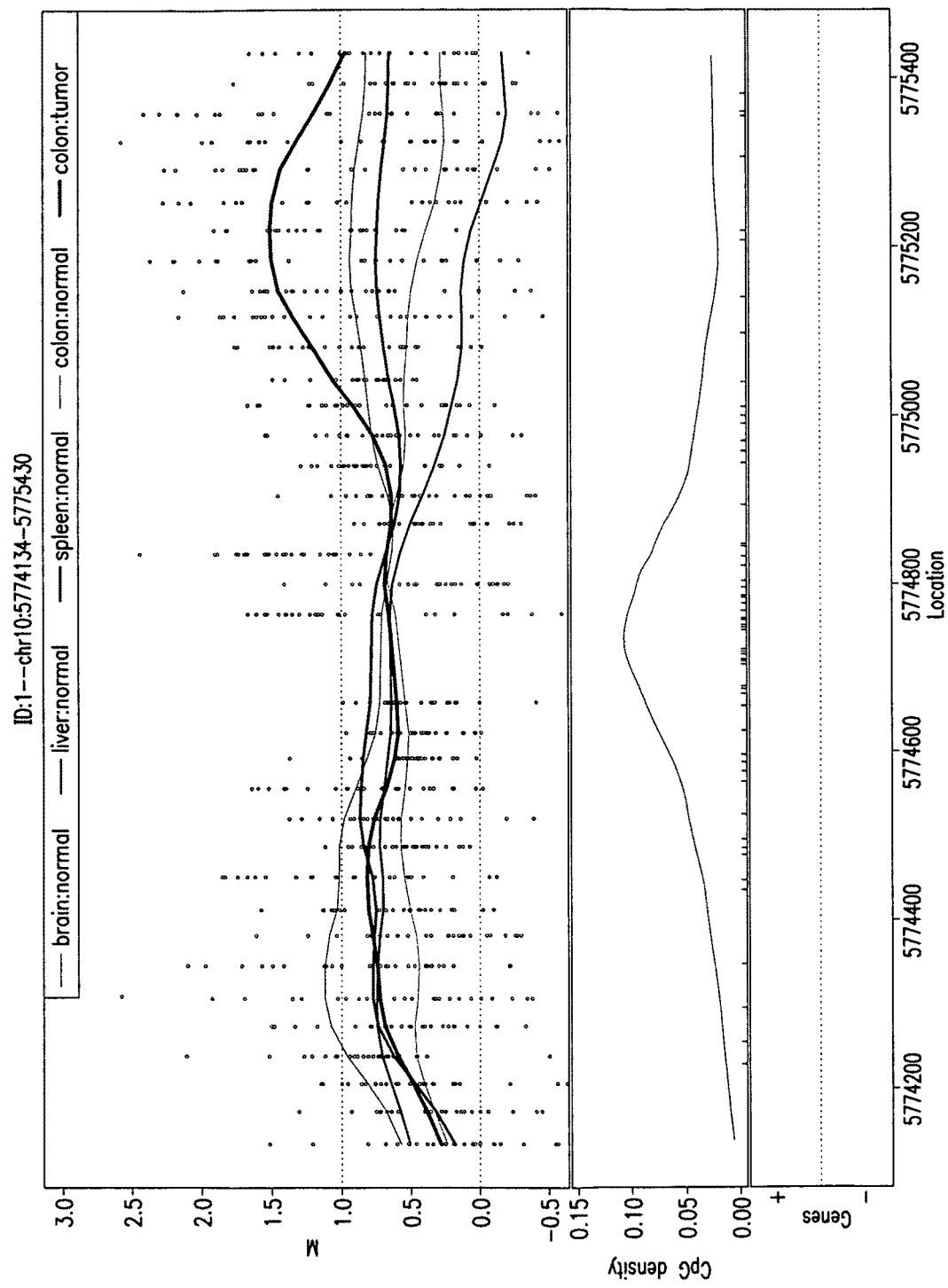
FIGS. 12A-J show representative plots of 10 C-DMRs. The upper panels are plots of M value versus genomic location for brain, liver, spleen, normal colon, and colon cancer. The middle panels provide the location of CpG dinucleotides with black tick marks on the x-axis. The lower panels provide gene annotation for the genomic region.
Figure 12B:
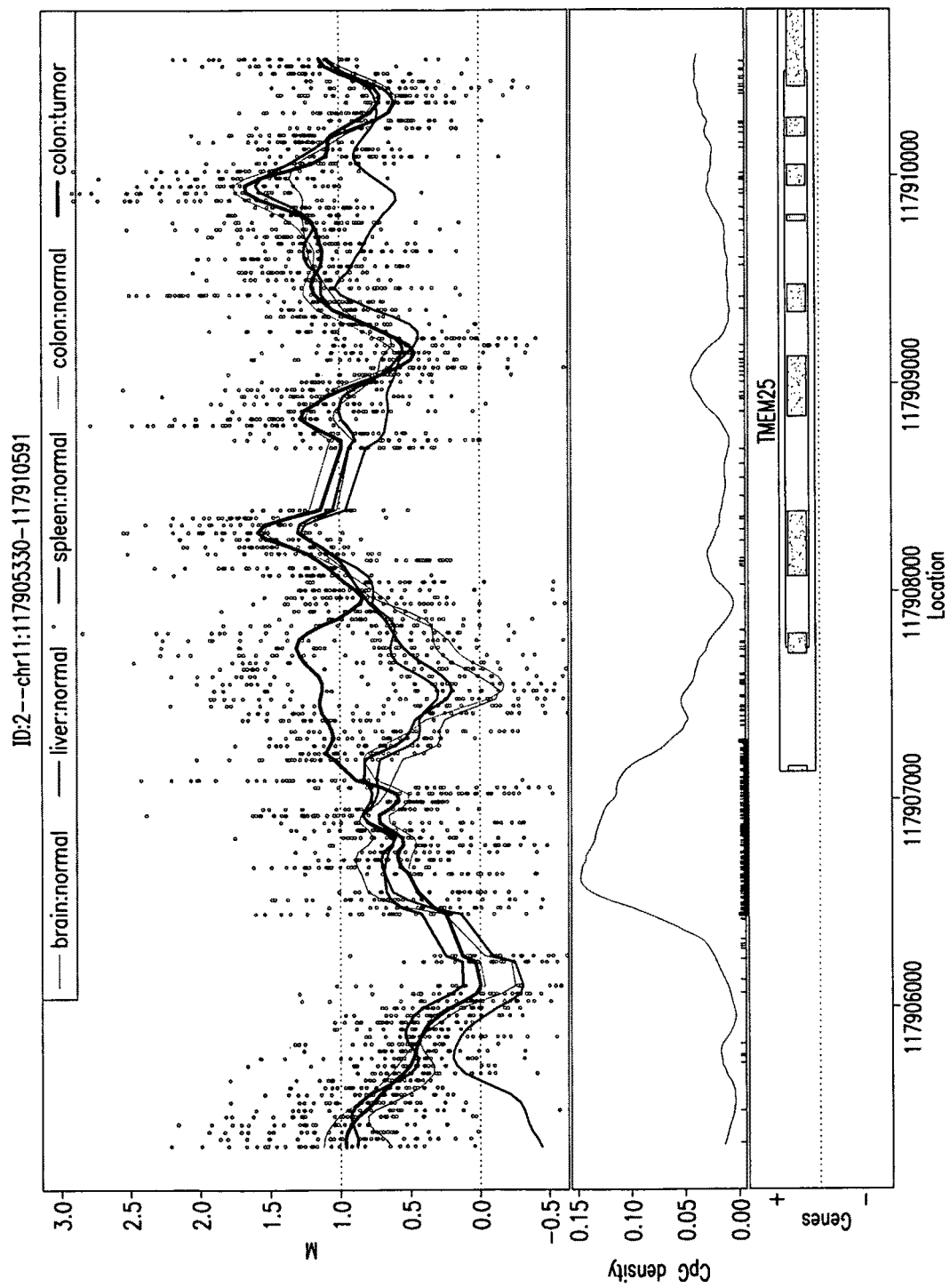
Figure 12C:
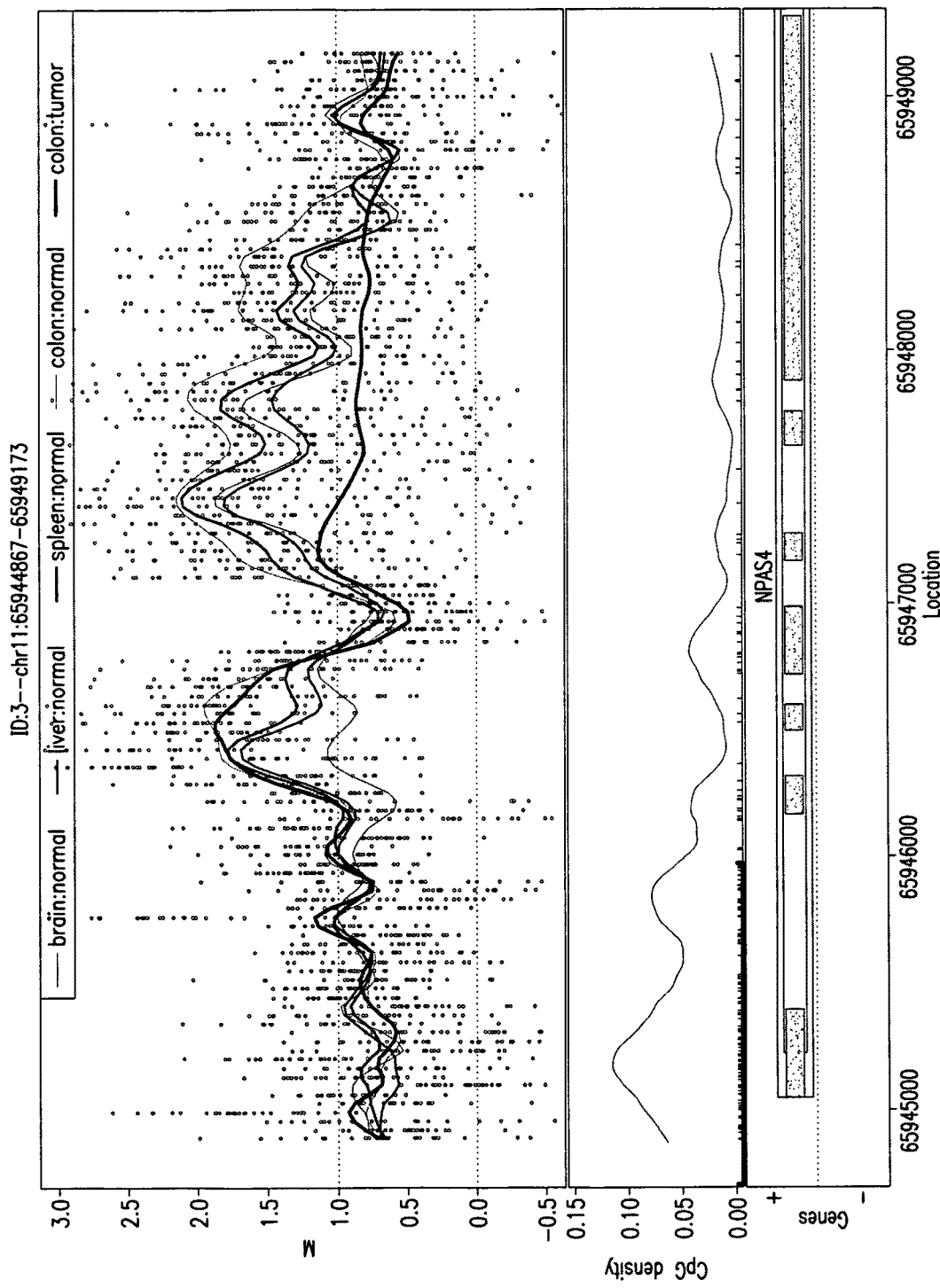
Figure 12D:
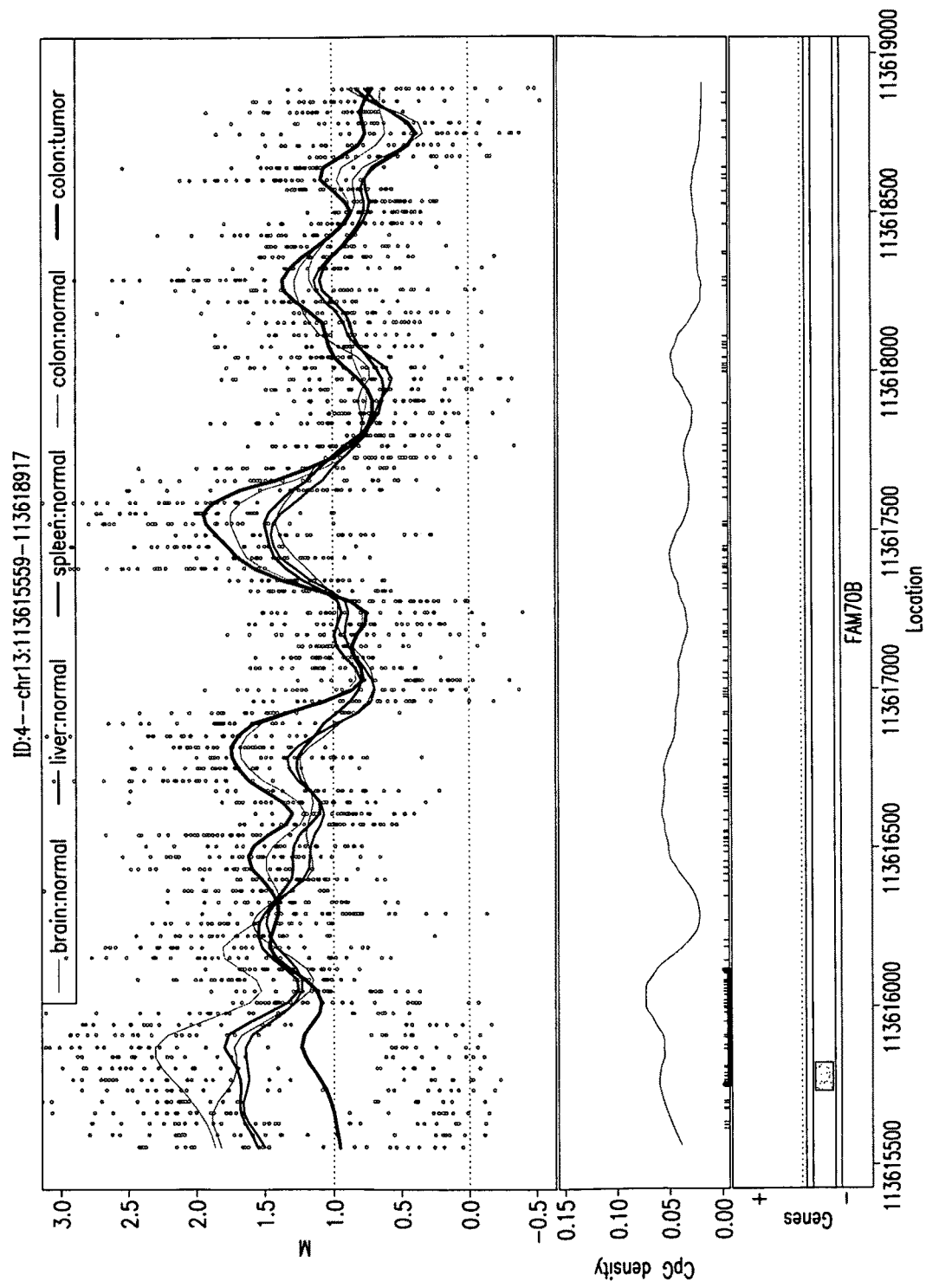
Figure 12E:
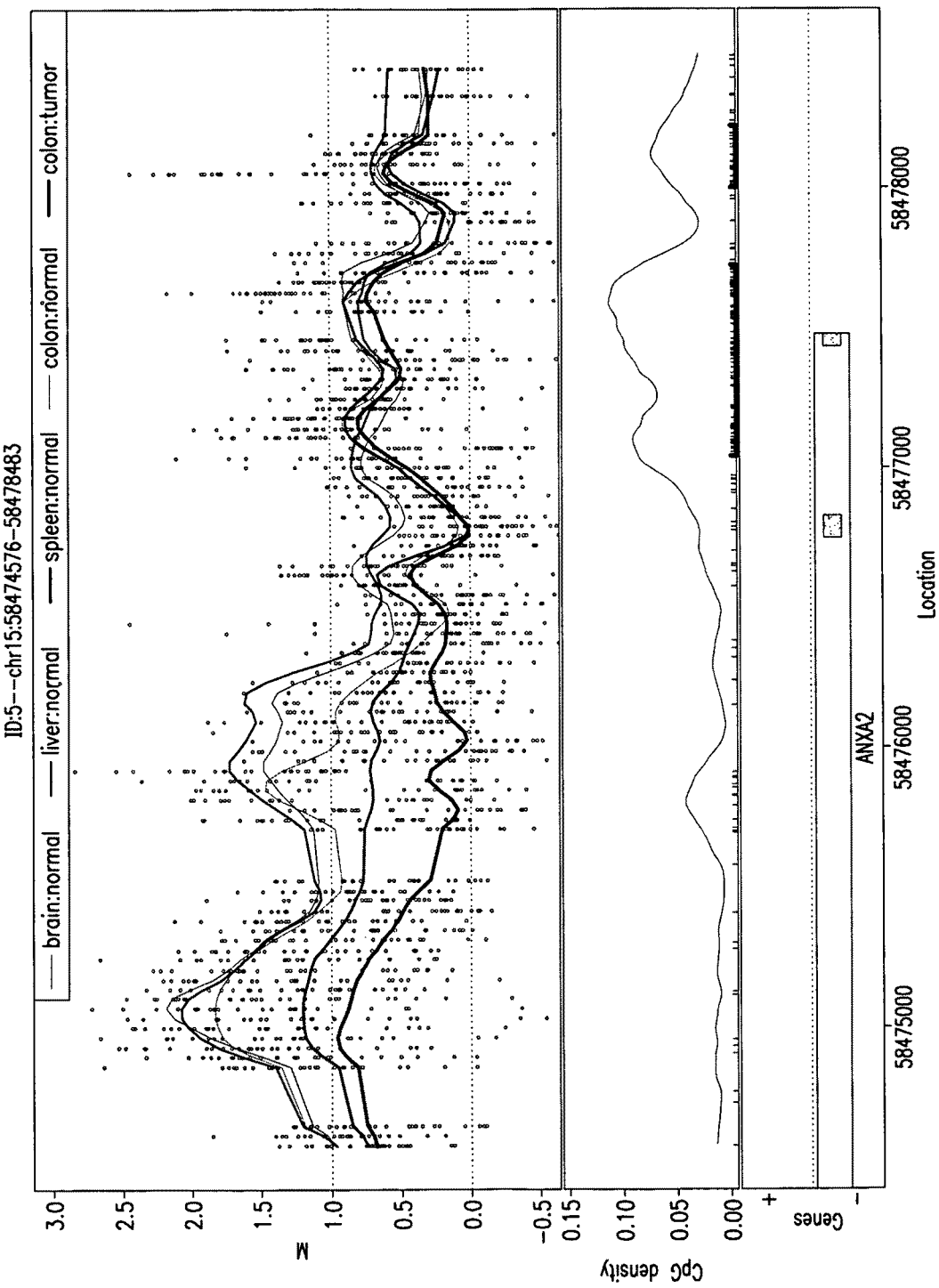
Figure 12F:
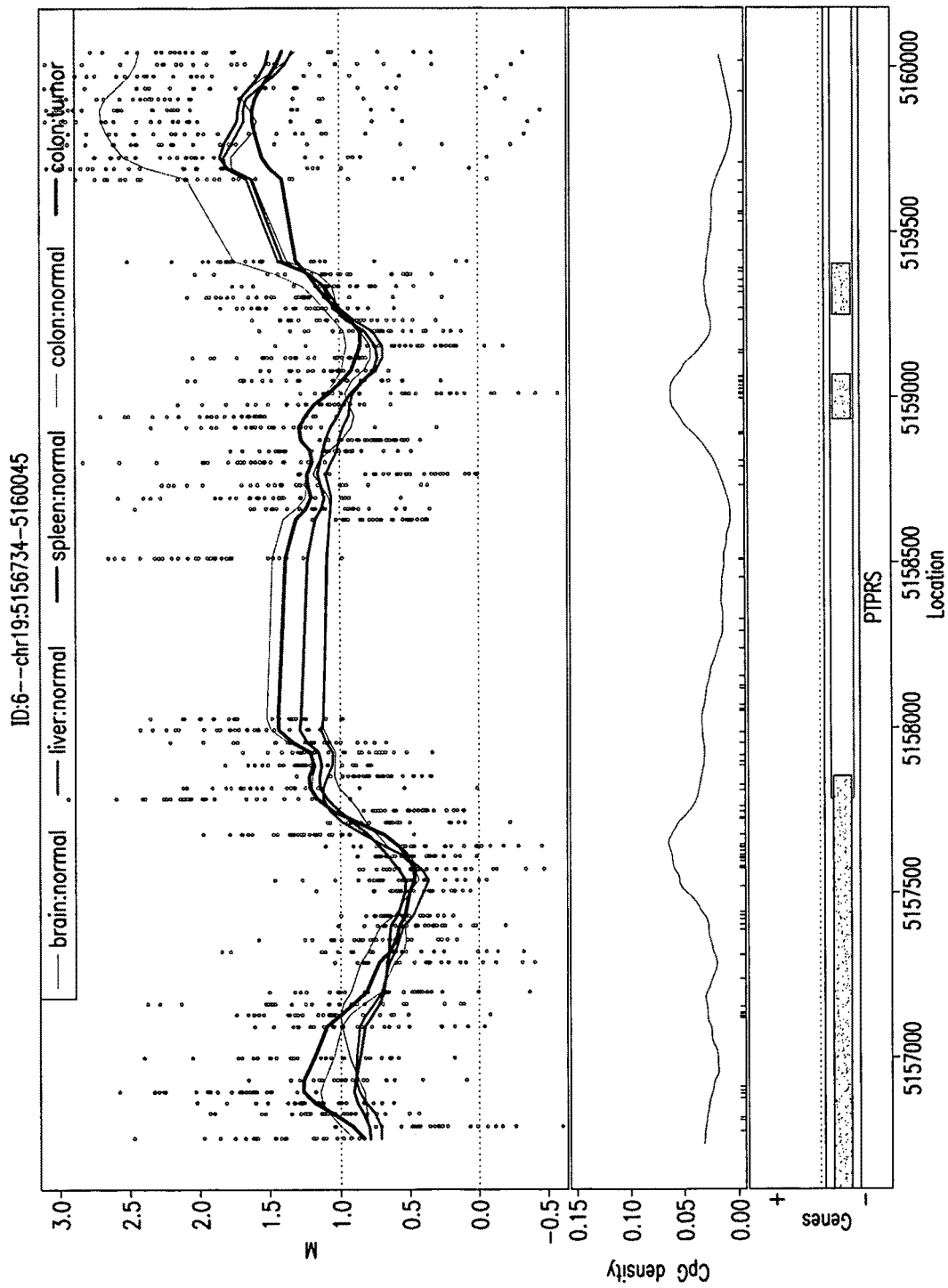
Figure 12G:
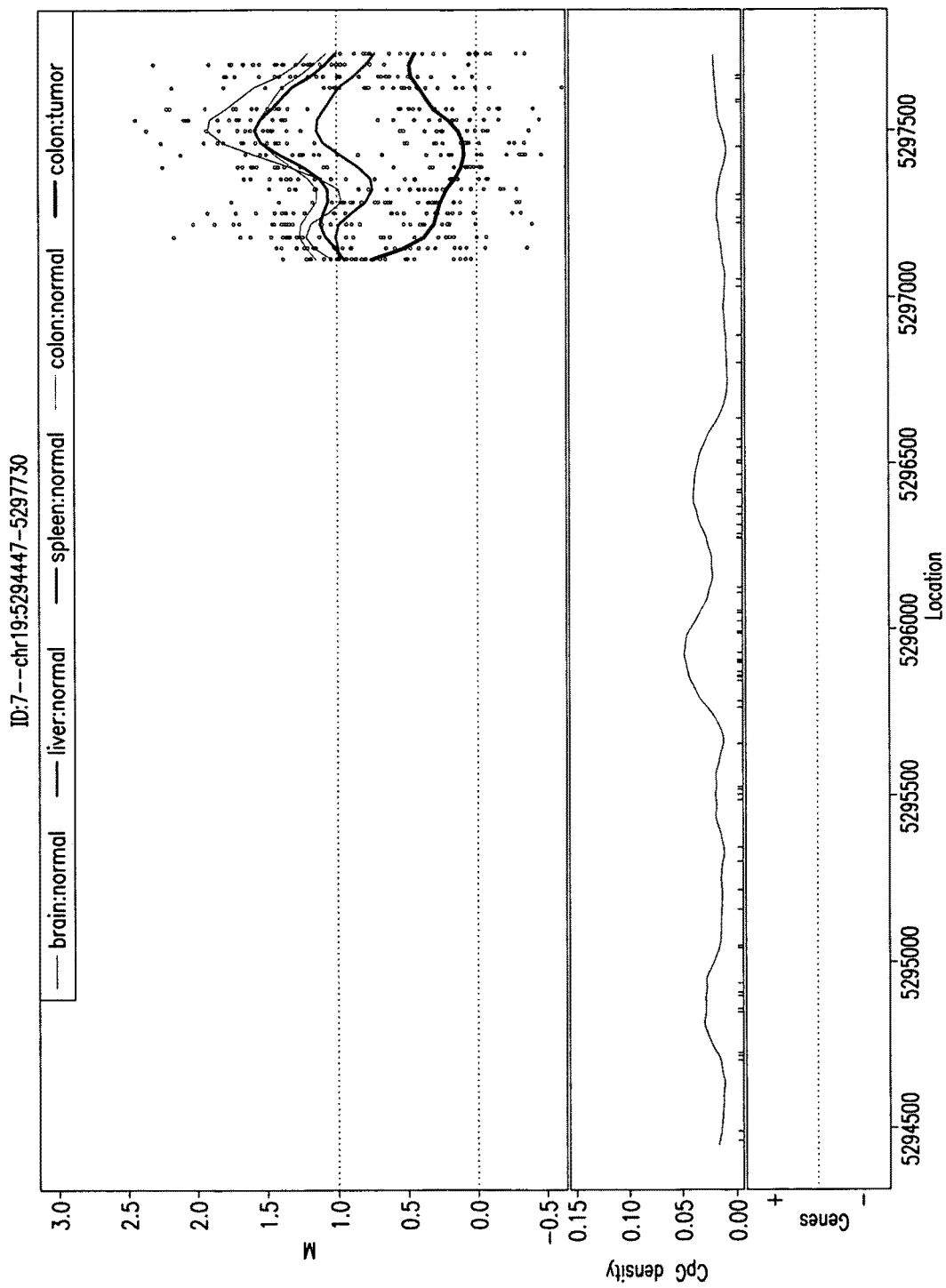
Figure 12H:
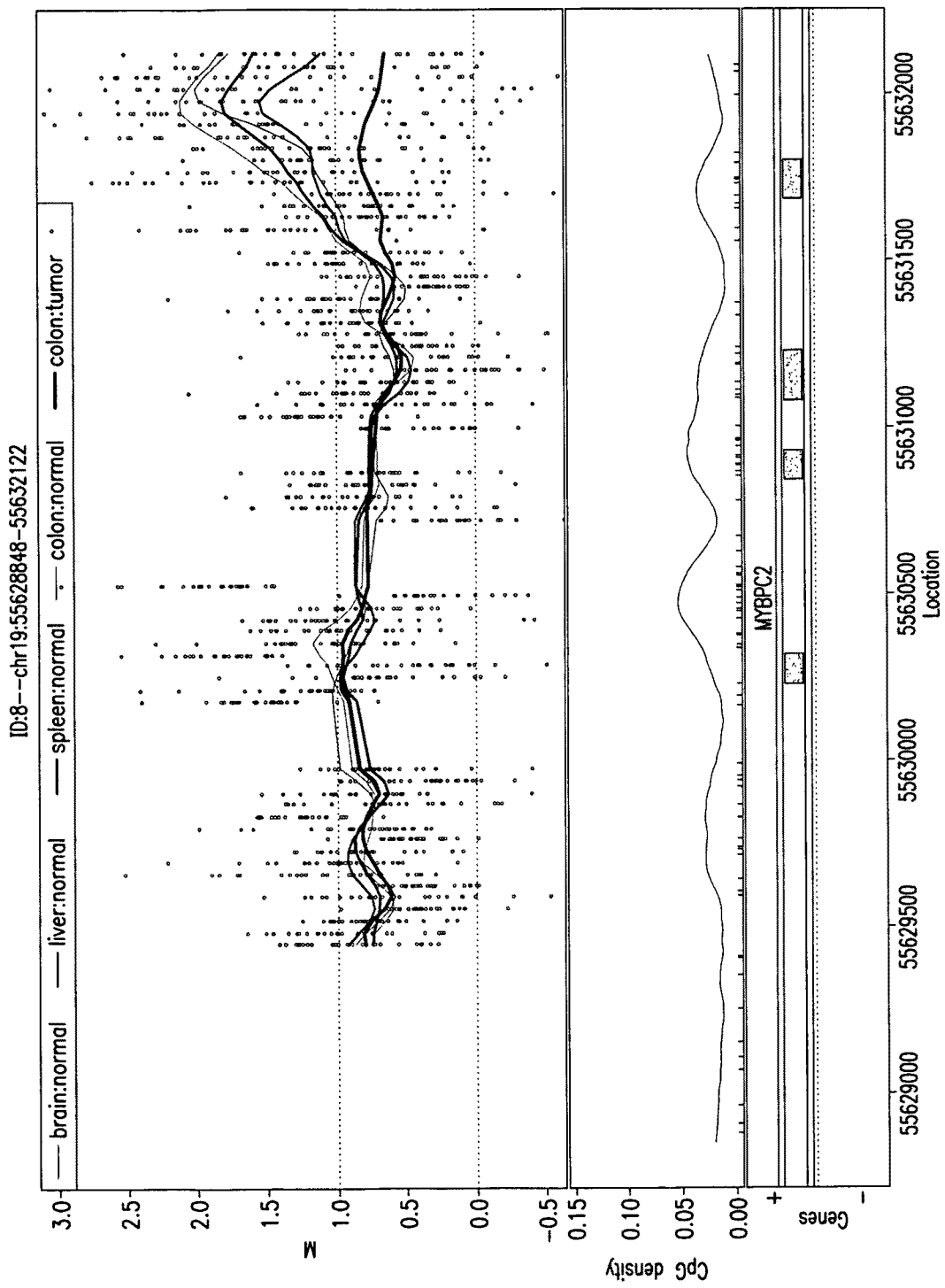
Figure 12I:
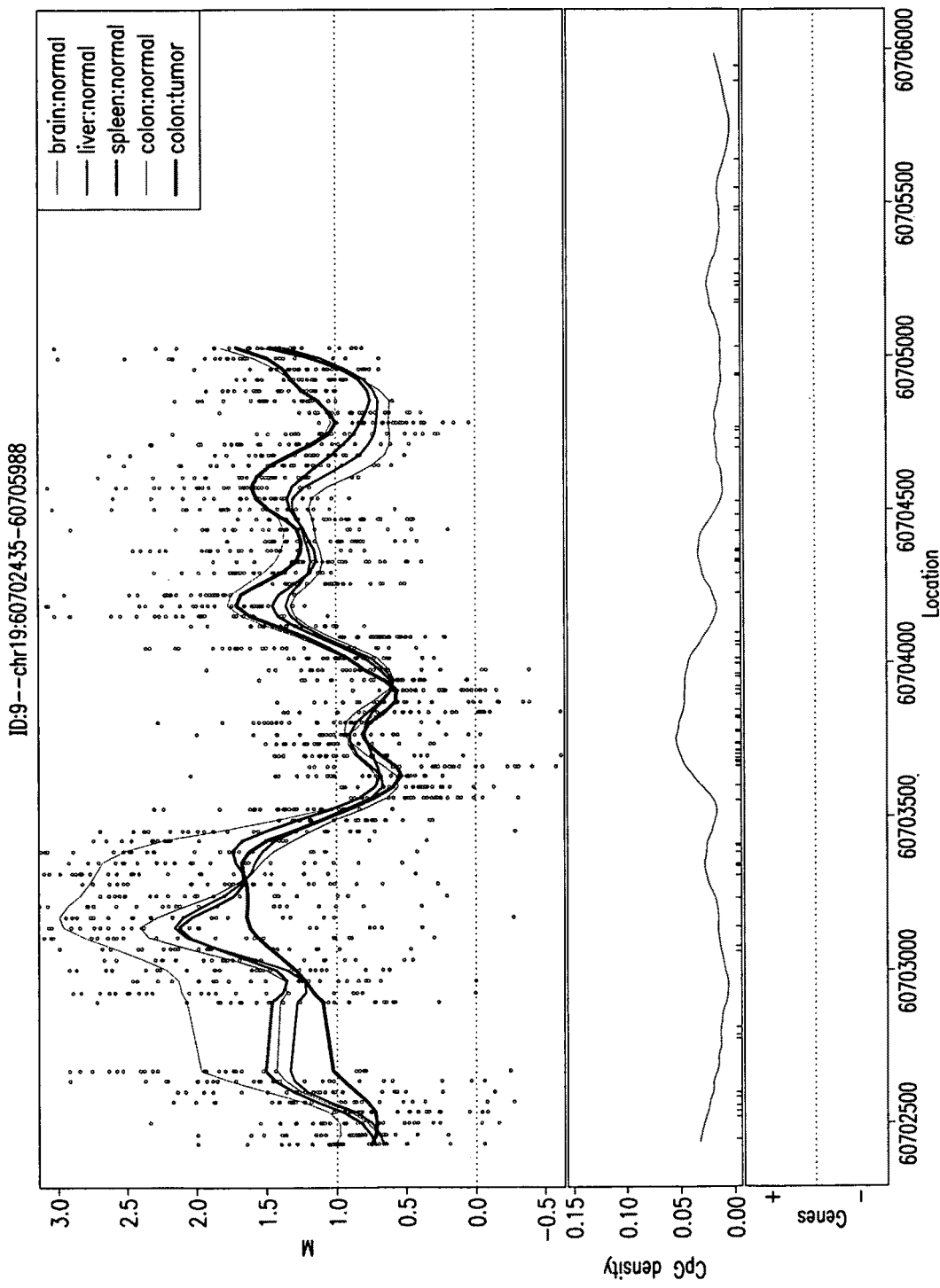
Figure 12J:
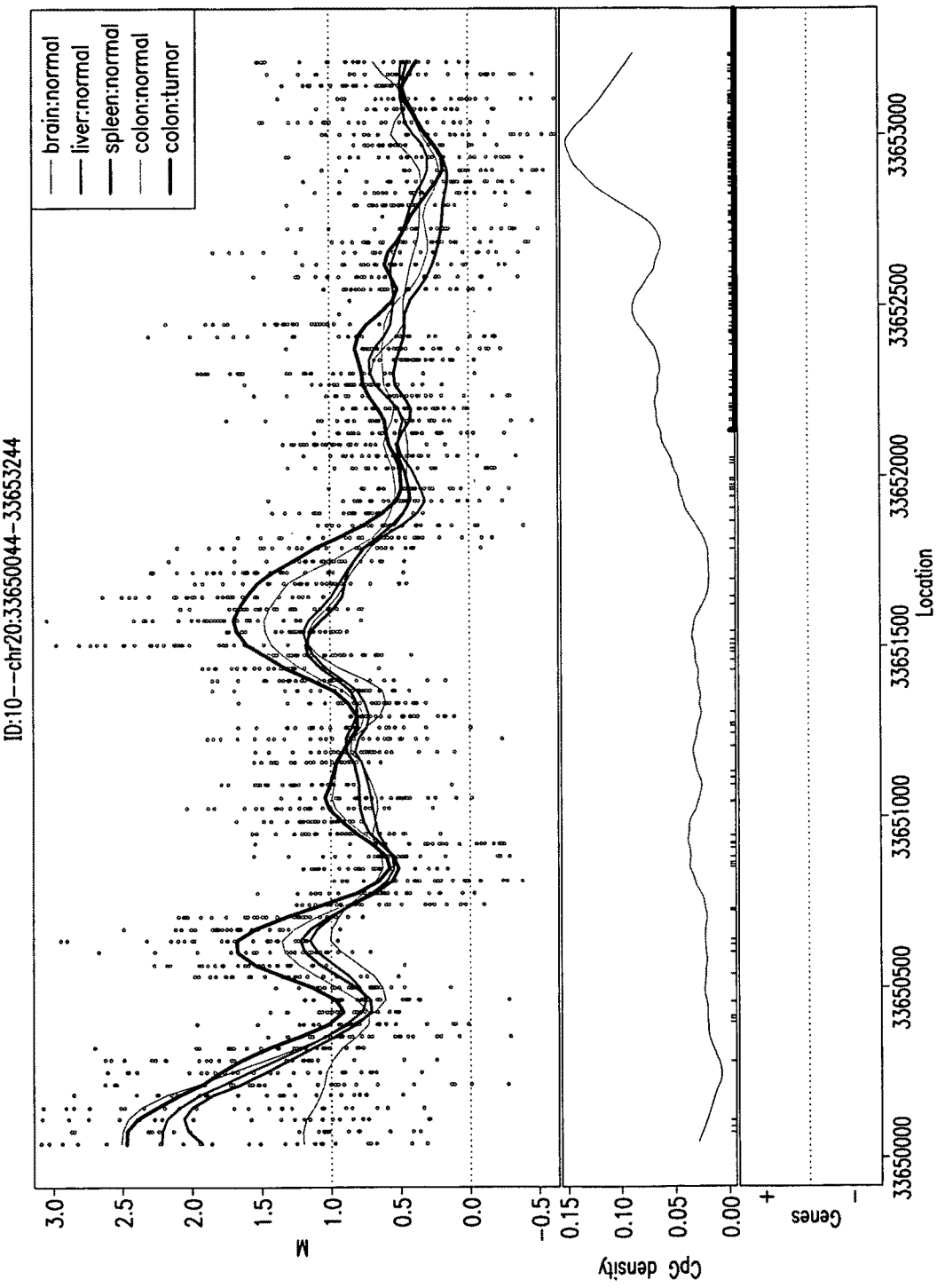
Figure 13A:
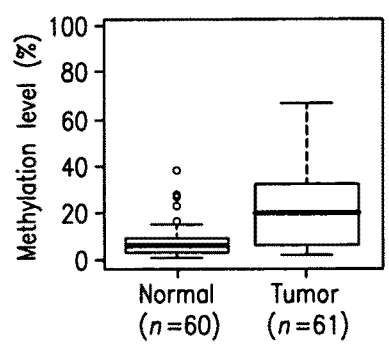
FIGS. 13A-E shows box plots of bisulfite pyrosequencing confirming the prevalence of 5 hypermethylated C-DMR shores in a large set of colon tumor and normal mucosa samples. Box-plots represent DNA methylation level measured using bisulfite pyrosequencing. A, distal-less homeobox 5 (DLX5); B, leucine rich repeat and fibronectin type III domain containing 5 (LRFN5); C, homeobox A3 (HOXA3)
Figure 13B:
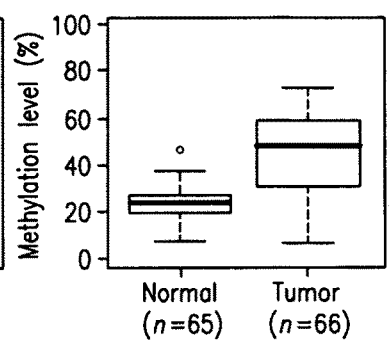
Figure 13C:
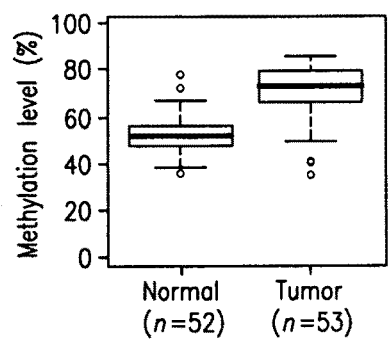
Figure 13D:
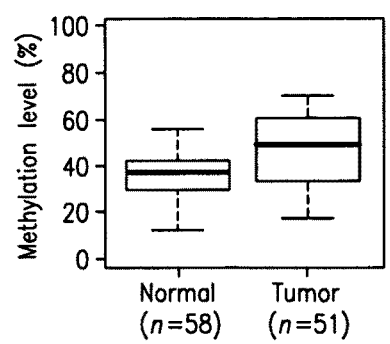
Figure 13E:
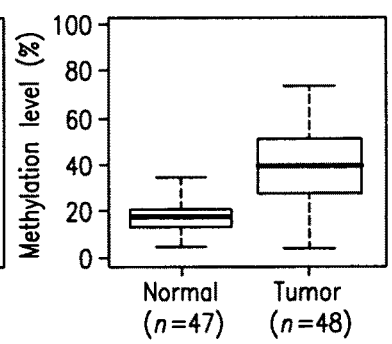
Figure 14A:
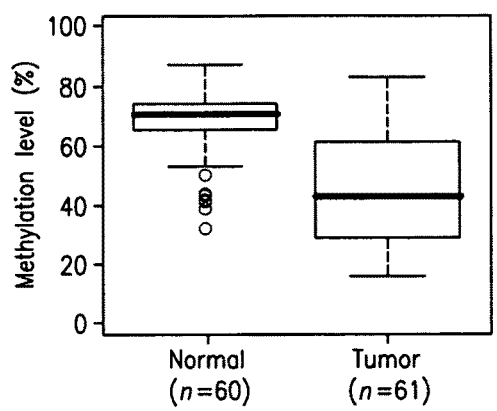
Figure 14B:
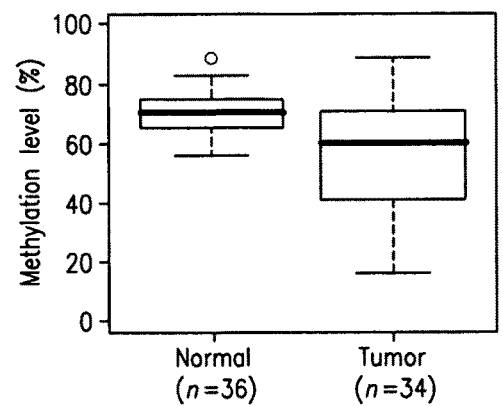
Figure 14C:
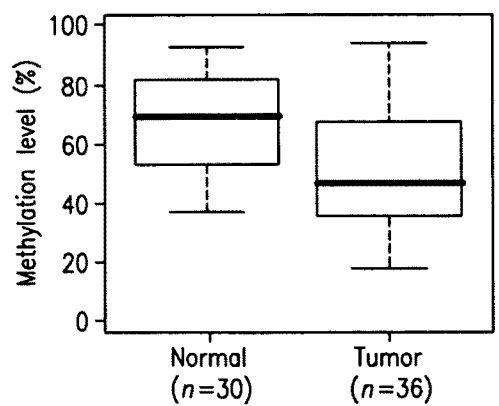
Figure 14D:
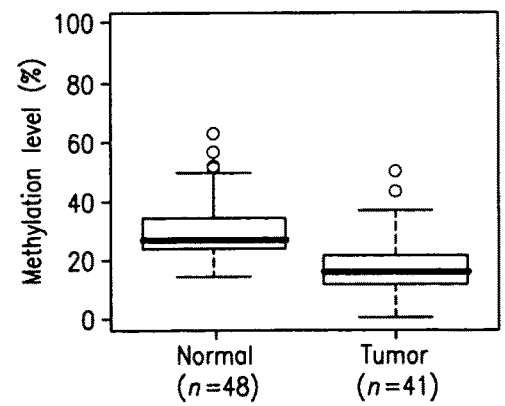

FIG. 11 illustrates that bisulfite pyrosequencing confirmed the prevalence of 4 hypomethylated C-DMR shores in a large set of colon tumor and normal mucosa samples. Box-plots represent DNA methylation level measured using bisulfite pyrosequencing. a, transmembrane protein 14A (TMEM14A); b, glutamate-rich 1 (ERICH1); c, family with sequence similarity 70, member B (FAM70C); d, prostate transmembrane protein, androgen induced 1 (TMEPA1), (n) equals the number of samples analyzed by pyrosequencing.

Mouse DNAm discriminates human tissues, even far from genes. A compelling argument for the functional importance of differential DNAm of CpG island shores would be their conservation across species. One might expect DMRs near transcriptional start sites to be conserved because the genes are conserved. However, when the relationship between gene-distant T-DMRs (2-10 kb away from an annotated gene) and sequence conservation using the phastCons28way table from the University of California Santa Cruz genome browser was examined, it was found that 48% of differentially methylated regions showed sequence conservation. Furthermore, 91% of DMRs were located within 1 kb of a highly conserved region (P<0.001).

To address whether the DNA methylation itself is conserved across species, a mouse CHARM array was created with ~2.1 million features independently of the human array. Tissue replicates were then isolated from each of three mice, corresponding to the tissues examined in the human T-DMR experiments, and then mapped these methylation data across species using the UCSC LiftOver tool. The interspecies correspondence of tissue-specific methylation was notable, and unsupervised clustering perfectly discriminated among the tissues, regardless of the species of origin (FIG. 6; P<10$^{-9}$). Perfect discrimination among the tissues was found even when the analysis was limited to gene-distant DMRs (FIGS. 12A-J; the complete set is available on the Nature Genetics website (nature.com/naturegenetics) see "Supplementary FIG. 4" in the Supplementary Information for Irizarry et al., Nature Genetics 41(2):178-186)). Thus, DNAm itself is highly conserved across 50 Myr of evolution (approximately 51% of mapped DNAm sites were conserved). It was also noticed relatively little heterogeneity in tissue-specific methylation in the mouse compared to the human (height of the cluster bars in FIG. 6), suggesting a genetic-epigenetic relationship, as the mice are inbred.

Figure 6:
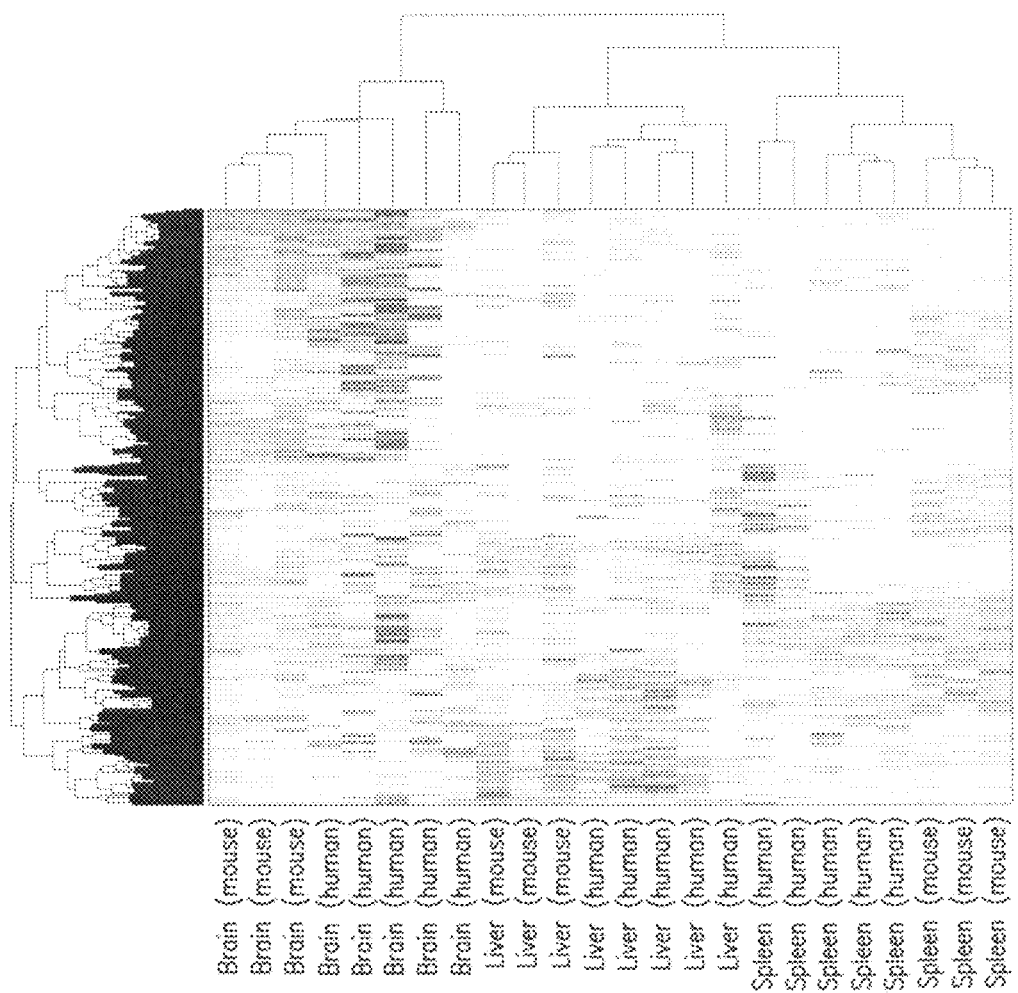
FIG. 6 shows a clustering of human tissue samples using mouse T-DMRs.

FIG. 6 shows clustering of human tissue samples using mouse T-DMRs resulted in perfect discrimination of tissues. The M values of all tissues from the 1,963 regions corresponding to mouse T-DMRs that mapped to the human genome were used for unsupervised hierarchical clustering. By definition, the mouse tissues were segregated. Notably, all of the human tissues were also completely discriminated by the regions that differ in mouse tissues. The three major branches in the dendrograms corresponded perfectly to tissue type regardless of species. Columns represent individual samples, and rows represent regions corresponding to mouse T-DMRs. The heat map shows M values, with some being more methylated and some being less methylated.

FIG. 12 illustrates that most cancer-specific differential DNA methylation was located at CpG island shores. The top 50 C-DMRs, ordered by statistical significance. Displays are as in FIG. 1b. The upper panels are plots of M value versus genomic location for brain, liver, spleen, normal colon, and colon cancer. Each point (shown only for normal colon and colon cancer) represented the methylation level of an individual sample for a given probe. The curve represents averaged smoothed M values, described in detail in the Methods. Due to the scale and standardization used, M values which range from –0.5 to 0.5 represent unmethylated sites as defined by the control probes, and values from 0.5 to 1.5 represent baseline levels of methylation. The middle panels provide the location of CpG dinucleotides with tick marks on the x-axis. CpG density was calculated across the region using a standard density estimator and is represented by the smoothed line. The location of the CpG island is denoted on the x-axis. The lower panels provide gene annotation for the genomic region. The thin outer line represents the transcript, the thin inner lines represent a coding region. Filled in boxes represent exons. On the y-axis, plus and minus marks denote sense and antisense gene transcription respectively.

Figure 7A:
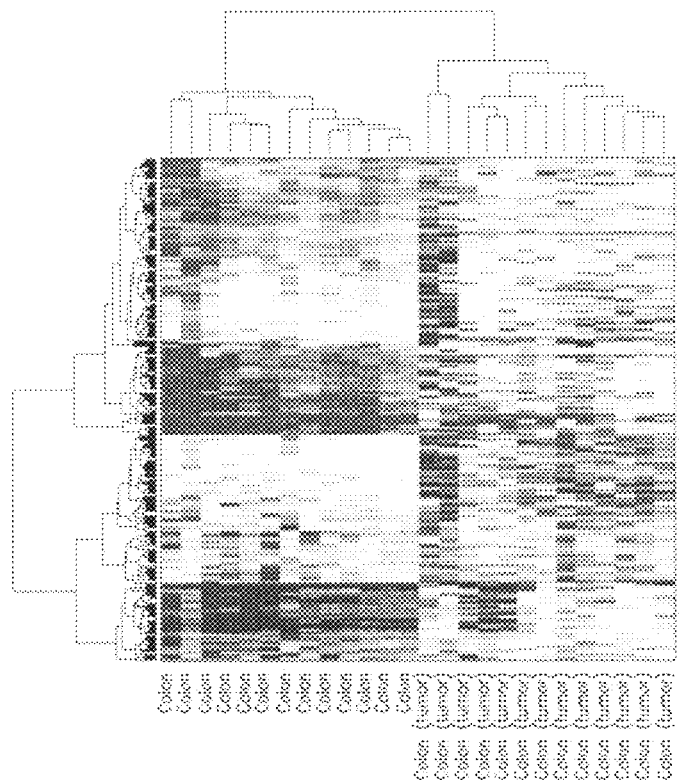
FIGS. 7A and B show a clustering of normal tissue samples using C-DMRs.
Figure 7B:
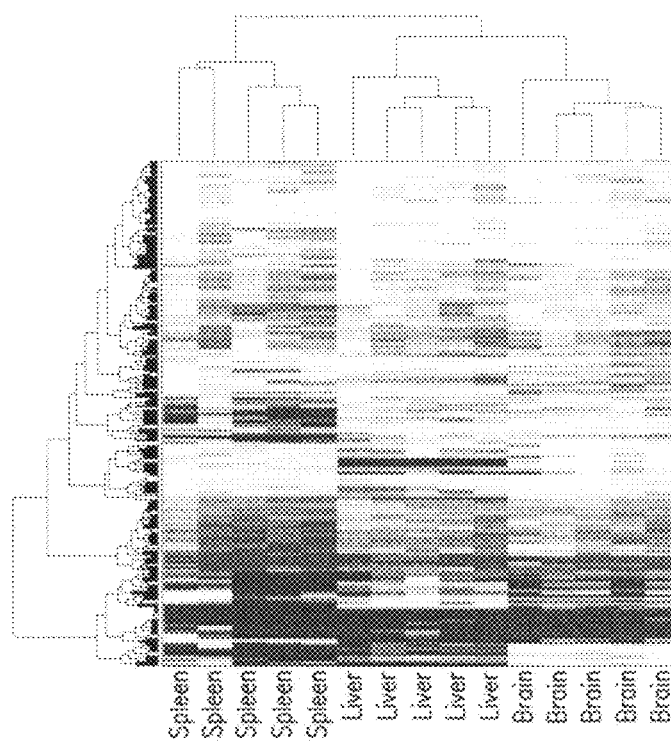

The location of C-DMRs overlaps that of T-DMRs. Because both C-DMRs and T-DMRs were located at CpG island shores, we then asked whether they occurred in similar locations. DMRs in which the methylation difference was from no methylation to some methylation, that is, those DMRs for which the gene expression data above showed a strong relationship between 'none-to-some' methylation and gene silencing were focused on. Notably, it was found that 52% of the C-DMRs overlapped a T-DMR, compared to only 22% expected by chance ($P<10^{-14}$), when using an FDR of 5% for defining T-DMRs. Although these data are significant, the definition of a T-DMR based on FDR of 5% is conservative. It was therefore also asked directly whether C-DMRs are enriched for tissue variation in DNAm by computing an averaged F-statistic (comparison of cross-tissue to within-tissue variation) at each C-DMR. The cross-tissue variation in normal tissues was significant at 64% of the C-DMRs, compared to 20% of randomly selected CpG regions on the array matched for size ($P<10^{-143}$). When DMRs were defined using an FDR of 5%, 1,229 of 2,707 C-DMRs overlapped a T-DMR, of which 265, 448 and 185 are brain-, liver- and spleen-specific, respectively, and 331 show variation among all of the tissues (Table 14; the complete data set is available on the Nature Genetics website (nature.com/naturegenetics) see "Supplementary Data 4" in the Supplementary Information for Irizarry et al., Nature Genetics 41(2):178-186). The colon C-DMRs were highly enriched for overlap with liver T-DMRs ($P<10^{-15}$), and liver was embryologically closest to colon of the autopsy tissues studied. For example, the C-DMR located in the CpG island shore upstream of the HS3ST4 (heparan sulfate D-glucosaminyl 3-O-sulfotransferase 4) gene is hypomethylated in colon cancer compared to normal colon and coincides with a T-DMR that distinguishes liver from other tissues (FIG. 1b). The correspondence between C-DMRs and T-DMRs was so marked that when unsupervised clustering of the normal brain, liver and spleen, using the M values from the C-DMRs was carried out, there was perfect discrimination of the tissues (FIG. 7).

Most tissue-specific methylation difference more commonly involves hypomethylation, although this varies by tissue type with 50% of liver, 62% of spleen, and 79% of brain DMRs representing hypomethylation, and cancer-specific methylation differences slightly more frequently involve hypermethylation (56%:44%). For both T-DMRs and C-DMRs, when there was differential methylation, it was common that at least one of the tissues was completely unmethylated (68% and 37%, respectively). Furthermore, hypomethylated C-DMRs were twice as likely to resemble another tissue type, such as liver, than were hypermethylated C-DMRs (82% versus 61%, $P<10^{-31}$), even though hypermethylated C-DMRs overlapped T-DMRs 1.5-fold more frequently than did hypomethylated C-DMRs (54% versus 35%, $P<10^{-21}$).

To further explore the relationship between differentiation and type of methylation change, Gene Ontology (GO) analysis was carried out for both hypomethylated and hypermethylated C-DMRs in the cancers (see Methods). The GO analysis showed enrichment for development and pluripotency-associated genes for both hyper- and hypomethylated C-DMRs ($P<0.01$) (Table 5). Hypomethylated C-DMRs were also enriched for genes associated with differentiated cellular functions for lineages other than the colon ($P<0.01$) (Table 5). Thus, cancer-specific DNA methylation predominantly involves the same sites that show normal DNAm variation among tissues, particularly at genes associated with development.

Next, the magnitude of differential methylation and variation in C-DMRs and T-DMRs were examined. The $\Delta M$ values for tissue and cancer DMRs differed markedly from nonmethylated controls or randomly selected regions (the latter have an average value comparable to controls but with significant tails, as by definition they may contain DMRs themselves) (FIGS. 8a-d). The $\Delta M$ values for normal tissues were comparable across the tissues, but the $\Delta M$ values between normal and cancer tissues were on average approximately half the $\Delta M$ between normal tissue pairs (FIG. 8e), which is logical given that the cancers are compared with their tissue of origin. Another difference between cancer and normal tissues was an increase in the inter-individual variation in M among the colon cancers, which was on average ~50% greater than the inter-individual variation among the normal colons (FIG. 8f), a result which may help to explain tumor cell heterogeneity. Given the strong inter-individual variability found in cancer, 205/2,707 C-DMRs were identified that were consistently differentially methylated between the colon tumor and matched normal mucosa from all 13 individuals examined (Table 18; the complete data set is available on the Nature Genetics website (nature.com/naturegenetics) see "Supplementary Data 4" in the Supplementary Information for Irizarry et al., Nature Genetics 41(2):178-186). These regions, heavily over-represented for development and morphogenesis genes, provide a smaller, more focused set of regions for biomarker discovery and carcinogenesis studies.

FIG. 7 shows clustering of normal tissue samples using C-DMRs resulted in perfect discrimination of tissues. The M values of all tissues from the 2,707 regions corresponding to C-DMRs were used for unsupervised hierarchical clustering. (a) By definition, the colon tumors and matched normal mucosa were segregated. The two major branches in the dendrograms corresponded perfectly to tissue type. (b) Notably, all of the normal brains, spleens and livers were also completely discriminated by the regions that differ in colon cancer. The three major branches in the dendrograms corresponded perfectly to tissue type. Columns represent individual samples, and rows represent regions corresponding to C-DMRs. The heat map shows M values, with some being more methylated and some being less methylated.

FIG. 8 shows the magnitude of differential methylation and variation in C-DMRs and T-DMRs. (a-d) Box plots of average ΔM values over all DMRs, compared to randomly chosen regions and unmethylated control regions, matched for length. (a) Liver versus brain. (b) Spleen versus brain. (c) Spleen versus liver. (d) Colon cancer versus normal colonic mucosa. (e) Differences in DNA methylation were greater in magnitude among normal tissues than were differences between colon tumors and matched normal mucosa. For all DMRs the average ΔM was computed. These values were then stratified into T-DMRs, hypermethylated C-DMRs and hypomethylated C-DMRs. T-DMRs were further stratified according to brain versus liver, brain versus spleen and liver versus spleen pairwise comparisons. The box plots represented absolute values of the ΔMs. (f) Inter-individual variation in M was larger among colon tumors than matched normal mucosa. For each C-DMR the average interindividual s.d. of the M values was computed. The box plots represent these values for normal colon mucosa and colon tumors.

FIG. 15 illustrates that gene expression was strongly correlated with C-DMRs at CpG island shores. For each colon tumor versus normal mucosa C-DMR the closest annotated gene on the Affymetrix HGU133A microarray was found, resulting in a total of 650 gene/C-DMR pairs. Plotted are log (base 2) ratios of colon tumor to normal expression against delta M values for colon tumor and normal DNAm. Dots represent C-DMRs located within 300 bp from the corresponding gene's transcriptional start site (TSS). Dots represent C-DMRs that are located from 300-2000 bp from the TSS of an annotated gene. Dots, in the middle, represent log ratios for all genes further than 2 kb from an annotated TSS.

FIG. 16 illustrates that differences in DNA methylation were greater in magnitude among normal tissues than were differences between colon tumors and matched normal mucosa. For all DMRs the average delta M was computed. These values were then stratified into T-DMRs, hypermethylated C-DMRs and hypomethylated C-DMRs. T-DMRs were further stratified according to brain versus liver, brain versus spleen, and liver versus spleen pair-wise comparisons. The box-plots represent absolute values of the delta Ms.

FIG. 17 shows that inter-individual variation in M was larger among colon tumors than matched normal mucosa. For each C-DMR the average inter-individual standard deviation of the M-values were computed. The box-plots represent these values for normal colon mucosa and colon tumors.

FIG. 18 demonstrates alternate gene transcription origin in colon tumors at a CpG island shore. A schematic overview of the PIP5K1A gene locus. C-DMR represents the genomic region that is hypomethylated in colon tumors as compared to normals. b, the arrow indicates a 220 bp fragment present in 3 colon tumors but not normal mucosa from the same individual amplified by the Sp3 primer and the 5' RACE anchor primer.

FIG. 19 shows an example of non-conventional CpG island, a C-DMR that was not adjacent to a conventionally defined CpG island. Upper panel: plot of M value versus genomic location for brain, liver, spleen, normal colon, colon tumor. Each point represented the methylation level of an individual sample for each probe across the region. The smoothed line represents averaged, smoothed M values for each tissue, described in detail in the methods. M values which range from −0.5 to 0.5 represent unmethylated points and values from 0.5 to 1.5 represent baseline levels of methylation due to the scale and standardization used. The middle panel provides the location of CpG dinucleotides with tick marks on the x-axis. CpG density was calculated across this region using a standard density estimator and is represented by the smoothed line. The location of non-conventional CpG islands, defined using Hidden Markov modeling, is denoted on the x-axis. The lower panel provides gene annotation for the genomic region. The thin outer line represents the start of transcription, the thin inner lines represent the start and end of a coding region. Filled in boxes represent exons. On the y-axis, plus and minus marks denote sense and antisense gene transcription respectively.

FIG. 20 illustrates the methylation of mouse T-DMRs completely discriminated tissues regardless of species of origin, even for T-DMRs >2 kb from an annotated gene. The M values of all tissues from the 957 regions corresponding to mouse T-DMRs that mapped to the human genome and were greater than 2 kb from an annotated gene were used for unsupervised hierarchical clustering. By definition, the mouse tissues were segregated. Surprisingly, all of the human tissues were also completely discriminated by the regions that differ in mouse tissues. The three major branches in the dendrograms correspond perfectly to tissue type regardless of species. Columns represent individual samples, and rows represent regions corresponding to mouse T-DMRs. The heatmap displays M values, with some being more methylated and some being less methylated.

Although the invention has been described with reference to the above examples, it will be understood that modifications and variations are encompassed within the spirit and scope of the invention. Accordingly, the invention is limited only by the following claims.

TABLE 1

Bisulfite pyrosequencing confirms differential DNA methylation at CpG island shores but not the associated island.

| Gene | Location[a] | Region | Tissue[b] | CG1 | CG2 | CG3 | CG4 | CG5 | CG6 | CG7 | CG8 | CG9 |
|------|-----------|--------|-----------|------|------|------|------|------|------|------|------|------|
| PCDH9 | +3,338 | Shore | Brain | 32 | 26 | 12 | 39 | 19 | 22 | | | |
| | | | Spleen | 91 | 71 | 31 | 76 | 66 | 60 | | | |
| | | | P value | <.001 | <.001 | <.001 | <.001 | <.001 | 0.003 | | | |
| | −267 | Island | Brain | 2 | 3 | 4 | 2 | 3 | 5 | 2 | 3 | 2 |
| | | | Spleen | 2 | 3 | 3 | 2 | 3 | 6 | 2 | 4 | 3 |
| | | | P value | 0.032 | 0.298 | 0.336 | 0.108 | 0.475 | 0.150 | 0.393 | 0.141 | 0.011 |
| HEY1 | +3,381 | Shore | Brain | 54 | 53 | 51 | 51 | | | | | |
| | | | Liver | 70 | 84 | 87 | 71 | | | | | |
| | | | P value | .023 | <.001 | <.001 | <.007 | | | | | |
| | +2,207 | Island | Brain | 4 | 7 | 3 | 4 | 4 | 5 | 1 | 8 | 5 |
| | | | Liver | 3 | 6 | 3 | 4 | 4 | 6 | 2 | 9 | 23 |
| | | | P value | 0.349 | 0.309 | 0.226 | 0.460 | 0.630 | 0.252 | 0.017 | 0.336 | 0.255 |

TABLE 1-continued

Bisulfite pyrosequencing confirms differential DNA methylation at CpG island shores but not the associated island.

| Gene | Location[a] | Region | Tissue[b] | | | | | | | | | |
|------|------|------|------|------|------|------|------|------|------|------|------|------|
| HAGH | +2,192 | Shore | Liver | 26 | 30 | 22 | 18 | 7 | 6 | 23 | 33 | |
| | | | Spleen | 93 | 93 | 82 | 56 | 20 | 20 | 86 | 95 | |
| | | | P value | <.001 | <.001 | <.001 | <.001 | <.001 | <.001 | 0.017 | 0.017 | |
| | +206 | Island | Liver | 2.1 | 1.1 | 2.1 | 3.4 | 2.3 | 6.7 | 2.7 | 2.2 | 3 |
| | | | Spleen | 2.2 | 1.6 | 2.9 | 3.7 | 2.2 | 2.2 | 2.1 | 2.1 | 3.6 |
| | | | P value | 0.608 | 0.207 | 0.433 | 0.803 | 0.058 | 0.342 | 0.262 | 0.529 | 0.504 |
| SLMO2 | +1,125 | Shore | Normal | 89 | 63 | 85 | 46 | 68 | 30 | 78 | 81 | 75 |
| | | | Tumor | 37 | 28 | 34 | 19 | 30 | 13 | 34 | 40 | 35 |
| | | | P value | <.001 | <.001 | <.001 | 0.005 | 0.002 | <.001 | <.001 | <.001 | 0.002 |
| | +40 | Island | Normal | 4 | 2 | 3 | 3 | 6 | 4 | 3 | 2 | 3 |
| | | | Tumor | 4 | 1 | 3 | 3 | 3 | 4 | 3 | 2 | 2 |
| | | | P value | 0.619 | 0.233 | 0.293 | 0.546 | 0.302 | 0.364 | 0.461 | 0.204 | 0.586 |

| Gene | Location[a] | Region | Tissue[b] | CG10 | CG11 | CG12 | CG13 | CG14 | CG15 | CG16 | CG17 | CG18 |
|------|------|------|------|------|------|------|------|------|------|------|------|------|
| PCDH9 | +3,338 | Shore | Brain | | | | | | | | | |
| | | | Spleen | | | | | | | | | |
| | | | P value | | | | | | | | | |
| | −267 | Island | Brain | 3 | 3 | 3 | 5 | 5 | 4 | 3 | 3 | 4 |
| | | | Spleen | 3 | 3 | 3 | 3 | 5 | 4 | 3 | 4 | 3 |
| | | | P value | 0.661 | 0.265 | 0.208 | 0.420 | 0.051 | 0.133 | 0.885 | 0.783 | 0.270 |
| HEY1 | +3,381 | Shore | Brain | | | | | | | | | |
| | | | Liver | | | | | | | | | |
| | | | P value | | | | | | | | | |
| | +2,207 | Island | Brain | 5 | 7 | 7 | 4 | | | | | |
| | | | Liver | 26 | 26 | 8 | 8 | | | | | |
| | | | P value | 0.179 | 0.238 | 0.432 | 0.001 | | | | | |
| HAGH | +2,192 | Shore | Liver | | | | | | | | | |
| | | | Spleen | | | | | | | | | |
| | | | P value | | | | | | | | | |
| | +206 | Island | Liver | 1.1 | 2.2 | 1.8 | 1.2 | 1.4 | 0.6 | 1.7 | 0.6 | 4.2 |
| | | | Spleen | 1.2 | 4.4 | 1.9 | 1.8 | 2.5 | 2.1 | 4.4 | 0.8 | 7.8 |
| | | | P value | 0.782 | 0.060 | 0.832 | 0.366 | 0.074 | 0.307 | 0.073 | 0.141 | 0.015 |
| SLMO2 | +1,125 | Shore | Normal | 82 | 40 | 85 | 81 | 43 | 65 | 76 | 76 | 87 |
| | | | Tumor | 36 | 18 | 38 | 36 | 19 | 30 | 39 | 37 | 46 |
| | | | P value | <.001 | 0.036 | <.001 | <.001 | <.001 | <.001 | <.001 | 0.003 | <.001 |
| | +40 | Island | Normal | 2 | 3 | 3 | 4 | 2 | 7 | 5 | | |
| | | | Tumor | 4 | 3 | 2 | 4 | 2 | 7 | 6 | | |
| | | | P value | 0.263 | 0.173 | 0.369 | 0.253 | 0.928 | 0.230 | 0.509 | | |

[a]Location represents distance in base pairs, + denoting upstream and − downstream, from the transcriptional start site to the closest CpG site measured by bisulfite pyrosequencing (CG1). CG1-18 denote individual CpG site measured by bisulfite pyrosequencing. Values are percent methylation. The coordinates for each CpG site measured by pyrosequencing are provided in Supplementary Table 7.
[b]Brain, spleen, and liver tissues are from the same individuals. Normal and tumor represent matched colon tumor and mucosa from the same individuals.

TABLE 2

Bisulfite pyrosequencing confirms differential DNA methylation at 4 additional CpG island shores

| Gene | Location[a] | Region | Tissue[b] | CG1 | CG2 | CG3 | CG4 | CG5 | CG6 |
|------|------|------|------|------|------|------|------|------|------|
| SEMA3C | −409 | Shore | Tumor | 31 | 32 | 32 | 34 | 31 | 26 |
| | | | Normal | 65 | 71 | 68 | 64 | 63 | 52 |
| | | | P value | <0.001 | <0.001 | <0.001 | <0.001 | <0.001 | <0.001 |
| DSCAML1 | +2,875 | Shore | Brain | 34 | 30 | 29 | 28 | 33 | 26 |
| | | | Liver | 86 | 79 | 87 | 89 | 76 | 71 |
| | | | P value | <0.001 | <0.001 | <0.001 | <0.001 | <0.001 | 0.004 |
| GPT2 | −2,984 | Shore | Spleen | 93 | 93 | 82 | 56 | 20 | 20 |
| | | | Liver | 26 | 30 | 22 | 18 | 7 | 5 |
| | | | Pvalue | <0.001 | <0.001 | <0.001 | <0.001 | <0.001 | <0.001 |
| ZNF532 | +1,127 | Shore | Liver | 97 | 96 | 92 | 93 | 79 | 96 |
| | | | Brain | 34 | 38 | 26 | 30 | 23 | 24 |
| | | | Pvalue | <0.001 | <0.001 | <0.001 | <0.001 | <0.001 | <0.001 |

| Gene | Location[a] | Region | Tissue[b] | CG7 | CG8 | CG9 | CG10 | CG11 | CG12 |
|------|------|------|------|------|------|------|------|------|------|
| SEMA3C | −409 | Shore | Tumor | 24 | 21 | 23 | 9 | 9 | 1 |
| | | | Normal | 58 | 41 | 43 | 21 | 17 | 2 |
| | | | P value | 0.007 | <0.001 | 0.001 | 0.003 | <0.001 | 0.048 |
| DSCAML1 | +2,875 | Shore | Brain | 33 | 26 | 38 | 23 | 26 | |
| | | | Liver | 88 | 82 | 98 | 70 | 77 | |
| | | | P value | <0.001 | <0.001 | <0.001 | <0.001 | <0.001 | |

TABLE 2-continued

Bisulfite pyrosequencing confirms differential DNA methylation at 4 additional CpG island shores

| GPT2 | −2,984 | Shore | Spleen | 86 | 95 |
|---|---|---|---|---|---|
| | | | Liver | 23 | 33 |
| | | | Pvalue | <0.001 | <0.001 |
| ZNF532 | +1,127 | Shore | Liver | 98 | 89 |
| | | | Brain | 22 | 21 |
| | | | Pvalue | <0.001 | <0.001 |

[a]Location is distance in base pairs, + denoting upstream and − downstream, from the transcriptional start site to closest CpG site measured by bisulfite pyrosequencing (CG1). CG1-12 denote individual CpG sites measured by bisulfite pyrosequencing. Values are percent methylation. The coordinates for each site are provided in Supplementary Table 7.
[b]Brain, spleen, and liver tissues are from the same individuals. Normal and tumor represent matched colon tumor and mucosa from the same individuals.

TABLE 3

Bisulfite pyrosequencing confirms differential DNA methylation at 9 C-DMRs in colon tumor and normal colon mucosa samples.

| C-DMR | Gene | CHARM methylation[a] | Normal mean[b] | Tumor mean[b] | CN[c] | CT[c] | Matched[d] | P |
|---|---|---|---|---|---|---|---|---|
| Chr7: 96491680-96494485 | DLX5 | T > N | 8 | 22 | 53 | 61 | 42 | $<10^{-6}$ |
| Chr14: 41147653-41148722 | LRFN5 | T > N | 23 | 44 | 61 | 65 | 55 | $<10^{-14}$ |
| Chr7: 27129188-27131713 | HOXA3 | T > N | 52 | 72 | 52 | 59 | 44 | $<10^{-16}$ |
| Chr13: 83352750-83353823 | SLITRK1 | T > N | 36 | 46 | 56 | 51 | 26 | 0.0009 |
| Chr3: 62335415-62336514 | FEZF2 | T > N | 16 | 40 | 42 | 48 | 39 | $<10^{-14}$ |
| Chr6: 52637426-52638797 | TMEM14A | N > T | 67 | 45 | 57 | 64 | 53 | $<10^{-11}$ |
| Chr8: 846979-849372 | ERICH1 | N > T | 71 | 56 | 30 | 34 | 23 | $<10^{-3}$ |
| Chr13: 113615559-113616275 | FAM70B | N > T | 67 | 50 | 38 | 36 | 29 | $<10^{-3}$ |
| Chr20: 55705356-55707713 | TMEPAI | N > T | 29 | 17 | 48 | 41 | 30 | $<10^{-6}$ |

CN = normal colon tissue;
CT = colon tumor
[a]Methylation level reported by CHARM from greatest to least.
[b]Mean methylation level reported by bisulfite pyrosequencing.
[c]Total number of colon samples included in the bisulfite pyrosequencing mean methylation level reported.
[d]Total number of colon tumor and normal samples from the same individual reported in the bisulfite pyrosequencing mean methylation level.

TABLE 4

Relationship between DNA methylation and gene expression for 2 T-DMRs and 6 C-DMRs

| Gene | Methylation[a] | Region | Type | Distance[b] | Distance[c] | Fold change[d] | P | Expression[e] |
|---|---|---|---|---|---|---|---|---|
| FZD3 | Brain < Liver | Upstream Shore | T-DMR | 844 bp | 7 bp | 28.2 | 0.002 | Brain > Liver |
| | Brain < Spleen | Shore | | 844 bp | 7 bp | 34.0 | <0.001 | Brain > Spleen |
| RBM38 | Brain > Spleen | Intragenic Shore | T-DMR | 1937 bp | 69 bp | 7.0 | 0.005 | Brain < Spleen |
| | Liver > Spleen | Shore | | 1937 bp | 69 bp | 4.0 | 0.136 | Liver < Spleen |
| NDN | Tumor > Normal | Promoter Shore | C-DMR | 47 bp | 0 bp | 4.2 | 0.025 | Normal > Tumor |
| TRAF1 | Tumor > Normal | Intragenic Shore | C-DMR | 724 bp | 0 bp | 2.8 | 0.025 | Normal > Tumor |
| ZNF804A | Tumor > Normal | Promoter Shore | C-DMR | 105 bp | 185 bp | 2.5 | 0.047 | Normal > Tumor |
| CHRM2 | Tumor > Normal | Promoter Shore | C-DMR | 433 bp | 0 bp | 2.0 | 0.346 | Normal > Tumor |
| NQO1 | Normal > Tumor | Promoter Shore | C-DMR | 146 bp | 216 bp | 2.8 | 0.004 | Tumor > Normal |
| SEMA3C | Normal > Tumor | Promoter Shore | C-DMR | 143 bp | 0 bp | 4.8 | 0.025 | Tumor > Normal |

[a]Methylation level reported by CHARM from greatest to least.
[b]Base pairs to canonical transcriptional start site from the DMR.
[c]Base pairs to an alternative transcriptional start site from the DMR.
[d]Fold change = $2^{-\Delta\Delta CT}$; $\Delta\Delta C_T$ is equal to ($C_{T\ tissue\ A\ target\ gene} - C_{T\ beta\ actin}$) − ($C_{T\ tissue\ B\ target\ gene} - C_{T\ beta\ actin}$).
[e]Tissue expression from greatest to least.
P was computed using a paired, two-tailed, t-test.

TABLE 5

Distribution of C-DMRs and T-DMRs.

| | | Total number | Percent |
|---|---|---|---|
| Cancer DMRs | | 2,707 | 100% |
| Colon DMRs | | | |
| | Tumor hypermethylated | 1,508 | 56% |
| | Tumor hypomethylated | 1,199 | 44% |
| Tissue DMRs | | 16,379 | 100% |
| Brain DMRs | | 8200 | |
| | Brain hypermethylated | 1717 | 21% |
| | Brain hypomethylated | 6483 | 79% |
| Liver DMRs | | 3511 | |
| | Liver hypermethylated | 1763 | 50% |
| | Liver hypomethylated | 1748 | 50% |
| Spleen DMRs | | 3186 | |
| | Spleen hypermethylated | 1208 | 38% |
| | Spleen hypomethylated | 1978 | 62% |
| Brain:Liver:Spleen DMRs | | 1482 | |

Brain:Liver:Spleen DMRs are regions that vary in methylation across all three tissues.

TABLE 6

Anchorage-independent growth of C-DMR associated genes assayed by soft agar analysis.

| Gene | Methylation status[a] | Expression[b] | Expression fold change[c] | Colonies HeLa | HeLa P[d] | Colonies HCT116 | HCT116 P[d] |
|---|---|---|---|---|---|---|---|
| NQO1 | Hypomethylated | T > N | 2.8 | 32 | 0.01 | 102 | 0.069 |
| ZNF804A | Hypermethylated | N > T | −2.5 | 19 | 0.27 | 79 | 0.005 |
| CHRM2 | Hypermethylated | N > T | −2.0 | 9 | <0.01 | 81 | 0.037 |
| Vector | N/A | N/A | N/A | 21 | N/A | 125 | N/A |

[a]Methylation level of colon tumor as compared to matched normal mucosa, reported by CHARM. Hypomethylated: some methylation in normal, none in tumor. Hypermethylated: some methylation in tumor, none in normal.
[b]Tissue expression from greatest to least.
[c]Fold change = $2^{-\Delta\Delta C_T}$; $\Delta\Delta C_T$ is equal to $(C_{T\ tissue\ A\ target\ gene} - C_{T\ beta\ actin}) - (C_{T\ tissue\ B\ target\ gene} - C_{T\ beta\ actin})$.
[d]Table shows the number of colonies, n = 4. P was computed using a paired, two-tailed, t-test.

TABLE 7

Location of CpG sites validated by bisulfite pyrosequencing

Chromosomal coordinates for CG1-CG9

| Gene | Region | Chr | CG1 | CG2 | CG3 | CG4 | CG5 |
|---|---|---|---|---|---|---|---|
| SLMO2 | Shore | 20 | 57049852 | 57049859 | 57049884 | 57049912 | 57049933 |
| SLMO2 | Island | 20 | 57051256 | 57051274 | 57051277 | 57051280 | 57051287 |
| PCDH9 | Shore | 13 | 66698906 | 66698964 | 66699018 | 66699044 | 66699123 |
| PCDH9 | Island | 13 | 66702731 | 66702734 | 66702745 | 66702747 | 66702753 |
| HEY1 | Shore | 8 | 80839112 | 80839160 | 80839206 | 80839272 | |
| HEY1 | Island | 8 | 80840367 | 80840374 | 80840376 | 80840382 | 80840385 |
| HAGH | Shore | 16 | 1814967 | 1814974 | 1814978 | 1815044 | 1815048 |
| HAGH | Island | 16 | 1816837 | 1816840 | 1816843 | 1816846 | 1816848 |
| SEMA3C | Shore | 7 | 80387012 | 80387355 | 80387019 | 80387340 | 80387067 |
| DSCAML1 | Shore | 11 | 117170021 | 117170072 | 117170149 | 117170209 | 117170224 |
| GPT2 | Shore | 16 | 45474293 | 45474335 | 45474389 | 45474480 | 45474502 |
| ZNF532 | Shore | 18 | 54683963 | 54683972 | 54683997 | 54684040 | 54684060 |

| Gene | Region | CG6 | CG7 | CG8 | CG9 |
|---|---|---|---|---|---|
| SLMO2 | Shore | 57049937 | 57049958 | 57049972 | 57050013 |
| SLMO2 | Island | 57051293 | 57051299 | 57051305 | 57051308 |
| PCDH9 | Shore | 66699126 | | | |
| PCDH9 | Island | 66702766 | 66702770 | 66702776 | 66702779 |
| HEY1 | Shore | | | | |
| HEY1 | Island | 80840389 | 80840391 | 80840399 | 80840409 |
| HAGH | Shore | 1815086 | 1815091 | 1815095 | |
| HAGH | Island | 1816851 | 1816868 | 1816873 | 1816875 |
| SEMA3C | Shore | 80387071 | 80387080 | 80387092 | 80387102 |
| DSCAML1 | Shore | 117170231 | 117170236 | 117170239 | 117170250 |
| GPT2 | Shore | 45474508 | 45474539 | 45474564 | |
| ZNF532 | Shore | 54684099 | 54684127 | 54684162 | |

Chromosomal coordinates for CG10-CG18

| Gene | Region | Chr | CG10 | CG11 | CG12 | CG13 | CG14 | CG15 | CG16 | CG17 | CG18 |
|---|---|---|---|---|---|---|---|---|---|---|---|
| SLMO2 | Shore | 20 | 57050041 | 57050045 | 57050047 | 57050057 | 57050099 | 57050109 | 57050116 | 57050141 | 57050171 |
| SLMO2 | Island | 20 | 57051310 | 57051317 | 57051305 | 57051327 | 57051329 | 57051337 | 57051347 | | |
| PCDH9 | Shore | 13 | | | | | | | | | |

TABLE 7-continued

Location of CpG sites validated by bisulfite pyrosequencing

| | | | | | | | | | | |
|---|---|---|---|---|---|---|---|---|---|---|
| PCDH9 | Island | 13 | 66702783 | 66702789 | 66702798 | 66702802 | 66702816 | 66702825 | 66702828 | 66702838 | 66702841 |
| HEY1 | Shore | 8 | | | | | | | | | |
| HEY1 | Island | 8 | 80840425 | 80840435 | 80840441 | 80840446 | | | | | |
| HAGH | Shore | 16 | | | | | | | | | |
| HAGH | Island | 16 | 1816895 | 1816904 | 1816909 | 1816913 | 1816927 | 1816929 | 1816933 | 1816935 | 1816953 |
| SEMA3C | Shore | 7 | 80387104 | 80387107 | 80387120 | | | | | | |
| DSCAML1 | Shore | 11 | 117170304 | 117170311 | | | | | | | |

TABLE 8

Primer sequences and annealing temperatures used for bisulfite pyrosequencing

| Gene | Region | Primer | Sequence (5'→3') | (SEQ ID NO'S) | Annealing temperature (° C.) | Nested annealing temperature (° C.) |
|---|---|---|---|---|---|---|
| SLMO2 | Island | Forward | ATAATGAGGTATAGAGGTTATA | 4 | 44 | |
| | | Reverse | AACATCTATATCAACAAACTAA | 5 | | |
| | | Nested forward | Bio-GAGGTTATATTTGTTTTTGTTT | 6 | | 45 |
| | | Nested reverse | Bio-AACTCTACCCAAAAATCAAA | 7 | | |
| | | Sequencing1 (F) | GGTTTTGTTTTAGTTTTG | 8 | | |
| | | Sequencing2 (R) | CAAAACTAAAACAAAACC | 9 | | |
| | Shore | Forward | GATATAGTAGGTTTTAGGATGTGT | 10 | 49 | |
| | | Reverse | TTACCACACTATTTTAATTAATATAACCT | 11 | | |
| | | Nested forward | AGGATGTGTTTTATTGAGTATA | 12 | | 43 |
| | | Nested reverse | Bio-AAAACCATTTATATTTTTAAAACT | 13 | | |
| | | Sequencing1 (F) | TGTTTTATTGAGTATAAATG | 14 | | |
| | | Sequencing2 (F) | GTGGTTTATATTTGTAATTT | 15 | | |
| | | Sequencing3 (F) | GAATTATTTGAGGTTAGGTG | 16 | | |
| | | Sequencing4 (F) | TGATTAATATGGTGAAATTT | 17 | | |
| | | Sequencing5 (F) | TTAAAAATATAAAAATTAGT | 18 | | |
| | | Sequencing6 (F) | GGAGGTTAAGGTAGGAGAAT | 19 | | |
| | | Sequencing7 (F) | GTTGTAGTGAGTTAAGAATA | 20 | | |
| HEY | Island | Forward | GAGGTGATTATAGGGAGTAT | 21 | 46 | |
| | | Reverse | AACCCTAAAATTTTCTTTTATTC | 22 | | |
| | | Nested forward | GTTTTGGGGTAGTAATAG | 23 | | 41 |
| | | Nested reverse | Bio-CTAAACATCATTAAAAAACTA | 24 | | |
| | | Sequencing (F) | GGTTTTTTAGGGAATGTGTT | 25 | | |
| | Shore | Forward | AAAGAGGTATTATTATTTATATATTTTGTGG | 26 | 49 | |
| | | Reverse | TATTAAACTTAAACCTAAAATTTCACATC | 27 | | |
| | | Nested forward | GGTAGTTTTAGGAAAATTAGG | 28 | | 45 |
| | | Nested reverse | Bio-AACTATTAATAACCCTAAATCC | 29 | | |
| | | Sequencing1 (F) | GTATTATTTAATTGATTATT | 30 | | |
| | | Sequencing2 (F) | ATATTTGTGAATTTGAGATT | 31 | | |

TABLE 8-continued

Primer sequences and annealing temperatures used for bisulfite pyrosequencing

| Gene | Region | Primer | Sequence (5'→3') | (SEQ ID NO'S) | Annealing temperature (° C.) | Nested annealing temperature (° C.) |
|---|---|---|---|---|---|---|
| | | Sequencing3 (F) | TTGGGGTTGGTAAATGTAGG | 32 | | |
| | | Sequencing4 (F) | AATGAGATTTAATTTATTAG | 33 | | |
| HAGH | Island | Forward | TAGGTTTGGTTTTGTTTATTTAG | 34 | 46 | |
| | | Reverse | CAATAACCTAAATACTACCATAATT | 35 | | |
| | | Nested forward | Bio-GTTGTTTAGGATTGTAAAATAT | 36 | | 44 |
| | | Nested reverse | Bio-AAAAAACCAACTACCTC | 37 | | |
| | | Sequencing1 (F) | TTGTTTTTAGTTAATTAG | 38 | | |
| | | Sequencing2 (F) | GTATAGTGGATTTTGGAGGT | 39 | | |
| | | Sequencing3 (R) | CTAATTAACTAAAAACAA | 40 | | |
| | | Sequencing4 (R) | ACCTCCAAAAATCCACTATAC | 41 | | |
| | Shore | Forward | AAGGAGTATAATAAGTAGAGTGTG | 42 | 49 | |
| | | Reverse | AAAACACCTCCCTAAATTATCAA | 43 | | |
| | | Nested forward | GTAGAAGGGTTGTGATAGGAT | 44 | | 48 |
| | | Nested reverse | Bio-CCTCCCTAAATTATCAACTTC | 45 | | |
| | | Sequencing1 (F) | GAAGGGTTGTGATAGGATTT | 46 | | |
| | | Sequencing2 (F) | ATAAATAAAAATATTGTTTA | 47 | | |
| | | Sequencing3 (F) | ATTTTAGTATTTTGGGAGGT | 48 | | |
| | | Sequencing4 (F) | AAATATAAAAATTAGTTGGG | 49 | | |
| | | Sequencing5 (F) | GGAGGTTGAGGTAGGAGATT | 50 | | |
| | | Sequencing6 (F) | AGGTAGAGGTTGTAGTGAGT | 51 | | |
| PCDH9 | Island | Forward | GTTGATTGTTTTTAGTTTTTTT | 52 | 45 | |
| | | Reverse | CGCAACCCAAAAATAACTATA | 53 | | |
| | | Nested forward | Bio-AAATTTGATTTTGGTTTTAGGAGA | 54 | | 49 |
| | | Nested reverse | Bio-ACTCCCCCATCTATACATTTTAA | 55 | | |
| | | Sequencing1 (F) | GTATTGAGTATGTTTTGTAGGGTT | 56 | | |
| | | Sequencing2 (R) | CTTCACTTAACAAAAAAATAT | 57 | | |
| | Shore | Forward | GAAAATGATTATGAGTAAATTTGGG | 58 | 49 | |
| | | Reverse | CTTAAAAATAAAAATAACAACCCACC | 59 | | |
| | | Nested forward | GAGTAAATTTGGGGTTATTGT | 60 | | 48 |
| | | Nested reverse | Bio-CCAATTTTCAACCAACCTATA | 61 | | |
| | | Sequencing1 (F) | AGAATAGTAATAATTATAGT | 62 | | |
| | | Sequencing2 (F) | TAGTTATTGTAAAAATGAAT | 63 | | |
| | | Sequencing3 (F) | TTGTTAAAATTTTTGTTTTT | 64 | | |
| | | Sequencing4 (F) | TAGTTGTTAAGTATAATTTA | 65 | | |
| SEMA3C | Shore | Forward | TGTATTTTTAGTAGAGATAGGGTTAG | 66 | 49 | |
| | | Reverse | TCTATTAACATAACTCAAAACAACC | 67 | | |

TABLE 8-continued

Primer sequences and annealing temperatures used for bisulfite pyrosequencing

| Gene | Region | Primer | Sequence (5'→3') | (SEQ ID NO'S) | Annealing temperature (° C.) | Nested annealing temperature (° C.) |
|---|---|---|---|---|---|---|
| | | Nested forward | TTAGTAGAGATAGGGTTAGG | 68 | | 46 |
| | | Nested reverse | Bio-CAAAACAACCTCTCCACATAA | 69 | | |
| | | Sequencing1 (F) | GATTTTTTGATTTAATGGTT | 70 | | |
| | | Sequencing2 (F) | TTAAAATAGGTTAAGATAAA | 71 | | |
| | | Sequencing3 (F) | TAATTTTGTTGATTTTTTTA | 72 | | |
| | | Sequencing4 (F) | TATTTTTAAATATAATTATA | 73 | | |
| DSCAML1 | Shore | Forward | TAGATATTGAATAGAATGTTGGAGA | 74 | 49 | |
| | | Reverse | ATTATTTCCATTCCTCTCAAAATAC | 75 | | |
| | | Nested forward | AGAATGTTGGAGATTTTTTTAATG | 76 | | 45 |
| | | Nested reverse | Bio-CCTTTTTTTTATAATACCTAAACT | 77 | | |
| | | Sequencing1 (F) | AGATTTTTTTAATGTTTTGA | 78 | | |
| | | Sequencing2 (F) | GAAGAATTATGAGTTTTTAT | 79 | | |
| | | Sequencing3 (F) | GAAAATAGGAATTTTAGTGT | 80 | | |
| | | Sequencing4 (F) | AGGTAATATAGATGTTGGTA | 81 | | |
| | | Sequencing5 (F) | TAAGGTAGTTATTGGAGATT | 82 | | |
| GPT2 | Shore | Forward | ATTGGGGAAGATTTTTATTTAGAG | 83 | 49 | |
| | | Reverse | CTAAATCCCAAATTCTCCATATAC | 84 | | |
| | | Nested forward | AGATTGAATATTTGGTTATTAAG | 85 | | 44 |
| | | Nested reverse | Bio-CTCTAAAATCCTTCCCCTTAA | 86 | | |
| | | Sequencing1 (F) | ATTTAGTGTAGATAAAGGTG | 87 | | |
| | | Sequencing2 (F) | GAGTTTAAATAATTTTTTAG | 88 | | |
| | | Sequencing3 (F) | GGAATATTTAAAGATATTTT | 89 | | |
| | | Sequencing4 (F) | TAGGTGTTATTTTGATTTTA | 90 | | |
| | | Sequencing5 (F) | AAATTTAGTTAAGTAGTGTA | 91 | | |
| ZNF532 | Shore | Forward | TTTAGAGTGGAGAAGAAATGTT | 92 | 49 | |
| | | Reverse | ATATTCCACATTAAACATATACCAC | 93 | | |
| | | Nested forward | GTTTAATGGGATTAGAGTGATTT | 94 | | 46 |
| | | Nested reverse | Bio-ATAAAAAACCTTTCAAATTAACAC | 95 | | |
| | | Sequencing1 (F) | GTGATYFTATGATGGTATTG | 96 | | |
| | | Sequencing2 (F) | GAGTTAGGTTTGGAAGGAAG | 97 | | |
| | | Sequencing3 (F) | ATGTGTTGTTTTGTATAAGA | 98 | | |
| | | Sequencing4 (F) | AAGGAAGGGTTTTATTAAAT | 99 | | |
| DLX5C | Shore | Forward | TATTTAGGGTATTTGGTTTTTTTT | 100 | 48 | |
| | | Reverse | AACCTAACTCCCTACCCACTTATCT | 101 | | |
| | | Nested forward | Bio-GGATTGTATTAGAAAAATATAGT | 102 | | 43 |
| | | Nested reverse | ACCCATATTTCCCTCCTAT | 103 | | |
| | | Sequencing (R) | CTACAACTCTATTTACCC | 104 | | |

TABLE 8-continued

Primer sequences and annealing temperatures used for bisulfite pyrosequencing

| Gene | Region | Primer | Sequence (5'→3') | (SEQ ID NO'S) | Annealing temperature (° C.) | Nested annealing temperature (° C.) |
|---|---|---|---|---|---|---|
| ERICH1 | Shore | Forward | TATTTTATTGTGGGAGTTTTTGGAG | 105 | 51 | |
| | | Reverse | AATAATCACATTTCTCACTTTTACCACTA | 106 | | |
| | | Nested forward | TGGGAGTTTTTGGAGTATAGT | 107 | | 42 |
| | | Nested reverse | TATATTTACCTATATTCCTATCT | 108 | | |
| | | Sequencing (R) | AATAAAATACATTTATTATCATT | 109 | | |
| FAM70B | Island | Forward | TTTTGTGTTTTGTTGTGGTGTG | 110 | 52 | |
| | | Reverse | CTAACTCCAAACTCCAAAACCATTA | 111 | | |
| | | Nested forward | GGAAATGAGATTATTGAGAG | 112 | | 46 |
| | | Nested reverse | Bio-CTCTCCTTCTATTACAACTAA | 113 | | |
| | | Sequencing (F) | TAGTTATTGGTAATTTTTAG | 114 | | |
| SLITRK1 | Shore | Forward | TTGATTTTGATTTGTTAGTTGTTTG | 115 | 48 | |
| | | Reverse | TATTCCAATATATACCCATCACCC | 116 | | |
| | | Nested forward | Bio-GGGGTTTAGGAGTAAAGGTT | 117 | | 45 |
| | | Nested reverse | CTACCCTATAAAAAAATCTTAAA | 118 | | |
| | | Sequencing (R) | ATTCCCAAAAATACCCTAAT | 119 | | |
| LRFN5 | Shore | Forward | TTGTTGTGGAGGAGTTTGTTAG | 120 | 48 | |
| | | Reverse | TCCAACCTACTCCTTATAAATC | 121 | | |
| | | Nested forward | TGGTTTGTATGAAAGGGAATAT | 122 | | 49 |
| | | Nested reverse | Bio-CCTACTCCTTATAAATCAAAACACC | 123 | | |
| | | Sequencing (F) | TTTAGTTGTATTGTTTT | 124 | | |
| FEZF2 | Shore | Forward | GTGTGGTTAGAGGTATAAGTAGA | 125 | 50 | |
| | | Reverse | TCAACCCTCTCAAAACTTATTCCTA | 126 | | |
| | | Nested forward | GTAGAGGGAAGAAAAGATTTTTTTT | 127 | | 49 |
| | | Nested reverse | Bio-CCCAATCCTCCCCCTTTC | 128 | | |
| | | Sequencing (F) | TTGTAGATTATTTTATTTG | 129 | | |
| TMEM14A | Island | Forward | TGGGTGGGTGTAGATATTTTGTTAT | 130 | 54 | |
| | | Reverse | ACAATCCTACACACACAAACCTTTA | 131 | | |
| | | Nested forward | Bio-TAGTGAAAGTTTTGGGAAATTTA | 132 | | 48 |
| | | Nested reverse | CTACACACACAAACCTTTAATAA | 133 | | |
| | | Sequencing (R) | ATTCATTTTAAAAAATAATCC | 134 | | |
| TMEPAI | Shore | Forward | TATTAATTAAATTGTTTTTAGGAAGGTAAT | 135 | 49 | |
| | | Reverse | AAATTTACATAAAACCACAACAAAC | 136 | | |
| | | Nested forward | GTTTTTAGGAAGGTAATTAGAA | 137 | | 45 |
| | | Nested reverse | Bio-TACAAAAACTTACCAAATCTATAT | 138 | | |
| | | Sequencing (F) | AAATTTTAAGAAGTTAGTA | 139 | | |

TABLE 8-continued

Primer sequences and annealing temperatures used for bisulfite pyrosequencing

| Gene | Region Primer | Sequence (5'→3') | (SEQ ID NO'S) | Annealing temperature (° C.) | Nested annealing temperature (° C.) |
|---|---|---|---|---|---|
| HOXA3 | Island Forward | GATTAATGAGTTATAGAGAGATGTTG | 140 | 48 | |
| | Reverse | AAGGAGTTAAAAGTTTTTGGAG | 141 | | |
| | Nested forward | GTTTAGGTTTTTTATTTTATAATG | 142 | | 43 |
| | Nested reverse | TAAGATTTGGTGAGGGTTTGT | 143 | | |
| | Sequencing (F) | GGGTGATTTATGAA | 144 | | |

Bio = 5' biotin added; F = forward; R = reverse

TABLE 9

Real time quantitative RT-PCR assays

| Gene | Assay ID (Applied Biosystems) |
|---|---|
| FZD3 | Hs00184043_m1 |
| RBM38 | Hs00766686_m1 |
| NDN | Hs00267349_s1 |
| TRAF1 | Hs00194638_m1 |
| ZNF804A | Hs00290118_s1 |
| CHRM2 | Hs00265208_s1 |
| NQO1 | Hs00168547_m1 |
| SEMA3C | Hs00170762_m1 |

TABLE 10

Regions with tissue-specific differential methylation (T-DMRs) at a FDR of 5%.

| chr | start | end | fdr | tissue Varying | brainM | liverM | spleenM |
|---|---|---|---|---|---|---|---|
| chr1 | 143786173 | 143787603 | 0 | brain | −0.11535 | 1.487259 | 1.302311 |
| chr1 | 8009359 | 8011113 | 0 | liver | 1.299418 | −0.0514 | 1.426635 |
| chr10 | 101831054 | 101831872 | 0 | liver | 1.292584 | −0.05296 | 1.304799 |
| chr12 | 131467604 | 131472462 | 0 | brain | 0.26132 | 1.456655 | 1.679197 |
| chr12 | 6531994 | 6532981 | 0 | All | −0.20912 | 1.254775 | 0.874488 |
| chr14 | 23089148 | 23090035 | 0 | All | −0.63109 | 1.535749 | 1.192863 |
| chr14 | 50629706 | 50630173 | 0 | All | −0.08017 | 1.408726 | 1.106452 |
| chr14 | 59165574 | 59166710 | 0 | brain | −0.14155 | 1.252699 | 1.205902 |
| chr15 | 75709049 | 75710128 | 0 | brain | −0.15474 | 1.309527 | 1.226063 |
| chr15 | 91163167 | 91164726 | 0 | All | −0.47387 | 1.249181 | 0.967742 |
| chr16 | 45472725 | 45475365 | 0 | liver | 1.345268 | −0.04038 | 1.356521 |
| chr16 | 45477675 | 45478565 | 0 | All | −0.55643 | 0.63018 | 1.629881 |
| chr18 | 54682827 | 54684488 | 0 | brain | −0.46482 | 1.381573 | 1.207633 |
| chr2 | 54538538 | 54540625 | 0 | All | −0.28043 | 1.191245 | 0.59945 |
| chr20 | 60184636 | 60188417 | 0 | liver | 1.335582 | −0.15525 | 1.454903 |
| chr4 | 99796292 | 99798038 | 0 | All | −0.53255 | 1.000455 | 0.477587 |
| chr5 | 98138988 | 98139704 | 0 | brain | 0.361833 | 1.754281 | 1.493639 |
| chr8 | 17314239 | 17314991 | 0 | brain | −0.11832 | 1.481885 | 1.356334 |
| chr8 | 75425908 | 75426276 | 0 | All | −0.3947 | 1.254908 | 0.888546 |
| chrX | 144713386 | 144714243 | 0 | brain | −0.03791 | 1.36192 | 1.560882 |
| chrX | 53131580 | 53132161 | 0 | brain | 0.355145 | 1.795164 | 1.815183 |
| chr17 | 73467744 | 73468595 | 1.72E-14 | All | 0.021405 | 1.358955 | 1.058227 |
| chr15 | 35173578 | 35175443 | 1.73E-14 | All | −0.25443 | 1.220796 | 0.644358 |
| chr7 | 129916095 | 129916949 | 2.55E-14 | All | 0.046312 | 1.436957 | 0.996807 |
| chr1 | 158637654 | 158638754 | 2.71E-14 | brain | −0.28314 | 1.130432 | 0.847571 |
| chr11 | 64877881 | 64878384 | 5.10E-14 | All | 0.041802 | 1.412251 | 1.04274 |
| chr6 | 97479869 | 97480719 | 8.58E-14 | brain | −0.17882 | 1.149061 | 1.019161 |
| chr20 | 6462584 | 6463175 | 1.57E-13 | brain | −0.07902 | 1.303117 | 1.070685 |
| chr17 | 71959149 | 71959442 | 1.79E-13 | All | −0.07652 | 1.36918 | 0.89536 |
| chr17 | 35473766 | 35475501 | 2.38E-13 | All | −0.51389 | 0.699964 | 0.36019 |
| chr7 | 130438711 | 130440952 | 2.63E-13 | All | −0.13901 | 1.122755 | 0.781425 |
| chr18 | 51240890 | 51242290 | 3.03E-13 | All | −0.29669 | 1.01559 | 0.812538 |
| chr14 | 52687631 | 52688222 | 3.07E-13 | All | −0.40997 | 0.899323 | 0.121039 |
| chr19 | 53707072 | 53707611 | 7.25E-13 | brain | −0.58951 | 0.757836 | 0.547046 |
| chr1 | 242283486 | 242284310 | 8.08E-13 | brain | 0.197052 | 1.546314 | 1.564309 |
| chr22 | 44837327 | 44840079 | 9.71E-13 | brain | −0.02283 | 1.364865 | 1.280148 |
| chr22 | 26520905 | 26522055 | 9.74E-13 | brain | −0.08032 | 1.409407 | 1.409504 |
| chr12 | 111302662 | 111303654 | 1.10E-12 | brain | 0.036707 | 1.361237 | 1.307891 |

TABLE 10-continued

Regions with tissue-specific differential methylation (T-DMRs) at a FDR of 5%.

| | | | | | | | |
|---|---|---|---|---|---|---|---|
| chr16 | 17468105 | 17468795 | 1.32E-12 | All | −0.01385 | 1.030508 | 1.451115 |
| chr6 | 53768814 | 53769599 | 1.33E-12 | brain | 0.134246 | 1.283679 | 1.070607 |
| chr12 | 121944796 | 121946259 | 1.42E-12 | All | −0.55677 | 0.652273 | −0.04003 |
| chr4 | 76775030 | 76775602 | 1.75E-12 | brain | 0.121772 | 1.391647 | 1.250962 |
| chr10 | 11089463 | 11090071 | 2.05E-12 | brain | 0.0384 | 1.278444 | 1.277885 |
| chr19 | 12974645 | 12975430 | 2.81E-12 | brain | 0.058949 | 1.312149 | 1.366242 |
| chr9 | 137121252 | 137121872 | 3.27E-12 | brain | 0.257197 | 1.567195 | 1.364371 |
| chr3 | 187560575 | 187561467 | 3.59E-12 | All | −0.06283 | 1.222911 | 0.556389 |
| chr13 | 43257042 | 43257653 | 4.49E-12 | brain | 0.003724 | 1.270532 | 1.252464 |
| chr14 | 23083610 | 23084323 | 4.84E-12 | brain | 0.332277 | 1.600948 | 1.536168 |
| chr20 | 4616137 | 4616745 | 5.79E-12 | All | −0.33653 | 0.970823 | 0.639435 |
| chr18 | 72330871 | 72331443 | 6.11E-12 | All | 0.090288 | 1.251749 | 0.784134 |
| chr7 | 75386078 | 75389998 | 6.67E-12 | liver | 1.552091 | 0.424268 | 1.543758 |
| chr16 | 30361878 | 30364176 | 7.04E-12 | liver | 1.264842 | −0.02377 | 1.218326 |
| chr1 | 234916923 | 234918037 | 7.40E-12 | brain | 0.188523 | 1.354653 | 1.349526 |
| chr1 | 227542393 | 227543223 | 8.16E-12 | brain | 0.301546 | 1.554823 | 1.484626 |
| chr9 | 111443165 | 111443953 | 9.23E-12 | All | −0.30158 | 0.969521 | 0.313406 |
| chr21 | 42514640 | 42515749 | 9.51E-12 | All | 0.229328 | 1.50122 | 1.077787 |
| chr21 | 25934681 | 25935782 | 9.57E-12 | brain | −0.47751 | 0.721757 | 0.472824 |
| chr19 | 58297027 | 58297933 | 1.01E-11 | All | −0.41847 | 0.779032 | 0.344519 |
| chrX | 48937108 | 48937860 | 1.08E-11 | brain | 0.388972 | 1.581553 | 1.611601 |
| chr1 | 33418284 | 33418931 | 1.11E-11 | All | 0.173928 | 1.468768 | 0.907082 |
| chr4 | 21557703 | 21559151 | 1.75E-11 | brain | 0.093552 | 1.124707 | 1.26124 |
| chr17 | 55509863 | 55510786 | 2.04E-11 | All | −0.59336 | 0.510877 | −0.04011 |
| chr21 | 45713907 | 45716550 | 2.04E-11 | liver | 0.993849 | −0.02669 | 1.158456 |
| chr2 | 100303365 | 100304155 | 2.09E-11 | brain | 0.079216 | 1.422576 | 1.363524 |
| chr2 | 9684653 | 9686112 | 2.40E-11 | brain | 0.168387 | 1.319339 | 1.180425 |
| chr13 | 66697473 | 66700370 | 2.92E-11 | brain | −0.11815 | 1.067169 | 1.241919 |
| chr8 | 120290407 | 120291436 | 3.22E-11 | All | 0.464379 | −0.30417 | 1.031852 |
| chr17 | 63963603 | 63964386 | 3.36E-11 | brain | −0.35063 | 0.832736 | 0.572111 |
| chr5 | 16236252 | 16237106 | 3.62E-11 | All | 1.603336 | 0.431418 | 1.063083 |
| chr15 | 27346324 | 27347653 | 3.86E-11 | brain | 0.177365 | 1.38589 | 1.150294 |
| chr8 | 9795653 | 9796645 | 3.97E-11 | brain | 0.23902 | 1.519226 | 1.537175 |
| chr15 | 21361048 | 21361947 | 4.66E-11 | brain | 0.131271 | 1.324638 | 1.362028 |
| chr13 | 43906353 | 43906790 | 4.81E-11 | brain | 0.212522 | 1.230147 | 1.332329 |
| chr20 | 21536810 | 21537175 | 5.08E-11 | brain | −0.00897 | 1.355417 | 1.309454 |
| chr6 | 87918996 | 87919649 | 5.11E-11 | All | −0.0929 | 1.110646 | 0.491515 |
| chr3 | 161040187 | 161040531 | 5.29E-11 | All | −0.12641 | 1.043576 | 0.432139 |
| chr16 | 85164000 | 85164607 | 5.63E-11 | spleen | 0.046453 | 0.061563 | 1.155534 |
| chr17 | 44038889 | 44039760 | 6.03E-11 | All | 0.112679 | 0.619602 | 1.416283 |
| chr12 | 113601482 | 113602777 | 6.22E-11 | All | −0.20773 | 0.730495 | 1.016832 |
| chr22 | 19463535 | 19464248 | 6.27E-11 | All | 1.134095 | 0.037807 | 1.449567 |
| chr9 | 99783345 | 99784242 | 6.35E-11 | brain | 0.238381 | 1.423687 | 1.133009 |
| chr10 | 104669419 | 104671001 | 6.57E-11 | brain | −0.0864 | 0.974036 | 1.172766 |
| chr6 | 52335546 | 52337567 | 6.57E-11 | brain | −0.14951 | 0.974944 | 0.765697 |
| chr8 | 80837473 | 80839800 | 6.74E-11 | brain | −0.13852 | 1.134604 | 0.980399 |
| chr1 | 200125551 | 200126951 | 8.29E-11 | All | 0.200372 | 1.343235 | 1.036733 |
| chr11 | 117169663 | 117170865 | 8.61E-11 | brain | 0.036012 | 1.319412 | 1.355828 |
| chr10 | 88272523 | 88272784 | 8.63E-11 | All | −0.05095 | 1.334199 | 0.977942 |
| chr3 | 160966443 | 160967336 | 9.13E-11 | brain | 0.193104 | 1.277767 | 1.047332 |
| chr10 | 69992084 | 69993085 | 9.34E-11 | All | −0.03598 | 1.004592 | 0.494343 |
| chr10 | 72314866 | 72316425 | 9.55E-11 | liver | 1.431814 | 0.293288 | 1.410689 |
| chr5 | 17272645 | 17273667 | 9.66E-11 | All | 0.335036 | 1.530197 | 1.121364 |
| chr19 | 57202145 | 57203221 | 1.10E-10 | brain | −0.19286 | 1.016431 | 0.97668 |
| chr7 | 139121047 | 139122912 | 1.11E-10 | All | −0.04716 | 0.405804 | 1.070219 |
| chr11 | 65816795 | 65817554 | 1.27E-10 | brain | 0.047017 | 1.183867 | 1.21434 |
| chr12 | 38783038 | 38784659 | 1.35E-10 | All | 0.13847 | 0.907052 | 1.253477 |
| chr18 | 70271478 | 70272306 | 1.48E-10 | brain | 0.477285 | 1.616985 | 1.601359 |
| chr12 | 8958831 | 8959862 | 1.58E-10 | All | −0.41555 | 0.731955 | 0.380007 |
| chr7 | 35542549 | 35543379 | 1.58E-10 | liver | 1.46152 | 0.187143 | 1.513851 |
| chr22 | 44856437 | 44856847 | 1.75E-10 | All | −0.21002 | 0.964414 | 0.570562 |
| chr9 | 113434267 | 113436690 | 1.75E-10 | liver | 1.110322 | −0.06272 | 1.188455 |
| chr3 | 182923902 | 182926235 | 1.78E-10 | All | −0.28218 | 0.719899 | 0.392404 |
| chr5 | 87600958 | 87602603 | 1.78E-10 | brain | 0.13372 | 1.234886 | 1.288835 |
| chr22 | 44840824 | 44842585 | 2.07E-10 | All | −0.32082 | 0.854645 | 0.468445 |
| chr15 | 35174959 | 35175429 | 2.09E-10 | All | −0.02782 | 1.121221 | 0.668461 |
| chr6 | 32226447 | 32227133 | 2.35E-10 | brain | −0.12679 | 1.21501 | 1.108105 |
| chr6 | 24468445 | 24468955 | 2.49E-10 | All | 0.204555 | 1.450305 | 1.08434 |
| chr11 | 67912958 | 67914011 | 2.65E-10 | liver | 1.672152 | 0.496634 | 1.725968 |
| chr15 | 49699745 | 49700848 | 2.69E-10 | All | 0.005382 | 1.100265 | 0.692709 |
| chr10 | 79064134 | 79065116 | 2.73E-10 | brain | −0.03703 | 1.057269 | 0.936404 |
| chr12 | 102757515 | 102758501 | 2.87E-10 | All | 0.464408 | −0.07212 | 1.247512 |
| chr1 | 244954765 | 244956165 | 3.36E-10 | All | 0.94556 | 0.057658 | 1.256526 |
| chr9 | 93748388 | 93749207 | 3.38E-10 | brain | 1.558837 | 0.457913 | 0.734517 |
| chr17 | 69717977 | 69719999 | 3.48E-10 | brain | 0.34338 | 1.370673 | 1.257086 |
| chr5 | 75735889 | 75737508 | 3.59E-10 | brain | 1.018357 | −0.06504 | 0.153059 |
| chr14 | 72427335 | 72428501 | 3.61E-10 | All | 0.110581 | 1.172443 | 0.708188 |
| chr4 | 108858341 | 108860158 | 3.69E-10 | All | 0.019132 | 1.121514 | 0.642438 |

TABLE 10-continued

Regions with tissue-specific differential methylation (T-DMRs) at a FDR of 5%.

| | | | | | | | |
|---|---|---|---|---|---|---|---|
| chr19 | 12956890 | 12957636 | 3.90E−10 | brain | 0.317379 | 1.422033 | 1.317791 |
| chr3 | 135095342 | 135095599 | 4.07E−10 | All | 0.345701 | 1.547571 | 1.201468 |
| chr12 | 119419408 | 119420682 | 4.32E−10 | All | −0.45368 | 0.64277 | 0.357627 |
| chr3 | 194442270 | 194443491 | 4.59E−10 | brain | 0.454163 | 1.59038 | 1.582465 |
| chr18 | 54678682 | 54681415 | 4.71E−10 | brain | −0.11259 | 0.889818 | 0.731549 |
| chr10 | 105441168 | 105442058 | 4.95E−10 | All | −0.07938 | 1.057892 | 0.58793 |
| chr4 | 41341411 | 41342111 | 5.00E−10 | brain | 0.015783 | 1.215938 | 1.249218 |
| chr8 | 80840243 | 80842031 | 5.22E−10 | All | −0.39056 | 0.633251 | 0.035054 |
| chr20 | 33336159 | 33337040 | 5.25E−10 | All | 0.496151 | −0.19458 | 1.042875 |
| chr1 | 120056929 | 120057765 | 5.64E−10 | All | 0.268229 | −0.0413 | 1.13111 |
| chr9 | 102276338 | 102277457 | 5.97E−10 | brain | 0.236111 | 1.305146 | 1.117734 |
| chr19 | 2651477 | 2652367 | 6.88E−10 | brain | −0.00437 | 1.22873 | 1.134348 |
| chr11 | 64858559 | 64859826 | 7.01E−10 | All | −0.13863 | 0.855243 | 0.225677 |
| chr12 | 48766660 | 48767337 | 7.56E−10 | All | 0.48622 | 1.564671 | 1.166946 |
| chr14 | 22839242 | 22839642 | 8.19E−10 | brain | −0.07093 | 1.088938 | 0.895761 |
| chr12 | 54406765 | 54407517 | 8.73E−10 | All | 0.079217 | 1.142971 | 0.765836 |
| chr6 | 71720614 | 71721830 | 8.87E−10 | All | 0.190403 | 1.277573 | 0.94305 |
| chr2 | 113632025 | 113632600 | 9.06E−10 | liver | 1.312823 | 0.278355 | 1.091582 |
| chr1 | 152568347 | 152569153 | 1.02E−09 | brain | 0.382712 | 1.416759 | 1.180129 |
| chr19 | 12986646 | 12989167 | 1.02E−09 | brain | 0.027941 | 1.171056 | 0.952401 |
| chr18 | 53172450 | 53172776 | 1.05E−09 | All | −0.18109 | 0.986896 | 0.438065 |
| chr22 | 42139152 | 42140849 | 1.07E−09 | brain | 0.489183 | 1.544282 | 1.580222 |
| chr8 | 94999343 | 95000446 | 1.08E−09 | All | −0.09493 | 0.967359 | 0.532637 |
| chr1 | 158321798 | 158322793 | 1.11E−09 | brain | 0.259199 | 1.387606 | 1.405033 |
| chr10 | 45328714 | 45329270 | 1.14E−09 | brain | 0.487386 | 1.627923 | 1.640054 |
| chr4 | 113519509 | 113520087 | 1.17E−09 | brain | 0.351665 | 1.428635 | 1.42591 |
| chr8 | 28406277 | 28406880 | 1.25E−09 | All | 0.102019 | 0.893019 | 1.44425 |
| chr6 | 31697055 | 31698136 | 1.31E−09 | All | −0.51951 | 0.524483 | 0.169974 |
| chr11 | 1668090 | 1669572 | 1.48E−09 | liver | 1.099981 | 0.049418 | 1.262819 |
| chr9 | 20609087 | 20610219 | 1.53E−09 | All | −0.38654 | 0.733972 | 0.290223 |
| chr4 | 17390836 | 17391751 | 1.57E−09 | All | −0.01514 | 0.610289 | 1.056951 |
| chr7 | 27144976 | 27145521 | 1.67E−09 | All | 0.104066 | 0.4646 | 1.284721 |
| chr13 | 100100517 | 100101056 | 1.69E−09 | brain | 0.126005 | 1.270831 | 1.278393 |
| chr17 | 67631765 | 67632456 | 1.70E−09 | brain | −0.08216 | 0.965589 | 1.168482 |
| chr8 | 139577318 | 139577719 | 1.74E−09 | All | 0.381754 | 1.528271 | 1.20125 |
| chr6 | 39302949 | 39304155 | 1.76E−09 | All | 1.220726 | 0.182266 | 0.696068 |
| chr1 | 159549832 | 159551072 | 1.97E−09 | All | 0.162422 | 0.860818 | 1.165009 |
| chr11 | 129374246 | 129376513 | 2.02E−09 | liver | 1.442827 | 0.09828 | 1.273512 |
| chr6 | 26332969 | 26333508 | 2.10E−09 | All | 0.091736 | 1.175461 | 0.869038 |
| chr10 | 31359338 | 31360454 | 2.14E−09 | All | −0.11936 | 0.893576 | 0.980227 |
| chr7 | 36157999 | 36159166 | 2.24E−09 | liver | 1.386701 | 0.239862 | 1.31825 |
| chr12 | 116111015 | 116111629 | 2.28E−09 | All | −0.39965 | 0.299806 | 0.840599 |
| chr12 | 24945492 | 24947103 | 2.30E−09 | brain | 0.018833 | 1.077256 | 0.926808 |
| chr19 | 39954301 | 39955362 | 2.35E−09 | All | 0.084007 | 1.085292 | 0.991353 |
| chr10 | 124212667 | 124215516 | 2.40E−09 | brain | 0.203019 | 1.299387 | 1.287902 |
| chr22 | 36999241 | 36999534 | 2.42E−09 | All | −0.30703 | 0.886854 | 0.445371 |
| chr5 | 72829082 | 72829798 | 2.47E−09 | All | −0.12689 | 0.443145 | 0.969204 |
| chr2 | 42647983 | 42648909 | 2.54E−09 | All | 0.059632 | 1.131059 | 0.652138 |
| chr5 | 108090358 | 108091228 | 2.54E−09 | All | 0.017378 | 1.041888 | 0.707126 |
| chr2 | 16071365 | 16072112 | 2.58E−09 | All | 0.337041 | 1.347634 | 0.952726 |
| chr10 | 105031159 | 105031629 | 2.62E−09 | All | −0.0494 | 0.688734 | 1.016566 |
| chr19 | 51170609 | 51171407 | 2.74E−09 | All | 0.264918 | 1.321571 | 1.394371 |
| chr4 | 120029760 | 120030128 | 2.89E−09 | All | −0.27772 | 0.816238 | 0.511608 |
| chr13 | 107664610 | 107665176 | 2.98E−09 | All | −0.05834 | 1.072254 | 0.649981 |
| chr1 | 206056315 | 206056820 | 3.15E−09 | brain | 0.066974 | 1.098728 | 1.003981 |
| chr8 | 26207367 | 26208013 | 3.17E−09 | brain | 0.038493 | 1.160728 | 0.947717 |
| chr13 | 112746460 | 112748715 | 3.18E−09 | brain | 0.427857 | 1.380589 | 1.457585 |
| chr2 | 74585982 | 74586242 | 3.20E−09 | liver | 1.767917 | 0.640233 | 1.667118 |
| chr12 | 7175952 | 7176212 | 3.28E−09 | All | −0.01499 | 1.1523 | 0.849905 |
| chr1 | 109626152 | 109626919 | 3.33E−09 | brain | −0.04827 | 0.99007 | 0.876846 |
| chr20 | 23291758 | 23292447 | 3.49E−09 | All | −0.321 | 0.800623 | 0.294726 |
| chr4 | 166520211 | 166521230 | 3.50E−09 | brain | 0.1225 | 1.28178 | 1.22046 |
| chr21 | 39678541 | 39679533 | 3.52E−09 | liver | 1.326263 | 0.256805 | 1.372241 |
| chr5 | 36278172 | 36279450 | 3.64E−09 | liver | 0.870676 | 0.007346 | 1.103939 |
| chrX | 53466762 | 53467199 | 3.82E−09 | All | −0.89696 | 0.218855 | −0.22092 |
| chr2 | 48611532 | 48612389 | 3.92E−09 | All | −0.04989 | 0.995592 | 0.480689 |
| chrX | 18355897 | 18356374 | 4.07E−09 | brain | −0.3703 | 0.699427 | 0.547643 |
| chr19 | 44581428 | 44584303 | 4.17E−09 | brain | 1.129111 | 0.159947 | 0.374427 |
| chr1 | 165182806 | 165183330 | 4.19E−09 | All | 0.078551 | 1.160163 | 0.736041 |
| chr17 | 68094833 | 68098785 | 4.24E−09 | brain | 0.199103 | 1.079328 | 1.153802 |
| chr17 | 4795197 | 4796159 | 4.26E−09 | liver | 1.18738 | 0.182585 | 1.068554 |
| chr19 | 55744809 | 55746038 | 4.26E−09 | brain | −0.03805 | 0.758509 | 1.008509 |
| chr6 | 2712261 | 2713113 | 4.71E−09 | All | −0.31861 | 0.757329 | 0.053413 |
| chr1 | 207913994 | 207914866 | 4.78E−09 | All | 1.048671 | 0.009665 | 0.479916 |
| chr1 | 228271526 | 228273514 | 4.85E−09 | All | 0.721839 | 0.263038 | 1.405718 |
| chr4 | 3341125 | 3342144 | 4.90E−09 | brain | 0.237939 | 1.277335 | 1.144417 |

TABLE 10-continued

Regions with tissue-specific differential methylation (T-DMRs) at a FDR of 5%.

| chr | name | annotation | region | island | distToIsla |
|---|---|---|---|---|---|
| chr1 | PDE4DIP | NM_022359 | overlaps 5' | cover | 0 |
| chr1 | ERRFI1 | NM_018948 | upstream | Shore | 0 |
| chr10 | CPN1 | NM_001308 | overlaps 5' | Far | 15878 |
| chr12 | GALNT9 | NM_021808 | upstream | Shore | 603 |
| chr12 | HOM-TES-103 | NM_001039670 | inside | Shore | 1705 |
| chr14 | THTPA | NM_024328 | downstream | Island | 0 |
| chr14 | TRIM9 | NM_052978 | inside | Island | 0 |
| chr14 | RTN1 | NM_206852 | inside | Shore | 251 |
| chr15 | LRRN6A | NM_032583 | inside | Shore | 1495 |
| chr15 | CHD2 | NM_001042572 | downstream | Far | 9081 |
| chr16 | GPT2 | NM_133443 | downstream | Shore | 0 |
| chr16 | GPT2 | NM_133443 | inside | Shore | 1217 |
| chr18 | ZNF532 | NM_018181 | inside | Shore | 559 |
| chr2 | SPTBN1 | NM_003128 | inside | Shore | 660 |
| chr20 | SS18L1 | NM_198935 | inside | Far | 2587 |
| chr4 | TSPAN5 | NM_005723 | inside | Shore | 127 |
| chr5 | RGMB | NM_173670 | inside | Shore | 781 |
| chr8 | MTMR7 | NM_004686 | inside | Shore | 0 |
| chr8 | GDAP1 | NM_001040875 | inside | Shore | 309 |
| chrX | SLITRK2 | NM_032539 | inside | Shore | 1945 |
| chrX | TSPYL2 | NM_022117 | inside | Far | 2034 |
| chr17 | FLJ45079 | NM_001001685 | upstream | Shore | 197 |
| chr15 | MEIS2 | NM_172315 | inside | Shore | 101 |
| chr7 | MEST | NM_177524 | inside | Shore | 1026 |
| chr1 | VANGL2 | NM_020335 | inside | Shore | 372 |
| chr11 | TIGD3 | NM_145719 | downstream | Shore | 130 |
| chr6 | KIAA1900 | NM_052904 | inside | Shore | 487 |
| chr20 | BMP2 | NM_001200 | downstream | Far | 232877 |
| chr17 | UBE2O | NM_022066 | inside | Shore | 541 |
| chr17 | THRA | NM_199334 | inside | Shore | 360 |
| chr7 | MKLN1 | NM_013255 | downstream | Shore | 0 |
| chr18 | TCF4 | NM_003199 | inside | Far | 165726 |
| chr14 | DDHD1 | NM_030637 | inside | Shore | 393 |
| chr19 | PSCD2 | NM_004228 | upstream | Shore | 320 |
| chr1 | ZNF238 | NM_006352 | inside | Shore | 587 |
| chr22 | C22orf26 | NM_018280 | upstream | Shore | 635 |
| chr22 | MN1 | NM_002430 | inside | Shore | 738 |
| chr12 | RPL6 | NM_000970 | downstream | cover | 0 |
| chr16 | XYLT1 | NM_022166 | inside | Far | 869871 |
| chr6 | LRRC1 | NM_018214 | inside | Shore | 0 |
| chr12 | VPS37B | NM_024667 | inside | Shore | 27 |
| chr4 | CDKL2 | NM_003948 | upstream | Shore | 0 |
| chr10 | CUGBP2 | NM_001025077 | inside | Far | 9377 |
| chr19 | NFIX | NM_002501 | inside | Shore | 74 |
| chr9 | OLFM1 | NM_006334 | inside | Shore | 579 |
| chr3 | DGKG | NM_001346 | inside | Shore | 0 |
| chr13 | CCDC122 | NM_144974 | downstream | Shore | 205 |
| chr14 | THTPA | NM_024328 | downstream | Far | 5519 |
| chr20 | PRNP | NM_000311 | inside | Shore | 263 |
| chr18 | FLJ44881 | NM_207461 | downstream | Shore | 295 |
| chr7 | POR | NM_000941 | inside | Far | 3367 |
| chr16 | SEPHS2 | NM_012248 | overlaps 3' | Shore | 55 |
| chr1 | ACTN2 | NM_001103 | inside | Shore | 0 |
| chr1 | C1orf96 | NM_145257 | inside | Shore | 1414 |
| chr9 | PALM2 | NM_001037293 | inside | Shore | 0 |
| chr21 | ABCG1 | NM_207174 | inside | Shore | 1439 |
| chr21 | JAM2 | NM_021219 | inside | Shore | 412 |
| chr19 | ZNF160 | NM_033288 | inside | Shore | 0 |
| chrX | SYP | NM_003179 | inside | Shore | 1759 |
| chr1 | TRIM62 | NM_018207 | inside | Shore | 269 |
| chr4 | KCNIP4 | NM_147182 | inside | Shore | 32 |
| chr17 | ABC1 | NM_022070 | inside | Shore | 6 |
| chr21 | COL18A1 | NM_030582 | inside | cover | 0 |
| chr2 | LONRF2 | NM_198461 | upstream | Shore | 56 |
| chr2 | YWHAQ | NM_006826 | inside | Shore | 1528 |
| chr13 | PCDH9 | NM_020403 | inside | Far | 2224 |
| chr8 | MAL2 | NM_052886 | inside | Shore | 4 |
| chr17 | WIPI1 | NM_017983 | inside | Shore | 558 |
| chr5 | FBXL7 | NM_012304 | upstream | Far | 2832 |
| chr15 | NDNL2 | NM_138704 | overlaps 3' | Shore | 1133 |
| chr8 | TNKS | NM_003747 | upstream | Shore | 1250 |
| chr15 | MKRN3 | NM_005664 | overlaps 3' | Far | 120705 |
| chr13 | TSC22D1 | NM_006022 | inside | Far | 2361 |
| chr20 | NKX2-2 | NM_002509 | upstream | Far | 84879 |
| chr6 | CGA | NM_000735 | upstream | Shore | 0 |
| chr3 | SCHIP1 | NM_014575 | inside | Far | 74473 |

TABLE 10-continued

Regions with tissue-specific differential methylation (T-DMRs) at a FDR of 5%.

| | | | | | |
|---|---|---|---|---|---|
| chr16 | FOXC2 | NM_005251 | upstream | Far | 2282 |
| chr17 | HOXB7 | NM_004502 | overlaps 3' | Shore | 483 |
| chr12 | TBX3 | NM_005996 | inside | Far | 2380 |
| chr22 | SERPIND1 | NM_000185 | inside | Far | 74742 |
| chr9 | ANP32B | NM_006401 | downstream | Shore | 561 |
| chr10 | CNNM2 | NM_199077 | inside | Shore | 117 |
| chr6 | PAQR8 | NM_133367 | inside | Shore | 0 |
| chr8 | HEY1 | NM_012258 | overlaps 3' | Shore | 336 |
| chr1 | TMEM58 | NM_198149 | inside | Far | 60230 |
| chr11 | DSCAML1 | NM_020693 | inside | Shore | 979 |
| chr10 | WAPAL | NM_015045 | upstream | Shore | 454 |
| chr3 | SCHIP1 | NM_014575 | inside | Shore | 729 |
| chr10 | CXXC6 | NM_030625 | inside | Shore | 1256 |
| chr10 | PCBD1 | NM_000281 | inside | Shore | 1319 |
| chr5 | BASP1 | NM_006317 | inside | Shore | 624 |
| chr19 | ZNF615 | NM_198480 | inside | Island | 0 |
| chr7 | TBXAS1 | NM_030984 | downstream | Shore | 963 |
| chr11 | TMEM151 | NM_153266 | inside | Shore | 284 |
| chr12 | SLC2A13 | NM_052885 | inside | Shore | 570 |
| chr18 | C18orf51 | NM_001044369 | inside | Far | 2280 |
| chr12 | PHC1 | NM_004426 | inside | Shore | 84 |
| chr7 | HERPUD2 | NM_022373 | downstream | Shore | 197 |
| chr22 | FLJ27365 | NM_207477 | downstream | Far | 3632 |
| chr9 | bA16L21.2.1 | NM_001015882 | inside | Shore | 241 |
| chr3 | SOX2 | NM_003106 | upstream | Shore | 865 |
| chr5 | TMEM161B | NM_153354 | upstream | Shore | 321 |
| chr22 | C22orf26 | NM_018280 | upstream | Far | 2055 |
| chr15 | MEIS2 | NM_172315 | inside | Shore | 53 |
| chr6 | PRRT1 | NM_030651 | inside | Shore | 0 |
| chr6 | KAAG1 | NM_181337 | upstream | Shore | 55 |
| chr11 | LRP5 | NM_002335 | inside | Shore | 624 |
| chr15 | DMXL2 | NM_015263 | inside | Shore | 611 |
| chr10 | KCNMA1 | NM_002247 | inside | Shore | 985 |
| chr12 | NT5DC3 | NM_001031701 | inside | Shore | 0 |
| chr1 | SCCPDH | NM_016002 | inside | Shore | 114 |
| chr9 | ROR2 | NM_004560 | inside | Shore | 1731 |
| chr17 | RPL38 | NM_000999 | upstream | Shore | 70 |
| chr5 | IQGAP2 | NM_006633 | inside | Shore | 0 |
| chr14 | DPF3 | NM_012074 | inside | Shore | 41 |
| chr4 | PAPSS1 | NM_005443 | inside | Shore | 136 |
| chr19 | NFIX | NM_002501 | downstream | Far | 10181 |
| chr3 | RAB6B | NM_016577 | inside | Shore | 654 |
| chr12 | DYNLL1 | NM_001037495 | overlaps 5' | Shore | 312 |
| chr3 | HRASLS | NM_020386 | inside | Shore | 206 |
| chr18 | ZNF532 | NM_018181 | overlaps 3' | Shore | 0 |
| chr10 | SH3PXD2A | NM_014631 | inside | Shore | 270 |
| chr4 | DKFZP686A01247 | NM_014988 | inside | Shore | 72 |
| chr8 | HEY1 | NM_012258 | inside | Island | 0 |
| chr20 | FAM83C | NM_178468 | overlaps 3' | Shore | 6 |
| chr1 | PHGDH | NM_006623 | inside | Shore | 0 |
| chr9 | TMEFF1 | NM_003692 | inside | Shore | 0 |
| chr19 | GNG7 | NM_052847 | inside | Shore | 1165 |
| chr11 | DPF2 | NM_006268 | inside | Shore | 140 |
| chr12 | SMARCD1 | NM_003076 | inside | Shore | 1064 |
| chr14 | BCL2L2 | NM_004050 | downstream | Shore | 710 |
| chr12 | CD63 | NM_001780 | inside | Shore | 767 |
| chr6 | B3GAT2 | NM_080742 | inside | Shore | 251 |
| chr2 | PSD4 | NM_012455 | downstream | Shore | 158 |
| chr1 | ATP8B2 | NM_001005855 | inside | Shore | 195 |
| chr19 | NFIX | NM_002501 | inside | Shore | 387 |
| chr18 | ST8SIA3 | NM_015879 | inside | Shore | 0 |
| chr22 | MPPED1 | NM_001044370 | inside | Shore | 753 |
| chr8 | PPM2C | NM_018444 | inside | Shore | 43 |
| chr1 | KCNJ9 | NM_004983 | inside | Shore | 436 |
| chr10 | 8-Mar | NM_001002266 | inside | Far | 69029 |
| chr4 | ALPK1 | NM_025144 | inside | Shore | 0 |
| chr8 | FZD3 | NM_017412 | downstream | Shore | 495 |
| chr6 | BAT2 | NM_004638 | inside | Shore | 52 |
| chr11 | HCCA2 | NM_053005 | inside | Far | 2351 |
| chr9 | MLLT3 | NM_004529 | inside | Shore | 509 |
| chr4 | C4orf30 | NM_017741 | downstream | Shore | 0 |
| chr7 | HOXA5 | NM_019102 | downstream | Shore | 66 |
| chr13 | TMTC4 | NM_032813 | upstream | Far | 23274 |
| chr17 | SOX9 | NM_000346 | inside | Island | 0 |
| chr8 | C8ORFK32 | NM_015912 | inside | Shore | 258 |
| chr6 | KCNK5 | NM_003740 | inside | Shore | 640 |
| chr1 | SDHC | NM_001035512 | overlaps 3' | Island | 0 |
| chr11 | PRDM10 | NM_020228 | inside | Shore | 387 |

TABLE 10-continued

Regions with tissue-specific differential methylation (T-DMRs) at a FDR of 5%.

| | | | | | |
|---|---|---|---|---|---|
| chr6 | HIST1H3E | NM_003532 | overlaps 3' | Shore | 0 |
| chr10 | ZNF438 | NM_182755 | upstream | Shore | 35 |
| chr7 | KIAA1706 | NM_030636 | downstream | Shore | 0 |
| chr12 | FBXO21 | NM_015002 | inside | Shore | 404 |
| chr12 | BCAT1 | NM_005504 | inside | Shore | 0 |
| chr19 | ZNF599 | NM_001007247 | inside | Shore | 126 |
| chr10 | HTRA1 | NM_002775 | inside | Shore | 437 |
| chr22 | C22orf5 | NM_012264 | promoter | Shore | 72 |
| chr5 | BTF3 | NM_001037637 | downstream | Shore | 0 |
| chr2 | MTA3 | NM_020744 | downstream | Shore | 442 |
| chr5 | FER | NM_005246 | downstream | Shore | 271 |
| chr2 | MYCN | NM_005378 | upstream | cover | 0 |
| chr10 | INA | NM_032727 | inside | Far | 3085 |
| chr19 | NOVA2 | NM_002516 | upstream | Far | 22266 |
| chr4 | SYNPO2 | NM_133477 | inside | Far | 52501 |
| chr13 | LIG4 | NM_002312 | overlaps 5' | Shore | 0 |
| chr1 | LOC148696 | NM_001039568 | downstream | Far | 51665 |
| chr8 | PPP2R2A | NM_002717 | inside | Shore | 1997 |
| chr13 | MCF2L | NM_024979 | inside | Shore | 1119 |
| chr2 | PCGF1 | NM_032673 | inside | Shore | 1308 |
| chr12 | CLSTN3 | NM_014718 | inside | Far | 57129 |
| chr1 | PSRC1 | NM_001005290 | inside | Shore | 103 |
| chr20 | GZF1 | NM_022482 | downstream | Shore | 352 |
| chr4 | CPE | NM_001873 | inside | Shore | 93 |
| chr21 | WRB | NM_004627 | inside | Shore | 0 |
| chr5 | C5orf33 | NM_153013 | promoter | Shore | 0 |
| chrX | RIBC1 | NM_144968 | inside | Shore | 265 |
| chr2 | FLJ46838 | NM_001007546 | inside | Shore | 243 |
| chrX | CDKL5 | NM_003159 | inside | Shore | 1550 |
| chr19 | IXL | NM_017592 | overlaps 5' | Shore | 718 |
| chr1 | C1orf32 | NM_199351 | inside | Shore | 159 |
| chr17 | SLC39A11 | NM_139177 | downstream | Shore | 581 |
| chr17 | ENO3 | NM_001976 | inside | Shore | 545 |
| chr19 | LOC554235 | NM_001024656 | upstream | Shore | 875 |
| chr6 | WRNIP1 | NM_020135 | inside | Shore | 487 |
| chr1 | G0S2 | NM_015714 | downstream | Shore | 200 |
| chr1 | GALNT2 | NM_004481 | inside | Shore | 694 |
| chr4 | RGS12 | NM_198227 | overlaps 3' | Far | 2387 |

FDR is false discovery rate.
Columns are chromosome, start, end, false discovery rate, tissue-specificity, brain M value, liver M value, spleen M value, gene, annotation, relation to gene, relation to CGI, distance to CGI

TABLE 11

Regions with cancer-specific differential methylation (C-DMRs) at a FDR of 5%.

| chr | start | end | deltaM | fdr | state | name | annotation | region | relation to Dist to CGI | Dist To CGI |
|---|---|---|---|---|---|---|---|---|---|---|
| chr10 | 5774977 | 5775480 | 0.88404 | 0 | Some methylation | ASB13 | NM_024701 | upstream | Far | 7274 |
| chr11 | 117907224 | 117907958 | 1.00157 | 0 | Some methylation | TMEM25 | NM_032780 | inside | Shore | 0 |
| chr11 | 65947037 | 65948698 | −0.88203 | 0 | Less methylation | NPAS4 | NM_178864 | inside | Shore | 1064 |
| chr13 | 113615559 | 113616275 | −0.91383 | 0 | Less methylation | FAM70B | NM_182614 | inside | cover | 0 |
| chr15 | 58474576 | 58476390 | −0.80517 | 0 | No methylation | ANXA2 | NM_001002857 | inside | Shore | 651 |
| chr19 | 5159373 | 5160095 | −1.01444 | 0 | Less methylation | PTPRS | NM_130854 | inside | Shore | 1469 |
| chr19 | 5297115 | 5297780 | −0.93292 | 0 | No methylation | PTPRS | NM_130854 | upstream | Far | 5054 |
| chr19 | 55631525 | 55632172 | −0.84621 | 0 | Less methylation | MYBPC2 | NM_004533 | inside | Far | 4036 |
| chr19 | 60702435 | 60703541 | −0.93061 | 0 | Less methylation | NAT14 | NM_020378 | upstream | Far | 3082 |
| chr20 | 33650044 | 33650445 | 0.881805 | 0 | More methylation | SPAG4 | NM_003116 | downstream | Shore | 1688 |
| chr21 | 37858818 | 37859555 | −1.16368 | 0 | No methylation | DYRK1A | NM_001396 | upstream | Shore | 402 |
| chr2 | 147061940 | 147063253 | −0.85834 | 0 | Less methylation | ACVR2A | NM_001616 | downstream | Shore | 91 |
| chr22 | 35335058 | 35336773 | −1.03729 | 0 | Less methylation | CACNG2 | NM_006078 | inside | Far | 44058 |

TABLE 11-continued

Regions with cancer-specific differential methylation (C-DMRs) at a FDR of 5%.

| chr | start | end | deltaM | fdr | state | name | annotation | region | relation to Dist to CGI | Dist To CGI |
|---|---|---|---|---|---|---|---|---|---|---|
| chr22 | 48414225 | 48414719 | −0.96407 | 0 | Less methylation | C22orf34 | NM_001039473 | inside | Shore | 1806 |
| chr3 | 193607217 | 193607552 | −0.93573 | 0 | Less methylation | FGF12 | NM_021032 | inside | Shore | 960 |
| chr3 | 82629728 | 82630444 | −0.83773 | 0 | Less methylation | GBE1 | NM_000158 | upstream | Far | 309227 |
| chr4 | 62618513 | 62619190 | −0.87267 | 0 | Less methylation | LPHN3 | NM_015236 | inside | Far | 552670 |
| chr5 | 1718578 | 1720081 | −1.00668 | 0 | Less methylation | MRPL36 | NM_032479 | downstream | Shore | 106 |
| chr6 | 52637426 | 52638797 | −0.88756 | 0 | No methylation | TMEM14A | NM_014051 | downstream | Shore | 0 |
| chr7 | 153219537 | 153220325 | −1.02674 | 0 | Less methylation | DPP6 | NM_001039350 | inside | Far | 2938 |
| chr7 | 27106893 | 27108170 | 0.882121 | 0 | More methylation | HOXA2 | NM_006735 | inside | Shore | 1536 |
| chr8 | 819298 | 820365 | −0.87447 | 0 | Less methylation | ERICH1 | NM_207332 | upstream | Shore | 1879 |
| chr9 | 94989150 | 94990319 | 0.845242 | 0 | Some methylation | WNK2 | NM_006648 | inside | Shore | 1494 |
| chrX | 135941512 | 135943110 | 0.904877 | 0 | Some methylation | GPR101 | NM_054021 | promoter | Island | 0 |
| chr13 | 24843229 | 24844191 | 0.835162 | 2.95E−12 | More methylation | ATP8A2 | NM_016529 | downstream | Shore | 0 |
| chr8 | 144543158 | 144544935 | −0.79612 | 3.04E−12 | Less methylation | RHPN1 | NM_052924 | upstream | Far | 9061 |
| chr20 | 15408602 | 15408931 | −0.87712 | 5.30E−12 | Less methylation | C20orf133 | NM_001033087 | inside | Far | 1092905 |
| chr19 | 43436599 | 43438474 | 0.828947 | 6.70E−12 | More methylation | PPP1R14A | NM_033256 | inside | Shore | 4 |
| chr7 | 27121979 | 27122917 | 0.793013 | 1.34E−11 | Some methylation | HOXA3 | NM_030661 | inside | Shore | 28 |
| chr10 | 129973472 | 129974329 | −0.79104 | 1.92E−11 | Less methylation | MKI67 | NM_002417 | upstream | Far | 19204 |
| chr7 | 129912736 | 129913242 | −0.82465 | 2.24E−11 | Less methylation | MEST | NM_177524 | downstream | Shore | 11 |
| chr15 | 90735153 | 90735977 | −0.78099 | 4.62E−11 | Less methylation | ST8SIA2 | NM_006011 | downstream | Shore | 1704 |
| chr22 | 36145002 | 36145832 | 0.778036 | 5.64E−11 | Some methylation | LRRC62 | NM_052906 | upstream | Shore | 0 |
| chr5 | 175019374 | 175020506 | −0.77323 | 7.72E−11 | Less methylation | HRH2 | NM_022304 | downstream | Shore | 1012 |
| chr8 | 118032313 | 118033443 | −0.76958 | 8.22E−11 | Less methylation | LOC441376 | NM_001025357 | upstream | Far | 12173 |
| chr7 | 27151643 | 27153628 | 0.72037 | 8.57E−11 | More methylation | HOXA6 | NM_024014 | inside | Shore | 0 |
| chr12 | 108883476 | 108884015 | −0.79921 | 8.98E−11 | Less methylation | GIT2 | NM_139201 | inside | Far | 34165 |
| chr7 | 4865828 | 4866751 | −0.75229 | 1.80E−10 | Less methylation | PAPOLB | NM_020144 | inside | Shore | 1111 |
| chr15 | 70198422 | 70199761 | −0.75665 | 2.30E−10 | No methylation | SENP8 | NM_145204 | inside | Shore | 366 |
| chr19 | 63146186 | 63149953 | −0.69314 | 2.31E−10 | Less methylation | ZNF256 | NM_005773 | inside | Shore | 545 |
| chr12 | 128898887 | 128900474 | −0.72032 | 3.16E−10 | No methylation | TMEM132D | NM_133448 | inside | Far | 5162 |
| chr1 | 14092469 | 14093393 | 0.743518 | 3.74E−10 | More methylation | PRDM2 | NM_012231 | upstream | Shore | 145 |
| chr20 | 56858718 | 56860946 | 0.682357 | 3.76E−10 | Some methylation | GNAS | NM_016592 | inside | cover | 0 |
| chr6 | 50873235 | 50873811 | −0.77277 | 3.81E−10 | Less methylation | TFAP2B | NM_003221 | downstream | Far | 21434 |
| chr9 | 101171244 | 101172098 | −0.74221 | 4.84E−10 | Less methylation | SEC61B | NM_006808 | upstream | Far | 72210 |
| chr7 | 145026589 | 145027407 | −0.73801 | 7.53E−10 | Less methylation | CNTNAP2 | NM_014141 | downstream | Far | 416556 |
| chr11 | 73980533 | 73981178 | −0.78485 | 8.52E−10 | Less methylation | POLD3 | NM_006591 | downstream | Shore | 0 |
| chr5 | 16236219 | 16237106 | −0.72798 | 1.00E−09 | No methylation | FBXL7 | NM_012304 | upstream | Far | 2799 |
| chr9 | 137437549 | 137438193 | −0.74586 | 1.27E−09 | Less methylation | KIAA0649 | NM_014811 | downstream | Far | 6096 |
| chr8 | 17060922 | 17062917 | −0.68442 | 1.34E−09 | Less methylation | ZDHHC2 | NM_016353 | inside | Shore | 1761 |

TABLE 11-continued

Regions with cancer-specific differential methylation (C-DMRs) at a FDR of 5%.

| chr | start | end | deltaM | fdr | state | name | annotation | region | relation to Dist to CGI | Dist To CGI |
|---|---|---|---|---|---|---|---|---|---|---|
| chr9 | 136758751 | 136759638 | −0.72195 | 1.46E−09 | Less methylation | COL5A1 | NM_000093 | inside | Far | 40696 |
| chr18 | 73809395 | 73809862 | −0.76199 | 1.78E−09 | Less methylation | GALR1 | NM_001480 | upstream | Far | 9620 |
| chr3 | 129687777 | 129688211 | 0.765371 | 1.99E−09 | Some methylation | GATA2 | NM_032638 | inside | Shore | 0 |
| chr3 | 191521264 | 191521946 | −0.73631 | 2.29E−09 | No methylation | CLDN1 | NM_021101 | inside | Shore | 562 |
| chr13 | 42886712 | 42887185 | −0.75536 | 2.66E−09 | No methylation | PIG38 | NM_017993 | inside | Far | 370673 |
| chr7 | 27147025 | 27148414 | 0.687423 | 2.78E−09 | More methylation | HOXA5 | NM_019102 | overlaps 3' | Shore | 724 |
| chr2 | 4028054 | 4028969 | −0.71686 | 2.80E−09 | Less methylation | ALLC | NM_199232 | upstream | cover | 0 |
| chr17 | 74692697 | 74693892 | −0.70553 | 2.93E−09 | Less methylation | LOC146713 | NM_001025448 | downstream | Shore | 873 |
| chr12 | 112557312 | 112558104 | −0.75314 | 3.06E−09 | Less methylation | LHX5 | NM_022363 | upstream | Far | 43177 |
| chr20 | 44094989 | 44097868 | −0.67672 | 3.15E−09 | No methylation | SLC12A5 | NM_020708 | inside | Shore | 634 |
| chr7 | 92075312 | 92075873 | −0.7558 | 3.60E−09 | Less methylation | CDK6 | NM_001259 | inside | Far | 17503 |
| chr7 | 50103520 | 50103993 | −0.74337 | 5.51E−09 | Less methylation | ZPBP | NM_007009 | promoter | Shore | 53 |
| chr2 | 172826386 | 172826961 | −0.72901 | 5.75E−09 | No methylation | DLX2 | NM_004405 | upstream | Far | 18042 |
| chr8 | 1032896 | 1034248 | −0.68718 | 5.85E−09 | Less methylation | ERICH1 | NM_207332 | upstream | Shore | 1718 |
| chr20 | 56841054 | 56842229 | −0.67616 | 7.76E−09 | No methylation | GNAS | NM_016592 | downstream | Far | 5761 |
| chr7 | 27129188 | 27131713 | 0.62826 | 7.80E−09 | More methylation | HOXA3 | NM_153631 | inside | cover | 0 |
| chr16 | 86201868 | 86205260 | −0.67852 | 9.80E−09 | Less methylation | JPH3 | NM_020655 | inside | Shore | 327 |
| chr18 | 32022373 | 32023451 | −0.68242 | 1.01E−08 | Less methylation | MOCOS | NM_017947 | inside | Shore | 230 |
| chr16 | 31139986 | 31140921 | −0.70124 | 1.03E−08 | Less methylation | TRIM72 | NM_001008274 | inside | Far | 2105 |
| chrX | 23042002 | 23042577 | −0.73787 | 1.05E−08 | Less methylation | DDX53 | NM_182699 | upstream | Far | 217628 |
| chr12 | 16648817 | 16649638 | 0.693703 | 1.13E−08 | Some methylation | LMO3 | NM_018640 | inside | Far | 693016 |
| chr11 | 2190993 | 2192468 | −0.65402 | 1.36E−08 | Less methylation | TH | NM_000360 | upstream | Far | 46172 |
| chr6 | 168586102 | 168588777 | 0.621865 | 1.36E−08 | More methylation | SMOC2 | NM_022138 | inside | Shore | 153 |
| chr4 | 172202321 | 172202941 | −0.71014 | 1.39E−08 | Less methylation | GALNT17 | NM_001034845 | downstream | Far | 767368 |
| chr20 | 3603786 | 3604568 | −0.69261 | 1.43E−08 | No methylation | ADAM33 | NM_025220 | inside | Shore | 1013 |
| chr7 | 1182527 | 1183550 | −0.70109 | 1.53E−08 | Less methylation | ZFAND2A | NM_182491 | upstream | Far | 15857 |
| chr2 | 242632926 | 242634574 | −0.69924 | 2.62E−08 | Less methylation | FLJ33590 | NM_173821 | upstream | Shore | 1740 |
| chr14 | 95577239 | 95578925 | −0.64697 | 3.05E−08 | No methylation | C14orf132 | NM_020215 | inside | Shore | 1084 |
| chr8 | 966339 | 968282 | −0.62553 | 3.25E−08 | Less methylation | ERICH1 | NM_207332 | upstream | Shore | 581 |
| chrX | 142544143 | 142544508 | −0.72871 | 3.62E−08 | Less methylation | SLITRK4 | NM_173078 | inside | Far | 4568 |
| chr7 | 50436454 | 50438081 | −0.63782 | 3.80E−08 | Less methylation | IKZF1 | NM_006060 | overlaps 5' | Shore | 560 |
| chr13 | 87123702 | 87125149 | 0.64054 | 3.98E−08 | Some methylation | SLITRK5 | NM_015567 | inside | cover | 0 |
| chr12 | 88272781 | 88274261 | −0.65038 | 4.42E−08 | Less methylation | DUSP6 | NM_001946 | upstream | Shore | 506 |
| chr13 | 112142200 | 112143003 | −0.6783 | 4.68E−08 | Less methylation | C13orf28 | NM_145248 | upstream | Far | 11335 |
| chr7 | 80386676 | 80389252 | −0.60191 | 4.84E−08 | No methylation | SEMA3C | NM_006379 | promoter | Shore | 14 |
| chr7 | 90064351 | 90065062 | 0.677011 | 5.06E−08 | Some methylation | PFTK1 | NM_012395 | downstream | Shore | 51 |
| chr8 | 100031456 | 100033208 | 0.618925 | 5.12E−08 | Some methylation | OSR2 | NM_053001 | inside | Shore | 842 |

TABLE 11-continued

Regions with cancer-specific differential methylation (C-DMRs) at a FDR of 5%.

| chr | start | end | deltaM | fdr | state | name | annotation | region | relation to Dist to CGI | Dist To CGI |
|---|---|---|---|---|---|---|---|---|---|---|
| chr13 | 110126686 | 110127336 | 0.682652 | 5.44E−08 | More methylation | FLJ12118 | NM_024537 | inside | Shore | 1831 |
| chr8 | 846979 | 849372 | −0.59665 | 5.47E−08 | Less methylation | ERICH1 | NM_207332 | upstream | Far | 6574 |
| chr11 | 103540808 | 103541706 | −0.6721 | 5.56E−08 | Less methylation | PDGFD | NM_025208 | upstream | Shore | 540 |
| chr3 | 28591265 | 28591843 | 0.687621 | 6.39E−08 | Some methylation | ZCWPW2 | NM_001040432 | upstream | Shore | 0 |
| chr8 | 98356982 | 98358151 | −0.64161 | 6.46E−08 | Less methylation | TSPYL5 | NM_033512 | inside | Shore | 629 |
| chr5 | 3586182 | 3587073 | −0.70608 | 6.57E−08 | Less methylation | IRX1 | NM_024337 | downstream | Shore | 1557 |
| chr20 | 4928754 | 4929383 | 0.695671 | 6.64E−08 | Some methylation | SLC23A2 | NM_005116 | inside | Far | 111977 |
| chr12 | 128900526 | 128905070 | −0.5668 | 8.89E−08 | Less methylation | TMEM132D | NM_133448 | inside | Shore | 566 |
| chr5 | 7900127 | 7901201 | −0.65677 | 9.34E−08 | Less methylation | FASTKD3 | NM_024091 | downstream | Shore | 1744 |
| chr19 | 35406489 | 35408138 | 0.619251 | 9.87E−08 | Some methylation | ZNF536 | NM_014717 | downstream | cover | 0 |
| chr7 | 3984090 | 3985861 | −0.6193 | 9.87E−08 | Less methylation | SDK1 | NM_152744 | inside | Far | 134310 |
| chr18 | 75366596 | 75367142 | −0.77008 | 1.07E−07 | Less methylation | NFATC1 | NM_172389 | inside | Far | 4639 |
| chr5 | 11954677 | 11955633 | −0.64541 | 1.12E−07 | Less methylation | CTNND2 | NM_001332 | inside | Shore | 917 |
| chr11 | 2243719 | 2244678 | −0.64164 | 1.20E−07 | Less methylation | ASCL2 | NM_005170 | downstream | Far | 2002 |
| chr9 | 137111474 | 137112189 | −0.65985 | 1.32E−07 | Less methylation | OLFM1 | NM_006334 | inside | Far | 3926 |
| chr7 | 32076356 | 32076691 | 0.709313 | 1.58E−07 | Some methylation | PDE1C | NM_005020 | inside | Shore | 0 |
| chr11 | 19323912 | 19324554 | 0.68291 | 1.77E−07 | Some methylation | E2F8 | NM_024680 | upstream | inside | 0 |
| chr20 | 59905352 | 59906092 | −0.67681 | 1.89E−07 | Less methylation | CDH4 | NM_001794 | inside | Shore | 1622 |
| chr11 | 134186796 | 134187368 | −0.6669 | 2.01E−07 | Less methylation | B3GAT1 | NM_018644 | upstream | Far | 48599 |
| chr7 | 142264591 | 142265022 | −0.68427 | 2.20E−07 | Less methylation | EPHB6 | NM_004445 | inside | Shore | 1283 |
| chr6 | 10501357 | 10502013 | 0.657096 | 2.24E−07 | Some methylation | TFAP2A | NM_001032280 | downstream | Far | 2273 |
| chr7 | 42233455 | 42234204 | 0.645604 | 2.40E−07 | More methylation | GLI3 | NM_000168 | upstream | Shore | 0 |
| chr12 | 38783074 | 38784521 | 0.600023 | 2.59E−07 | More methylation | SLC2A13 | NM_052885 | inside | Shore | 708 |
| chr8 | 117611158 | 117611838 | −0.64748 | 3.10E−07 | Less methylation | EIF3S3 | NM_003756 | downstream | Far | 225273 |
| chr11 | 31966319 | 31967492 | −0.63749 | 3.15E−07 | No methylation | RCN1 | NM_002901 | downstream | Shore | 699 |
| chr17 | 14831980 | 14832519 | −0.66274 | 3.17E−07 | Less methylation | FLJ45831 | NM_001001684 | upstream | Far | 272136 |
| chr21 | 42057731 | 42059424 | −0.58952 | 3.54E−07 | Less methylation | RIPK4 | NM_020639 | inside | Shore | 0 |
| chr11 | 133791126 | 133793856 | −0.56461 | 3.77E−07 | No methylation | B3GAT1 | NM_018644 | upstream | Far | 2997 |
| chr8 | 22469866 | 22470840 | −0.62573 | 3.77E−07 | Less methylation | SORBS3 | NM_005775 | inside | Far | 4286 |
| chr3 | 129686645 | 129687266 | 0.658959 | 3.87E−07 | More methylation | GATA2 | NM_032638 | inside | Shore | 916 |
| chr1 | 221053963 | 221054618 | −0.65816 | 4.06E−07 | Less methylation | FLJ43505 | NM_207468 | upstream | Shore | 249 |
| chr10 | 3499370 | 3500060 | −0.64479 | 4.34E−07 | No methylation | PITRM1 | NM_014889 | upstream | Far | 8794 |
| chr20 | 48778557 | 48780262 | −0.59546 | 4.34E−07 | No methylation | PARD6B | NM_032521 | downstream | Shore | 510 |
| chr7 | 152249022 | 152250754 | −0.63648 | 4.67E−07 | Less methylation | ACTR3B | NM_020445 | upstream | Far | 2095 |
| chr12 | 130718351 | 130718755 | −0.68171 | 4.82E−07 | Less methylation | SFRS8 | NM_004592 | downstream | Far | 5588 |
| chr14 | 57669356 | 57669927 | −0.65813 | 5.16E−07 | Less methylation | C14orf37 | NM_001001872 | inside | Far | 18117 |
| chr10 | 101273308 | 101274941 | 0.602562 | 5.43E−07 | Some methylation | NKX2-3 | NM_145285 | downstream | Shore | 378 |

TABLE 11-continued

Regions with cancer-specific differential methylation (C-DMRs) at a FDR of 5%.

| chr | start | end | deltaM | fdr | state | name | annotation | region | relation to Dist to CGI | Dist To CGI |
|---|---|---|---|---|---|---|---|---|---|---|
| chr18 | 491107 | 491721 | 0.648047 | 5.52E−07 | More methylation | COLEC12 | NM_130386 | upstream | Shore | 385 |
| chr16 | 25608094 | 25609031 | −0.61772 | 5.78E−07 | No methylation | HS3ST4 | NM_006040 | downstream | Shore | 1425 |
| chr19 | 50669649 | 50670313 | 0.642613 | 5.96E−07 | More methylation | FOSB | NM_006732 | overlaps 5' | Shore | 1547 |
| chr11 | 132451977 | 132454794 | −0.55094 | 6.61E−07 | Less methylation | OPCML | NM_001012393 | inside | Far | 2108 |
| chr13 | 100427918 | 100428562 | −0.64421 | 6.75E−07 | Less methylation | VGCNL1 | NM_052867 | downstream | Far | 302194 |
| chr19 | 4505154 | 4505870 | −0.62946 | 6.75E−07 | Less methylation | SEMA6B | NM_020241 | inside | Shore | 1066 |
| chr7 | 139121471 | 139122220 | 0.626218 | 6.75E−07 | More methylation | TBXAS1 | NM_030984 | downstream | Shore | 1655 |
| chr10 | 1437553 | 1439093 | −0.59022 | 6.89E−07 | Less methylation | ADARB2 | NM_018702 | inside | Far | 7539 |
| chr13 | 67580738 | 67581346 | −0.63959 | 6.96E−07 | Less methylation | PCDH9 | NM_020403 | upstream | Far | 875559 |
| chr3 | 174341049 | 174341309 | −0.70742 | 7.33E−07 | Less methylation | SPATA16 | NM_031955 | inside | Far | 254652 |
| chr15 | 67494729 | 67495415 | −0.63108 | 7.40E−07 | No methylation | KIF23 | NM_004856 | inside | Shore | 323 |
| chr12 | 52430235 | 52431287 | 0.615375 | 7.52E−07 | Some methylation | CALCOCO1 | NM_020898 | upstream | Island | 0 |
| chr1 | 32992444 | 32992959 | 0.649479 | 8.12E−07 | Some methylation | KIAA1522 | NM_020888 | inside | Shore | 0 |
| chr14 | 52326048 | 52327349 | −0.60366 | 8.12E−07 | No methylation | GNPNAT1 | NM_198066 | inside | Shore | 65 |
| chr6 | 80711271 | 80712497 | −0.59439 | 8.33E−07 | Less methylation | ELOVL4 | NM_022726 | inside | Shore | 966 |
| chr5 | 132392 | 134486 | −0.57195 | 8.95E−07 | Less methylation | KIAA1909 | NM_052909 | downstream | Shore | 1942 |
| chr3 | 148446946 | 148448043 | −0.61085 | 9.51E−07 | Less methylation | ZIC4 | NM_032153 | downstream | Far | 111759 |
| chr13 | 113548234 | 113549273 | 0.600339 | 9.66E−07 | More methylation | GAS6 | NM_000820 | inside | Shore | 99 |
| chr11 | 133445488 | 133446499 | −0.61556 | 1.00E−06 | Less methylation | JAM3 | NM_032801 | inside | Shore | 597 |
| chr22 | 47455137 | 47456387 | −0.58401 | 1.05E−06 | Less methylation | FAM19A5 | NM_015381 | inside | Far | 4801 |
| chr8 | 132984463 | 132985363 | −0.6234 | 1.10E−06 | Less methylation | KIAA0143 | NM_015137 | downstream | Shore | 141 |
| chr2 | 100303400 | 100304122 | 0.61944 | 1.14E−06 | More methylation | LONRF2 | NM_198461 | upstream | Shore | 89 |
| chr17 | 22902924 | 22903499 | −0.63407 | 1.14E−06 | Less methylation | KSR1 | NM_014238 | inside | Far | 53125 |
| chr1 | 206062462 | 206063842 | 0.573914 | 1.22E−06 | Some methylation | LOC148696 | NM_001039568 | overlaps 5' | Far | 44643 |
| chr5 | 134553843 | 134554653 | 0.610755 | 1.28E−06 | More methylation | H2AFY | NM_138609 | downstream | Shore | 173 |
| chr22 | 46984389 | 46985561 | −0.58562 | 1.31E−06 | Less methylation | LOC388915 | NM_001010902 | upstream | Shore | 218 |
| chr19 | 40896785 | 40897432 | 0.623253 | 1.34E−06 | More methylation | ZBTB32 | NM_014383 | inside | Shore | 1492 |
| chr7 | 149667145 | 149668311 | 0.582745 | 1.37E−06 | More methylation | RARRES2 | NM_002889 | inside | Shore | 81 |
| chr4 | 81341228 | 81342411 | 0.593058 | 1.40E−06 | More methylation | PRDM8 | NM_020226 | inside | Shore | 121 |
| chr12 | 4889976 | 4890592 | 0.629828 | 1.42E−06 | Some methylation | KCNA1 | NM_000217 | downstream | inside | 0 |
| chr19 | 36535109 | 36535822 | 0.615047 | 1.43E−06 | More methylation | TSHZ3 | NM_020856 | upstream | Shore | 0 |
| chr10 | 24025406 | 24026498 | −0.60568 | 1.43E−06 | No methylation | C10orf67 | NM_153714 | upstream | Shore | 422 |
| chr19 | 38866174 | 38866577 | −0.67497 | 1.47E−06 | Less methylation | CHST8 | NM_022467 | downstream | Shore | 607 |
| chr19 | 16876414 | 16876750 | −0.6835 | 1.49E−06 | Less methylation | CPAMD8 | NM_015692 | inside | Far | 6557 |
| chr11 | 31780765 | 31782078 | 0.584509 | 1.55E−06 | Some methylation | PAX6 | NM_000280 | inside | Shore | 241 |
| chr11 | 45645190 | 45645996 | −0.6053 | 1.70E−06 | Less methylation | CHST1 | NM_003654 | upstream | Shore | 1119 |
| chr13 | 21140646 | 21141497 | 0.598118 | 1.82E−06 | Some methylation | FGF9 | NM_002010 | downstream | Shore | 0 |

TABLE 11-continued

Regions with cancer-specific differential methylation (C-DMRs) at a FDR of 5%.

| chr | start | end | deltaM | fdr | state | name | annotation | region | relation to Dist to CGI | Dist To CGI |
|---|---|---|---|---|---|---|---|---|---|---|
| chr8 | 53636369 | 53637193 | −0.60042 | 1.87E−06 | Less methylation | UNQ9433 | NM_207413 | inside | Far | 2904 |
| chr10 | 102097628 | 102098179 | −0.64186 | 2.02E−06 | No methylation | SCD | NM_005063 | inside | Shore | 0 |
| chr13 | 109229161 | 109231936 | −0.52866 | 2.19E−06 | Less methylation | IRS2 | NM_003749 | inside | Shore | 531 |
| chr15 | 53707187 | 53707654 | −0.63505 | 2.19E−06 | Less methylation | PRTG | NM_173814 | inside | Far | 38667 |
| chr11 | 1861758 | 1862726 | −0.58891 | 2.22E−06 | Less methylation | LSP1 | NM_001013255 | inside | Shore | 1848 |
| chr20 | 24399098 | 24400197 | 0.576246 | 2.35E−06 | Some methylation | C20orf39 | NM_024893 | inside | Island | 0 |
| chr13 | 113850874 | 113851696 | 0.595891 | 2.36E−06 | More methylation | RASA3 | NM_007368 | inside | Far | 2472 |
| chr6 | 7413675 | 7414250 | −0.61922 | 2.43E−06 | Less methylation | RIOK1 | NM_153005 | upstream | Far | 72267 |
| chr10 | 124898365 | 124898865 | 0.631343 | 2.63E−06 | Some methylation | HMX2 | NM_005519 | inside | inside | 0 |
| chr7 | 5360462 | 5361424 | 0.593453 | 2.65E−06 | More methylation | SLC29A4 | NM_153247 | upstream | Shore | 974 |
| chr14 | 100996473 | 100997806 | −0.5653 | 2.71E−06 | Less methylation | DIO3 | NM_001362 | downstream | Shore | 725 |
| chr19 | 13473726 | 13475470 | −0.56537 | 2.71E−06 | Less methylation | CACNA1A | NM_023035 | inside | Far | 2282 |
| chr8 | 3257254 | 3257862 | −0.61199 | 2.86E−06 | Less methylation | CSMD1 | NM_033225 | inside | Far | 389899 |
| chr16 | 49141667 | 49142498 | −0.59792 | 2.87E−06 | Less methylation | NKD1 | NM_033119 | inside | Shore | 701 |
| chr5 | 158465126 | 158466712 | 0.548688 | 2.93E−06 | Some methylation | EBF1 | NM_024007 | upstream | cover | 0 |
| chr19 | 3240846 | 3241491 | −0.60751 | 2.96E−06 | Less methylation | BRUNOL5 | NM_021938 | inside | Far | 2776 |
| chr6 | 5946646 | 5947326 | 0.603987 | 2.96E−06 | Some methylation | NRN1 | NM_016588 | inside | Shore | 144 |
| chr7 | 154079253 | 154079678 | −0.65898 | 3.29E−06 | Less methylation | DPP6 | NM_001936 | inside | Far | 93314 |
| chr8 | 144372893 | 144373912 | −0.59142 | 3.41E−06 | No methylation | LOC338328 | NM_178172 | upstream | Far | 9171 |
| chr16 | 4101996 | 4102769 | 0.594061 | 3.47E−06 | Some methylation | ADCY9 | NM_001116 | inside | Far | 2040 |
| chr20 | 61186086 | 61186916 | −0.58801 | 3.49E−06 | Less methylation | BHLHB4 | NM_080606 | upstream | Shore | 1296 |
| chr1 | 203580235 | 203580810 | 0.611495 | 3.58E−06 | More methylation | KLHDC8A | NM_018203 | inside | Shore | 36 |
| chr2 | 128944074 | 128944714 | −0.61563 | 3.59E−06 | Less methylation | HS6ST1 | NM_004807 | upstream | Shore | 357 |
| chr20 | 48848947 | 48849522 | 0.611074 | 3.65E−06 | More methylation | BCAS4 | NM_017843 | inside | Far | 3398 |
| chr18 | 75183050 | 75183445 | 0.635066 | 3.79E−06 | More methylation | ATP9B | NM_198531 | inside | Far | 5006 |
| chr6 | 133602937 | 133603652 | 0.618352 | 3.94E−06 | More methylation | EYA4 | NM_172103 | downstream | Shore | 127 |
| chr9 | 97304533 | 97306736 | 0.542219 | 4.02E−06 | More methylation | PTCH1 | NM_000264 | inside | Shore | 1560 |

DeltaM is cancer minus normal.
FDR is false discovery rate.
State: "Some methylation" means some methylation in tumor, none in normal; "Less methylation" means less in tumor than normal. "More methylation" means more in tumor than normal; "No methylation" means none in tumor, some in normal.
Columns are chromosome, start, end, delta M, fdr, overall methylation state, gene, annotation, relation to gene, relation to CGI, distance to CGI

TABLE 12

Relationship between tissue methylation-specific gene expression and experimental demethylation

| Gene Description | Mean expression (AZA) | meanHCT116 | AZA/HCT116 (mean) | AZA_expression_direction | AZA P-value | TISSUES_Diff_expression (L − B) | TISSUES expression P-value |
|---|---|---|---|---|---|---|---|
| MEF2C | 1.50 | 0.94 | 1.60 | increase | 0.0167 | −5.4 | 1.10E−05 |
| CCK | 1.68 | 0.96 | 1.74 | increase | 0.0256 | −5.2 | 4.50E−05 |
| NTRK2 | 2.11 | 0.95 | 2.23 | increase | 0.0167 | −4.7 | 4.40E−05 |
| SNCA | 0.86 | 0.52 | 1.67 | increase | 0.0256 | −4.3 | 6.30E−05 |

TABLE 12-continued

Relationship between tissue methylation-specific gene expression and experimental demethylation

| | | | | | | | |
|---|---|---|---|---|---|---|---|
| HSPA8 | 5.33 | 2.89 | 1.85 | increase | 0.0167 | −3.3 | 0.00053 |
| WRB | 0.88 | 0.56 | 1.57 | increase | 0.0256 | −2.2 | 0.00037 |
| PIN | 1.17 | 0.67 | 1.75 | increase | 0.0167 | −1.8 | 6.90E−05 |
| SOX9 | 2.78 | 1.81 | 1.53 | increase | 0.0167 | −1.6 | 0.0042 |
| KAL1 | 1.79 | 1.04 | 1.73 | increase | 0.0256 | −1.5 | 0.00058 |
| FYN | 0.91 | 0.58 | 1.57 | increase | 0.0167 | −1.5 | 0.0071 |
| ABCC5 | 1.49 | 0.90 | 1.65 | increase | 0.0256 | −1.5 | 4.20E−05 |
| MTMR6 | 1.72 | 1.11 | 1.55 | increase | 0.0476 | −1 | 0.0039 |
| SHC1 | 1.99 | 1.17 | 1.70 | increase | 0.0167 | 1 | 8.00E−04 |
| S100A10 | 1.27 | 0.84 | 1.51 | increase | 0.0167 | 1.1 | 0.0014 |
| IFITM3 | 2.65 | 1.26 | 2.11 | increase | 0.0256 | 1.2 | 0.056 |
| IFITM3 | 3.12 | 1.05 | 2.97 | increase | 0.0167 | 1.2 | 0.056 |
| DUSP6 | 6.10 | 3.29 | 1.85 | increase | 0.0167 | 1.3 | 0.004 |
| ACADVL | 1.71 | 1.12 | 1.53 | increase | 0.0167 | 1.3 | 0.012 |
| MT2A | 3.31 | 2.20 | 1.50 | increase | 0.0256 | 1.6 | 0.044 |
| KCNJ8 | 2.57 | 1.23 | 2.08 | increase | 0.0455 | 1.7 | 0.00052 |
| MT1X | 3.15 | 2.08 | 1.52 | increase | 0.0167 | 1.9 | 0.052 |
| NFKBIA | 2.04 | 1.07 | 1.91 | increase | 0.0167 | 2.2 | 0.00014 |
| SDC4 | 2.88 | 1.48 | 1.95 | increase | 0.0167 | 2.2 | 0.004 |
| CD14 | 1.75 | 0.82 | 2.14 | increase | 0.0455 | 2.4 | 0.0081 |
| EGFR | 2.02 | 1.12 | 1.81 | increase | 0.0256 | 2.5 | 0.00029 |
| GLDC | 1.32 | 0.70 | 1.88 | increase | 0.0256 | 2.7 | 0.00087 |
| IGFBP3 | 0.44 | 0.04 | 11.24 | increase | 0.0167 | 2.8 | 2.70E−05 |
| GCH1 | 1.14 | 0.73 | 1.55 | increase | 0.0167 | 3.3 | 0.0069 |

| Gene Description | TISSUES_expression_direction_in_hypomethylated_tissue | TISSUES_deltaM (L − B) | TISSUES_Methylation FDR | T-DMR Location |
|---|---|---|---|---|
| MEF2C | increase | 0.74 | 3.60E−05 | Far |
| CCK | increase | 0.84 | 4.90E−05 | Shore |
| NTRK2 | increase | 0.48 | 0.0089 | Far |
| SNCA | increase | 0.36 | 0.0089 | Shore |
| HSPA8 | increase | 0.42 | 0.0089 | Shore |
| WRB | decrease | −0.52 | 0.0089 | Shore |
| PIN | increase | 1.1 | 1.00E−07 | Shore |
| SOX9 | increase | 0.77 | 0.00035 | Shore |
| KAL1 | increase | 0.55 | 0.0017 | Shore |
| FYN | increase | 0.6 | 0.0012 | Shore |
| ABCC5 | increase | 0.93 | 1.40E−08 | Shore |
| MTMR6 | increase | 0.79 | 0.00025 | Far |
| SHC1 | decrease | 1 | 5.50E−07 | Far |
| S100A10 | increase | −0.49 | 0.0089 | Shore |
| IFITM3 | increase | −0.56 | 0.0045 | Shore |
| IFITM3 | increase | −0.56 | 0.0045 | Shore |
| DUSP6 | decrease | −1.4 | 9.90E−14 | Far |
| ACADVL | decrease | 0.62 | 0.0012 | Far |
| MT2A | increase | −0.91 | 8.40E−08 | Shore |
| KCNJ8 | increase | −0.58 | 0.0077 | Shore |
| MT1X | increase | −0.46 | 0.0089 | Shore |
| NFKBIA | increase | −0.69 | 0.00097 | Far |
| SDC4 | increase | −0.44 | 0.0089 | Shore |
| CD14 | increase | −0.46 | 0.0056 | Shore |
| EGFR | increase | −0.67 | 3.00E−04 | Shore |
| GLDC | increase | −0.81 | 0.00058 | Shore |
| IGFBP3 | increase | 0.48 | 0.0058 | Shore |
| GCH1 | increase | −0.54 | 0.00053 | Shore |

Data for AZA and HCT116 gene expression data was obtained from Gius et al. (Gius et al., Cancer Cell, 6: 361-71, 2004).
AZA represents expression data from HCT116 cells treated with 5-aza-2'-deoxycytidine
TISSUES represents data (methylation and expression) from liver and brain samples examined in the current study.
L = liver,
B = brain,
deltaM is differential methylation

TABLE 13

Relationship between tissue methylation-specific gene expression and experimental demethylation

| Gene Description | Mean expression (DKO) | meanHCT116 | DKO/HCT116 (mean) | DKO_expression_direction | DKO p-value | TISSUES_Diff_expression (L − B) | TISSUES expression P-value |
|---|---|---|---|---|---|---|---|
| BASP1 | 1.2362 | 0.5882 | 2.1017 | increased | 0.0014 | −5.3 | 6.10E−07 |
| TUBA1A | 0.9824 | 0.4569 | 2.1499 | increased | 0.0001 | −4.1 | 3.70E−06 |
| TUBB2B | 1.6697 | 0.5768 | 2.8949 | increased | 0 | −3.9 | 2.30E−05 |
| PRKAR2B | 1.4493 | 0.896 | 1.6175 | increased | 0.0064 | −3.5 | 2.00E−05 |

TABLE 13-continued

Relationship between tissue methylation-specific gene expression and experimental demethylation

| Gene | | | | | | | |
|---|---|---|---|---|---|---|---|
| TUBB4 | 2.0428 | 0.8001 | 2.5532 | increased | 0.0057 | −3.4 | 2.90E−05 |
| YWHAE | 1.5439 | 1.0142 | 1.5222 | increased | 0.0276 | −2.9 | 7.60E−05 |
| YWHAQ | 1.6098 | 0.7673 | 2.098 | increased | 0.0191 | −2.7 | 0.00011 |
| NDUFA5 | 1.0375 | 0.6292 | 1.6489 | increased | 0.0198 | −2.5 | 0.006 |
| MAPRE2 | 1.9434 | 1.2365 | 1.5717 | increased | 0.0264 | −2.4 | 8.40E−06 |
| HSPA8 | 1.3072 | 0.7291 | 1.7929 | increased | 0.009 | −2.2 | 0.0015 |
| NTRK2 | 1.4017 | 0.8025 | 1.7468 | increased | 0.008 | −2.2 | 0.0041 |
| STMN1 | 1.9323 | 0.9595 | 2.0139 | increased | 0.0002 | −2.2 | 0.00012 |
| PPP2CA | 1.905 | 1.1691 | 1.6295 | increased | 0.0476 | −2.1 | 0.0024 |
| APPBP2 | 1.8646 | 1.2318 | 1.5138 | increased | 0.0028 | −1.9 | 4.60E−05 |
| DCK | 1.4481 | 0.85 | 1.7038 | increased | 0.0003 | −1.9 | 0.00097 |
| PIN1 | 1.5581 | 0.6673 | 2.3351 | increased | 0 | −1.8 | 6.90E−05 |
| PPP1CB | 2.218 | 1.3206 | 1.6796 | increased | 0.0384 | −1.5 | 0.0094 |
| AP1S2 | 1.8289 | 1.0252 | 1.7839 | increased | 0.0331 | −1.5 | 0.00045 |
| TPI1 | 1.1161 | 0.6111 | 1.8266 | increased | 0.0001 | −1.4 | 0.00055 |
| AP2B1 | 1.8708 | 1.1524 | 1.6234 | increased | 0.0106 | −1.4 | 4.50E−05 |
| FGF12 | 1.0432 | 0.5635 | 1.8512 | increased | 0.0021 | −1.3 | 0.0048 |
| SGCE | 1.6516 | 0.7029 | 2.3498 | increased | 0.0001 | −1.2 | 0.00054 |
| CAP1 | 1.6185 | 1.021 | 1.5852 | increased | 0.0163 | −1.2 | 0.0068 |
| H2AFX | 1.5148 | 0.954 | 1.5878 | increased | 0.0017 | −1.1 | 0.00058 |
| RAD51C | 2.0561 | 1.1202 | 1.8354 | increased | 0.0002 | −1 | 0.0017 |

| Gene Description | TISSUES_expression_direction_in_hypomethylated_tissue | TISSUES_deltaM (L − B) | TISSUES_Methylation FDR | T-DMR Location |
|---|---|---|---|---|
| BASP1 | increased | 0.5 | 0.0089 | Shore |
| TUBA1A | increased | 0.69 | 0.00047 | Shore |
| TUBB2B | increased | 0.53 | 0.0089 | Shore |
| PRKAR2B | increased | 0.66 | 0.0089 | Far |
| TUBB4 | increased | 0.61 | 0.00067 | Shore |
| YWHAE | increased | 0.63 | 0.003 | Shore |
| YWHAQ | increased | 0.52 | 0.0048 | Shore |
| NDUFA5 | increased | 0.66 | 0.0037 | Shore |
| MAPRE2 | increased | 0.53 | 0.0089 | Shore |
| HSPA8 | increased | 0.42 | 0.0089 | Shore |
| NTRK2 | increased | 0.48 | 0.0089 | Far |
| STMN1 | increased | 0.93 | 3.50E−07 | Shore |
| PPP2CA | increased | 0.66 | 8.70E−05 | Shore |
| APPBP2 | increased | 0.4 | 0.0089 | Shore |
| DCK | increased | 0.54 | 0.0089 | Far |
| PIN1 | increased | 1.1 | 1.00E−07 | Shore |
| PPP1CB | increased | 0.54 | 0.0089 | Shore |
| AP1S2 | increased | 0.63 | 0.0089 | Shore |
| TPI1 | increased | 0.45 | 0.0089 | Shore |
| AP2B1 | increased | 0.5 | 0.0089 | Shore |
| FGF12 | increased | 0.67 | 0.00031 | Shore |
| SGCE | increased | 0.35 | 0.0089 | Shore |
| CAP1 | increased | 0.51 | 0.0089 | Shore |
| H2AFX | increased | 0.62 | 0.0013 | Shore |
| RAD51C | increased | 0.59 | 0.0069 | Shore |

Data for DKO and HCT116 gene expression data was obtained from Gius et al. (Gius et al., Cancer Cell, 6: 361-71, 2004).
DKO represents expression data from HCT116 cells with a genetic knockout of DNA methylatransferases 1 and 3b
TISSUES represents data (methylation and expression) from liver and brain samples examined in the current study.
L = liver,
B = brain,
deltaM is differential methylation

TABLE 14

Regions with tissue-specific differential methylation (T-DMRs) and differential methylation in colon cancer (C-DMRs) at a FDR of 5%.

| chr | start | end | tumorstate | similartissue | name | annotation | region | island | Dist To CGI |
|---|---|---|---|---|---|---|---|---|---|
| chr10 | 5774977 | 5775480 | Some methylation | brain | ASB13 | NM_024701 | upstream | Far | 7274 |
| chr21 | 37858818 | 37859555 | No methylation | brain | DYRK1A | NM_001396 | upstream | Shore | 402 |
| chr11 | 73980533 | 73981178 | Less methylation | brain | POLD3 | NM_006591 | downstream | Shore | 0 |
| chr7 | 92075312 | 92075873 | Less methylation | brain | CDK6 | NM_001259 | inside | Far | 17503 |
| chr6 | 168586102 | 168588777 | More methylation | brain | SMOC2 | NM_022138 | inside | Shore | 153 |

TABLE 14-continued

Regions with tissue-specific differential methylation (T-DMRs) and differential methylation in colon cancer (C-DMRs) at a FDR of 5%.

| chr | start | end | tumorstate | similartissue | name | annotation | region | island | Dist To CGI |
|---|---|---|---|---|---|---|---|---|---|
| chr9 | 137111474 | 137112189 | Less methylation | brain | OLFM1 | NM_006334 | inside | Far | 3926 |
| chr7 | 42233455 | 42234204 | More methylation | brain | GLI3 | NM_000168 | upstream | Shore | 0 |
| chr1 | 221053963 | 221054618 | Less methylation | brain | FLJ43505 | NM_207468 | upstream | Shore | 249 |
| chr10 | 3499370 | 3500060 | No methylation | brain | PITRM1 | NM_014889 | upstream | Far | 8794 |
| chr19 | 4505154 | 4505870 | Less methylation | brain | SEMA6B | NM_020241 | inside | Shore | 1066 |
| chr12 | 52430235 | 52431287 | Some methylation | brain | CALCOCO1 | NM_020898 | upstream | Island | 0 |
| chr6 | 80711271 | 80712497 | Less methylation | brain | ELOVL4 | NM_022726 | inside | Shore | 966 |
| chr8 | 132984463 | 132985363 | Less methylation | brain | KIAA0143 | NM_015137 | downstream | Shore | 141 |
| chr7 | 149667145 | 149668311 | More methylation | brain | RARRES2 | NM_002889 | inside | Shore | 81 |
| chr19 | 13473726 | 13475470 | Less methylation | brain | CACNA1A | NM_023035 | inside | Far | 2282 |
| chr8 | 3257254 | 3257862 | Less methylation | brain | CSMD1 | NM_033225 | inside | Far | 389899 |
| chr20 | 48848947 | 48849522 | More methylation | brain | BCAS4 | NM_017843 | inside | Far | 3398 |
| chr6 | 133602937 | 133603652 | More methylation | brain | EYA4 | NM_172103 | downstream | Shore | 127 |
| chr17 | 41333049 | 41334735 | Less methylation | brain | MAPT | NM_005910 | inside | Far | 2213 |
| chr9 | 73954546 | 73955019 | No methylation | brain | GDA | NM_004293 | inside | Shore | 0 |
| chr20 | 33336261 | 33337040 | No methylation | brain | FAM83C | NM_178468 | overlaps 3' | Shore | 108 |
| chr1 | 20383082 | 20384429 | Less methylation | brain | UBXD3 | NM_152376 | downstream | Shore | 518 |
| chr11 | 64244495 | 64245421 | Less methylation | brain | NRXN2 | NM_015080 | inside | Shore | 1648 |
| chr7 | 121736808 | 121737526 | Some methylation | brain | FEZF1 | NM_001024613 | upstream | Shore | 0 |
| chr13 | 20184958 | 20186542 | No methylation | brain | IL17D | NM_138284 | inside | Far | 7069 |
| chr10 | 112248574 | 112249464 | Some methylation | brain | DUSP5 | NM_004419 | inside | Shore | 0 |
| chrX | 120009921 | 120011075 | Less methylation | brain | GLUD2 | NM_012084 | inside | Shore | 270 |
| chr17 | 8846444 | 8846986 | Some methylation | brain | NTN1 | NM_004822 | downstream | Shore | 0 |
| chrX | 74062751 | 74063503 | Less methylation | brain | KIAA2022 | NM_001008537 | upstream | Shore | 850 |
| chr7 | 142205460 | 142206135 | Some methylation | brain | PRSS2 | NM_002770 | upstream | Shore | 84 |
| chr15 | 76344533 | 76345543 | Less methylation | brain | DNAJA4 | NM_018602 | inside | Shore | 0 |
| chr7 | 101853738 | 101854712 | More methylation | brain | PRKRIP1 | NM_024653 | overlaps 5' | Far | 5898 |
| chr14 | 102437341 | 102437847 | More methylation | brain | TRAF3 | NM_003300 | inside | Far | 5743 |
| chr9 | 37022893 | 37023922 | More methylation | brain | PAX5 | NM_016734 | inside | Shore | 213 |
| chr10 | 3818645 | 3819574 | Less methylation | brain | KLF6 | NM_001300 | upstream | Shore | 519 |
| chr7 | 12694278 | 12696066 | No methylation | brain | ARL4A | NM_005738 | inside | Shore | 505 |
| chr20 | 47529867 | 47531270 | No methylation | brain | KCNB1 | NM_004975 | inside | Shore | 649 |
| chr20 | 49590611 | 49591553 | Some methylation | brain | NFATC2 | NM_173091 | inside | Shore | 758 |
| chr9 | 122729717 | 122730552 | More methylation | brain | TRAF1 | NM_005658 | upstream | Shore | 40 |
| chr10 | 22807699 | 22808944 | Less methylation | brain | PIP5K2A | NM_005028 | downstream | Shore | 643 |
| chr7 | 38634847 | 38635894 | Less methylation | brain | AMPH | NM_001635 | inside | Shore | 1070 |
| chr12 | 55902867 | 55903735 | More methylation | brain | NXPH4 | NM_007224 | inside | Shore | 1301 |

TABLE 14-continued

Regions with tissue-specific differential methylation (T-DMRs) and differential methylation in colon cancer (C-DMRs) at a FDR of 5%.

| chr | start | end | tumorstate | similartissue | name | annotation | region | island | Dist To CGI |
|---|---|---|---|---|---|---|---|---|---|
| chr19 | 47263128 | 47264262 | No methylation | brain | GRIK5 | NM_002088 | upstream | Far | 7513 |
| chr18 | 68357323 | 68359390 | No methylation | brain | CBLN2 | NM_182511 | inside | Shore | 564 |
| chr7 | 92076105 | 92076398 | No methylation | brain | CDK6 | NM_001259 | inside | Far | 18296 |
| chr15 | 88348758 | 88349331 | Less methylation | brain | ZNF710 | NM_198526 | inside | Shore | 1843 |
| chr19 | 46525737 | 46526942 | Some methylation | brain | TGFB1 | NM_000660 | downstream | Shore | 1912 |
| chr8 | 10955476 | 10957641 | Less methylation | brain | XKR6 | NM_173683 | inside | Shore | 969 |
| chr7 | 150958618 | 150959472 | Less methylation | brain | PRKAG2 | NM_024429 | inside | Far | 26959 |
| chr10 | 49550539 | 49551086 | More methylation | brain | ARHGAP22 | NM_021226 | upstream | Far | 15932 |
| chr11 | 63821175 | 63822065 | Some methylation | brain | KCNK4 | NM_033310 | inside | Shore | 1268 |
| chr16 | 34067297 | 34067906 | Less methylation | brain | LOC649159 | NM_001040069 | upstream | Shore | 548 |
| chr7 | 5224659 | 5225234 | More methylation | brain | WIPI2 | NM_001033520 | inside | Far | 8213 |
| chr19 | 14487242 | 14488698 | Less methylation | brain | DNAJB1 | NM_006145 | inside | Shore | 708 |
| chr6 | 160690246 | 160691751 | Less methylation | brain | SLC22A3 | NM_021977 | inside | Shore | 0 |
| chr19 | 2239906 | 2240688 | More methylation | brain | C19orf35 | NM_198532 | upstream | Shore | 207 |
| chr10 | 103579583 | 103580518 | Some methylation | brain | KCNIP2 | NM_173194 | inside | Island | 0 |
| chr7 | 121738145 | 121739034 | Some methylation | brain | FEZF1 | NM_001024613 | upstream | Shore | 0 |
| chr13 | 101842566 | 101843905 | No methylation | brain | FGF14 | NM_175929 | inside | Shore | 776 |
| chr2 | 935104 | 935722 | Some methylation | brain | SNTG2 | NM_018968 | downstream | Shore | 0 |
| chr2 | 88531875 | 88532417 | More methylation | brain | FLJ25369 | NM_152670 | downstream | Shore | 33 |
| chr5 | 1555785 | 1556980 | More methylation | brain | AYTL2 | NM_024830 | inside | Far | 7498 |
| chr11 | 66892179 | 66893553 | More methylation | brain | CLCF1 | NM_013246 | inside | Far | 2910 |
| chr10 | 23425480 | 23426204 | No methylation | brain | MSRB2 | NM_012228 | inside | Shore | 396 |
| chr3 | 5002243 | 5003439 | Less methylation | brain | BHLHB2 | NM_003670 | upstream | Shore | 0 |
| chr2 | 174898625 | 174899336 | More methylation | brain | FLJ46347 | NM_001005303 | downstream | Shore | 0 |
| chr19 | 37859830 | 37860375 | More methylation | brain | RGS9BP | NM_207391 | inside | Shore | 0 |
| chr15 | 91430517 | 91431653 | No methylation | brain | RGMA | NM_020211 | inside | Shore | 779 |
| chr10 | 101283725 | 101284669 | Some methylation | brain | NKX2-3 | NM_145285 | inside | Shore | 0 |
| chr20 | 9436915 | 9438354 | More methylation | brain | C20orf103 | NM_012261 | downstream | Shore | 1026 |
| chr15 | 28985194 | 28985874 | More methylation | brain | KIAA1018 | NM_014967 | inside | Shore | 1510 |
| chr1 | 57861340 | 57861987 | Less methylation | brain | DAB1 | NM_021080 | inside | Far | 198115 |
| chr1 | 55123414 | 55124391 | Less methylation | brain | DHCR24 | NM_014762 | inside | Shore | 660 |
| chr18 | 22385126 | 22385774 | Some methylation | brain | KCTD1 | NM_198991 | inside | Shore | 0 |
| chr13 | 111762553 | 111763273 | Some methylation | brain | SOX1 | NM_005986 | downstream | Shore | 87 |
| chr10 | 124218023 | 124218949 | Less methylation | brain | HTRA1 | NM_002775 | inside | Far | 5793 |
| chr13 | 99424284 | 99425382 | Some methylation | brain | ZIC5 | NM_033132 | upstream | Shore | 1935 |
| chr13 | 36147816 | 36148563 | Less methylation | brain | LOC400120 | NM_203451 | inside | Shore | 1353 |
| chr8 | 120755795 | 120756355 | Less methylation | brain | ENPP2 | NM_001040092 | upstream | Far | 157624 |

TABLE 14-continued

Regions with tissue-specific differential methylation (T-DMRs) and differential methylation in colon cancer (C-DMRs) at a FDR of 5%.

| chr | start | end | tumorstate | similartissue | name | annotation | region | island | Dist To CGI |
|---|---|---|---|---|---|---|---|---|---|
| chr8 | 145074517 | 145075008 | More methylation | brain | PLEC1 | NM_201384 | inside | Shore | 394 |
| chr1 | 35164297 | 35165947 | Less methylation | brain | ZMYM6 | NM_007167 | downstream | Shore | 1387 |
| chr5 | 72958425 | 72958969 | Less methylation | brain | UTP15 | NM_032175 | upstream | Shore | 142 |
| chr18 | 42166935 | 42167750 | Some methylation | brain | RNF165 | NM_152470 | downstream | Shore | 0 |
| chr15 | 90198817 | 90201147 | Some methylation | brain | SLCO3A1 | NM_013272 | inside | Shore | 131 |
| chr13 | 25694712 | 25696110 | No methylation | brain | RNF6 | NM_005977 | promoter | Shore | 0 |
| chr10 | 121290732 | 121291137 | More methylation | brain | RGS10 | NM_001005339 | inside | Shore | 331 |
| chr10 | 119281507 | 119283969 | Some methylation | brain | EMX2 | NM_004098 | downstream | Shore | 0 |
| chr2 | 45010614 | 45011650 | Some methylation | brain | SIX3 | NM_005413 | downstream | Shore | 61 |
| chr10 | 101831054 | 101831872 | Less methylation | brain | CPN1 | NM_001308 | overlaps 5' | Far | 15878 |
| chr7 | 2305691 | 2306476 | More methylation | brain | SNX8 | NM_013321 | inside | Far | 13679 |
| chr20 | 54635841 | 54636933 | Some methylation | brain | TFAP2C | NM_003222 | downstream | inside | 0 |
| chr7 | 102577345 | 102577848 | No methylation | brain | NAPE-PLD | NM_198990 | upstream | Shore | 0 |
| chr20 | 54632900 | 54633442 | Some methylation | brain | TFAP2C | NM_003222 | downstream | Shore | 244 |
| chr6 | 106657399 | 106658118 | Some methylation | brain | PRDM1 | NM_182907 | inside | Far | 16321 |
| chr10 | 89410644 | 89411916 | Less methylation | brain | PAPSS2 | NM_001015880 | inside | Shore | 637 |
| chr5 | 139705099 | 139705722 | No methylation | brain | HBEGF | NM_001945 | inside | Shore | 0 |
| chr7 | 55344238 | 55344779 | More methylation | brain | LANCL2 | NM_018697 | downstream | Far | 34680 |
| chr19 | 45414041 | 45414847 | Less methylation | brain | TTC9B | NM_152479 | inside | Shore | 97 |
| chr16 | 71648030 | 71648287 | Some methylation | brain | ATBF1 | NM_006885 | upstream | Shore | 728 |
| chr3 | 184362174 | 184362794 | More methylation | brain | LAMP3 | NM_014398 | inside | Shore | 174 |
| chr9 | 2232790 | 2233418 | No methylation | brain | SMARCA2 | NM_003070 | upstream | Shore | 688 |
| chr17 | 35277006 | 35277374 | More methylation | brain | ZPBP2 | NM_198844 | downstream | Shore | 297 |
| chr2 | 27336168 | 27336881 | Less methylation | brain | SLC30A3 | NM_003459 | inside | Shore | 1496 |
| chr6 | 170702309 | 170703586 | Less methylation | brain | PSMB1 | NM_002793 | inside | Shore | 463 |
| chr2 | 100089371 | 100089913 | Less methylation | brain | AFF3 | NM_002285 | inside | Far | 2198 |
| chr13 | 32487129 | 32487948 | More methylation | brain | KL | NM_153683 | downstream | Shore | 0 |
| chr16 | 88601552 | 88602716 | More methylation | brain | DBNDD1 | NM_024043 | inside | Far | 3168 |
| chr17 | 40746938 | 40747474 | Some methylation | brain | MAP3K14 | NM_003954 | inside | Far | 2200 |
| chr7 | 76881860 | 76882613 | More methylation | brain | LOC54103 | NM_017439 | upstream | Shore | 163 |
| chr9 | 109287301 | 109288864 | Some methylation | brain | KLF4 | NM_004235 | inside | Shore | 705 |
| chr19 | 36536018 | 36538335 | Some methylation | brain | TSHZ3 | NM_020856 | upstream | Shore | 0 |
| chr19 | 1811760 | 1812617 | No methylation | brain | KLF16 | NM_031918 | inside | Shore | 94 |
| chr7 | 44051835 | 44052197 | Some methylation | brain | DBNL | NM_001014436 | inside | Shore | 563 |
| chr13 | 111760735 | 111762537 | Some methylation | brain | SOX1 | NM_005986 | downstream | Shore | 69 |
| chr1 | 243387598 | 243388628 | More methylation | brain | EFCAB2 | NM_032328 | upstream | Shore | 728 |
| chr11 | 67008185 | 67008540 | More methylation | brain | AIP | NM_003977 | inside | Shore | 745 |

TABLE 14-continued

Regions with tissue-specific differential methylation (T-DMRs) and differential methylation in colon cancer (C-DMRs) at a FDR of 5%.

| chr | start | end | tumorstate | similartissue | name | annotation | region | island | Dist To CGI |
|---|---|---|---|---|---|---|---|---|---|
| chr1 | 3816414 | 3816740 | More methylation | brain | C1orf174 | NM_207356 | upstream | Far | 2098 |
| chr20 | 41978520 | 41978954 | Some methylation | brain | C20orf100 | NM_032883 | inside | Shore | 0 |
| chr4 | 54663443 | 54664534 | Some methylation | brain | GSH2 | NM_133267 | upstream | Shore | 623 |
| chr8 | 101641754 | 101641969 | Less methylation | brain | ANKRD46 | NM_198401 | upstream | Shore | 474 |
| chr6 | 10506685 | 10507236 | More methylation | brain | TFAP2A | NM_001032280 | inside | Shore | 0 |
| chr9 | 125811111 | 125813109 | Some methylation | brain | LHX2 | NM_004789 | downstream | Island | 0 |
| chr2 | 71358949 | 71359598 | Less methylation | brain | ZNF638 | NM_001014972 | downstream | Shore | 1208 |
| chr2 | 50910673 | 50911104 | Less methylation | brain | NRXN1 | NM_004801 | inside | Far | 196922 |
| chr11 | 75599856 | 75600608 | More methylation | brain | WNT11 | NM_004626 | upstream | Island | 0 |
| chr13 | 111776858 | 111777751 | Some methylation | brain | SOX1 | NM_005986 | upstream | Shore | 438 |
| chr8 | 133756854 | 133758207 | No methylation | brain | LRRC6 | NM_012472 | overlaps 5' | Island | 0 |
| chr21 | 43964727 | 43965443 | Less methylation | brain | PDXK | NM_003681 | inside | Shore | 468 |
| chr2 | 65072672 | 65073755 | Less methylation | brain | SLC1A4 | NM_003038 | inside | Shore | 1956 |
| chr12 | 112388093 | 112389548 | Some methylation | brain | LHX5 | NM_022363 | inside | inside | 0 |
| chr11 | 128070356 | 128071042 | Some methylation | brain | FLI1 | NM_002017 | inside | Shore | 135 |
| chr7 | 29814368 | 29815975 | Less methylation | brain | SCRN1 | NM_014766 | downstream | Shore | 1092 |
| chr13 | 111767784 | 111768464 | Some methylation | brain | SOX1 | NM_005986 | downstream | Shore | 101 |
| chr1 | 110412699 | 110412994 | More methylation | brain | ALX3 | NM_006492 | inside | inside | 0 |
| chr15 | 87749926 | 87751409 | Some methylation | brain | RHCG | NM_016321 | downstream | Island | 0 |
| chr21 | 45692055 | 45692558 | Less methylation | brain | COL18A1 | NM_130445 | inside | Far | 6999 |
| chr4 | 42096924 | 42097709 | More methylation | brain | ATP8A1 | NM_006095 | downstream | Shore | 1365 |
| chr10 | 119295529 | 119296699 | Some methylation | brain | EMX2 | NM_004098 | inside | Shore | 171 |
| chr18 | 9902703 | 9903140 | Less methylation | brain | VAPA | NM_194434 | downstream | Shore | 324 |
| chr11 | 119937785 | 119939272 | Less methylation | brain | ARHGEF12 | NM_015313 | upstream | Shore | 760 |
| chr13 | 66699432 | 66700406 | Less methylation | brain | PCDH9 | NM_020403 | inside | Far | 2188 |
| chr21 | 45319964 | 45320506 | Some methylation | brain | ADARB1 | NM_001033049 | inside | Shore | 64 |
| chr8 | 11586977 | 11587378 | Some methylation | brain | GATA4 | NM_002052 | downstream | Shore | 0 |
| chr14 | 34941365 | 34942010 | Some methylation | brain | NFKBIA | NM_020529 | inside | Shore | 788 |
| chr9 | 963736 | 964822 | Some methylation | brain | DMRT3 | NM_021240 | downstream | Shore | 460 |
| chr11 | 7489950 | 7490879 | Some methylation | brain | PPFIBP2 | NM_003621 | downstream | Shore | 251 |
| chr9 | 135226940 | 135227305 | More methylation | brain | SURF4 | NM_033161 | inside | Far | 4822 |
| chr3 | 195887111 | 195887789 | More methylation | brain | FAM43A | NM_153690 | downstream | Shore | 0 |
| chr11 | 62449546 | 62449908 | More methylation | brain | CHRM1 | NM_000738 | upstream | Shore | 41 |
| chr7 | 5237174 | 5238382 | More methylation | brain | WIPI2 | NM_001033520 | inside | Far | 2538 |
| chr1 | 119335409 | 119336717 | Some methylation | brain | TBX15 | NM_152380 | upstream | Shore | 472 |
| chr7 | 157176767 | 157177234 | Some methylation | brain | PTPRN2 | NM_002847 | inside | inside | 0 |
| chr7 | 99059893 | 99060630 | More methylation | brain | ZNF498 | NM_145115 | inside | Far | 7072 |

TABLE 14-continued

Regions with tissue-specific differential methylation (T-DMRs) and differential methylation in colon cancer (C-DMRs) at a FDR of 5%.

| chr | start | end | tumorstate | similartissue | name | annotation | region | island | Dist To CGI |
|---|---|---|---|---|---|---|---|---|---|
| chr4 | 99799616 | 99800611 | No methylation | brain | TSPAN5 | NM_005723 | upstream | Shore | 433 |
| chr1 | 163470852 | 163471256 | Some methylation | brain | LMX1A | NM_177398 | inside | Shore | 0 |
| chr14 | 72673969 | 72674259 | Less methylation | brain | PSEN1 | NM_000021 | inside | Shore | 469 |
| chr15 | 50862519 | 50863517 | More methylation | brain | ONECUT1 | NM_004498 | inside | Shore | 0 |
| chr7 | 157748940 | 157749938 | More methylation | brain | PTPRN2 | NM_002847 | inside | Shore | 1574 |
| chr5 | 125957145 | 125958451 | No methylation | brain | ALDH7A1 | NM_001182 | inside | Shore | 49 |
| chr9 | 137135684 | 137136292 | Less methylation | brain | OLFM1 | NM_014279 | inside | Shore | 899 |
| chr3 | 193611789 | 193611977 | Less methylation | brain | FGF12 | NM_004113 | inside | Shore | 1104 |
| chr3 | 10834684 | 10835283 | Less methylation | brain | SLC6A11 | NM_014229 | inside | Shore | 1237 |
| chr3 | 35654544 | 35655159 | Less methylation | brain | ARPP-21 | NM_016300 | downstream | Shore | 354 |
| chr4 | 54669495 | 54670070 | More methylation | brain | GSH2 | NM_133267 | upstream | Shore | 74 |
| chr11 | 71467385 | 71467930 | No methylation | brain | NUMA1 | NM_006185 | inside | Shore | 1103 |
| chr20 | 61838213 | 61838785 | Some methylation | brain | LIME1 | NM_017806 | overlaps 3' | Shore | 614 |

Columns are chromosome, start, end, methylation level of tumor, tissue-specificity, gene, annotation, relation to gene, relation to CGI, distance to CGI

TABLE 15

Gene ontology functional categories enriched in hypermethylated C-DMRs (P < 0.01)

| GOBPID | Pvalue | OddsRatio | ExpCount | Count | Size | Term | Region |
|---|---|---|---|---|---|---|---|
| GO: 0065007 | 1.75E−15 | 1.434797 | 1049.09 | 1221 | 3840 | biological regulation | inside |
| GO: 0006355 | 2.40E−13 | 1.500956 | 504.3282 | 632 | 1846 | regulation of transcription, DNA-dependent | inside/promoter |
| GO: 0022008 | 1.49E−12 | 2.556799 | 66.11453 | 117 | 242 | neurogenesis | inside/promoter |
| GO: 0032774 | 2.03E−12 | 1.47175 | 517.4418 | 641 | 1894 | RNA biosynthetic process | inside/promoter |
| GO: 0019219 | 1.13E−11 | 1.442249 | 545.5814 | 667 | 1997 | regulation of nucleobase, nucleoside, nucleotide and nucleic acid metabolic process | inside/promoter |
| GO: 0006350 | 2.42E−11 | 1.431476 | 552.1383 | 672 | 2021 | transcription | inside/promoter |
| GO: 0010468 | 9.44E−11 | 1.410716 | 569.6231 | 687 | 2085 | regulation of gene expression | inside |
| GO: 0007399 | 3.96E−10 | 2.235828 | 69.90378 | 116 | 263 | nervous system development | inside |
| GO: 0019222 | 7.12E−10 | 1.374211 | 622.0776 | 737 | 2277 | regulation of metabolic process | inside |
| GO: 0007275 | 2.63E−09 | 1.905658 | 100.0965 | 152 | 395 | multicellular organismal development | inside/promoter |
| GO: 0050794 | 2.78E−09 | 1.36836 | 612.7722 | 721 | 2297 | regulation of cellular process | inside |
| GO: 0007155 | 3.54E−09 | 1.735154 | 143.9767 | 204 | 527 | cell adhesion | inside |
| GO: 0048667 | 1.03E−08 | 3.004827 | 30.59846 | 59 | 112 | neuron morphogenesis during differentiation | inside/promoter |
| GO: 0031175 | 2.06E−08 | 2.788835 | 33.87686 | 63 | 124 | neurite development | inside/promoter |

TABLE 15-continued

Gene ontology functional categories enriched in hypermethylated C-DMRs
(P < 0.01)

| GOBPID | Pvalue | OddsRatio | ExpCount | Count | Size | Term | Region |
|---|---|---|---|---|---|---|---|
| GO: 0006366 | 5.56E−07 | 1.574135 | 154.0851 | 206 | 564 | transcription from RNA polymerase II promoter | inside |
| GO: 0048598 | 6.02E−07 | 3.034178 | 22.67564 | 44 | 83 | embryonic morphogenesis | inside/promoter |
| GO: 0006813 | 7.63E−07 | 2.392713 | 36.60887 | 63 | 134 | potassium ion transport | inside |
| GO: 0048731 | 2.51E−06 | 1.509823 | 163.7593 | 214 | 629 | system development | inside |
| GO: 0007268 | 4.80E−06 | 2.061921 | 46.00111 | 73 | 169 | synaptic transmission | inside |
| GO: 0001501 | 6.53E−06 | 2.073943 | 43.98528 | 70 | 161 | skeletal development | inside |
| GO: 0007166 | 7.82E−06 | 1.380202 | 258.195 | 316 | 947 | cell surface receptor linked signal transduction | inside/promoter |
| GO: 0048663 | 8.67E−06 | 16.02797 | 3.824807 | 12 | 14 | neuron fate commitment | inside/promoter |
| GO: 0009887 | 1.12E−05 | 1.725707 | 77.15602 | 110 | 283 | organ morphogenesis | inside |
| GO: 0048858 | 1.20E−05 | 1.975596 | 47.81009 | 74 | 175 | cell projection morphogenesis | inside/promoter |
| GO: 0007411 | 1.37E−05 | 3.379597 | 14.20643 | 29 | 52 | axon guidance | inside |
| GO: 0032989 | 1.71E−05 | 1.806973 | 62.01652 | 91 | 227 | cellular structure morphogenesis | inside |
| GO: 0007417 | 1.77E−05 | 4.033628 | 4.162579 | 15 | 210 | central nervous system development | promoter/inside |
| GO: 0045165 | 1.78E−05 | 5.117343 | 7.884457 | 19 | 29 | cell fate commitment | inside |
| GO: 0050877 | 3.16E−05 | 1.457508 | 153.5387 | 196 | 562 | neurological system process | inside |
| GO: 0030182 | 4.77E−05 | 4.13478 | 3.500752 | 13 | 180 | neuron differentiation | promoter/inside |
| GO: 0003002 | 6.81E−05 | 3.011824 | 14.43907 | 28 | 53 | regionalization | inside |
| GO: 0030198 | 7.50E−05 | 4.234686 | 8.469216 | 19 | 31 | extracellular matrix organization and biogenesis | inside |
| GO: 0007165 | 0.000112 | 1.27058 | 370.8697 | 428 | 1393 | signal transduction | inside |
| GO: 0007498 | 0.000119 | 3.462613 | 10.65482 | 22 | 39 | mesoderm development | inside |
| GO: 0006811 | 0.000179 | 1.761983 | 50.34717 | 73 | 186 | ion transport | inside/promoter |
| GO: 0016481 | 0.000212 | 1.621181 | 69.11973 | 95 | 253 | negative regulation of transcription | inside |
| GO: 0008286 | 0.000212 | 4.1309 | 7.649615 | 17 | 28 | insulin receptor signaling pathway | inside |
| GO: 0007223 | 0.00022 | 5.786819 | 5.19081 | 13 | 19 | Wnt receptor signaling pathway, calcium modulating pathway | inside |
| GO: 0048518 | 0.000234 | 1.314643 | 236.0452 | 281 | 864 | positive regulation of biological process | inside |
| GO: 0007156 | 0.00028 | 1.973959 | 32.23766 | 50 | 118 | homophilic cell adhesion | inside |
| GO: 0007409 | 0.000289 | 2.697344 | 14.67244 | 27 | 54 | axonogenesis | inside/promoter |
| GO: 0006928 | 0.000332 | 1.539749 | 81.96016 | 109 | 300 | cell motility | inside |
| GO: 0000122 | 0.000357 | 1.94508 | 32.51086 | 50 | 119 | negative regulation of transcription from RNA polymerase II promoter | inside |

TABLE 15-continued

Gene ontology functional categories enriched in hypermethylated C-DMRs
(P < 0.01)

| GOBPID | Pvalue | OddsRatio | ExpCount | Count | Size | Term | Region |
|---|---|---|---|---|---|---|---|
| GO: 0051253 | 0.000364 | 1.720385 | 49.72249 | 71 | 182 | negative regulation of RNA metabolic process | inside |
| GO: 0048869 | 0.000389 | 1.879478 | 26.48193 | 44 | 1336 | cellular developmental process | promoter |
| GO: 0030901 | 0.000399 | 30.11077 | 0.158574 | 3 | 8 | midbrain development | promoter/inside |
| GO: 0019933 | 0.000447 | 2.434235 | 17.21163 | 30 | 63 | cAMP-mediated signaling | inside |
| GO: 0048523 | 0.000503 | 1.381743 | 142.3193 | 176 | 525 | negative regulation of cellular process | inside |
| GO: 0009790 | 0.000527 | 3.008165 | 10.78958 | 21 | 40 | embryonic development | inside |
| GO: 0007169 | 0.000542 | 3.862582 | 2.834518 | 10 | 143 | transmembrane receptor protein tyrosine kinase signaling pathway | promoter/inside |
| GO: 0045941 | 0.000581 | 1.568199 | 68.30013 | 92 | 250 | positive regulation of transcription | inside |
| GO: 0035107 | 0.000665 | 3.174262 | 9.562018 | 19 | 35 | appendage morphogenesis | inside/promoter |
| GO: 0060173 | 0.000665 | 3.174262 | 9.562018 | 19 | 35 | limb development | inside/promoter |
| GO: 0035295 | 0.00079 | 1.99814 | 26.22725 | 41 | 96 | tube development | inside |
| GO: 0009792 | 0.000941 | 2.036269 | 24.04165 | 38 | 88 | embryonic development ending in birth or egg hatching | inside |
| GO: 0006817 | 0.001021 | 2.34154 | 16.39203 | 28 | 60 | phosphate transport | inside |
| GO: 0035270 | 0.001048 | 3.649792 | 7.092567 | 15 | 26 | endocrine system development | inside |
| GO: 0001709 | 0.001066 | 3.642225 | 7.103214 | 15 | 26 | cell fate determination | inside/promoter |
| GO: 0030326 | 0.001093 | 3.244364 | 8.469216 | 17 | 31 | embryonic limb morphogenesis | inside/promoter |
| GO: 0043583 | 0.00125 | 2.813623 | 10.65482 | 20 | 39 | ear development | inside |
| GO: 0051254 | 0.001323 | 1.583569 | 56.00611 | 76 | 205 | positive regulation of RNA metabolic process | inside |
| GO: 0001649 | 0.00135 | 3.73849 | 6.556812 | 14 | 24 | osteoblast differentiation | inside |
| GO: 0016477 | 0.001648 | 3.088396 | 3.84543 | 11 | 194 | cell migration | promoter |
| GO: 0001756 | 0.001671 | 5.336521 | 4.098008 | 10 | 15 | somitogenesis | inside |
| GO: 0030154 | 0.001739 | 1.236387 | 282.3619 | 323 | 1062 | cell differentiation | inside |
| GO: 0009953 | 0.001796 | 3.338246 | 7.376414 | 15 | 27 | dorsal/ventral pattern formation | inside |
| GO: 0007420 | 0.0018 | 2.174124 | 17.64753 | 29 | 65 | brain development | inside |
| GO: 0031325 | 0.001905 | 1.420589 | 91.79537 | 116 | 336 | positive regulation of cellular metabolic process | inside |
| GO: 0031016 | 0.002219 | 7.112091 | 3.005206 | 8 | 11 | pancreas development | inside |
| GO: 0030878 | 0.002221 | 15.99486 | 1.912404 | 6 | 7 | thyroid gland development | inside |
| GO: 0045597 | 0.002287 | 2.243075 | 15.57243 | 26 | 57 | positive regulation of cell differentiation | inside |
| GO: 0042472 | 0.002303 | 3.398158 | 6.830013 | 14 | 25 | inner ear morphogenesis | inside |
| GO: 0001654 | 0.002407 | 2.671956 | 10.38162 | 19 | 38 | eye development | inside |

TABLE 15-continued

Gene ontology functional categories enriched in hypermethylated C-DMRs
(P < 0.01)

| GOBPID | Pvalue | OddsRatio | ExpCount | Count | Size | Term | Region |
|---|---|---|---|---|---|---|---|
| GO: 0048534 | 0.002449 | 1.718494 | 34.96967 | 50 | 128 | hemopoietic or lymphoid organ development | inside |
| GO: 0001764 | 0.002689 | 2.838035 | 9.015617 | 17 | 33 | neuron migration | inside |
| GO: 0009653 | 0.002713 | 1.700625 | 35.04919 | 50 | 132 | anatomical structure morphogenesis | inside |
| GO: 0007267 | 0.002732 | 1.482421 | 66.00984 | 86 | 245 | cell-cell signaling | inside |
| GO: 0045944 | 0.002991 | 1.705597 | 34.42327 | 49 | 126 | positive regulation of transcription from RNA polymerase II promoter | inside |
| GO: 0048666 | 0.003085 | 4.51368 | 4.323974 | 10 | 16 | neuron development | inside |
| GO: 0006812 | 0.003153 | 1.368558 | 103.8162 | 128 | 380 | cation transport | inside |
| GO: 0007507 | 0.003355 | 2.047192 | 18.26662 | 29 | 67 | heart development | inside |
| GO: 0003007 | 0.003369 | 4.446488 | 4.371208 | 10 | 16 | heart morphogenesis | inside |
| GO: 0048513 | 0.003421 | 1.838106 | 17.14586 | 29 | 865 | organ development | promoter |
| GO: 0042311 | 0.003551 | 11.5716 | 0.317149 | 3 | 16 | vasodilation | promoter |
| GO: 0030855 | 0.003746 | 3.114549 | 7.103214 | 14 | 26 | epithelial cell differentiation | inside |
| GO: 0045761 | 0.004025 | 2.670723 | 9.288818 | 17 | 34 | regulation of adenylate cyclase activity | inside |
| GO: 0007595 | 0.004249 | 10.74396 | 0.336971 | 3 | 17 | lactation | promoter |
| GO: 0007369 | 0.004843 | 3.66869 | 5.19081 | 11 | 19 | gastrulation | inside |
| GO: 0030902 | 0.004843 | 3.66869 | 5.19081 | 11 | 19 | hindbrain development | inside |
| GO: 0001935 | 0.005025 | 10.02667 | 0.356792 | 3 | 18 | endothelial cell proliferation | promoter |
| GO: 0042136 | 0.005064 | 5.333333 | 3.278406 | 8 | 12 | neurotransmitter biosynthetic process | inside |
| GO: 0048839 | 0.005371 | 6.288015 | 0.713585 | 4 | 36 | inner ear development | promoter |
| GO: 0002052 | 0.005562 | Inf | 1.092802 | 4 | 4 | positive regulation of neuroblast proliferation | inside |
| GO: 0009249 | 0.005562 | Inf | 1.092802 | 4 | 4 | protein lipoylation | inside |
| GO: 0021871 | 0.005562 | Inf | 1.092802 | 4 | 4 | forebrain regionalization | inside |
| GO: 0045885 | 0.005562 | Inf | 1.092802 | 4 | 4 | positive regulation of survival gene product activity | inside |
| GO: 0001505 | 0.005663 | 1.970186 | 18.03123 | 28 | 66 | regulation of neurotransmitter levels | inside |
| GO: 0048732 | 0.005765 | 2.527244 | 9.547686 | 17 | 35 | gland development | inside |
| GO: 0006814 | 0.005976 | 1.839114 | 22.12924 | 33 | 81 | sodium ion transport | inside |
| GO: 0006023 | 0.006192 | 3.81075 | 4.644409 | 10 | 17 | aminoglycan biosynthetic process | inside |
| GO: 0042127 | 0.006293 | 1.345211 | 97.53259 | 119 | 357 | regulation of cell proliferation | inside |
| GO: 0030324 | 0.006442 | 2.403541 | 10.38162 | 18 | 38 | lung development | inside |
| GO: 0002062 | 0.006821 | 7.996328 | 2.185604 | 6 | 8 | chondrocyte differentiation | inside |
| GO: 0040018 | 0.006821 | 7.996328 | 2.185604 | 6 | 8 | positive regulation of multicellular organism growth | inside |
| GO: 0007611 | 0.006957 | 2.306642 | 11.20122 | 19 | 41 | learning and/or memory | inside |

TABLE 15-continued

Gene ontology functional categories enriched in hypermethylated C-DMRs
(P < 0.01)

| GOBPID | Pvalue | OddsRatio | ExpCount | Count | Size | Term | Region |
|---|---|---|---|---|---|---|---|
| GO: 0045661 | 0.007037 | 13.32416 | 1.639203 | 5 | 6 | regulation of myoblast differentiation | inside |
| GO: 0045773 | 0.007037 | 13.32416 | 1.639203 | 5 | 6 | positive regulation of axon extension | inside |
| GO: 0007154 | 0.007222 | 1.475146 | 52.15117 | 68 | 2631 | cell communication | promoter |
| GO: 0009880 | 0.007599 | 2.891016 | 6.830013 | 13 | 25 | embryonic pattern specification | inside |
| GO: 0030321 | 0.007689 | 19.97143 | 0.138753 | 2 | 7 | transepithelial chloride transport | promoter |
| GO: 0031018 | 0.007689 | 19.97143 | 0.138753 | 2 | 7 | endocrine pancreas development | promoter |
| GO: 0008015 | 0.007821 | 3.285874 | 2.279507 | 7 | 115 | blood circulation | promoter |
| GO: 0000165 | 0.008109 | 1.644346 | 30.87166 | 43 | 113 | MAPKKK cascade | inside |
| GO: 0007215 | 0.008131 | 3.260608 | 5.46401 | 11 | 20 | glutamate signaling pathway | inside |
| GO: 0051056 | 0.008464 | 1.474653 | 50.8153 | 66 | 186 | regulation of small GTPase mediated signal transduction | inside |
| GO: 0007204 | 0.008553 | 5.435497 | 0.812694 | 4 | 41 | elevation of cytosolic calcium ion concentration | promoter |
| GO: 0006936 | 0.008566 | 3.225464 | 2.319151 | 7 | 117 | muscle contraction | promoter |
| GO: 0040011 | 0.008827 | 1.964954 | 16.11883 | 25 | 59 | locomotion | inside |
| GO: 0030900 | 0.008854 | 2.292153 | 10.64347 | 18 | 39 | forebrain development | inside |
| GO: 0031324 | 0.009247 | 1.322222 | 98.62539 | 119 | 361 | negative regulation of cellular metabolic process | inside |
| GO: 0042592 | 0.009255 | 1.337753 | 90.42937 | 110 | 331 | homeostatic process | inside |
| GO: 0002009 | 0.009685 | 2.920795 | 6.26769 | 12 | 23 | morphogenesis of an epithelium | inside |
| GO: 0001656 | 0.009895 | 2.910563 | 6.283612 | 12 | 23 | metanephros development | inside |
| GO: 0042445 | 0.00997 | 2.136582 | 12.29402 | 20 | 45 | hormone metabolic process | inside |

TABLE 16

Gene ontology functional categories enriched in hypomethylated C-DMRs
(P < 0.01)

| GOBPID | Pvalue | OddsRatio | ExpCount | Count | Size | Term | Region |
|---|---|---|---|---|---|---|---|
| GO: 0032501 | 7.53E−07 | 1.311239 | 504.7175 | 590 | 2357 | multicellular organismal process | inside |
| GO: 0007155 | 2.18E−06 | 1.601385 | 112.8494 | 157 | 527 | cell adhesion | inside |
| GO: 0032502 | 5.33E−05 | 1.245694 | 503.4327 | 572 | 2351 | developmental process | inside |
| GO: 0006816 | 9.88E−05 | 2.422182 | 18.41566 | 34 | 86 | calcium ion transport | inside |
| GO: 0007165 | 0.000127 | 1.308432 | 258.2146 | 308 | 1226 | signal transduction | inside |
| GO: 0009887 | 0.000132 | 1.632507 | 64.02653 | 91 | 299 | organ morphogenesis | inside |
| GO: 0051056 | 0.000185 | 1.814148 | 39.82921 | 61 | 186 | regulation of small GTPase mediated signal transduction | inside |
| GO: 0007399 | 0.000207 | 1.405645 | 134.4771 | 171 | 628 | nervous system development | inside |

TABLE 16-continued

Gene ontology functional categories enriched in hypomethylated C-DMRs
(P < 0.01)

| GOBPID | Pvalue | OddsRatio | ExpCount | Count | Size | Term | Region |
|---|---|---|---|---|---|---|---|
| GO: 0048731 | 0.000231 | 1.401666 | 134.76 | 171 | 641 | system development | inside |
| GO: 0006812 | 0.000257 | 1.522005 | 81.37151 | 110 | 380 | cation transport | inside |
| GO: 0007154 | 0.000309 | 1.636925 | 55.3083 | 79 | 271 | cell communication | inside |
| GO: 0006817 | 0.00031 | 2.64056 | 12.84813 | 25 | 60 | phosphate transport | inside |
| GO: 0048667 | 0.000336 | 2.058652 | 23.98318 | 40 | 112 | neuron morphogenesis during differentiation | inside |
| GO: 0007409 | 0.00043 | 2.069855 | 22.69837 | 38 | 106 | axonogenesis | inside |
| GO: 0001525 | 0.000486 | 2.076003 | 22.05596 | 37 | 103 | angiogenesis | inside |
| GO: 0003015 | 0.000486 | 3.163871 | 8.351286 | 18 | 39 | heart process | inside |
| GO: 0032989 | 0.000504 | 1.657806 | 48.60877 | 70 | 227 | cellular structure morphogenesis | inside |
| GO: 0035023 | 0.000542 | 2.353129 | 15.41776 | 28 | 72 | regulation of Rho protein signal transduction | inside |
| GO: 0030879 | 0.000937 | 7.363679 | 2.569627 | 8 | 12 | mammary gland development | inside |
| GO: 0008016 | 0.001128 | 3.10623 | 7.494744 | 16 | 35 | regulation of heart contraction | inside |
| GO: 0006811 | 0.001488 | 2.18175 | 15.51374 | 27 | 74 | ion transport | inside |
| GO: 0031175 | 0.001662 | 1.828747 | 26.55281 | 41 | 124 | neurite development | inside |
| GO: 0006820 | 0.001971 | 1.806743 | 26.76694 | 41 | 125 | anion transport | inside |
| GO: 0048858 | 0.002059 | 1.654343 | 37.47372 | 54 | 175 | cell projection morphogenesis | inside |
| GO: 0050801 | 0.002091 | 1.644364 | 38.33026 | 55 | 179 | ion homeostasis | inside |
| GO: 0001568 | 0.002126 | 1.768872 | 28.48003 | 43 | 133 | blood vessel development | inside |
| GO: 0048661 | 0.002212 | 18.39035 | 1.284813 | 5 | 6 | positive regulation of smooth muscle cell proliferation | inside |
| GO: 0007268 | 0.002312 | 1.542972 | 50.32185 | 69 | 235 | synaptic transmission | inside |
| GO: 0006813 | 0.002495 | 1.749208 | 28.69416 | 43 | 134 | potassium ion transport | inside |
| GO: 0030324 | 0.00321 | 2.681625 | 8.137151 | 16 | 38 | lung development | inside |
| GO: 0050877 | 0.003314 | 1.32209 | 120.3442 | 147 | 562 | neurological system process | inside |
| GO: 0006029 | 0.003629 | 10.84488 | 0.312344 | 3 | 30 | proteoglycan metabolic process | promoter |
| GO: 0051147 | 0.004404 | 7.357712 | 1.92722 | 6 | 9 | regulation of muscle cell differentiation | inside |
| GO: 0008299 | 0.005816 | 5.151501 | 2.569627 | 7 | 12 | isoprenoid biosynthetic process | inside |
| GO: 0007265 | 0.005855 | 1.529967 | 41.75643 | 57 | 195 | Ras protein signal transduction | inside |
| GO: 0005513 | 0.006372 | 9.194002 | 1.498949 | 5 | 7 | detection of calcium ion | inside |
| GO: 0009395 | 0.006372 | 9.194002 | 1.498949 | 5 | 7 | phospholipid catabolic process | inside |
| GO: 0003001 | 0.007507 | 2.029051 | 13.2764 | 22 | 62 | generation of a signal involved in cell-cell signaling | inside |
| GO: 0043062 | 0.008118 | 1.973458 | 14.13295 | 23 | 66 | extracellular structure organization and biogenesis | inside |
| GO: 0007528 | 0.009022 | 5.517581 | 2.141355 | 6 | 10 | neuromuscular junction development | inside |
| GO: 0007613 | 0.009022 | 5.517581 | 2.141355 | 6 | 10 | memory | inside |
| GO: 0045884 | 0.009022 | 5.517581 | 2.141355 | 6 | 10 | regulation of survival gene product expression | inside |
| GO: 0048659 | 0.009022 | 5.517581 | 2.141355 | 6 | 10 | smooth muscle cell proliferation | inside |
| GO: 0007242 | 0.0098 | 1.194127 | 242.8297 | 274 | 1134 | intracellular signaling cascade | inside |

TABLE 16-continued

Gene ontology functional categories enriched in hypomethylated C-DMRs (P < 0.01)

| GOBPID | Pvalue | OddsRatio | ExpCount | Count | Size | Term | Region |
|---|---|---|---|---|---|---|---|
| GO: 0030949 | 0.009808 | Inf | 0.642407 | 3 | 3 | positive regulation of vascular endothelial growth factor receptor signaling pathway | inside |
| GO: 0035313 | 0.009808 | Inf | 0.642407 | 3 | 3 | wound healing, spreading of epidermal cells | inside |
| GO: 0045662 | 0.009808 | Inf | 0.642407 | 3 | 3 | negative regulation of myoblast differentiation | inside |
| GO: 0045740 | 0.009808 | Inf | 0.642407 | 3 | 3 | positive regulation of DNA replication | inside |

TABLE 17

Regions with tissue-specific differential methylation (T-DMRs) at a FDR of 5% in *mus musculus*.

| chromosome | start | end |
|---|---|---|
| chr10 | 126979292 | 126980671 |
| chr10 | 127656871 | 127658217 |
| chr10 | 24887401 | 24889329 |
| chr10 | 28888124 | 28888716 |
| chr10 | 33988268 | 33988975 |
| chr10 | 53437662 | 53438762 |
| chr10 | 67306310 | 67306619 |
| chr10 | 76555574 | 76556749 |
| chr10 | 79735316 | 79736395 |
| chr11 | 100635649 | 100638591 |
| chr11 | 102212266 | 102212933 |
| chr11 | 115107596 | 115109335 |
| chr11 | 115111691 | 115113355 |
| chr11 | 120394702 | 120395960 |
| chr1 | 134507754 | 134508470 |
| chr11 | 3811935 | 3812582 |
| chr1 | 157570104 | 157573766 |
| chr11 | 57912170 | 57913262 |
| chr1 | 158417149 | 158418321 |
| chr11 | 58766015 | 58766738 |
| chr11 | 59954757 | 59955965 |
| chr1 | 162825603 | 162826433 |
| chr1 | 162979500 | 162980205 |
| chr11 | 63695421 | 63696067 |
| chr11 | 70847335 | 70849134 |
| chr11 | 78365131 | 78365880 |
| chr11 | 79408077 | 79409420 |
| chr11 | 81782037 | 81782297 |
| chr11 | 83112200 | 83113213 |
| chr11 | 84336675 | 84338372 |
| chr1 | 186509025 | 186510266 |
| chr1 | 186697870 | 186699731 |
| chr1 | 193522768 | 193523343 |
| chr11 | 98586369 | 98587025 |
| chr11 | 98587096 | 98589090 |
| chr12 | 108421230 | 108422853 |
| chr12 | 113167928 | 113169389 |
| chr12 | 30114031 | 30115188 |
| chr12 | 30240986 | 30242545 |
| chr12 | 31879295 | 31880075 |
| chr12 | 53621042 | 53623143 |
| chr12 | 55778410 | 55779489 |
| chr12 | 58362526 | 58363068 |
| chr12 | 60013490 | 60014134 |
| chr12 | 70826084 | 70826557 |
| chr12 | 70827383 | 70827994 |
| chr12 | 71143556 | 71145601 |
| chr12 | 71263656 | 71264508 |
| chr12 | 73151554 | 73155106 |
| chr12 | 83257544 | 83259350 |
| chr12 | 99300922 | 99301356 |
| chr13 | 49157646 | 49158486 |
| chr13 | 52165707 | 52166249 |
| chr13 | 55162752 | 55164518 |
| chr13 | 55477782 | 55479287 |
| chr13 | 58353772 | 58354380 |
| chr13 | 58818797 | 58820212 |
| chr13 | 70203147 | 70204256 |
| chr13 | 70633047 | 70633499 |
| chr14 | 102537320 | 102538579 |
| chr14 | 104219050 | 104219694 |
| chr14 | 20310849 | 20311379 |
| chr14 | 24418637 | 24419041 |
| chr14 | 30097079 | 30098320 |
| chr14 | 50925011 | 50925826 |
| chr14 | 53864878 | 53866395 |
| chr14 | 54043521 | 54045533 |
| chr14 | 54515663 | 54516328 |
| chr14 | 64214773 | 64215654 |
| chr14 | 84989766 | 84990308 |
| chr15 | 100321886 | 100322823 |
| chr15 | 101114047 | 101116123 |
| chr15 | 102016174 | 102017697 |
| chr15 | 102321308 | 102321977 |
| chr15 | 27417171 | 27417674 |
| chr15 | 27968069 | 27968486 |
| chr15 | 39684465 | 39687107 |
| chr15 | 68759467 | 68761004 |
| chr15 | 68761548 | 68763148 |
| chr15 | 78543180 | 78543923 |
| chr15 | 79602362 | 79603288 |
| chr15 | 82533583 | 82534176 |
| chr15 | 85508940 | 85510281 |
| chr15 | 85564473 | 85565120 |
| chr15 | 89202174 | 89205204 |
| chr15 | 91204682 | 91205405 |
| chr15 | 96467000 | 96469097 |
| chr15 | 96570462 | 96571826 |
| chr16 | 24114726 | 24115655 |
| chr16 | 32564545 | 32567256 |
| chr16 | 42108443 | 42109471 |
| chr16 | 85052975 | 85055043 |
| chr17 | 12502541 | 12503011 |
| chr17 | 27384570 | 27385268 |
| chr17 | 28786279 | 28786821 |
| chr17 | 34443844 | 34444281 |
| chr17 | 34739247 | 34740179 |
| chr17 | 56073635 | 56074076 |
| chr17 | 63187176 | 63187802 |
| chr17 | 73446574 | 73447083 |
| chr17 | 73983627 | 73984097 |
| chr17 | 80466736 | 80468474 |

TABLE 17-continued

Regions with tissue-specific differential methylation (T-DMRs) at a FDR of 5% in *mus musculus*.

| chromosome | start | end |
| --- | --- | --- |
| chr17 | 84696081 | 84698211 |
| chr18 | 25868426 | 25868929 |
| chr18 | 34988882 | 34989739 |
| chr18 | 36789615 | 36790328 |
| chr18 | 37945287 | 37947408 |
| chr18 | 38992510 | 38993187 |
| chr18 | 60729232 | 60731679 |
| chr18 | 61044585 | 61044998 |
| chr18 | 65349251 | 65349859 |
| chr18 | 75560629 | 75561096 |
| chr1 | 91413137 | 91414588 |
| chr19 | 25178728 | 25179405 |
| chr19 | 34813801 | 34814130 |
| chr19 | 44354649 | 44355473 |
| chr19 | 45043522 | 45045155 |
| chr19 | 46817593 | 46818555 |
| chr19 | 54252753 | 54254455 |
| chr19 | 55802705 | 55803957 |
| chr19 | 5955473 | 5957745 |
| chr19 | 8906711 | 8907458 |
| chr2 | 104208681 | 104210622 |
| chr2 | 130849724 | 130850548 |
| chr2 | 163238725 | 163239474 |
| chr2 | 179955182 | 179957788 |
| chr2 | 33190742 | 33192554 |
| chr2 | 65841897 | 65843222 |
| chr2 | 93621671 | 93622925 |
| chr3 | 121522532 | 121522894 |
| chr3 | 121522949 | 121524010 |
| chr3 | 121802762 | 121803376 |
| chr3 | 127151720 | 127152797 |
| chr3 | 135373833 | 135375158 |
| chr3 | 83096129 | 83096809 |
| chr3 | 83137592 | 83139735 |
| chr3 | 87004578 | 87005432 |
| chr4 | 117381676 | 117383055 |
| chr4 | 125561574 | 125562182 |
| chr4 | 136994230 | 136995186 |
| chr4 | 138238001 | 138239488 |
| chr4 | 148063477 | 148065006 |
| chr4 | 150869280 | 150870206 |
| chr4 | 154185273 | 154188604 |
| chr4 | 35285562 | 35286638 |
| chr4 | 42972011 | 42973852 |
| chr4 | 42973973 | 42974614 |
| chr4 | 59310854 | 59311432 |
| chr4 | 98613661 | 98614914 |
| chr5 | 107645478 | 107646164 |
| chr5 | 113458417 | 113459346 |
| chr5 | 115071773 | 115072276 |
| chr5 | 124865500 | 124866267 |
| chr5 | 143070755 | 143071267 |
| chr5 | 143233197 | 143234288 |
| chr5 | 65627192 | 65629135 |
| chr5 | 90008195 | 90009248 |
| chr6 | 101163944 | 101165305 |
| chr6 | 119284067 | 119284606 |
| chr6 | 124825932 | 124826609 |
| chr6 | 147219158 | 147219979 |
| chr6 | 38843094 | 38844092 |
| chr6 | 55608676 | 55609270 |
| chr6 | 83108264 | 83109323 |
| chr6 | 83150997 | 83151731 |
| chr6 | 83403666 | 83405735 |
| chr6 | 85995461 | 85996279 |
| chr6 | 90432664 | 90433797 |
| chr7 | 113850061 | 113850390 |
| chr7 | 121496715 | 121497551 |
| chr7 | 127061589 | 127063103 |
| chr7 | 127063311 | 127064541 |
| chr7 | 130484240 | 130486315 |
| chr7 | 139037295 | 139038319 |
| chr7 | 140624014 | 140624754 |
| chr7 | 140757459 | 140759046 |
| chr7 | 15951594 | 15952451 |
| chr7 | 18081819 | 18082463 |
| chr7 | 24596110 | 24596727 |
| chr7 | 24954217 | 24954966 |
| chr7 | 26968540 | 26971209 |
| chr7 | 27442446 | 27443207 |
| chr7 | 29225581 | 29226432 |
| chr7 | 30151377 | 30151814 |
| chr7 | 30822453 | 30823520 |
| chr7 | 45652166 | 45653161 |
| chr7 | 49647288 | 49647932 |
| chr7 | 55711682 | 55712182 |
| chr7 | 79389572 | 79390003 |
| chr7 | 96825159 | 96825599 |
| chr8 | 111425321 | 111427570 |
| chr8 | 111588936 | 111589513 |
| chr8 | 111633592 | 111634305 |
| chr8 | 112137088 | 112141065 |
| chr8 | 112859398 | 112860273 |
| chr8 | 124619935 | 124620738 |
| chr8 | 4257372 | 4258328 |
| chr8 | 47706238 | 47707539 |
| chr8 | 48784788 | 48786354 |
| chr8 | 87673614 | 87674328 |
| chr8 | 87782082 | 87783422 |
| chr9 | 106313871 | 106314629 |
| chr9 | 106534209 | 106534400 |
| chr9 | 108047150 | 108047903 |
| chr9 | 108453798 | 108454337 |
| chr9 | 110094621 | 110095928 |
| chr9 | 110100907 | 110102298 |
| chr9 | 114690009 | 114691953 |
| chr9 | 21385742 | 21386110 |
| chr9 | 36584091 | 36585669 |
| chr9 | 44627976 | 44630076 |
| chr9 | 45183701 | 45184379 |
| chr9 | 64820556 | 64821893 |
| chr9 | 66150149 | 66150724 |
| chr9 | 69092444 | 69093502 |
| chr9 | 83050145 | 83051215 |
| chr9 | 95362984 | 95365053 |
| chr9 | 99241977 | 99242273 |
| chr9 | 99242400 | 99245369 |
| chrX | 147681816 | 147682532 |
| chr10 | 28888088 | 28888716 |
| chr10 | 53437662 | 53438762 |
| chr10 | 80900473 | 80901327 |
| chr1 | 108000968 | 108002063 |
| chr11 | 102212266 | 102212933 |
| chr11 | 109235707 | 109237233 |
| chr11 | 22662409 | 22662984 |
| chr11 | 3811935 | 3812546 |
| chr11 | 53612110 | 53613003 |
| chr1 | 158417149 | 158418321 |
| chr11 | 58765982 | 58766738 |
| chr1 | 162979533 | 162980205 |
| chr1 | 166291190 | 166292146 |
| chr11 | 69841848 | 69842984 |
| chr11 | 70847302 | 70848750 |
| chr11 | 83464295 | 83464906 |
| chr1 | 186430240 | 186431931 |
| chr1 | 186697939 | 186699731 |
| chr1 | 187102071 | 187102469 |
| chr11 | 94938664 | 94939659 |
| chr11 | 96105595 | 96107038 |
| chr11 | 96133733 | 96134386 |
| chr11 | 96143071 | 96143511 |
| chr11 | 97613914 | 97614906 |
| chr11 | 98587132 | 98589159 |
| chr12 | 111186780 | 111187702 |
| chr12 | 30241655 | 30242545 |
| chr12 | 45197481 | 45198904 |
| chr12 | 53621042 | 53623212 |
| chr12 | 55778410 | 55779555 |
| chr12 | 70827419 | 70827994 |
| chr12 | 71263656 | 71264541 |

TABLE 17-continued

Regions with tissue-specific differential methylation (T-DMRs) at a FDR of 5% in *mus musculus*.

| chromosome | start | end |
|---|---|---|
| chr12 | 73151554 | 73155106 |
| chr12 | 83257544 | 83259284 |
| chr12 | 99300922 | 99301392 |
| chr13 | 21513212 | 21513649 |
| chr13 | 35745963 | 35748082 |
| chr13 | 49157646 | 49158525 |
| chr13 | 52540971 | 52542658 |
| chr13 | 55477782 | 55479254 |
| chr13 | 58353808 | 58354380 |
| chr13 | 58818728 | 58820212 |
| chr14 | 104219050 | 104219694 |
| chr1 | 41549409 | 41549774 |
| chr14 | 19166845 | 19167417 |
| chr14 | 30097112 | 30098248 |
| chr14 | 51166853 | 51167672 |
| chr14 | 53733790 | 53734791 |
| chr14 | 53865226 | 53866395 |
| chr14 | 54043521 | 54045602 |
| chr14 | 63546684 | 63549154 |
| chr14 | 64214773 | 64215754 |
| chr14 | 65819186 | 65820690 |
| chr14 | 7008650 | 7010062 |
| chr15 | 100321886 | 100322856 |
| chr15 | 27417132 | 27417674 |
| chr15 | 27968069 | 27968486 |
| chr15 | 37079209 | 37080133 |
| chr15 | 39490076 | 39490510 |
| chr1 | 55352211 | 55352609 |
| chr15 | 68759313 | 68760932 |
| chr15 | 79919013 | 79919906 |
| chr15 | 85508940 | 85509726 |
| chr15 | 97252471 | 97253256 |
| chr16 | 42108443 | 42109435 |
| chr16 | 57391719 | 57392402 |
| chr16 | 58352052 | 58352837 |
| chr1 | 66402075 | 66402928 |
| chr16 | 81084948 | 81085859 |
| chr16 | 85051940 | 85055848 |
| chr17 | 34443844 | 34444281 |
| chr17 | 5451100 | 5452848 |
| chr1 | 77394488 | 77395317 |
| chr18 | 25868426 | 25868929 |
| chr18 | 32701107 | 32702376 |
| chr18 | 34988219 | 34989670 |
| chr18 | 37945468 | 37947408 |
| chr18 | 60745072 | 60745914 |
| chr18 | 61044585 | 61044998 |
| chr18 | 69685663 | 69686202 |
| chr1 | 91765466 | 91766315 |
| chr19 | 43658075 | 43659637 |
| chr19 | 5117032 | 5117184 |
| chr19 | 55802945 | 55803713 |
| chr19 | 58130598 | 58131158 |
| chr2 | 113628540 | 113629780 |
| chr2 | 148368993 | 148369534 |
| chr2 | 148369553 | 148369951 |
| chr2 | 179955743 | 179957821 |
| chr2 | 92232293 | 92234278 |
| chr2 | 93621635 | 93622925 |
| chr3 | 127151720 | 127152764 |
| chr3 | 135374094 | 135375194 |
| chr3 | 136611345 | 136612055 |
| chr3 | 138741405 | 138741737 |
| chr3 | 144130403 | 144131566 |
| chr3 | 28784766 | 28785098 |
| chr3 | 87004578 | 87005465 |
| chr4 | 114409124 | 114411976 |
| chr4 | 125561505 | 125562182 |
| chr4 | 133522280 | 133523272 |
| chr4 | 135299619 | 135300935 |
| chr4 | 148149542 | 148150642 |
| chr4 | 154186710 | 154188227 |
| chr4 | 41756406 | 41756948 |
| chr5 | 113546929 | 113547504 |
| chr5 | 116169864 | 116171999 |
| chr5 | 143070791 | 143071297 |
| chr5 | 52679340 | 52680512 |
| chr6 | 119284067 | 119284606 |
| chr6 | 145003894 | 145005549 |
| chr6 | 147219194 | 147220132 |
| chr6 | 52105770 | 52106804 |
| chr6 | 52109489 | 52110473 |
| chr6 | 52118616 | 52120690 |
| chr6 | 52130359 | 52133065 |
| chr6 | 52134341 | 52135335 |
| chr6 | 55608676 | 55609444 |
| chr6 | 88170526 | 88171206 |
| chr6 | 88839352 | 88840134 |
| chr7 | 121496679 | 121497518 |
| chr7 | 130484240 | 130486315 |
| chr7 | 18081786 | 18082427 |
| chr7 | 26968690 | 26971209 |
| chr7 | 44735606 | 44736776 |
| chr7 | 44919263 | 44920252 |
| chr7 | 45652130 | 45653257 |
| chr7 | 62297270 | 62297671 |
| chr7 | 79389605 | 79390003 |
| chr7 | 96825159 | 96825491 |
| chr8 | 108238955 | 108239740 |
| chr8 | 111425321 | 111427570 |
| chr8 | 112137124 | 112138948 |
| chr8 | 112139103 | 112141065 |
| chr8 | 122007273 | 122007887 |
| chr8 | 124535330 | 124537432 |
| chr8 | 124620001 | 124620738 |
| chr8 | 127546771 | 127548576 |
| chr8 | 14113008 | 14113968 |
| chr8 | 60218064 | 60218813 |
| chr9 | 106313871 | 106314527 |
| chr9 | 108119711 | 108121117 |
| chr9 | 108453798 | 108454337 |
| chr9 | 21385742 | 21386077 |
| chr9 | 45183767 | 45185397 |
| chr9 | 66150221 | 66150724 |
| chr9 | 72490554 | 72492061 |
| chr9 | 83601188 | 83601727 |
| chr9 | 89629425 | 89629895 |
| chr10 | 126979364 | 126980638 |
| chr10 | 127020412 | 127022913 |
| chr10 | 127656943 | 127658217 |
| chr10 | 41890728 | 41891096 |
| chr10 | 80692225 | 80693889 |
| chr1 | 108001004 | 108001925 |
| chr11 | 103160706 | 103161842 |
| chr11 | 109293793 | 109294485 |
| chr11 | 115111730 | 115113316 |
| chr11 | 120237470 | 120237940 |
| chr11 | 120611069 | 120611503 |
| chr11 | 120766874 | 120767062 |
| chr11 | 22662409 | 22662984 |
| chr1 | 135191990 | 135192493 |
| chr1 | 139952104 | 139952436 |
| chr1 | 163084626 | 163084958 |
| chr11 | 69180232 | 69180594 |
| chr11 | 69180685 | 69181225 |
| chr11 | 78365131 | 78365880 |
| chr1 | 193522768 | 193523343 |
| chr12 | 113168003 | 113169353 |
| chr12 | 118743027 | 118744363 |
| chr12 | 31879325 | 31880075 |
| chr12 | 58362526 | 58363068 |
| chr12 | 60013490 | 60014101 |
| chr12 | 71144570 | 71145463 |
| chr12 | 84942362 | 84943216 |
| chr12 | 86635810 | 86637096 |
| chr12 | 87778503 | 87779744 |
| chr13 | 40897757 | 40899363 |
| chr13 | 52165707 | 52166249 |
| chr13 | 52987856 | 52990349 |
| chr13 | 92215958 | 92216461 |

TABLE 17-continued

Regions with tissue-specific differential methylation (T-DMRs) at a FDR of 5% in *mus musculus*.

| chromosome | start | end |
|---|---|---|
| chr14 | 120387491 | 120388301 |
| chr14 | 46395955 | 46396851 |
| chr14 | 50829932 | 50832484 |
| chr14 | 50832626 | 50833966 |
| chr14 | 56055810 | 56057340 |
| chr15 | 102015649 | 102016017 |
| chr15 | 10928320 | 10928886 |
| chr15 | 37079176 | 37080133 |
| chr15 | 76133841 | 76134551 |
| chr15 | 78236579 | 78237388 |
| chr15 | 85564542 | 85565081 |
| chr15 | 88692381 | 88692779 |
| chr15 | 89202174 | 89205168 |
| chr15 | 89384916 | 89385488 |
| chr15 | 97252471 | 97253256 |
| chr16 | 24114972 | 24115619 |
| chr16 | 57391719 | 57392402 |
| chr1 | 66935142 | 66935648 |
| chr16 | 84715521 | 84716705 |
| chr16 | 92895397 | 92895810 |
| chr17 | 12502580 | 12503011 |
| chr17 | 24422788 | 24423243 |
| chr17 | 28786279 | 28786785 |
| chr17 | 45349645 | 45350289 |
| chr17 | 80466736 | 80468438 |
| chr17 | 84696258 | 84698178 |
| chr18 | 36789687 | 36790328 |
| chr18 | 60729268 | 60731718 |
| chr18 | 60732259 | 60732978 |
| chr18 | 65349251 | 65349859 |
| chr18 | 70653550 | 70654152 |
| chr18 | 75548120 | 75548380 |
| chr19 | 25178692 | 25179405 |
| chr19 | 29115205 | 29115927 |
| chr19 | 34813837 | 34814130 |
| chr19 | 34942556 | 34943841 |
| chr19 | 37238481 | 37239098 |
| chr19 | 37328982 | 37330121 |
| chr19 | 43654651 | 43655382 |
| chr1 | 94901325 | 94902392 |
| chr19 | 54252753 | 54254134 |
| chr19 | 5955777 | 5957547 |
| chr2 | 163238827 | 163239474 |
| chr2 | 30028984 | 30029874 |
| chr2 | 58379608 | 58380903 |
| chr2 | 58381061 | 58381699 |
| chr3 | 121523021 | 121523974 |
| chr3 | 121894506 | 121894976 |
| chr3 | 83096129 | 83096809 |
| chr3 | 83137592 | 83139768 |
| chr4 | 105959139 | 105959501 |
| chr4 | 105959592 | 105960239 |
| chr4 | 135411138 | 135412272 |
| chr4 | 138238949 | 138239419 |
| chr4 | 140403814 | 140404461 |
| chr4 | 148149575 | 148150570 |
| chr4 | 148628253 | 148628720 |
| chr4 | 149697690 | 149698580 |
| chr4 | 150869421 | 150870134 |
| chr4 | 35285775 | 35286638 |
| chr4 | 40456117 | 40456761 |
| chr4 | 59310821 | 59311432 |
| chr4 | 97328719 | 97329291 |
| chr5 | 113197288 | 113198073 |
| chr5 | 113458495 | 113459346 |
| chr5 | 116706401 | 116708027 |
| chr5 | 118239146 | 118240513 |
| chr5 | 123395820 | 123396041 |
| chr5 | 124865500 | 124866234 |
| chr5 | 65627192 | 65629135 |
| chr6 | 119382061 | 119382708 |
| chr6 | 124629874 | 124631263 |
| chr6 | 31119916 | 31120566 |
| chr6 | 85903153 | 85903656 |
| chr6 | 88156373 | 88156597 |
| chr7 | 127061589 | 127063136 |
| chr7 | 132958148 | 132959237 |
| chr7 | 140624014 | 140624754 |
| chr7 | 140757459 | 140757896 |
| chr7 | 15951594 | 15952415 |
| chr7 | 29942884 | 29943006 |
| chr7 | 30662992 | 30664459 |
| chr7 | 49211159 | 49211842 |

TABLE 18

Regions with consistent cancer-specific differential methylation (C-DMRs) at a FDR of 5%.

| chr | start | end | deltaM | fdr | gene name | relation | TSS distance | CGI | distToCGI |
|---|---|---|---|---|---|---|---|---|---|
| chr7 | 153219537 | 153220325 | −1.02674 | 0.00000131 | DPP6 | inside | 1096601 | Far | −2938 |
| chr21 | 37858785 | 37859555 | −1.08401 | 0.00000164 | DYRK1A | upstream | 49238 | Shore | −369 |
| chr11 | 117907224 | 117907958 | 1.00157 | 0.00000328 | TMEM25 | inside | 3800 | Shore | 0 |
| chr19 | 5159412 | 5160095 | −1.02228 | 0.00000628 | PTPRS | inside | 131718 | Shore | 1469 |
| chr11 | 65947037 | 65948698 | −0.88203 | 0.00000638 | NPAS4 | inside | 2054 | Shore | −1064 |
| chr22 | 35335058 | 35337265 | −0.87143 | 0.00000665 | CACNG2 | inside | 91583 | Far | −44058 |
| chr19 | 60702504 | 60703541 | −0.94123 | 0.00000892 | NAT14 | upstream | 11758 | Far | 3082 |
| chrX | 135941512 | 135943110 | 0.904877 | 0.0000093 | GPR101 | promoter | 14 | Island | 0 |
| chr6 | 52637426 | 52638797 | −0.88756 | 0.000013 | TMEM14A | downstream | 20544 | Shore | 0 |
| chr7 | 27106893 | 27108203 | 0.870706 | 0.0000156 | HOXA2 | inside | 715 | Shore | 1503 |
| chr5 | 1718233 | 1720117 | −0.85903 | 0.0000205 | MRPL36 | downstream | 132828 | Shore | 70 |
| chr19 | 5297115 | 5297780 | −0.93292 | 0.0000226 | PTPRS | upstream | 5302 | Far | −5054 |
| chr2 | 147061970 | 147063253 | −0.86015 | 0.0000229 | ACVR2A | downstream | 1341608 | Shore | −121 |
| chr8 | 819298 | 820365 | −0.87447 | 0.0000243 | ERICH1 | upstream | 148073 | Shore | 1879 |
| chr22 | 48414225 | 48414719 | −0.96407 | 0.0000249 | C22orf34 | inside | 22470 | Shore | −1806 |
| chr13 | 113615559 | 113616275 | −0.91383 | 0.000027 | FAM70B | inside | 35597 | cover | 0 |
| chr15 | 58474612 | 58476390 | −0.81855 | 0.0000399 | ANXA2 | inside | 1086 | Shore | 651 |
| chr7 | 3984567 | 3985861 | −0.84076 | 0.0000663 | SDK1 | inside | 285898 | Far | 134310 |
| chr20 | 33650044 | 33650409 | 0.946503 | 0.0000695 | SPAG4 | downstream | 21969 | Shore | 1724 |
| chr13 | 24843229 | 24844069 | 0.886019 | 0.0000738 | ATP8A2 | downstream | 649349 | Shore | 0 |
| chr4 | 62618513 | 62619190 | −0.87267 | 0.0000761 | LPHN3 | inside | 1571 | Far | −552670 |
| chr3 | 193607217 | 193607552 | −0.93573 | 0.0001116 | FGF12 | inside | 1153 | Shore | 960 |
| chr10 | 5774977 | 5775480 | 0.88404 | 0.00012066 | ASB13 | upstream | 26431 | Far | −7274 |

TABLE 18-continued

Regions with consistent cancer-specific differential methylation (C-DMRs) at a FDR of 5%.

| chr | start | end | deltaM | fdr | gene name | relation | TSS distance | CGI | distToCGI |
|---|---|---|---|---|---|---|---|---|---|
| chr3 | 82629728 | 82630444 | −0.83773 | 0.00014135 | GBE1 | upstream | 736294 | Far | 309227 |
| chr15 | 70198455 | 70199761 | −0.825 | 0.00014832 | SENP8 | inside | 20595 | Shore | −399 |
| chr8 | 144543158 | 144544971 | −0.7704 | 0.00017229 | RHPN1 | upstream | 7196 | Far | −9061 |
| chr19 | 63146186 | 63149398 | −0.7009 | 0.00020946 | ZNF256 | inside | 1490 | Shore | 1100 |
| chr7 | 27121979 | 27122917 | 0.793013 | 0.00021477 | HOXA3 | inside | 2821 | Shore | −28 |
| chr10 | 129973472 | 129974329 | −0.79104 | 0.00024398 | MKI67 | upstream | 158828 | Far | −19204 |
| chr5 | 175019374 | 175020470 | −0.78658 | 0.00032057 | HRH2 | downstream | 23691 | Shore | −1012 |
| chr15 | 90735153 | 90736013 | −0.77464 | 0.0003365 | ST8SIA2 | downstream | 76946 | Shore | 1668 |
| chr20 | 15408602 | 15408931 | −0.87712 | 0.00036397 | C20orf133 | inside | 572907 | Far | 1092905 |
| chr12 | 128898887 | 128900474 | −0.72032 | 0.00038766 | TMEM132D | inside | 53691 | Far | 5162 |
| chr20 | 56858718 | 56860982 | 0.659681 | 0.00039705 | GNAS | inside | 58661 | cover | 0 |
| chr8 | 118032349 | 118033443 | −0.77052 | 0.00039943 | LOC441376 | upstream | 7947 | Far | −12209 |
| chr19 | 55631492 | 55632172 | −0.78998 | 0.00040909 | MYBPC2 | inside | 29216 | Far | −4003 |
| chr7 | 27151538 | 27154015 | 0.661581 | 0.00040909 | HOXA6 | covers | 0 | Shore | 0 |
| chr22 | 36144969 | 36145868 | 0.759849 | 0.00041153 | LRRC62 | upstream | 43445 | Shore | 0 |
| chr20 | 16499527 | 16500276 | −0.77576 | 0.00043547 | C20orf23 | inside | 1801 | Shore | 1560 |
| chr7 | 4865828 | 4866751 | −0.75229 | 0.00043806 | PAPOLB | inside | 1399 | Shore | 1111 |
| chr8 | 17060922 | 17062917 | −0.68442 | 0.0005137 | ZDHHC2 | inside | 61694 | Shore | −1761 |
| chr12 | 108883476 | 108884015 | −0.79921 | 0.00055912 | GIT2 | inside | 34467 | Far | 34165 |
| chr1 | 14092469 | 14093393 | 0.743518 | 0.00056075 | PRDM2 | upstream | 68308 | Shore | −145 |
| chr9 | 101171277 | 101172098 | −0.75185 | 0.00056896 | SEC61B | upstream | 138557 | Far | −72243 |
| chr7 | 27129188 | 27131713 | 0.62826 | 0.00063513 | HOXA3 | inside | 1450 | cover | 0 |
| chr9 | 94987821 | 94990808 | 0.598843 | 0.00069825 | WNK2 | inside | 131865 | Shore | −165 |
| chr7 | 145026589 | 145027407 | −0.73801 | 0.00073506 | CNTNAP2 | downstream | 2721611 | Far | 416556 |
| chr5 | 16236219 | 16237106 | −0.72798 | 0.00074772 | FBXL7 | upstream | 243320 | Far | −2799 |
| chr6 | 168586102 | 168588777 | 0.621865 | 0.00078025 | SMOC2 | inside | 221818 | Shore | −153 |
| chr7 | 27147025 | 27148381 | 0.688088 | 0.00079587 | HOXA5 | overlaps 3' | 1430 | Shore | 757 |
| chr6 | 50873235 | 50873811 | −0.77277 | 0.00080038 | TFAP2B | downstream | 45822 | Far | 21434 |
| chr9 | 136758751 | 136759638 | −0.72195 | 0.000835 | COL5A1 | inside | 116868 | Far | 40696 |
| chr17 | 74692733 | 74693892 | −0.71657 | 0.00085162 | LOC146713 | downstream | 237673 | Shore | −909 |
| chr20 | 44094989 | 44097479 | −0.68354 | 0.00086367 | SLC12A5 | inside | 24716 | Shore | −634 |
| chr12 | 128900559 | 128905004 | −0.58154 | 0.00089325 | TMEM132D | inside | 49161 | Shore | 632 |
| chr9 | 137437549 | 137438193 | −0.74586 | 0.00103233 | KIAA0649 | downstream | 82366 | Far | 6096 |
| chr8 | 1032932 | 1034329 | −0.68718 | 0.00109097 | ERICH1 | upstream | 361707 | Shore | 1637 |
| chr20 | 56841054 | 56842229 | −0.67616 | 0.00110609 | GNAS | downstream | 77414 | Far | 5761 |
| chr11 | 2190993 | 2192468 | −0.65402 | 0.00113066 | TH | upstream | 41383 | Far | −46172 |
| chr7 | 80386676 | 80389252 | −0.60191 | 0.00118778 | SEMA3C | promoter | 74 | Shore | −14 |
| chr8 | 846979 | 849372 | −0.59665 | 0.00119103 | ERICH1 | upstream | 175754 | Far | −6574 |
| chr3 | 191521264 | 191521946 | −0.73631 | 0.00122064 | CLDN1 | inside | 962 | Shore | 562 |
| chr3 | 193338227 | 193339771 | −0.67305 | 0.00123738 | FGF12 | downstream | 268934 | Far | 268741 |
| chr16 | 86201868 | 86205260 | −0.67852 | 0.00127148 | JPH3 | inside | 83999 | Shore | 327 |
| chr22 | 48392638 | 48393144 | −0.76072 | 0.00128536 | C22orf34 | downstream | 44045 | Shore | 1818 |
| chr8 | 966339 | 968246 | −0.6265 | 0.00129586 | ERICH1 | upstream | 295114 | Shore | −581 |
| chr11 | 73980533 | 73981178 | −0.78485 | 0.00133142 | POLD3 | downstream | 50234 | Shore | 0 |
| chr18 | 32022373 | 32023451 | −0.68242 | 0.00135317 | MOCOS | inside | 79230 | Shore | −230 |
| chr18 | 73809395 | 73809862 | −0.76199 | 0.00144347 | GALR1 | upstream | 698315 | Far | 9620 |
| chr13 | 113548528 | 113549312 | 0.70947 | 0.00145514 | GAS6 | inside | 41083 | Shore | −393 |
| chr3 | 129687744 | 129688211 | 0.759315 | 0.00151474 | GATA2 | inside | 6506 | Shore | 0 |
| chr14 | 95577239 | 95578964 | −0.6455 | 0.00151879 | C14orf132 | inside | 50921 | Shore | −1084 |
| chr7 | 92075312 | 92075740 | −0.77713 | 0.00152285 | CDK6 | inside | 225407 | Far | −17503 |
| chr12 | 16648850 | 16649638 | 0.700737 | 0.00155156 | LMO3 | inside | 1059 | Far | −693049 |
| chr19 | 43436533 | 43438474 | 0.71493 | 0.00159765 | PPP1R14A | inside | 537 | Shore | 4 |
| chr7 | 50436490 | 50438081 | −0.63971 | 0.00161044 | IKZF1 | overlaps 5' | 0 | Shore | −596 |
| chr13 | 42886712 | 42887185 | −0.75536 | 0.00161901 | PIG38 | inside | 252469 | Far | 370673 |
| chr8 | 100031420 | 100033208 | 0.611014 | 0.00162763 | OSR2 | inside | 291 | Shore | −806 |
| chr16 | 31139986 | 31140921 | −0.70124 | 0.00167576 | TRIM72 | inside | 3089 | Far | 2105 |
| chr13 | 87123702 | 87125116 | 0.642127 | 0.00169358 | SLITRK5 | inside | 4752 | cover | 0 |
| chr2 | 172826761 | 172826901 | −0.72901 | 0.00172973 | DLX2 | upstream | 150663 | Far | −18042 |
| chr12 | 88272781 | 88274261 | −0.65038 | 0.00193625 | DUSP6 | promoter | 2355 | Shore | −506 |
| chr7 | 50103520 | 50103993 | −0.74337 | 0.00198218 | ZPBP | promoter | 149 | Shore | −53 |
| chr7 | 1182527 | 1183550 | −0.70109 | 0.00201859 | ZFAND2A | upstream | 16204 | Far | −15857 |
| chrX | 23042002 | 23042541 | −0.75918 | 0.00206093 | DDX53 | upstream | 111878 | Far | 217664 |
| chr8 | 98356982 | 98358151 | −0.64161 | 0.00212045 | TSPYL5 | inside | 1200 | Shore | 629 |
| chr11 | 132451645 | 132454794 | −0.55186 | 0.00212594 | OPCML | inside | 452818 | Far | 2108 |
| chr4 | 172202321 | 172202941 | −0.71014 | 0.00212594 | GALNT17 | downstream | 1996342 | Far | 767368 |
| chr11 | 133791126 | 133793856 | −0.56461 | 0.00224415 | B3GAT1 | upstream | 4105 | Far | −2997 |
| chr7 | 129912706 | 129913314 | −0.69892 | 0.00255614 | MEST | overlaps 3' | 20050 | Shore | 0 |
| chr12 | 38783104 | 38784488 | 0.607732 | 0.00260186 | SLC2A13 | inside | 1439 | Shore | 741 |
| chr13 | 112142200 | 112143003 | −0.6783 | 0.00268194 | C13orf28 | upstream | 5199 | Far | 11335 |
| chr7 | 90064351 | 90065026 | 0.683928 | 0.00268194 | PFTK1 | downstream | 612813 | Shore | −51 |
| chr11 | 103540808 | 103541706 | −0.6721 | 0.0027228 | PDGFD | promoter | 572 | Shore | −540 |
| chr21 | 42057698 | 42059424 | −0.5888 | 0.00274344 | RIPK4 | inside | 893 | Shore | 0 |
| chr2 | 4028568 | 4028969 | −0.73928 | 0.00285588 | ALLC | upstream | 300436 | Island | 0 |
| chr11 | 2243752 | 2244711 | −0.64164 | 0.00286305 | ASCL2 | downstream | 4046 | Shore | 1969 |
| chr5 | 11954677 | 11955633 | −0.64541 | 0.00287742 | CTNND2 | inside | 1476 | Shore | 917 |

TABLE 18-continued

Regions with consistent cancer-specific differential methylation (C-DMRs) at a FDR of 5%.

| chr | start | end | deltaM | fdr | gene name | relation | TSS distance | CGI | distToCGI |
|---|---|---|---|---|---|---|---|---|---|
| chr5 | 7900127 | 7901165 | −0.66262 | 0.00292092 | FASTKD3 | downstream | 20949 | Shore | 1780 |
| chr13 | 109229281 | 109231903 | −0.54967 | 0.00303226 | IRS2 | inside | 5011 | Shore | 564 |
| chr13 | 110126656 | 110127336 | 0.674417 | 0.00312403 | FLJ12118 | inside | 29127 | Shore | 1831 |
| chr20 | 48778557 | 48780262 | −0.59546 | 0.00331501 | PARD6B | downstream | 23421 | Shore | 510 |
| chr14 | 100997052 | 100997806 | −0.66962 | 0.00337263 | DIO3 | downstream | 101733 | Shore | −1304 |
| chr3 | 28591265 | 28591843 | 0.687621 | 0.00340596 | ZCWPW2 | upstream | 49632 | Shore | 0 |
| chr11 | 133445524 | 133446466 | −0.65981 | 0.0036033 | JAM3 | inside | 80392 | Shore | −633 |
| chr5 | 132392 | 134453 | −0.57597 | 0.00364751 | KIAA1909 | downstream | 108624 | Shore | 1975 |
| chrX | 142544143 | 142544478 | −0.74381 | 0.0037556 | SLITRK4 | inside | 6206 | Far | 4598 |
| chr20 | 4928754 | 4929383 | 0.695671 | 0.00377388 | SLC23A2 | inside | 761 | Far | 111977 |
| chr12 | 112557273 | 112558104 | −0.69254 | 0.00396112 | LHX5 | upstream | 163014 | Far | −43138 |
| chr16 | 85092993 | 85096638 | 0.487544 | 0.0039899 | FOXF1 | downstream | 8931 | Shore | 0 |
| chr10 | 1437553 | 1439129 | −0.58557 | 0.00404802 | ADARB2 | inside | 330540 | Far | −7539 |
| chr2 | 242632887 | 242634574 | −0.66358 | 0.00405778 | FLJ33590 | upstream | 168241 | Shore | 1740 |
| chr2 | 4028054 | 4028513 | −0.72737 | 0.00406756 | ALLC | upstream | 299922 | Shore | 11 |
| chr19 | 35406489 | 35407329 | 0.646091 | 0.00410688 | ZNF536 | upstream | 333475 | Shore | 60 |
| chr7 | 42233455 | 42234204 | 0.645604 | 0.0041366 | GLI3 | upstream | 4036 | Shore | 0 |
| chr3 | 174341049 | 174341237 | −0.80111 | 0.00415651 | SPATA16 | inside | 457 | Far | 254724 |
| chr5 | 3586182 | 3587073 | −0.70608 | 0.00415651 | IRX1 | downstream | 67442 | Shore | 1557 |
| chr8 | 22469866 | 22470840 | −0.62573 | 0.00420667 | SORBS3 | inside | 18110 | Far | −4286 |
| chr6 | 10501022 | 10502013 | 0.654216 | 0.00428802 | TFAP2A | downstream | 18579 | Shore | −1938 |
| chr11 | 31966319 | 31967492 | −0.63749 | 0.00433957 | RCN1 | downstream | 116160 | Shore | −699 |
| chr1 | 206062462 | 206063805 | 0.576185 | 0.00447616 | LOC148696 | overlaps 5' | 0 | Far | 44680 |
| chr22 | 47267034 | 47267870 | −0.63064 | 0.00447616 | FAM19A5 | downstream | 265877 | Shore | −1327 |
| chr6 | 80711271 | 80712497 | −0.59439 | 0.00450821 | ELOVL4 | inside | 1443 | Shore | 966 |
| chr22 | 47455137 | 47456387 | −0.58401 | 0.00455126 | FAM19A5 | inside | 77360 | Far | −4801 |
| chr11 | 134186796 | 134187368 | −0.6669 | 0.00469367 | B3GAT1 | upstream | 399775 | Far | −48599 |
| chr19 | 13474169 | 13475470 | −0.62291 | 0.00469367 | CACNA1A | inside | 2846 | Far | 2282 |
| chr16 | 25608094 | 25609031 | −0.61772 | 0.00474948 | HS3ST4 | downstream | 447477 | Shore | 1425 |
| chr8 | 117611158 | 117611838 | −0.64748 | 0.00474948 | EIF3S3 | downstream | 225404 | Far | 225273 |
| chr20 | 3603573 | 3604604 | −0.59867 | 0.00496688 | ADAM33 | inside | 6133 | Shore | −800 |
| chr20 | 59905352 | 59906092 | −0.67681 | 0.00503732 | CDH4 | inside | 39601 | Shore | −1622 |
| chr14 | 52326048 | 52327382 | −0.59637 | 0.00514462 | GNPNAT1 | inside | 750 | Shore | 32 |
| chr22 | 46984389 | 46985561 | −0.58562 | 0.00514462 | LOC388915 | upstream | 66632 | Shore | −218 |
| chr7 | 152249022 | 152250754 | −0.63648 | 0.00515666 | ACTR3B | upstream | 65627 | Far | 2095 |
| chr7 | 27108458 | 27111260 | 0.508493 | 0.00515666 | HOXA2 | overlaps 5' | 0 | cover | 0 |
| chr5 | 158465126 | 158466712 | 0.548688 | 0.00532789 | EBF1 | upstream | 5780 | cover | 0 |
| chr7 | 149667109 | 149668386 | 0.570024 | 0.00536522 | RARRES2 | inside | 1252 | Shore | 6 |
| chr10 | 3499370 | 3500060 | −0.64479 | 0.00540278 | PITRM1 | upstream | 294368 | Far | −8794 |
| chr11 | 31780765 | 31782111 | 0.582076 | 0.00542795 | PAX6 | inside | 7322 | Shore | 208 |
| chr7 | 139121471 | 139122253 | 0.621564 | 0.00552964 | TBXAS1 | downstream | 244217 | Shore | 1622 |
| chr17 | 14831980 | 14832519 | −0.66274 | 0.00555532 | FLJ45831 | upstream | 207736 | Far | 272136 |
| chr3 | 148446946 | 148448043 | −0.61085 | 0.00563299 | ZIC4 | downstream | 159053 | Far | 111759 |
| chr18 | 11140361 | 11141025 | −0.64161 | 0.00567218 | FAM38B | upstream | 452548 | Shore | −425 |
| chr19 | 4505154 | 4505834 | −0.63538 | 0.00569843 | SEMA6B | inside | 3668 | Shore | 1102 |
| chr4 | 81341228 | 81342411 | 0.593058 | 0.0057248 | PRDM8 | inside | 2092 | Shore | 121 |
| chr13 | 100427954 | 100428562 | −0.65947 | 0.00583131 | VGCNL1 | downstream | 438251 | Far | −302230 |
| chr1 | 221053963 | 221054618 | −0.65816 | 0.00595319 | FLJ43505 | upstream | 63194 | Shore | 249 |
| chr9 | 97304533 | 97306772 | 0.538529 | 0.00598058 | PTCH1 | inside | 3879 | Shore | 1524 |
| chr10 | 134597978 | 134600218 | −0.58526 | 0.00606339 | C10orf93 | inside | 5835 | Far | 5435 |
| chr10 | 24025367 | 24026498 | −0.60529 | 0.00611915 | C10orf67 | upstream | 351590 | Shore | −383 |
| chr19 | 50669649 | 50670313 | 0.642613 | 0.00611915 | FOSB | overlaps 5' | 0 | Shore | −1547 |
| chr18 | 491107 | 491721 | 0.648047 | 0.006232 | COLEC12 | promoter | 423 | Shore | −385 |
| chr17 | 41333049 | 41334735 | −0.54819 | 0.00626049 | MAPT | inside | 126808 | Far | −2213 |
| chr12 | 52430235 | 52431320 | 0.598153 | 0.00636111 | CALCOCO1 | upstream | 22750 | Island | 0 |
| chr13 | 67580738 | 67581346 | −0.63959 | 0.00640466 | PCDH9 | upstream | 878275 | Far | 875559 |
| chr5 | 134553843 | 134554638 | 0.606657 | 0.00641924 | H2AFY | downstream | 208137 | Shore | 137 |
| chr12 | 122813965 | 122816002 | −0.551 | 0.00652206 | ATP6V0A2 | upstream | 3575 | Shore | −758 |
| chr20 | 24399131 | 24400197 | 0.576626 | 0.00652206 | C20orf39 | inside | 194969 | Island | 0 |
| chr2 | 100303439 | 100304155 | 0.61944 | 0.00664131 | LONRF2 | upstream | 11041 | Shore | 56 |
| chr13 | 21140646 | 21141533 | 0.594077 | 0.0067472 | FGF9 | downstream | 32650 | Shore | 0 |
| chr8 | 132984463 | 132985363 | −0.6234 | 0.00679303 | KIAA0143 | downstream | 109587 | Shore | 141 |
| chr11 | 1861791 | 1862726 | −0.59254 | 0.006901 | LSP1 | inside | 7341 | Shore | −1881 |
| chr10 | 101273278 | 101274941 | 0.562231 | 0.00691655 | NKX2-3 | downstream | 11326 | Shore | −348 |
| chr13 | 113850844 | 113851732 | 0.592061 | 0.00694773 | RASA3 | inside | 64464 | Far | 2436 |
| chr7 | 32076356 | 32076765 | 0.715435 | 0.00699473 | PDE1C | promoter | 863 | Shore | 0 |
| chr11 | 45645190 | 45645996 | −0.6053 | 0.00701046 | CHST1 | promoter | 1443 | Shore | −1119 |
| chr19 | 16876450 | 16876750 | −0.74637 | 0.00701046 | CPAMD8 | inside | 121718 | Far | −6593 |
| chr8 | 53636408 | 53637226 | −0.60042 | 0.00702621 | UNQ9433 | inside | 3338 | Far | 2871 |
| chr15 | 24571127 | 24572559 | −0.55445 | 0.00705782 | GABRB3 | promoter | 1108 | Shore | −1091 |
| chr6 | 133605067 | 133606789 | 0.529372 | 0.00708955 | EYA4 | inside | 287568 | Shore | 0 |
| chr12 | 88266873 | 88268978 | −0.49621 | 0.0072177 | DUSP6 | inside | 1448 | Shore | 321 |
| chr17 | 782607 | 784014 | −0.56251 | 0.00723386 | NXN | inside | 45745 | Far | 12943 |
| chr19 | 36535076 | 36535822 | 0.607202 | 0.00734784 | TSHZ3 | upstream | 73062 | Shore | 0 |
| chr13 | 20184925 | 20186542 | −0.53392 | 0.00741367 | IL17D | inside | 8693 | Far | 7069 |

TABLE 18-continued

Regions with consistent cancer-specific differential methylation (C-DMRs) at a FDR of 5%.

| chr | start | end | deltaM | fdr | gene name | relation | TSS distance | CGI | distToCGI |
|---|---|---|---|---|---|---|---|---|---|
| chr17 | 22902924 | 22903499 | −0.63407 | 0.00763111 | KSR1 | inside | 71344 | Far | 53125 |
| chr1 | 32992405 | 32992989 | 0.632486 | 0.00780208 | KIAA1522 | inside | 20168 | Shore | 0 |
| chr15 | 32835765 | 32836849 | −0.56319 | 0.00792371 | CX36 | promoter | 1785 | Shore | −993 |
| chr12 | 130718351 | 130718755 | −0.68171 | 0.00801157 | SFRS8 | downstream | 131479 | Far | −5588 |
| chr13 | 36392772 | 36394298 | 0.523296 | 0.00801157 | ALG5 | downstream | 77178 | Shore | −20 |
| chr20 | 61186047 | 61186916 | −0.58658 | 0.00801157 | BHLHB4 | upstream | 77261 | Shore | 1296 |
| chr11 | 19323912 | 19324590 | 0.644909 | 0.00802925 | E2F8 | upstream | 104830 | inside | 0 |
| chr12 | 111302662 | 111303588 | 0.576207 | 0.00820783 | RPL6 | downstream | 28237 | Island | 0 |
| chr15 | 97011564 | 97012941 | 0.531506 | 0.0082802 | IGF1R | inside | 306092 | Shore | 0 |
| chr16 | 49141667 | 49142498 | −0.59792 | 0.00837144 | NKD1 | inside | 83643 | Shore | −701 |
| chr14 | 57669356 | 57669957 | −0.63311 | 0.00853784 | C14orf37 | inside | 18642 | Far | 18087 |
| chr8 | 144372893 | 144373912 | −0.59142 | 0.0085565 | LOC338328 | promoter | 2476 | Far | 9171 |
| chr9 | 124022303 | 124023189 | 0.590922 | 0.00861269 | LHX6 | inside | 7615 | Shore | 0 |
| chr19 | 3240846 | 3241458 | −0.61842 | 0.0086692 | BRUNOL5 | inside | 6612 | Far | 2809 |
| chr16 | 4101996 | 4102769 | 0.594061 | 0.00884063 | ADCY9 | inside | 3417 | Far | 2040 |
| chr12 | 4889938 | 4890628 | 0.61045 | 0.00889841 | KCNA1 | close to 3' | 1662 | inside | 0 |
| chr3 | 151719593 | 151721472 | −0.52881 | 0.00895651 | SERP1 | downstream | 25645 | Far | 24824 |
| chr19 | 41058856 | 41059386 | −0.6366 | 0.00903448 | APLP1 | inside | 3151 | Shore | −1192 |
| chr7 | 71437052 | 71438143 | −0.55387 | 0.00903448 | CALN1 | inside | 1752 | Shore | 550 |
| chr9 | 37023001 | 37023958 | 0.572428 | 0.00919216 | PAX5 | inside | 517 | Shore | 177 |
| chr20 | 33336228 | 33337040 | −0.58612 | 0.00921203 | FAM83C | overlaps 3' | 6598 | Shore | −75 |
| chr7 | 5360426 | 5361424 | 0.575878 | 0.00931195 | SLC29A4 | upstream | 50199 | Shore | 974 |
| chr18 | 75366596 | 75367142 | −0.77008 | 0.00935217 | NFATC1 | inside | 23167 | Far | 4639 |
| chr6 | 7413675 | 7414250 | −0.61922 | 0.00939254 | RIOK1 | upstream | 50409 | Far | 72267 |
| chr11 | 64244495 | 64245421 | −0.57059 | 0.00943306 | NRXN2 | inside | 1814 | Shore | 1648 |
| chr16 | 7291114 | 7292175 | −0.5578 | 0.00949411 | A2BP1 | inside | 408671 | Far | 2159 |
| chr8 | 3257254 | 3257862 | −0.61199 | 0.00949411 | CSMD1 | inside | 1581873 | Far | −389899 |
| chr5 | 88221043 | 88221995 | 0.573951 | 0.00955551 | MEF2C | upstream | 6264 | Island | 0 |
| chr13 | 99440030 | 99441015 | 0.573722 | 0.00959662 | ZIC2 | upstream | 3012 | Shore | 0 |
| chr10 | 102811316 | 102812341 | −0.55274 | 0.00965857 | KAZALD1 | overlaps 3' | 2996 | inside | 0 |
| chr17 | 71291527 | 71292204 | −0.59686 | 0.00988864 | H3F3B | upstream | 4073 | Shore | 237 |
| chr10 | 112248574 | 112249464 | 0.566331 | 0.00999474 | DUSP5 | inside | 11825 | Shore | 0 |

DeltaM is cancer minus normal. FDR is false discovery rate.
Columns are chromosome, start, end, delta M, fdr, gene, relation to gene, distance to TSS, relation to CGI, distance to CGI

What is claimed is:

1. A method of detecting colon cancer in a subject comprising:
   a) determining a methylation status of nucleic acid sequences in a sample from a tissue suspected of having colon cancer and a sample from a normal tissue of the subject,
   wherein determining the methylation status comprises:
      i) contacting the nucleic acid sequences of each sample with a plurality of control probes that selectively hybridize to genomic regions without CpG regions;
      ii) generating M values for the plurality of control probes for each sample;
      iii) calculating an averaged M value for each sample using the generated M values to define a value for unmethylated nucleic acid sequences for each sample;
      iv) contacting the nucleic acid sequences of each sample with a second plurality of probes that selectively hybridize to genomic regions with CpG regions;
      v) generating M values for the second plurality of probes and comparing the generated M values to the average M value for each sample to determine the methylation status of the nucleic acid sequences of each sample; and
      vi) comparing the methylation status of each sample to identify cancer-specific differential methylated regions (C-DMRs) in the sample from the tissue suspected of having colon cancer, wherein the presence of C-DMRs in the sample from the tissue suspected of having colon cancer is indicative of colon cancer, thereby detecting colon cancer in the subject; and
   b) administering a cancer therapy to the subject.

2. The method of claim 1, wherein the nucleic acid sequences are within a gene.

3. The method of claim 1, wherein the nucleic acid sequences are upstream or downstream of a gene.

4. The method of claim 1, wherein the methylation status is hypomethylation.

5. The method of claim 1, wherein the methylation status is hypermethylation.

6. The method of claim 1, further comprising performing one or more techniques selected from the group consisting of a nucleic acid amplification, polymerase chain reaction (PCR), methylation specific PCR, bisulfite pyrosequencing, single-strand conformation polymorphism (SSCP) analysis, restriction analysis, microarray technology, and proteomics.

* * * * *

UNITED STATES PATENT AND TRADEMARK OFFICE
CERTIFICATE OF CORRECTION

| | | |
|---|---|---|
| PATENT NO. | : 10,927,415 B2 | Page 1 of 1 |
| APPLICATION NO. | : 12/625240 | |
| DATED | : February 23, 2021 | |
| INVENTOR(S) | : Andrew P. Feinberg | |

It is certified that error appears in the above-identified patent and that said Letters Patent is hereby corrected as shown below:

In the Specification

Column 1, Lines 13-16 reads:
"This invention was made in part with government support under Grant Nos. P50HG003233 and R37CA54358 awarded by the National Institutes of Health. The United States government has certain rights in this invention."

Should read:
--This invention was made with government support under Grant Nos. HG003233, GM083084 and CA054358 awarded by the National Institutes of Health. The government has certain rights in the invention.--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*